(12) United States Patent
Drescher et al.

(10) Patent No.: US 8,969,552 B2
(45) Date of Patent: Mar. 3, 2015

(54) ARYLSULFONYLMETHYL OR ARYLSULFONAMIDE SUBSTITUTED AROMATIC COMPOUNDS SUITABLE FOR TREATING DISORDERS THAT RESPOND TO MODULATION OF THE DOPAMINE D3 RECEPTOR

(75) Inventors: Karla Drescher, Dossenheim (DE); Andreas Haupt, Schwetzingen (DE); Liliane Unger, Ludwigshafen (DE); Sean C. Turner, Mannheim (DE); Wilfried Braje, Mannheim (DE); Roland Grandel, Dossenheim (DE); Christophe Henry, Munich (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 1626 days.

(21) Appl. No.: 11/665,428

(22) PCT Filed: Oct. 14, 2005

(86) PCT No.: PCT/EP2005/011091
§ 371 (c)(1),
(2), (4) Date: Mar. 7, 2008

(87) PCT Pub. No.: WO2006/040178
PCT Pub. Date: Apr. 20, 2006

(65) Prior Publication Data
US 2009/0012074 A1    Jan. 8, 2009

Related U.S. Application Data

(60) Provisional application No. 60/711,942, filed on Aug. 26, 2005, provisional application No. 60/618,776, filed on Oct. 14, 2004.

(51) Int. Cl.
*C07C 311/44* (2006.01)
*C07D 207/10* (2006.01)
(Continued)

(52) U.S. Cl.
CPC ............. *C07C 311/21* (2013.01); *C07C 311/29* (2013.01); *C07C 311/44* (2013.01);
(Continued)

(58) Field of Classification Search
None
See application file for complete search history.

(56) References Cited

U.S. PATENT DOCUMENTS 6,706,757 B2    3/2004    Greenblatt et al.

FOREIGN PATENT DOCUMENTS

| WO | WO 97/45403 | * | 12/1997 | ............ C07C 311/05 |
| WO | WO 03/013507 | * | 2/2003 | ............ A61K 31/40 |
| WO | WO 03/013507 A1 | | 2/2003 | |
| WO | WO 2004/112785 | * | 12/2004 | ........... A61K 31/428 |
| WO | WO 2004/112785 A1 | | 12/2004 | |

OTHER PUBLICATIONS

J.C. Schwartz et al., The Dopamine $D_3$ Receptor as a Target for Antipsychotics, in Novel Antipsychotic Drugs, H.Y. Meltzer, Ed. Raven Press, New York, 1992, pp. 135-144.
M. Dooley et al., Drugs and Aging 1998, 12, 495-514.
J. N. Joyce, Pharmacology and Therapeutics 2001, 90, pp. 231-59 "The Dopamine $D_3$ Receptor as a Therapeutic Target for Antipsychotic and Antiparkinsonian Drugs".
P. Sokoloff et al., Localization and Function of the $D_3$ Dopamine Receptor, Arzneim. Frosch./Drug Res. 42(I), 224 (1992).
P. Sokoloff et al., Molecular Cloning and Characterization of a Novel Dopamine Receptor ($D_3$) as a Target for Neuroleptics, Nature, 347, 146 (1990).
D. Cussac et al, "The novel antagonist, 533084, and GR218, 231 interact selectively with cloned native, rat dopamine $D_3$ receptors as compared with native, rat dopamine $D_2$ receptors" European Journal of Pharmacology, vol, 394, 2000, pp. 47-50, XP002367384.

* cited by examiner

*Primary Examiner* — Alicia L Otton
(74) *Attorney, Agent, or Firm* — Lisa V. Mueller; Michael Best & Friedrich LLP

(57) ABSTRACT

The present invention relates to aromatic compounds of the formula I

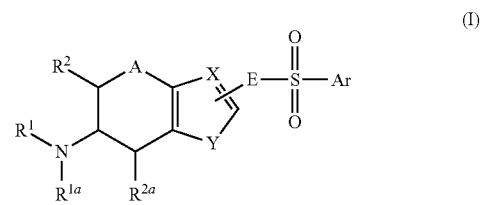

(I)

wherein Ar is phenyl or an aromatic 5- or 6-membered C-bound heteroaromatic radical, wherein Ar may carry 1 radical $R^a$ and wherein Ar may also carry 1 or 2 radicals $R^b$;
X is N or CH;
Y is O, S, —CH=N—, —CH=CH— or —N=CH—;
A is $CH_2$, O or S;
E is $CR^6R^7$ or $NR^3$;
$R^1$ is $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;
$R^{1a}$ is H, $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, or $R^{1a}$ and $R^2$ together are $(CH_2)_n$ with n being 2 or 3, or $R^{1a}$ and $R^{2a}$ together are $(CH_2)_n$ with n being 2 or 3;
$R^2$ and $R^{2a}$ are independently of each other H, $CH_3$, $CH_2F$, $CHF_2$ or $CF_3$;
$R^3$ is H or $C_1$-$C_4$-alkyl;
$R^6$, $R^7$ independently of each other are selected from H, $C_1$-$C_2$-alkyl and fluorinated $C_1$-$C_2$-alkyl;
and the physiologically tolerated acid addition salts thereof. The invention also relates to the use of a compound of the formula I or a pharmaceutically acceptable salt thereof for preparing a pharmaceutical composition for the treatment of a medical disorder susceptible to treatment with a dopamine D3 receptor ligand.

25 Claims, No Drawings

(51) Int. Cl.
*C07D 211/10* (2006.01)
*C07D 215/38* (2006.01)
*C07D 263/32* (2006.01)
*C07D 413/04* (2006.01)
*C07C 311/21* (2006.01)
*C07C 311/29* (2006.01)
*C07D 239/84* (2006.01)
*C07D 277/82* (2006.01)
*C07D 311/04* (2006.01)
*C07D 491/04* (2006.01)

(52) U.S. Cl.
CPC ......... *C07C2101/02* (2013.01); *C07C 2102/10* (2013.01); *C07D 207/10* (2013.01); *C07D 211/10* (2013.01); *C07D 215/38* (2013.01); *C07D 239/84* (2013.01); *C07D 263/32* (2013.01); *C07D 277/82* (2013.01); *C07D 311/04* (2013.01); *C07D 413/04* (2013.01); *C07D 491/04* (2013.01)
USPC ........... 544/160; 546/101; 548/235; 548/247; 548/377.1; 548/543; 564/80

ARYLSULFONYLMETHYL OR ARYLSULFONAMIDE SUBSTITUTED AROMATIC COMPOUNDS SUITABLE FOR TREATING DISORDERS THAT RESPOND TO MODULATION OF THE DOPAMINE D3 RECEPTOR

CROSS-REFERENCE TO RELATED APPLICATIONS

This is a U.S. National Stage Entry of International Patent Application No. PCT/EP2005/011091, filed on Oct. 14, 2005, which claims priority to U.S. patent application Ser. No. 60/711,942, filed on Aug. 26, 2005, and U.S. patent application Ser. No. 60/618,776, filed on Oct. 14, 2004, the entire contents of all of which are fully incorporated herein by reference.

BACKGROUND OF THE INVENTION

The present invention relates to novel arylsulfonylmethyl- and arylsulfonamide substituted aromatic compounds. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, namely the $D_1$ and $D_2$ receptors. More recently, a third subtype was found, namely the $D_3$ receptor which appears to mediate some effects of antipsychotics and antiparkinsonians (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine $D_3$ Receptor as a Therapeutic Target for Antipsychotic and Antiparkinsonian Drugs").

Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

WO 97/45403 discloses inter alia 6-aminotetraline compounds having an affinity for the dopamine $D_3$ receptor. Some of these compounds possess a certain selectivity for the dopamine $D_3$ receptor in comparison with their affinity for the $D_2$ receptor. They have therefore been proposed as being suitable for treating diseases of the central nervous system. Unfortunately their affinity and selectivity towards the $D_3$ receptor is only moderate or their pharmacological profile are not satisfactory. Consequently there is an ongoing need to provide new compounds, which either have an high affinity and an improved selectivity. The compounds should also have good pharmacological profile, e.g. a high brain plasma ratio, a high bioavailability, good metabolic stability or a decreased inhibition of the mitochondrial respiration.

SUMMARY OF THE INVENTION

The invention is based on the object of providing compounds which act as highly selective dopamine $D_3$ receptor ligands. This object is surprisingly achieved by means of arylsulfonylmethyl substituted aromatic compounds and by arylsulfonamide substituted aromatic compounds of the formula I

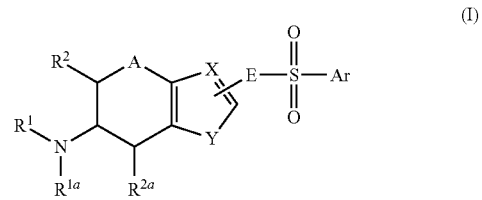

wherein

Ar is phenyl or an aromatic 5- or 6-membered C-bound heteroaromatic radical, wherein Ar may carry 1 radical $R^a$ and wherein Ar may carry 1 or 2 further radicals $R^b$;

$R^a$ being selected from the group consisting of $C_1$-$C_6$-alkyl, $C_2$-$C_6$-alkenyl, fluorinated $C_2$-$C_6$-alkenyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy; $C_1$-$C_6$-alkoxy-$C_1$-$C_4$-alkoxy, COOH, $NR^4R^5$, $CH_2NR^4R^5$, $ONR^4R^5$, NHC(O)$NR^4R^5$, C(O)$NR^4R^5$, $SO_2NR^4R^5$, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenyl, phenoxy, benzyloxy and a 3- to 7-membered heterocyclic radical, wherein the five last mentioned radicals may carry 1, 2, 3 or 4 radicals selected from halogen, cyano, OH, oxo, CN, and the radicals $R^a$, $R^b$ being, independently from each other, selected from halogen, cyano, nitro, OH, methyl, methoxy, fluoromethyl, difluoromethyl, trifluoromethyl, fluoromethoxy, difluoromethoxy and trifluoromethoxy, the radical $R^a$ and one radical $R^b$, if present and bound to two adjacent carbon atoms of phenyl, may form a 5- or 6-membered heterocyclic or carbocylic ring which is fused to the phenyl ring and which is unsubstituted or which may carry 1, 2 or 3 radicals selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl;

provided that if Ar is phenyl, $R^{2a}$ is hydrogen and $R^{2b}$ is hydrogen and A is $CH_2$, Ar carries 1 radical $R^a$ which is different from methyl, methoxy, trifluormethyl and trifluoromethoxy, and optionally 1 or 2 radicals $R^b$;

X is N or CH;
Y is O, S, —CH=N—, —CH=CH— or —N=CH—;
A is $CH_2$, O or S;
E is $CR^6R^7$ or $NR^3$;
$R^1$ is $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;
$R^{1a}$ is H, $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, or $R^{1a}$ and $R^2$ together are $(CH_2)_n$ with n being 2 or 3, or $R^{1a}$ and $R^{2a}$ together are $(CH_2)_n$ with n being 2 or 3;
$R^2$ and $R^{2a}$ each independently are H, $CH_3$, $CH_2F$, $CHF_2$ or $CF_3$
$R^3$ is H or $C_1$-$C_4$-alkyl;
$R^4$, $R^5$ independently of each other are selected from H, $C_1$-$C_2$-alkyl, $C_1$-$C_2$-alkoxy and fluorinated $C_1$-$C_2$-alkyl; and
$R^6$, $R^7$ independently of each other are selected from H, $C_1$-$C_2$-alkyl and fluorinated $C_1$-$C_2$-alkyl, in particular hydrogen;

and the physiologically tolerated acid addition salts of these compounds.

The present invention therefore relates to bicyclic aromatic compounds of the general formula I and to their physiologically tolerated acid addition salts.

The present invention also relates to a pharmaceutical composition which comprises at least one aromatic of the formula I and/or at least one physiologically tolerated acid addition salt of I, where appropriate together with physiologically acceptable carriers and/or auxiliary substances.

The present invention also relates to a method for treating disorders which respond to influencing by dopamine $D_3$ receptor antagonists or dopamine $D_3$ agonists; said method comprising administering an effective amount of at least one aromatic compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include, in particular, disorders and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the above mentioned indications. Provided the compounds of the formula I of a given constitution may exist in different spatial arrangements, for example if they possess one or more centers of asymmetry, poly-substituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The pre-fix $C_n$-$C_m$ indicates in each case the possible number of carbon atoms in the group.

The term halogen denotes in each case fluorine, bromine, chlorine or iodine, in particular fluorine or chlorine.

$C_1$-$C_4$ Alkyl (and likewise in $C_1$-$C_4$ hydroxyalkyl, $C_1$-$C_6$ alkoxy-$C_1$-$C_4$-alkyl, $C_1$-$C_4$ alkylcarbonyl, $C_1$-$C_4$ alkylcarbonylamino, $C_1$-$C_4$ alkylcarbonyloxy, $C_1$-$C_4$ alkylthio, $C_1$-$C_4$ alkylsulfinyl, $C_1$-$C_4$ alkylsulfonyl etc.) is a straight-chain or branched alkyl group having from 1 to 4 carbon atoms. Examples of an alkyl group are methyl, ethyl, n-propyl, iso-propyl, n-butyl, 2-butyl, iso-butyl or tert-butyl.

$C_1$-$C_6$ Alkyl (and likewise in $C_1$-$C_6$ hydroxyalkyl, $C_1$-$C_6$ alkoxy-$C_1$-$C_4$-alkyl, $C_1$-$C_6$ alkylcarbonyl, $C_1$-$C_6$ alkylcarbonylamino, $C_1$-$C_6$ alkylcarbonyloxy, $C_1$-$C_6$ alkylthio, $C_1$-$C_6$ alkylsulfinyl, $C_1$-$C_6$ alkylsulfonyl etc.) is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Fluorinated $C_1$-$C_6$ alkyl (and likewise in fluorinated $C_1$-$C_6$ alkylcarbonyl, fluorinated $C_1$-$C_6$ alkylcarbonylamino, fluorinated $C_1$-$C_6$ alkylcarbonyloxy, fluorinated $C_1$-$C_6$ alkylthio, fluorinated $C_1$-$C_6$ alkylsulfinyl, fluorinated $C_1$-$C_6$ alkylsulfonyl etc.) is a straight-chain or branched alkyl group having from 1 to 6, in particular 1 to 4 carbon atoms, more preferably 1 to 3 carbon atoms, wherein at least one, e.g. 1, 2, 3, 4 or all of the hydrogen atoms are replaced by a fluorine atoms such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2- difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, etc.;

Branched $C_3$-$C_6$-alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl 1-methyl-1-ethylpropyl.

$C_1$-$C_6$ Alkoxy (and likewise in $C_1$-$C_6$ alkoxycarbonyl, $C_1$-$C_6$ alkoxy-$C_1$-$C_4$ alkyl, $C_1$-$C_6$ alkoxy-$C_1$-$C_4$ alkoxy and $C_1$-$C_6$ hydroxyalkoxy) is a straight-chain or branched alkyl group having from 1 to 6, in particular 1 to 4 carbon atoms, which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy;

Fluorinated $C_1$-$C_6$ alkoxy (and likewise in fluorinated $C_1$-$C_6$alkoxycarbonyl) is a straight-chain or branched alkoxy group having from 1 to 6, in particular 1 to 4 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc.;

$C_3$-$C_6$ Cycloalkyl is a cycloaliphatic radical having from 3 to 6 C atoms, such as cyclopropyl, cyclobutyl and cyclopentyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl.

Fluorinated $C_3$-$C_6$ cycloalkyl is a cycloaliphatic radical having from 3 to 6 C atoms, such as cyclopropyl, cyclobutyl and cyclopentyl, wherein at least one, e.g. 1, 2, 3, 4 or all of the hydrogen atoms are replaced by a fluorine atoms such as in 1-fluorocyclopropyl, 2-fluorocyclopropyl, 2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 C-atoms, e.g. vinyl, allyl (2-propen-1-yl), 1-propen-1-yl, 2-propen-2-yl, methallyl(2-methylprop-2-en-1-yl) and the like. $C_3$-$C_4$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl and the like $C_1$-$C_6$ hydroxyalkyl is an alkyl radical having from 1 to 6 carbon atoms as defined above, wherein one hydrogen atom is replaced by hydroxy. Examples comprise hydroxymethyl, 2-hydroxyethyl, 1-hydroxyethyl, 3-hydroxypropyl, 2-hydroxypropyl, 1-methyl-1-hydroxyethyl and the like.

$C_1$-$C_6$ hydroxyalkoxy is an alkoxy radical having from 1 to 6, preferably from 2 to 4 carbon atoms as defined above, wherein one hydrogen atom is replaced by hydroxy. Examples comprise 2-hydroxyethyl, 3-hydroxypropyl, 2-hydroxypropyl, 1-methyl-2-hydroxyethyl and the like.

$C_1$-$C_6$ alkoxy-$C_1$-$C_4$-alkyl is an alkyl radical having from 1 to 4 carbon atoms as defined above, wherein one hydrogen atom is replaced by $C_1$-$C_6$ alkoxy. Examples comprise methoxymethyl, 2-methoxyethyl, 1-methoxyethyl, 3-methoxypropyl, 2-methoxypropyl, 1-methyl-1-methoxyethyl, ethoxymethyl, 2-ethoxyethyl, 1-ethoxyethyl, 3-ethoxypropyl, 2-ethoxypropyl, 1-methyl-1-ethoxyethyl and the like.

$C_1$-$C_6$ alkoxy-$C_1$-$C_4$-alkoxy is an alkoxy radical having from 1 to 4 carbon atoms as defined above, wherein one hydrogen atom is replaced by $C_1$-$C_6$ alkoxy. Examples comprise methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

$C_1$-$C_6$ alkylcarbonyl is a radical of the formula R—C(O)—, wherein R is an alkyl radical having from 1 to 6 carbon atoms as defined above. Examples comprise acetyl, propionyl, n-butylryl, 2-methylpropionyl, pivalyl and the like.

$C_1$-$C_6$ alkylcarbonylamino is a radical of the formula R—C(O)—NH—, wherein R is an alkyl radical having from 1 to 6 carbon atoms as defined above. Examples comprise acetamido, propionamido, n-butyramido, 2-methylpropanamido, 2,2-dimethylpropionamido and the like.

$C_1$-$C_6$ alkylcarbonyloxy is a radical of the formula R—C(O)—O—, wherein R is an alkyl radical having from 1 to 6 carbon atoms as defined above. Examples comprise acetyloxy, propionyloxy, n-butyryloxy, 2-methylpropionyloxy, 2,2-dimethylpropionyloxy and the like.

$C_1$-$C_6$ alkylthio is a radical of the formula R—S—, wherein R is an alkyl radical having from 1 to 6 carbon atoms as defined above. Examples comprise methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl;

$C_1$-$C_6$ alkylsulfinyl is a radical of the formula R—S(O)—, wherein R is an alkyl radical having from 1 to 6 carbon atoms as defined above. Examples comprise methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl;

$C_1$-$C_6$ alkylsulfonyl is a radical of the formula R—S(O)$_2$—, wherein R is an alkyl radical having from 1 to 6 carbon atoms as defined above. Examples comprise methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl;

fluorinated $C_1$-$C_6$ alkylcarbonyl is a radical of the formula R—C(O)—, wherein R is a fluorinated alkyl radical having from 1 to 6 carbon atoms as defined above. Examples comprise fluoroacetyl, difluoroacetyl, trifluoroacetyl, (R)-1-fluoroethylcarbonyl, (S)-1-fluoroethylcarbonyl, 2-fluoroethylcarbonyl, 1,1-difluoroethylcarbonyl, 2,2-difluoroethylcarbonyl, 2,2,2-trifluoroethylcarbonyl, (R)-1-fluoropropylcarbonyl, (S)-1-fluoropropylcarbonyl, 2-fluoropropylcarbonyl, 3-fluoropropylcarbonyl, 1,1-difluoropropylcarbonyl, 2,2-difluoropropylcarbonyl, 3,3-difluoropropylcarbonyl, 3,3,3-trifluoropropylcarbonyl, (R)-2-fluoro-1-methylethylcarbonyl, (S)-2-fluoro-1-methylethylcarbonyl, (R)-2,2-difluoro-1-methylethylcarbonyl, (S)-2,2-difluoro-1-methylethylcarbonyl, (R)-1,2-difluoro-1-methylethylcarbonyl, (S)-1,2-difluoro-1-methylethylcarbonyl, (R)-2,2,2-trifluoro-1-methylethylcarbonyl, (S)-2,2,2-trifluoro-1-methylethylcarbonyl, 2-fluoro-1-(fluoromethyl)ethylcarbonyl, 1-(difluoromethyl)-2,2-difluoroethylcarbonyl, (R)-1-fluorobutylcarbonyl, (S)-1-fluorobutylcarbonyl, 2-fluorobutylcarbonyl, 3-fluorobutylcarbonyl, 4-fluorobutylcarbonyl, 1,1-difluorobutylcarbonyl, 2,2-difluorobutylcarbonyl, 3,3-difluorobutylcarbonyl, 4,4-difluorobutylcarbonyl, 4,4,4-trifluorobutylcarbonyl, etc.;

fluorinated $C_1$-$C_6$ alkylcarbonylamino is a radical of the formula R—C(O)—NH—, wherein R is a fluorinated alkyl radical having from 1 to 6 carbon atoms as defined above. Examples comprise fluoroacetamido, difluoroacetamido, trifluoroacetamido, (R)-1-fluoroethylcarbonylamino, (S)-1-fluoroethylcarbonylamino, 2-fluoroethylcarbonylamino, 1,1-difluoroethylcarbonylamino, 2,2-difluoroethylcarbonylamino, 2,2,2-trifluoroethylcarbonylamino, (R)-1-fluoropropylcarbonylamino, (S)-1-fluoropropylcarbonylamino, 2-fluoropropylcarbonylamino, 3-fluoropropylcarbonylamino, 1,1-difluoropropylcarbonylamino, 2,2-difluoropropylcarbonylamino, 3,3-difluoropropylcarbonylamino, 3,3,3-trifluoropropylcarbonylamino, (R)-2-fluoro-1-methylethylcarbonylamino, (S)-2-fluoro-1-methylethylcarbonylamino, (R)-2,2-difluoro-1-methylethylcarbonylamino, (S)-2,2-difluoro-1-methylethylcarbonylamino, (R)-1,2-difluoro-1-methylethylcarbonylamino, (S)-1,2-difluoro-1-methylethylcarbonylamino, (R)-2,2,2-trifluoro-1-methylethylcarbonylamino, (S)-2,2,2-trifluoro-1-methylethylcarbonylamino, 2-fluoro-1-(fluoromethyl)ethylcarbonylamino, 1-(difluoromethyl)-2,2-difluoroethylcarbonylamino, (R)-1-fluorobutylcarbonylamino, (S)-1-fluorobutylcarbonylamino, 2-fluorobutylcarbonylamino, 3-fluorobutylcarbonylamino, 4-fluorobutylcarbonylamino, 1,1-difluorobutylcarbonylamino, 2,2-difluorobutylcarbonylamino, 3,3-difluorobutylcarbonylamino, 4,4-difluorobutylcarbonylamino, 4,4,4-trifluorobutylcarbonylamino, etc., fluorinated $C_1$-$C_6$ alkylcarbonyloxy is a radical of the formula R—C(O)—O—, wherein R is a fluorinated alkyl radical having from 1 to 6 carbon atoms as defined above fluoroacetyl, difluoroacetyl, trifluoroacetyl, (R)-1-fluoroethylcarbonyloxy, (S)-1-fluoroethylcarbonyloxy, 2-fluoroethylcarbonyloxy, 1,1-difluoroethylcarbonyloxy, 2,2-difluoroethylcarbonyloxy, 2,2,2-trifluoroethylcarbonyloxy, (R)-1-fluoropropylcarbonyloxy, (S)-1-fluoropropylcarbonyloxy, 2-fluoropropylcarbonyloxy, 3-fluoropropylcarbonyloxy, 1,1-difluoropropylcarbonyloxy, 2,2-difluoropropylcarbonyloxy, 3,3-difluoropropylcarbonyloxy, 3,3,3-trifluoropropylcarbonyloxy, (R)-2-fluoro-1-methylethylcarbonyloxy, (S)-2-fluoro-1-methylethylcarbonyloxy, (R)-2,2-difluoro-1-methylethylcarbonyloxy, (S)-2,2-difluoro-1-methylethylcarbonyloxy, (R)-1,2-difluoro-1-methylethylcarbonyloxy, (S)-1,2-difluoro-1-methylethylcarbonyloxy, (R)-2,2,2-trifluoro-1-methylethylcarbonyloxy, (S)-2,2,2-trifluoro-1-methylethylcarbonyloxy, 2-fluoro-1-(fluoromethyl)ethylcarbonyloxy, 1-(difluoromethyl)-2,2-difluoroethylcarbonyloxy, (R)-1-fluorobutylcarbonyloxy, (S)-1-fluorobutylcarbonyloxy, 2-fluorobutylcarbonyloxy, 3-fluorobutylcarbonyloxy, 4-fluorobutylcarbonyloxy, 1,1-difluorobutylcarbonyloxy, 2,2-difluorobutylcarbonyloxy, 3,3-difluorobutylcarbonyloxy, 4,4-difluorobutylcarbonyloxy, 4,4,4-trifluorobutylcarbonyloxy, etc.;

fluorinated $C_1$-$C_6$ alkylthio is a radical of the formula R—S—, wherein R is a fluorinated alkyl radical having from 1 to 6 carbon atoms as defined above. Examples comprise fluoromethylthio, difluoromethylthio, trifluoromethylthio, (R)-1-fluoroethylthio, (S)-1-fluoroethylthio, 2-fluoroethylthio, 1,1-difluoroethylthio, 2,2-difluoroethylthio, 2,2,2-trifluoroethylthio, (R)-1-fluoropropylthio, (S)-1-fluoropropylthio, 2-fluoropropylthio, 3-fluoropropylthio, 1,1-difluoropropylthio, 2,2-difluoropropylthio, 3,3-difluoropropylthio, 3,3,3-trifluoropropylthio, (R)-2-fluoro-1-methylethylthio, (S)-2-fluoro-1-methylethylthio, (R)-2,2-difluoro-1-methylethylthio, (S)-2,2-difluoro-1-methylethylthio, (R)-1,2-difluoro-1-methylethylthio, (S)-1,2-difluoro-1-methylethylthio, (R)-2,2,2-trifluoro-1-methylethylthio, (S)-2,2,2-trifluoro-1-methylethylthio, 2-fluoro-1-(fluoromethyl)ethylthio, 1-(difluoromethyl)-2,2-difluoroethylthio, (R)-1-fluorobutylthio, (S)-1-fluorobutylthio, 2-fluorobutylthio, 3-fluorobutylthio, 4-fluorobutylthio, 1,1-difluorobutylthio, 2,2-difluorobutylthio, 3,3-difluorobutylthio, 4,4-difluorobutylthio, 4,4,4-trifluorobutylthio, etc.;

fluorinated $C_1$-$C_6$ alkylsulfinyl is a radical of the formula R—S(O)—, wherein R is a fluorinated alkyl radical having from 1 to 6 carbon atoms as defined above. Examples comprise fluoromethylsulfinyl, difluoromethylsulfinyl, trifluoromethylsulfinyl, (R)-1-fluoroethylsulfinyl, (S)-1-fluoroethylsulfinyl, 2-fluoroethylsulfinyl, 1,1-difluoroethylsulfinyl, 2,2-difluoroethylsulfinyl, 2,2,2-trifluoroethylsulfinyl, (R)-1-fluoropropylsulfinyl, (S)-1-fluoropropylsulfinyl, 2-fluoropropylsulfinyl, 3-fluoropropylsulfinyl, 1,1-difluoropropylsulfinyl, 2,2-difluoropropylsulfinyl, 3,3-difluoropropylsulfinyl, 3,3,3-trifluoropropylsulfinyl, (R)-2-fluoro-1-methylethylsulfinyl, (S)-2-fluoro-1-methylethylsulfinyl, (R)-2,2-difluoro-1-methylethylsulfinyl, (S)-2,2-difluoro-1-methylethylsulfinyl, (R)-1,2-difluoro-1-methylethylsulfinyl, (S)-1,2-difluoro-1-methylethylsulfinyl, (R)-2,2,2-trifluoro-1-methylethylsulfinyl, (S)-2,2,2-trifluoro-1-methylethylsulfinyl, 2-fluoro-1-(fluoromethyl)ethylsulfinyl, 1-(difluoromethyl)-2,2-difluoroethylsulfinyl, (R)-1-fluorobutylsulfinyl, (S)-1-fluorobutylsulfinyl, 2-fluorobutylsulfinyl, 3-fluorobutylsulfinyl, 4-fluorobutylsulfinyl, 1,1-difluorobutylsulfinyl, 2,2-difluorobutylsulfinyl, 3,3-difluorobutylsulfinyl, 4,4-difluorobutylsulfinyl, 4,4,4-trifluorobutylsulfinyl, etc.;

fluorinated $C_1$-$C_6$ alkylsulfonyl is a radical of the formula R—S(O)$_2$—, wherein R is a fluorinated alkyl radical having from 1 to 6 carbon atoms as defined above. Examples comprise fluoromethylsulfonyl, difluoromethylsulfonyl, trifluoromethylsulfonyl, (R)-1-fluoroethylsulfonyl, (S)-1-fluoroethylsulfonyl, 2-fluoroethylsulfonyl, 1,1-difluoroethylsulfonyl, 2,2-difluoroethylsulfonyl, 2,2,2-trifluoroethylsulfonyl, (R)-1-fluoropropylsulfonyl, (S)-1-fluoropropylsulfonyl, 2-fluoropropylsulfonyl, 3-fluoropropylsulfonyl, 1,1-difluoropropylsulfonyl, 2,2-difluoropropylsulfonyl, 3,3-difluoropropylsulfonyl, 3,3,3-trifluoropropylsulfonyl, (R)-2-fluoro-1-methylethylsulfonyl, (S)-2-fluoro-1-methylethylsulfonyl, (R)-2,2-difluoro-1-methylethylsulfonyl, (S)-2,2-difluoro-1-methylethylsulfonyl, (R)-1,2-difluoro-1-methylethylsulfonyl, (S)-1,2-difluoro-1-methylethylsulfonyl, (R)-2,2,2-trifluoro-1-methylethylsulfonyl, (S)-2,2,2-trifluoro-1-methylethylsulfonyl, 2-fluoro-1-(fluoromethyl)ethylsulfonyl, 1-(difluoromethyl)-2,2-difluoroethylsulfonyl, (R)-1-fluorobutylsulfonyl, (S)-1-fluorobutylsulfonyl, 2-fluorobutylsulfonyl, 3-fluorobutylsulfonyl, 4-fluorobutylsulfonyl, 1,1-difluorobutylsulfonyl, 2,2-difluorobutylsulfonyl, 3,3-difluorobutylsulfonyl, 4,4-difluorobutylsulfonyl, 4,4,4-trifluorobutylsulfonyl, etc.

3- to 7-membered heterocyclic radicals comprise saturated heterocyclic radicals, which generally have 3-, 4-, 5-, 6- or 7 ring forming atoms (ring members), unsaturated non-aromatic heterocyclic radicals, which generally have 5-, 6- or 7 ring forming atoms, and heteroaromatic radicals, which generally have 5-, 6- or 7 ring forming atoms. The heterocyclic radicals may be bound via a carbon atom (C-bound) or an nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of 3- to 7-membered, saturated heterocyclic radicals comprise 1- or 2-aziridinyl, 1-, 2- or 3-azetidinyl, 1-, 2- or 3-pyrrolidinyl, 1-, 2-, 3- or 4-piperidinyl, 1-, 2- or 3-morpholinyl, 1-, 2- or 3-thiomorpholinyl, 1-, 2- or 3-piperazinyl, 1-, 2- or 4-oxazolidinyl, 1-, 3- or 4-isoxazolidinyl, 2-oxiranyl, 2- or 3-oxetanyl, 2- or 3-oxolanyl, 2-, 3- or 4-oxanyl, 1,3-dioxolan-2- or 4-yl and the like, which may be unsubstituted or which may carry 1, 2 or 3 of the aforementioned radicals $R^a$ and/or $R^b$.

Unsaturated non-aromatic heterocyclic radicals, are heterocyclic radicals which generally have 5-, 6- or 7 ring forming atoms and which have 1 or 2 doublebonds that do not form an aromatic p-electron system. Examples are 2,3-dihydropyrrolyl, 3,4-dihydropyrrolyl, 2,3-dihydrofuranyl, 3,4-dihydrofuranyl, 2,3-dihydrothiophenyl, 3,4-dihydrothiophenyl, 1,2-dihydropyridinyl, 2,3-Dihydropyridiynl, 3,4-dihydropyridinyl, 1,2,3,4-tetrahydropyridinyl, 2,3,4,5-tetrahydropyridinyl, and the like.

5- or 6-membered heteroaromatic radicals are heteroaromatic cyclic radicals, wherein the cyclic radical has 5 or 6 atoms which form the ring (ring members) and wherein generally 1, 2, 3 or 4 ring member atoms are selected from O, S and N, the other ring member atoms being carbon atoms. The heteroaromatic radicals may be bound via a carbon atom (C-bound) or an nitrogen atom (N-bound). Preferred heteroaromatic radicals comprise 1 nitrogen atom as ring member atom and optionally 1, 2 or 3 further heteroatoms as ring members, which are selected, independently of each other from O, S and N. Likewise preferred heteroaromatic radicals comprise 1 heteroatom as ring member, which is selected from O, S and N, and optionally 1, 2 or 3 further nitrogen atoms as ring members. Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadizolyl, [1,3,4]-oxadizolyl, 4- or 5-[1,2,3]-thiadiazolyl, [1,2,5]-thiadiazolyl, 3- or 5-[1,2,4]-thiadizolyl or [1,3,4]-thiadiazolyl, which may be unsubstituted or which may carry 1, 2 or 3 of the aforementioned radicals $R^a$ and/or $R^b$.

A skilled person will appreciate that the radical -E-SO$_2$—Ar is bound to one of those carbon atoms of the aromatic part of the bicyclic moiety in formula I which carry a hydrogen atom, thereby substituting said hydrogen atom. Preferably the radical -E-SO$_2$—Ar is not bound to a carbon atom, which is adjacent to a bridgehead carbon atom. A skilled person will further appreciate that for Y being —CH═N— the carbon atom is attached to the bridgehead carbon atom while for Y being —N═CH— the nitrogen atom is attached to the carbon atom.

Preferably, Ar is phenyl or an aromatic 5- or 6-membered C-bound heteroaromatic radical, comprising 1 nitrogen atom as ring member and 0, 1, 2 or 3 further heteroatoms, independently of each other, selected from O, S and N, as ring members which may be unsubstituted or which may carry 1, 2 or 3 of the aforementioned radicals $R^a$ and/or $R^b$. Amongst these heteroaromatic radicals those are preferred, which comprise 1, 2 or 3 nitrogen atoms and no further heteroatom as ring members, or 1 or 2 nitrogen atoms and 1 atom, selected from O and S, as ring members. However, thienyl and furyl are likewise preferred. Particularly preferred radicals Ar are 2- or 3-thienyl, 2-, 3- or 4-pyridyl, 2-, 4- or 5-pyrimidinyl, 2-, 3- or 5-thiazolyl, 1,2,4-triazol-3-yl, 1,2,3-triazol-4-yl, 1,3,4-thiadiazol-2-yl, in particular 2-thienyl, 2-pyrimidinyl, 5-pyrimidinyl, 2-pyridinyl and more particularly phenyl which may be unsubstituted or which may carry 1, 2 or 3 of the aforementioned radicals $R^a$ and/or $R^b$.

Preferably the aromatic radical Ar carries one radical $R^a$ and optionally one or two further radicals $R^b$ as mentioned above, $R^b$ being particularly selected from methyl, fluorinated methyl, halogen, more preferably from fluorine or chlorine.

The aforementioned 5-membered heteroaromatic radicals Ar preferably one radical $R^a$ in the 3-position (related to the position of the $SO_2$-radical) and optionally one or two further radicals $R^b$, which are preferably selected from halogen, in particular fluorine or chlorine.

Phenyl and the aforementioned 6-membered heteroaromatic radicals Ar preferably carry one radical $R^a$ in the 4-position (related to the position of the $SO_2$-radical) and optionally one or two further radicals $R^b$, which are preferably selected from halogen, in particular fluorine or chlorine.

In a very preferred embodiment of the invention Ar is phenyl that carries a radical $R^a$ in the 4-position of the phenyl ring and optionally 1 or 2 further radicals $R^b$, which are preferably selected from halogen, in particular from fluorine or chlorine.

In another preferred embodiment of the invention Ar is 2-pyrimidinyl that carries a radical $R^a$ in the 5-position of the pyrimidine ring and optionally 1 or 2 further radicals $R^b$, which are preferably selected from halogen, in particular from fluorine or chlorine.

In a further preferred embodiment of the invention Ar is 5-pyrimidinyl that carries a radical $R^a$ in the 2-position of the pyrimidine ring and optionally 1 or 2 further radicals $R^b$, which are preferably selected from halogen, in particular from fluorine or chlorine.

In a further preferred embodiment of the invention Ar is 2-thienyl that carries a radical $R^a$ in the 3-position of the thiophene ring and optionally 1 or 2 further radicals $R^b$, which are preferably selected from halogen, in particular from fluorine or chlorine.

Preferably Ar carries 1 radical $R^a$ which is different from $CH_3$, $OCH_3$, $CF_3$, $OCF_3$, $NH_2$, $SO_2NH_2$, acetamido, $C_2$-$C_6$-alkoxy or acetyl.

In a preferred embodiment Ar carries 1 radical $R^a$ which selected from the group consisting of $C_2$-$C_6$-alkyl, $C_3$-$C_6$-cycloalkyl, $C_2$-$C_6$-alkoxy, fluorinated $C_2$-$C_6$-alkyl, fluorinated $C_3$-$C_6$-cycloalkyl, fluorinated $C_2$-$C_6$-alkoxy, $NR^4R^5$, 1-aziridinyl, azetidin-1-yl, pyrrolidin-1-yl or piperidin-1-yl, wherein the last four mentioned radicals may be fluorinated, a phenyl group and an aromatic 5- or 6-membered C-bound heteroaromatic radical, comprising 1 nitrogen atom as ring member and 0, 1, 2 or 3 further heteroatoms, independently of each other, selected from O, S and N, wherein the last two mentioned radicals may carry 1, 2, 3 or 4 radicals selected from Halogen and the radicals $R^a$, and wherein Ar may carry 1 or 2 further radicals $R^b$, which are independently from each other selected from halogen, cyano, methyl, fluoromethyl, difluoromethyl, trifluoromethyl, difluoromethoxy and trifluoromethoxy. In this embodiment $R^4$, $R^5$ are, independently of each other, preferably selected from H, $C_1$-$C_2$-alkyl and fluorinated $C_1$-$C_2$-alkyl. Preferably one of the radicals $R^4$ or $R^5$ is different from hydrogen. One of the radicals $R^4$ or $R^5$ may also be $C_1$-$C_2$-alkoxy.

In a very preferred embodiment, the radical Ar preferably carries one radical $R^a$, which has the formula $R^{a'}$

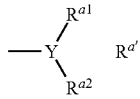

wherein
Y is N, CH or CF,
$R^{a1}$ and $R^{a2}$ are independently of each other selected from $C_1$-$C_2$-alkyl, $C_1$-$C_2$-alkoxy, fluorinated $C_1$-$C_2$-alkyl, provided for Y being CH or CF one of the radicals $R^{a1}$ or $R^{a2}$ may also be hydrogen or fluorine, or
$R^{a1}$ and $R^{a2}$ together form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein m is 2, 3, 4, 5 or 6;

In particular
$R^{a1}$ and $R^{a2}$ are independently of each other selected from $C_1$-$C_2$-alkyl, in particular methyl, fluorinated $C_1$-$C_2$-alkyl, in particular fluoromethyl, difluoromethyl or trifluoromethyl, provided for Y being CH or CF one of the radicals $R^{a1}$ or $R^{a2}$ may also be hydrogen or fluorine, or
$R^{a1}$ and $R^{a2}$ form a radical $(CH_2)_m$ wherein 1 or 2 of the hydrogen atoms may be replaced by fluorine and wherein m is 2, 3 or 4, in particular $CH_2$—$CH_2$, CHF—$CH_2$ $CF_2$—$CH_2$, $CH_2$—$CH_2$—$CH_2$, CHF—$CH_2$—$CH_2$, $CF_2$—$CH_2$—$CH_2$, $CH_2$—CHF—$CH_2$, $CH_2$—$CF_2$—$CH_2$.

In case $R^{a1}$ and $R^{a2}$ are different from each other, the radical of the aforementioned formula $R^{a'}$ may have either (R)- or (S)-configuration with regard to the Y-moiety.

Examples for preferred radicals of the formula $R^{a'}$ comprise isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-fluoro-1-methylethyl cyclopropyl, cyclobutyl, 1-fluorocyclopropyl, (R)- and (S)-2,2-difluorocyclopropyl, (R)- and (S)-2-fluorocyclopropyl.

Also preferred are radicals $R^{a'}$ wherein one of $R^{a1}$ or $R^{a2}$ is $C_1$-$C_2$-alkoxy and the other other of $R^{a1}$ or $R^{a2}$ is selected from H, $C_1$-$C_2$-alkyl, in particular methyl, fluorinated $C_1$-$C_2$-alkyl, in particular fluoromethyl, difluoromethyl or trifluoromethyl. Examples comprise N-methoxy-N-methylamino, N-methoxyamino and N-ethoxyamino.

Preferred radicals of the formula $R^{a'}$ also comprise those wherein Y is nitrogen and wherein $R^{a1}$ and $R^{a2}$ form a radical $(CH_2)_m$ wherein 1 or 2 of the hydrogen atoms may be replaced by fluorine, methyl, trifluoromethyl, methoxy or oxo and wherein m is 2, 3, 4 or 5. Examples comprise azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, piperidin-1-yl, 2-methylpiperidin-1-yl, (S)-2-methylpiperidin-1-yl and (R)-2-methylpiperidin-1-yl.

Likewise preferred are radicals $R^{a'}$, wherein $R^{a1}$ and $R^{a2}$ together form a radical $(CH_2)_m$ wherein 1 or 2 of the hydrogen atoms may be replaced by fluorine, hydroxy, oxo, $C_1$-$C_2$- alkyl or $C_1$-$C_2$-alkoxy, wherein one $CH_2$ moiety is replaced by O, S, S=O, $SO_2$ or N—$R^c$, $R^c$ being hydrogen or $C_1$-$C_2$-alkyl and wherein m is 2, 3, 4, 5 or 6. Examples for preferred radicals of the formula $R^{a'}$ also comprise 4-morpholinyl, 4-thiomorpholinyl, 4-(1,1-dioxo)thiomorpholinyl, piperazin-1-yl, 4-methylpiperazin-1-yl, 2-oxo-oxazolidin-3-yl, pyrrolidin-2-yl, (S)-pyrrolidin-2-yl, (R)-pyrrolidin-2-yl, pyrrolidin-3-yl, (S)-pyrrolidin-3-yl, (R)pyrrolidin-3-yl, 2-fluoropyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl and (R)-1-methylpyrrolidin-3-yl.

Amongst the radicals of the formula $R^{a'}$ those are preferred which carry 1, 2, 3 or 4, in particular 1, 2 or 3 fluorine atoms.

In a further preferred embodiment Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl. Amongst these radicals $R^a$, preference is given to radicals selected from 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadizolyl, [1,3,4]-oxadizolyl, 4- or 5-[1,2,3]-thiadiazolyl, [1,2,5]-thiadiazolyl, 3- or 5-[1,2,4]-thiadizolyl or [1,3,4]-thiadiazolyl, in particular from 2- or 3-furanyl, 2- or 3-thienyl, 1-, 2- or 3-pyrrolyl, pyrazolyl, imidazolyl, oxazolyl, isoxazolyl, 1,3,4-thiadiazolyl, 1,2,4-triazolyl, 1,2,3-triazolyl and tetrazolyl, where the heteroaromatic radical may be unsubstituted or may carry 1 to 3 substituents as given above. Preferred substituents on heteroaromatic $R^a$ are selected from halogen, $C_1$-$C_4$-alkyl, $C_1$-$C_4$-alkoxy, fluorinated $C_1$-$C_4$-alkyl and fluorinated $C_1$-$C_4$-alkoxy.

In a further preferred embodiment Ar carries 1 radical $R^a$ which selected from the group consisting of $CHF_2$, $CH_2F$, $OCHF_2$ and $OCH_2F$, with $OCHF_2$ being preferred. In this embodiment Ar may also carry 1 or 2 further radicals $R^b$, which are independently from each other selected from halogen, cyano, methyl, fluoromethyl, difluoromethyl, trifluoromethyl, difluoromethoxy and trifluoromethoxy. Preferably Ar carries no further radical $R^b$. In this embodiment Ar is preferably phenyl which carries 1 radical $R^a$ which selected from the group consisting of $CHF_2$, $CH_2F$, $OCHF_2$ and $OCH_2F$, with $OCHF_2$ being preferred. In this embodiment Ar is preferably phenyl, which carries $R^a$ in the 4 position with respect to the $SO_2$-group.

In another embodiment of the invention, Ar carries 1 radical $R^a$ which selected from the group consisting of $C_2$-$C_6$-alkenyl, fluorinated $C_2$-$C_6$-alkenyl, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $CH_2NR^4R^5$, $ONR^4R^5$, NHC(O)$NR^4R^5$, C(O)$NR^4R^5$, $SO_2NR^4R^5$, $C_1$-$C_6$-alkylcarbonyl, fluorinated $C_2$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenoxy, benzyloxy and a 5- or 6-membered N-bound heteroaromatic radical, wherein the four last mentioned radicals may carry 1, 2, 3 or 4 radicals selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl.

In another embodiment of the invention, Ar is phenyl, which carries 1 radical $R^a$ and at least one radical $R^b$ and wherein $R^a$ and one radical $R^b$ are bound to two adjacent carbon atoms of phenyl and form a 5- or 6-membered heterocyclic or carbocyclic ring which is fused to the phenyl ring and which is unsubstituted or which may carry 1, 2 or 3 radicals as given above. Examples of a phenyl ring fused to a saturated or unsaturated 5- or 6-membered carbocyclic or heterocyclic ring comprise indenyl, indanyl, naphthyl, tetralin, benzofuranyl, 2,3-dihydrobenzofuranyl, benzothienyl, indolyl, indazolyl, benzimidazolyl, benzoxathiazolyl, benzoxadiazolyl, benzothiadiazolyl; benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals. Preferred substituents for the saturated or unsaturated 5- or 6-membered carbocyclic or heterocyclic ring fused to the phenyl ring are selected from halogen, $C_1$-$C_4$-alkyl, $C_1$-$C_4$-alkoxy, fluorinated $C_1$-$C_4$-alkyl and fluorinated $C_1$-$C_4$-alkoxy.

The radical $R^1$ is preferably $C_2$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl, in particular $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, more preferably n-propyl, fluorinated linear $C_2$-$C_3$-alkyl or 1-propen-3-yl, in particular n-propyl or 1-propen-3-yl.

Preferably, the moiety E is N—$R^3$, wherein $R^3$ is as defined above. $R^3$ is in particular H or methyl and most preferred H.

One preferred embodiment of the invention relates to compounds, wherein $R^{1a}$ is hydrogen and $R^2$ and $R^{2a}$ have the meanings given above. In particular $R^2$ and/or $R^{2a}$ is (are) also hydrogen. For $R^2$ or $R^{2a}$ being different from hydrogen the radicals $R^2$ (or $R^{2a}$) and $NR^1R^{1a}$ may be located cis- or trans.

Another preferred embodiment of the invention relates to compounds, wherein $R^{1a}$ and $R^2$ or $R^{1a}$ and $R^{2a}$ together form a moiety $(CH_2)_n$, wherein n is as defined above and in particular 2 or 3. Thereby a fused ring is formed, which may be trans-fused or cis-fused.

A further preferred embodiment of the invention relates to compounds, wherein $R^{1a}$ is $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, in particular n-propyl, fluorinated linear $C_2$-$C_3$-alkyl or 1-propen-3-yl, more particularly propyl or 1-propen-3-yl. In this embodiment $R^2$ and $R^{2a}$ have the meanings given above. In particular $R^2$ and/or $R^{2a}$ is (are) also hydrogen. For $R^2$ or $R^{2a}$ being different from hydrogen the radicals $R^2$ (or $R^{2a}$) and $NR^1R^{1a}$ may be located cis- or trans. The carbon atom of the bicyclic core that carries the radical $NR^1R^{1a}$ may have (R) or (S) configuration.

One embodiment of the invention relates to compounds of the formula I, wherein X is CH. In this embodiment Y is preferably —CH=N—, —CH=CH— or —N=CH— and in particular —CH=CH—. In particular this embodiment relates to compounds of the general formulae Ia, Ib and Ic,

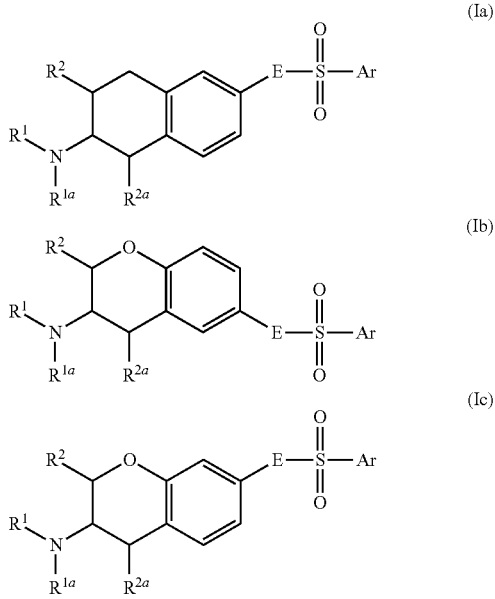

wherein $R^1$, $R^{1a}$, $R^2$, $R^{2a}$, $R^3$, E and Ar have the meanings given above and to the physiologically tolerated acid addition salts of these compounds. The preferences given above for $R^1$, $R^{1a}$, $R^2$, $R^{2a}$, $R^3$, E and Ar naturally apply to formulae Ia, Ib and Ic.

Preferred embodiments of compounds Ia, Ib and Ic are compounds wherein $R^2$ and $R^{2a}$ are hydrogen. These compounds are also referred to as compounds Iaa, Iba and Ica.

Other preferred embodiments of compounds Ia are those, wherein $R^{2a}$ is hydrogen and $R^{1a}$ together with $R^2$ is 1,3-propandiyl. These compounds are also referred to as compounds Iab.

Further preferred embodiments of compounds Ia are those, wherein $R^2$ is hydrogen and $R^{1a}$ together with $R^{2a}$ is 1,3-propandiyl. These compounds are also referred to as compounds Iac.

Most preferred are compounds Iaa and the physiologically tolerated acid addition salts of Iaa. In formula Iaa, Ar is preferably phenyl which carries a radical $R^a$ in the 4-position of the phenyl ring. Amongst these, compounds Iaa are preferred, wherein $R^a$ is a radical $R^{a'}$ as defined above. Likewise preferred are compounds Iaa, wherein Ar is phenyl which carries a radical $R^a$ in the 4-position, the radical $R^a$ being selected from $CHF_2$, $CH_2F$, $OCHF_2$ and $OCH_2F$, with $OCHF_2$ being preferred. In compounds Iaa, $R^1$ is preferably $C_2$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl, in particular $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, more preferably n-propyl, fluorinated linear $C_2$-$C_3$-alkyl or 1-propen-3-yl, in particular n-propyl or 1-propen-3-yl. A very preferred example of compounds Iaa is the compound Iaa, wherein $R^1$ is n-propyl and Ar is 4-difluoromethoxyphenyl. Therefore, a very preferred embodiment of the invention relates to compounds of the formula Iaa, wherein $R^1$ is n-propyl and Ar is 4-difluoromethoxyphenyl and to the physiologically tolerated acid addition salts thereof, includes the pure S- and R-stereoisomers and mixtures of S- and R-stereoisomers thereof.

In compounds Ia, Ib and Ic and likewise in compounds Iaa, Iba and Ica, the carbon atom to which the radical $R^1R^{1a}N$ is bound, may have S- or R configuration. The invention includes the pure S- and R-stereoisomers and mixtures of S- and R-stereoisomers.

Examples for preferred compounds Iaa, Iab, Iac, Iba and Ica are given in the following tables A-1, A-2, A-3, A-4 and A-5.

Table A-1: Compounds of the formula Iaa, including the pure S-isomers, the pure R-isomers and the racemic mixtures, wherein $R^{1a}$ is H and Ar and $R^1$ have the meaning given in one row of table A.

Table A-2: Compounds of the formula Iba, including the pure S-isomers, the pure R-isomers and the racemic mixtures, wherein $R^{1a}$ is H and Ar and $R^1$ have the meaning given in one row of table A.

Table A-3: Compounds of the formula Ica, including the pure S-isomers, the pure R-isomers and the racemic mixtures, wherein $R^{1a}$ is H and Ar and $R^1$ have the meaning given in one row of table A.

Table A-4:

Compounds of the formula Iab, wherein Ar and $R^1$ have the meaning given in one row of table A, wherein $R^2$ and $NR^1R^2$ are mutually trans, including the pure S/R-isomers, the pure R/S-isomers and the racemic mixtures.

Table A-5:

Compounds of the formula Iab, wherein Ar and $R^1$ have the meaning given in one row of table A, wherein $R^{2a}$ and $NR^1R^2$ are mutually trans, including the pure S/R-isomers, the pure R/S-isomers and the racemic mixtures.

Another embodiment of the invention, relates to compounds of the formula I, wherein X is N. In this embodiment Y is preferably S, —CH=N— or —CH=CH— and in particular S or —CH=N—. In particular this embodiment relates to compounds of the general formulae Ic and Id,

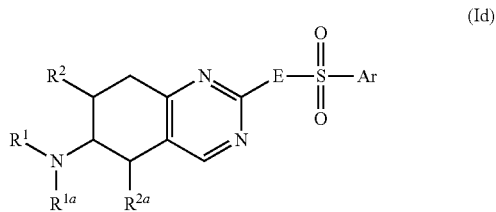

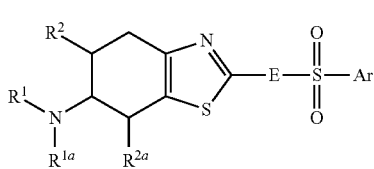

(Ie)

wherein $R^1$, $R^{1a}$, $R^2$, $R^{2a}$, $R^3$, E and Ar have the meanings given above. The preferences given above for $R^1$, $R^{1a}$, $R^2$, $R^{2a}$, $R^3$, E and Ar naturally apply to formulae Id and Ie. Preferred embodiments of compounds Id and Ie are compounds wherein $R^2$ and $R^{2a}$ are hydrogen. These compounds are also referred to as compounds Ida and Iea.

Examples for preferred compounds Ida and Iea are given in the following tables A-6 and A-7.

Table A-6:

Compounds of the formula Iaa, wherein Ar and $R^1$ have the meaning given in one row of table A, including the pure S-isomers, the pure R-isomers and the racemic mixtures.

Table A-7:

Compounds of the formula Iba, wherein Ar and $R^1$ have the meaning given in one row of table A, including the pure S-isomers, the pure R-isomers and the racemic mixtures.

TABLE A

| No. | $R^1$ | Ar |
|---|---|---|
| 1. | propyl | 4-ethylphenyl |
| 2. | propyl | 4-propylphenyl |
| 3. | propyl | 4-isopropylphenyl |
| 4. | propyl | 4-sec-butylphenyl |
| 5. | propyl | 4-isobutylphenyl |
| 6. | propyl | 4-(1,1-dimethylpropyl)-phenyl |
| 7. | propyl | 4-vinylphenyl |
| 8. | propyl | 4-isopropenylphenyl |
| 9. | propyl | 4-(fluoromethyl)phenyl |
| 10. | propyl | 3-(fluoromethyl)phenyl |
| 11. | propyl | 2-(fluoromethyl)phenyl |
| 12. | propyl | 4-(difluoromethyl)phenyl |
| 13. | propyl | 3-(difluoromethyl)phenyl |
| 14. | propyl | 2-(difluoromethyl)phenyl |
| 15. | propyl | 4-(trifluoromethyl)phenyl |
| 16. | propyl | 3-(trifluoromethyl)phenyl |
| 17. | propyl | 2-(trifluoromethyl)phenyl |
| 18. | propyl | 4-(1-fluoroethyl)-phenyl |
| 19. | propyl | 4-((S)-1-fluoroethyl)-phenyl |
| 20. | propyl | 4-((R)-1-fluoroethyl)-phenyl |
| 21. | propyl | 4-(2-fluoroethyl)-phenyl |
| 22. | propyl | 4-(1,1-difluoroethyl)-phenyl |
| 23. | propyl | 4-(2,2-difluoroethyl)-phenyl |
| 24. | propyl | 4-(2,2,2-trifluoroethyl)-phenyl |
| 25. | propyl | 4-(3-fluoropropyl)-phenyl |
| 26. | propyl | 4-(2-fluoropropyl)-phenyl |
| 27. | propyl | 4-((S)-2-fluoropropyl)-phenyl |
| 28. | propyl | 4-((R)-2-fluoropropyl)-phenyl |
| 29. | propyl | 4-(3,3-difluoropropyl)-phenyl |
| 30. | propyl | 4-(3,3,3-trifluoropropyl)-phenyl |
| 31. | propyl | 4-(1-fluoro-1-methylethyl)-phenyl |
| 32. | propyl | 4-(2-fluoro-1-methylethyl)-phenyl |
| 33. | propyl | 4-((S)-2-fluoro-1-methylethyl)-phenyl |
| 34. | propyl | 4-((R)-2-fluoro-1-methylethyl)-phenyl |
| 35. | propyl | 4-(2,2-difluoro-1-methylethyl)-phenyl |
| 36. | propyl | 4-((S)-2,2-difluoro-1-methylethyl)-phenyl |
| 37. | propyl | 4-((R)-2,2-difluoro-1-methylethyl)-phenyl |
| 38. | propyl | 4-(2,2,2-trifluoro-1-methylethyl)-phenyl |
| 39. | propyl | 4-((S)-2,2,2-trifluoro-1-methylethyl)-phenyl |
| 40. | propyl | 4-((R)-2,2,2-trifluoro-1-methylethyl)-phenyl |
| 41. | propyl | 4-(2-fluoro-1-fluoromethylethyl)-phenyl |
| 42. | propyl | 4-(1-difluoromethyl-2,2-difluoroethyl)-phenyl |
| 43. | propyl | 4-(1,1-dimethyl-2-fluoroethyl)-phenyl |
| 44. | propyl | 4-ethoxyphenyl |
| 45. | propyl | 4-propoxyphenyl |
| 46. | propyl | 4-isopropoxyphenyl |
| 47. | propyl | 4-butoxyphenyl |
| 48. | propyl | 4-(fluoromethoxy)-phenyl |
| 49. | propyl | 4-(difluoromethoxy)-phenyl |
| 50. | propyl | 4-(2-fluoroethoxy)-phenyl |
| 51. | propyl | 4-(2,2-difluoroethoxy)-phenyl |
| 52. | propyl | 4-(2,2,2-trifluoroethoxy)-phenyl |
| 53. | propyl | 4-(1,1,2,2-tetrafluoroethoxy)-phenyl |
| 54. | propyl | 4-cyclopropylphenyl |
| 55. | propyl | 4-cyclobutylphenyl |
| 56. | propyl | 4-cyclopentylphenyl |
| 57. | propyl | 4-(2,2-difluorocyclopropyl)-phenyl |
| 58. | propyl | 2-fluoro-4-isopropylphenyl |
| 59. | propyl | 3-fluoro-4-isopropylphenyl |
| 60. | propyl | 4-(1-hydroxy-1-methylethyl)-phenyl |
| 61. | propyl | 4-(2-hydroxy-2-methylpropyl)-phenyl |
| 62. | propyl | 4-acetylphenyl |
| 63. | propyl | 4-carboxyphenyl |
| 64. | propyl | 4-(O-benzyl)-phenyl |
| 65. | propyl | 4-(2-methoxyethoxy)-phenyl |
| 66. | propyl | 4-($CH_2$—$N(CH_3)_2$)-phenyl |
| 67. | propyl | 4-(NH—CO—$NH_2$)-phenyl |
| 68. | propyl | 4-(methylsulfanyl)-phenyl |
| 69. | propyl | 4-(fluoromethylsulfanyl)-phenyl |
| 70. | propyl | 4-(difluoromethylsulfanyl)-phenyl |
| 71. | propyl | 4-(trifluoromethylsulfanyl)-phenyl |
| 72. | propyl | 4-(methylsulfonyl)-phenyl |
| 73. | propyl | 4-(N-methoxy-N-methyl-amino)-phenyl |
| 74. | propyl | 4-(methoxyamino)-phenyl |
| 75. | propyl | 4-(ethoxyamino)-phenyl |
| 76. | propyl | 4-(N-methylaminooxy)-phenyl |
| 77. | propyl | 4-(N,N-dimethylaminooxy)-phenyl |
| 78. | propyl | 4-(azetidin-1-yl)-phenyl |
| 79. | propyl | 4-(2-methylazetidin-1-yl)-phenyl |
| 80. | propyl | 4-((S)-2-methylazetidin-1-yl)-phenyl |
| 81. | propyl | 4-((R)-2-methylazetidin-1-yl)-phenyl |
| 82. | propyl | 4-(3-fluoroazetidin-1-yl)-phenyl |
| 83. | propyl | 4-(3-methoxyazetidin-1-yl)-phenyl |
| 84. | propyl | 4-(3-hydroxyazetidin-1-yl)-phenyl |
| 85. | propyl | 4-(pyrrolidin-1-yl)-phenyl |
| 86. | propyl | 4-(pyrrolidin-2-yl)-phenyl |
| 87. | propyl | 4-((S)-pyrrolidin-2-yl)-phenyl |
| 88. | propyl | 4-((R)-pyrrolidin-2-yl)-phenyl |
| 89. | propyl | 4-(pyrrolidin-3-yl)-phenyl |
| 90. | propyl | 4-((S)-pyrrolidin-3-yl)-phenyl |
| 91. | propyl | 4-((R)-pyrrolidin-3-yl)-phenyl |
| 92. | propyl | 4-(2-fluoropyrrolidin-1-yl)-phenyl |
| 93. | propyl | 4-((S)-2-fluoropyrrolidin-1-yl)-phenyl |
| 94. | propyl | 4-((R)-2-fluoropyrrolidin-1-yl)-phenyl |
| 95. | propyl | 4-(3-fluoropyrrolidin-1-yl)-phenyl |
| 96. | propyl | 4-((S)-3-fluoropyrrolidin-1-yl)-phenyl |
| 97. | propyl | 4-((R)-3-fluoropyrrolidin-1-yl)-phenyl |
| 98. | propyl | 4-(2,2-difluoropyrrolidin-1-yl)-phenyl |
| 99. | propyl | 4-(3,3-difluoropyrrolidin-1-yl)-phenyl |
| 100. | propyl | 4-(2-methylpyrrolidin-1-yl)-phenyl |
| 101. | propyl | 4-((S)-2-methylpyrrolidin-1-yl)-phenyl |
| 102. | propyl | 4-((R)-2-methylpyrrolidin-1-yl)-phenyl |
| 103. | propyl | 4-(3-methylpyrrolidin-1-yl)-phenyl |
| 104. | propyl | 4-((S)-3-methylpyrrolidin-1-yl)-phenyl |
| 105. | propyl | 4-((R)-3-methylpyrrolidin-1-yl)-phenyl |
| 106. | propyl | 4-(1-methylpyrrolidin-2-yl)-phenyl |
| 107. | propyl | 4-((S)-1-methylpyrrolidin-2-yl)-phenyl |
| 108. | propyl | 4-((R)-1-methylpyrrolidin-2-yl)-phenyl |
| 109. | propyl | 4-(1-methylpyrrolidin-3-yl)-phenyl |
| 110. | propyl | 4-((S)-1-methylpyrrolidin-3-yl)-phenyl |
| 111. | propyl | 4-((R)-1-methylpyrrolidin-3-yl)-phenyl |
| 112. | propyl | 4-(2,2-dimethylpyrrolidin-1-yl)-phenyl |
| 113. | propyl | 4-(3,3-dimethylpyrrolidin-1-yl)-phenyl |
| 114. | propyl | 4-(2-trifluoromethylpyrrolidin-1-yl)-phenyl |
| 115. | propyl | 4-((S)-2-trifluoromethylpyrrolidin-1-yl)-phenyl |
| 116. | propyl | 4-((R)-2-trifluoromethylpyrrolidin-1-yl)-phenyl |
| 117. | propyl | 4-(3-trifluoromethylpyrrolidin-1-yl)-phenyl |
| 118. | propyl | 4-((S)-3-trifluoromethylpyrrolidin-1-yl)-phenyl |

TABLE A-continued

| No. | R¹ | Ar |
|---|---|---|
| 119. | propyl | 4-((R)-3-trifluoromethylpyrrolidin-1-yl)-phenyl |
| 120. | propyl | 4-(2-oxopyrrolidin-1-yl)-phenyl |
| 121. | propyl | 4-(2-oxo-oxazolidin-3-yl)-phenyl |
| 122. | propyl | 4-(piperidin-1-yl)-phenyl |
| 123. | propyl | 4-(2-methylpiperidin-1-yl)-phenyl |
| 124. | propyl | 4-((S)-2-methylpiperidin-1-yl)-phenyl |
| 125. | propyl | 4-((R)-2-methylpiperidin-1-yl)-phenyl |
| 126. | propyl | 4-(piperazin-1-yl)-phenyl |
| 127. | propyl | 4-(4-methylpiperazin-1-yl)-phenyl |
| 128. | propyl | 4-(morpholin-4-yl)-phenyl |
| 129. | propyl | 4-(thiomorpholin-4-yl)-phenyl |
| 130. | propyl | 4-(1-oxo-thiomorpholin-4-yl)-phenyl |
| 131. | propyl | 4-(1,1-dioxo-thiomorpholin-4-yl)-phenyl |
| 132. | propyl | 4-(pyrrol-1-yl)-phenyl |
| 133. | propyl | 4-(pyrrol-2-yl)-phenyl |
| 134. | propyl | 4-(pyrrol-3-yl)-phenyl |
| 135. | propyl | 4-(1-methylpyrrol-2-yl)-phenyl |
| 136. | propyl | 4-(1-methylpyrrol-3-yl)-phenyl |
| 137. | propyl | 4-(furan-2-yl)-phenyl |
| 138. | propyl | 4-(furan-3-yl)-phenyl |
| 139. | propyl | 4-(thiophen-2-yl)-phenyl |
| 140. | propyl | 4-(thiophen-3-yl)-phenyl |
| 141. | propyl | 4-(5-propylthien-2-yl)-phenyl |
| 142. | propyl | 4-(pyrazol-1-yl)-phenyl |
| 143. | propyl | 4-(pyrazol-3-yl)-phenyl |
| 144. | propyl | 4-(pyrazol-4-yl)-phenyl |
| 145. | propyl | 4-(1-methyl-1H-pyrazol-4-yl)-phenyl |
| 146. | propyl | 4-(1-ethyl-1H-pyrazol-4-yl)-phenyl |
| 147. | propyl | 4-(1-methyl-1H-pyrazol-5-yl)-phenyl |
| 148. | propyl | 4-(1H-imidazol-2-yl)-phenyl |
| 149. | propyl | 4-(imidazol-1-yl)-phenyl |
| 150. | propyl | 4-(1-methylimidazol-2-yl)-phenyl |
| 151. | propyl | 4-(oxazol-2-yl)-phenyl |
| 152. | propyl | 4-(oxazol-4-yl)-phenyl |
| 153. | propyl | 4-(oxazol-5-yl)-phenyl |
| 154. | propyl | 4-(isoxazol-3-yl)-phenyl |
| 155. | propyl | 4-(isoxazol-4-yl)-phenyl |
| 156. | propyl | 4-(isoxazol-5-yl)-phenyl |
| 157. | propyl | 4-([1,2,3]-triazol-1-yl)-phenyl |
| 158. | propyl | 4-([1,2,4]-triazol-1-yl)-phenyl |
| 159. | propyl | 4-([1,2,3]-triazol-2-yl)-phenyl |
| 160. | propyl | 4-(4H-[1,2,4]-triazol-3-yl)-phenyl |
| 161. | propyl | 4-([1,2,4]-triazol-4-yl)-phenyl |
| 162. | propyl | 4-(2H-[1,2,3]-triazol-4-yl)-phenyl |
| 163. | propyl | 4-(4-methyl-4H-[1,2,4]-triazol-3-yl)-phenyl |
| 164. | propyl | 4-(2-methyl-2H-[1,2,3]-triazol-4-yl)-phenyl |
| 165. | propyl | 4-([1,3,4]-oxadiazol-2-yl)-phenyl |
| 166. | propyl | 4-([1,2,4]-oxadiazol-3-yl)-phenyl |
| 167. | propyl | 4-([1,2,4]-oxadiazol-5-yl)-phenyl |
| 168. | propyl | 4-([1,2,3]-oxadiazol-4-yl)-phenyl |
| 169. | propyl | 4-([1,2,3]-oxadiazol-5-yl)-phenyl |
| 170. | propyl | 4-([1,2,3]-thiadiazol-4-yl)-phenyl |
| 171. | propyl | 4-(1H-tetrazol-5-yl)-phenyl |
| 172. | propyl | 4-(tetrazol-1-yl)-phenyl |
| 173. | propyl | 4-(2-methyl-2H-tetrazol-5-yl)-phenyl |
| 174. | propyl | 4-(1-methyl-1H-tetrazol-5-yl)-phenyl |
| 175. | propyl | 4-furazan-3-yl-phenyl |
| 176. | propyl | 4-(pyrid-2-yl)-phenyl |
| 177. | propyl | 4-(pyrid-3-yl)-phenyl |
| 178. | propyl | 4-(pyrid-4-yl)-phenyl |
| 179. | propyl | 4-(pyrimidin-2-yl)-phenyl |
| 180. | propyl | 4-(pyrimidin-4-yl)-phenyl |
| 181. | propyl | 4-(pyrimidin-5-yl)-phenyl |
| 182. | propyl | 5-isopropylthiophen-2-yl |
| 183. | propyl | 2-chlorothiophen-5-yl |
| 184. | propyl | 2,5-dichlorothiophen-4-yl |
| 185. | propyl | 2,3-dichlorothiophen-5-yl |
| 186. | propyl | 2-chloro-3-nitrothiophen-5-yl |
| 187. | propyl | 2-(phenylsulfonyl)-thiophen-5-yl |
| 188. | propyl | 2-(pyridin-2-yl)thiophen-5-yl |
| 189. | propyl | 2-(5-(trifluoromethyl)isoxazol-3-yl)-thiophen-5-yl |
| 190. | propyl | 2-(2-methylthiazol-4-yl)-thiophen-5-yl |
| 191. | propyl | 1-methyl-1H-imidazol-4-yl |
| 192. | propyl | 1,2-dimethyl-1H-imidazol-4-yl |
| 193. | propyl | 3,5-dimethylisoxazol-4-yl |
| 194. | propyl | thiazol-2-yl |
| 195. | propyl | 4-methylthiazol-2-yl |
| 196. | propyl | 4-isopropylthiazol-2-yl |
| 197. | propyl | 4-trifluoromethylthiazol-2-yl |
| 198. | propyl | 5-methylthiazol-2-yl |
| 199. | propyl | 5-isopropylthiazol-2-yl |
| 200. | propyl | 5-trifluoromethylthiazol-2-yl |
| 201. | propyl | 2,4-dimethylthiazol-5-yl |
| 202. | propyl | 2-acetamido-4-methylthiazol-5-yl |
| 203. | propyl | 4H-[1,2,4]triazol-3-yl |
| 204. | propyl | 5-methyl-4H-[1,2,4]triazol-3-yl |
| 205. | propyl | 4-methyl-4H-[1,2,4]triazol-3-yl |
| 206. | propyl | 5-isopropyl-4H-[1,2,4]triazol-3-yl |
| 207. | propyl | 5-trifluoromethyl-4H-[1,2,4]triazol-3-yl |
| 208. | propyl | 4,5-dimethyl-4H-[1,2,4]triazol-3-yl |
| 209. | propyl | 5-isopropyl-4-methyl-4H-[1,2,4]triazol-3-yl |
| 210. | propyl | 5-trifluoromethyl-4-methyl-4H-[1,2,4]triazol-3-yl |
| 211. | propyl | [1,3,4]thiadiazol-2-yl |
| 212. | propyl | 5-methyl-[1,3,4]thiadiazol-2-yl |
| 213. | propyl | 5-isopropyl-[1,3,4]thiadiazol-2-yl |
| 214. | propyl | 5-trifluoromethyl-[1,3,4]thiadiazol-2-yl |
| 215. | propyl | 3-bromo-2-chloropyrid-5-yl |
| 216. | propyl | 2-(4-morpholino)-pyrid-5-yl |
| 217. | propyl | 2-phenoxypyrid-5-yl |
| 218. | propyl | (2-isopropyl)-pyrimidin-5-yl |
| 219. | propyl | (5-isopropyl)-pyrimidin-2-yl |
| 220. | propyl | 8-quinolyl |
| 221. | propyl | 5-isoquinolyl |
| 222. | propyl | 2-(2,2,2-trifluoroacetyl)-1,2,3,4-tetrahydroisoquinolin-7-yl |
| 223. | propyl | 5-chloro-3-methylbenzothiophen-2-yl |
| 224. | propyl | 3,4-dihydro-4-methyl-2H-benzo[b][1,4]oxazinyl |
| 225. | propyl | benzothiazol-6-yl |
| 226. | propyl | benzo[2,1,3]oxadiazol-4-yl |
| 227. | propyl | 5-chlorobenzo[1,2,5]oxadiazolyl |
| 228. | propyl | 7-chlorobenzo[2,1,3]oxadiazol-4-yl |
| 229. | propyl | benzo[2,1,3]thiadiazol-4-yl |
| 230. | ethyl | 4-propylphenyl |
| 231. | ethyl | 4-ethylphenyl |
| 232. | ethyl | 4-isopropylphenyl |
| 233. | ethyl | 4-sec-butylphenyl |
| 234. | ethyl | 4-isobutylphenyl |
| 235. | ethyl | 4-(1,1-dimethylpropyl)-phenyl |
| 236. | ethyl | 4-vinylphenyl |
| 237. | ethyl | 4-isopropenylphenyl |
| 238. | ethyl | 4-(fluoromethyl)phenyl |
| 239. | ethyl | 3-(fluoromethyl)phenyl |
| 240. | ethyl | 2-(fluoromethyl)phenyl |
| 241. | ethyl | 4-(difluoromethyl)phenyl |
| 242. | ethyl | 3-(difluoromethyl)phenyl |
| 243. | ethyl | 2-(difluoromethyl)phenyl |
| 244. | ethyl | 4-(trifluoromethyl)phenyl |
| 245. | ethyl | 3-(trifluoromethyl)phenyl |
| 246. | ethyl | 2-(trifluoromethyl)phenyl |
| 247. | ethyl | 4-(1-fluoroethyl)-phenyl |
| 248. | ethyl | 4-((S)-1-fluoroethyl)-phenyl |
| 249. | ethyl | 4-((R)-1-fluoroethyl)-phenyl |
| 250. | ethyl | 4-(2-fluoroethyl)-phenyl |
| 251. | ethyl | 4-(1,1-difluoroethyl)-phenyl |
| 252. | ethyl | 4-(2,2-difluoroethyl)-phenyl |
| 253. | ethyl | 4-(2,2,2-trifluoroethyl)-phenyl |
| 254. | ethyl | 4-(3-fluoropropyl)-phenyl |
| 255. | ethyl | 4-(2-fluoropropyl)-phenyl |
| 256. | ethyl | 4-((S)-2-fluoropropyl)-phenyl |
| 257. | ethyl | 4-((R)-2-fluoropropyl)-phenyl |
| 258. | ethyl | 4-(3,3-difluoropropyl)-phenyl |
| 259. | ethyl | 4-(3,3,3-trifluoropropyl)-phenyl |
| 260. | ethyl | 4-(1-fluoro-1-methylethyl)-phenyl |
| 261. | ethyl | 4-(2-fluoro-1-methylethyl)-phenyl |
| 262. | ethyl | 4-((S)-2-fluoro-1-methylethyl)-phenyl |
| 263. | ethyl | 4-((R)-2-fluoro-1-methylethyl)-phenyl |
| 264. | ethyl | 4-(2,2-difluoro-1-methylethyl)-phenyl |
| 265. | ethyl | 4-((S)-2,2-difluoro-1-methylethyl)-phenyl |
| 266. | ethyl | 4-((R)-2,2-difluoro-1-methylethyl)-phenyl |
| 267. | ethyl | 4-(2,2,2-trifluoro-1-methylethyl)-phenyl |
| 268. | ethyl | 4-((S)-2,2,2-trifluoro-1-methylethyl)-phenyl |
| 269. | ethyl | 4-((R)-2,2,2-trifluoro-1-methylethyl)-phenyl |

TABLE A-continued

| No. | R¹ | Ar |
|---|---|---|
| 270. | ethyl | 4-(2-fluoro-1-fluoromethylethyl)-phenyl |
| 271. | ethyl | 4-(1-difluoromethyl-2,2-difluoroethyl)-phenyl |
| 272. | ethyl | 4-(1,1-dimethyl-2-fluoroethyl)-phenyl |
| 273. | ethyl | 4-ethoxyphenyl |
| 274. | ethyl | 4-propoxyphenyl |
| 275. | ethyl | 4-isopropoxyphenyl |
| 276. | ethyl | 4-butoxyphenyl |
| 277. | ethyl | 4-(fluoromethoxy)-phenyl |
| 278. | ethyl | 4-(difluoromethoxy)-phenyl |
| 279. | ethyl | 4-(2-fluoroethoxy)-phenyl |
| 280. | ethyl | 4-(2,2-difluoroethoxy)-phenyl |
| 281. | ethyl | 4-(2,2,2-trifluoroethoxy)-phenyl |
| 282. | ethyl | 4-(1,1,2,2-tetrafluoroethoxy)-phenyl |
| 283. | ethyl | 4-cyclopropylphenyl |
| 284. | ethyl | 4-cyclobutylphenyl |
| 285. | ethyl | 4-cyclopentylphenyl |
| 286. | ethyl | 4-(2,2-difluorocyclopropyl)-phenyl |
| 287. | ethyl | 2-fluoro-4-isopropylphenyl |
| 288. | ethyl | 3-fluoro-4-isopropylphenyl |
| 289. | ethyl | 4-(1-hydroxy-1-methylethyl)-phenyl |
| 290. | ethyl | 4-(2-hydroxy-2-methylpropyl)-phenyl |
| 291. | ethyl | 4-acetylphenyl |
| 292. | ethyl | 4-carboxyphenyl |
| 293. | ethyl | 4-(O-benzyl)-phenyl |
| 294. | ethyl | 4-(2-methoxyethoxy)-phenyl |
| 295. | ethyl | 4-(CH$_2$-N(CH$_3$)$_2$)-phenyl |
| 296. | ethyl | 4-(NH-CO-NH$_2$)-phenyl |
| 297. | ethyl | 4-(methylsulfanyl)-phenyl |
| 298. | ethyl | 4-(fluoromethylsulfanyl)-phenyl |
| 299. | ethyl | 4-(difluoromethylsulfanyl)-phenyl |
| 300. | ethyl | 4-(trifluoromethylsulfanyl)-phenyl |
| 301. | ethyl | 4-(methylsulfonyl)-phenyl |
| 302. | ethyl | 4-(N-methoxy-N-methyl-amino)-phenyl |
| 303. | ethyl | 4-(methoxyamino)-phenyl |
| 304. | ethyl | 4-(ethoxyamino)-phenyl |
| 305. | ethyl | 4-(N-methylaminooxy)-phenyl |
| 306. | ethyl | 4-(N,N-dimethylaminooxy)-phenyl |
| 307. | ethyl | 4-(azetidin-1-yl)-phenyl |
| 308. | ethyl | 4-(2-methylazetidin-1-yl)-phenyl |
| 309. | ethyl | 4-((S)-2-methylazetidin-1-yl)-phenyl |
| 310. | ethyl | 4-((R)-2-methylazetidin-1-yl)-phenyl |
| 311. | ethyl | 4-(3-fluoroazetidin-1-yl)-phenyl |
| 312. | ethyl | 4-(3-methoxyazetidin-1-yl)-phenyl |
| 313. | ethyl | 4-(3-hydroxyazetidin-1-yl)-phenyl |
| 314. | ethyl | 4-(pyrrolidin-1-yl)-phenyl |
| 315. | ethyl | 4-(pyrrolidin-2-yl)-phenyl |
| 316. | ethyl | 4-((S)-pyrrolidin-2-yl)-phenyl |
| 317. | ethyl | 4-((R)-pyrrolidin-2-yl)-phenyl |
| 318. | ethyl | 4-(pyrrolidin-3-yl)-phenyl |
| 319. | ethyl | 4-((S)-pyrrolidin-3-yl)-phenyl |
| 320. | ethyl | 4-((R)-pyrrolidin-3-yl)-phenyl |
| 321. | ethyl | 4-(2-fluoropyrrolidin-1-yl)-phenyl |
| 322. | ethyl | 4-((S)-2-fluoropyrrolidin-1-yl)-phenyl |
| 323. | ethyl | 4-((R)-2-fluoropyrrolidin-1-yl)-phenyl |
| 324. | ethyl | 4-(3-fluoropyrrolidin-1-yl)-phenyl |
| 325. | ethyl | 4-((S)-3-fluoropyrrolidin-1-yl)-phenyl |
| 326. | ethyl | 4-((R)-3-fluoropyrrolidin-1-yl)-phenyl |
| 327. | ethyl | 4-(2,2-difluoropyrrolidin-1-yl)-phenyl |
| 328. | ethyl | 4-(3,3-difluoropyrrolidin-1-yl)-phenyl |
| 329. | ethyl | 4-(2-methylpyrrolidin-1-yl)-phenyl |
| 330. | ethyl | 4-((S)-2-methylpyrrolidin-1-yl)-phenyl |
| 331. | ethyl | 4-((R)-2-methylpyrrolidin-1-yl)-phenyl |
| 332. | ethyl | 4-(3-methylpyrrolidin-1-yl)-phenyl |
| 333. | ethyl | 4-((S)-3-methylpyrrolidin-1-yl)-phenyl |
| 334. | ethyl | 4-((R)-3-methylpyrrolidin-1-yl)-phenyl |
| 335. | ethyl | 4-(1-methylpyrrolidin-2-yl)-phenyl |
| 336. | ethyl | 4-((S)-1-methylpyrrolidin-2-yl)-phenyl |
| 337. | ethyl | 4-((R)-1-methylpyrrolidin-2-yl)-phenyl |
| 338. | ethyl | 4-(1-methylpyrrolidin-3-yl)-phenyl |
| 339. | ethyl | 4-((S)-1-methylpyrrolidin-3-yl)-phenyl |
| 340. | ethyl | 4-((R)-1-methylpyrrolidin-3-yl)-phenyl |
| 341. | ethyl | 4-(2,2-dimethylpyrrolidin-1-yl)-phenyl |
| 342. | ethyl | 4-(3,3-dimethylpyrrolidin-1-yl)-phenyl |
| 343. | ethyl | 4-(2-trifluoromethylpyrrolidin-1-yl)-phenyl |
| 344. | ethyl | 4-((S)-2-trifluoromethylpyrrolidin-1-yl)-phenyl |
| 345. | ethyl | 4-((R)-2-trifluoromethylpyrrolidin-1-yl)-phenyl |
| 346. | ethyl | 4-(3-trifluoromethylpyrrolidin-1-yl)-phenyl |
| 347. | ethyl | 4-((S)-3-trifluoromethylpyrrolidin-1-yl)-phenyl |
| 348. | ethyl | 4-((R)-3-trifluoromethylpyrrolidin-1-yl)-phenyl |
| 349. | ethyl | 4-(2-oxopyrrolidin-1-yl)-phenyl |
| 350. | ethyl | 4-(2-oxo-oxazolidin-3-yl)-phenyl |
| 351. | ethyl | 4-(piperidin-1-yl)-phenyl |
| 352. | ethyl | 4-(2-methylpiperidin-1-yl)-phenyl |
| 353. | ethyl | 4-((S)-2-methylpiperidin-1-yl)-phenyl |
| 354. | ethyl | 4-((R)-2-methylpiperidin-1-yl)-phenyl |
| 355. | ethyl | 4-(piperazin-1-yl)-phenyl |
| 356. | ethyl | 4-(4-methylpiperazin-1-yl)-phenyl |
| 357. | ethyl | 4-(morpholin-4-yl)-phenyl |
| 358. | ethyl | 4-(thiomorpholin-4-yl)-phenyl |
| 359. | ethyl | 4-(1-oxo-thiomorpholin-4-yl)-phenyl |
| 360. | ethyl | 4-(1,1-dioxo-thiomorpholin-4-yl)-phenyl |
| 361. | ethyl | 4-(pyrrol-1-yl)-phenyl |
| 362. | ethyl | 4-(pyrrol-2-yl)-phenyl |
| 363. | ethyl | 4-(pyrrol-3-yl)-phenyl |
| 364. | ethyl | 4-(1-methylpyrrol-2-yl)-phenyl |
| 365. | ethyl | 4-(1-methylpyrrol-3-yl)-phenyl |
| 366. | ethyl | 4-(furan-2-yl)-phenyl |
| 367. | ethyl | 4-(furan-3-yl)-phenyl |
| 368. | ethyl | 4-(thiophen-2-yl)-phenyl |
| 369. | ethyl | 4-(thiophen-3-yl)-phenyl |
| 370. | ethyl | 4-(5-propylthien-2-yl)-phenyl |
| 371. | ethyl | 4-(pyrazol-1-yl)-phenyl |
| 372. | ethyl | 4-(pyrazol-3-yl)-phenyl |
| 373. | ethyl | 4-(pyrazol-4-yl)-phenyl |
| 374. | ethyl | 4-(1-methyl-1H-pyrazol-4-yl)-phenyl |
| 375. | ethyl | 4-(1-ethyl-1H-pyrazol-4-yl)-phenyl |
| 376. | ethyl | 4-(1-methyl-1H-pyrazol-5-yl)-phenyl |
| 377. | ethyl | 4-(1H-imidazol-2-yl)-phenyl |
| 378. | ethyl | 4-(imidazol-1-yl)-phenyl |
| 379. | ethyl | 4-(1-methylimidazol-2-yl)-phenyl |
| 380. | ethyl | 4-(oxazol-2-yl)-phenyl |
| 381. | ethyl | 4-(oxazol-4-yl)-phenyl |
| 382. | ethyl | 4-(oxazol-5-yl)-phenyl |
| 383. | ethyl | 4-(isoxazol-3-yl)-phenyl |
| 384. | ethyl | 4-(isoxazol-4-yl)-phenyl |
| 385. | ethyl | 4-(isoxazol-5-yl)-phenyl |
| 386. | ethyl | 4-([1,2,3]-triazol-1-yl)-phenyl |
| 387. | ethyl | 4-([1,2,4]-triazol-1-yl)-phenyl |
| 388. | ethyl | 4-([1,2,3]-triazol-2-yl)-phenyl |
| 389. | ethyl | 4-(4H-[1,2,4]-triazol-3-yl)-phenyl |
| 390. | ethyl | 4-([1,2,4]-triazol-4-yl)-phenyl |
| 391. | ethyl | 4-(2H-[1,2,3]-triazol-4-yl)-phenyl |
| 392. | ethyl | 4-(4-methyl-4H-[1,2,4]-triazol-3-yl)-phenyl |
| 393. | ethyl | 4-(2-methyl-2H-[1,2,3]-triazol-4-yl)-phenyl |
| 394. | ethyl | 4-([1,3,4]-oxadiazol-2-yl)-phenyl |
| 395. | ethyl | 4-([1,2,4]-oxadiazol-3-yl)-phenyl |
| 396. | ethyl | 4-([1,2,4]-oxadiazol-5-yl)-phenyl |
| 397. | ethyl | 4-([1,2,3]-oxadiazol-4-yl)-phenyl |
| 398. | ethyl | 4-([1,2,3]-oxadiazol-5-yl)-phenyl |
| 399. | ethyl | 4-([1,2,3]-thiadiazol-4-yl)-phenyl |
| 400. | ethyl | 4-(1H-tetrazol-5-yl)-phenyl |
| 401. | ethyl | 4-(tetrazol-1-yl)-phenyl |
| 402. | ethyl | 4-(2-methyl-2H-tetrazol-5-yl)-phenyl |
| 403. | ethyl | 4-(1-methyl-1H-tetrazol-5-yl)-phenyl |
| 404. | ethyl | 4-furazan-3-yl-phenyl |
| 405. | ethyl | 4-(pyrid-2-yl)-phenyl |
| 406. | ethyl | 4-(pyrid-3-yl)-phenyl |
| 407. | ethyl | 4-(pyrid-4-yl)-phenyl |
| 408. | ethyl | 4-(pyrimidin-2-yl)-phenyl |
| 409. | ethyl | 4-(pyrimidin-4-yl)-phenyl |
| 410. | ethyl | 4-(pyrimidin-5-yl)-phenyl |
| 411. | ethyl | 5-isopropylthiophen-2-yl |
| 412. | ethyl | 2-chlorothiophen-5-yl |
| 413. | ethyl | 2,5-dichlorothiophen-4-yl |
| 414. | ethyl | 2,3-dichlorothiophen-5-yl |
| 415. | ethyl | 2-chloro-3-nitrothiophen-5-yl |
| 416. | ethyl | 2-(phenylsulfonyl)-thiophen-5-yl |
| 417. | ethyl | 2-(pyridin-2-yl)thiophen-5-yl |

TABLE A-continued

| No. | R¹ | Ar |
|---|---|---|
| 418. | ethyl | 2-(5-(trifluoromethyl)isoxazol-3-yl)-thiophen-5-yl |
| 419. | ethyl | 2-(2-methylthiazol-4-yl)-thiophen-5-yl |
| 420. | ethyl | 1-methyl-1H-imidazol-4-yl |
| 421. | ethyl | 1,2-dimethyl-1H-imidazol-4-yl |
| 422. | ethyl | 3,5-dimethylisoxazol-4-yl |
| 423. | ethyl | thiazol-2-yl |
| 424. | ethyl | 4-methylthiazol-2-yl |
| 425. | ethyl | 4-isopropylthiazol-2-yl |
| 426. | ethyl | 4-trifluoromethylthiazol-2-yl |
| 427. | ethyl | 5-methylthiazol-2-yl |
| 428. | ethyl | 5-isopropylthiazol-2-yl |
| 429. | ethyl | 5-trifluoromethylthiazol-2-yl |
| 430. | ethyl | 2,4-dimethylthiazol-5-yl |
| 431. | ethyl | 2-acetamido-4-methylthiazol-5-yl |
| 432. | ethyl | 4H-[1,2,4]triazol-3-yl |
| 433. | ethyl | 5-methyl-4H-[1,2,4]triazol-3-yl |
| 434. | ethyl | 4-methyl-4H-[1,2,4]triazol-3-yl |
| 435. | ethyl | 5-isopropyl-4H-[1,2,4]triazol-3-yl |
| 436. | ethyl | 5-trifluoromethyl-4H-[1,2,4]triazol-3-yl |
| 437. | ethyl | 4,5-dimethyl-4H-[1,2,4]triazol-3-yl |
| 438. | ethyl | 5-isopropyl-4-methyl-4H-[1,2,4]triazol-3-yl |
| 439. | ethyl | 5-trifluoromethyl-4-methyl-4H-[1,2,4]triazol-3-yl |
| 440. | ethyl | [1,3,4]thiadiazol-2-yl |
| 441. | ethyl | 5-methyl-[1,3,4]thiadiazol-2-yl |
| 442. | ethyl | 5-isopropyl-[1,3,4]thiadiazol-2-yl |
| 443. | ethyl | 5-trifluoromethyl-[1,3,4]thiadiazol-2-yl |
| 444. | ethyl | 3-bromo-2-chloropyrid-5-yl |
| 445. | ethyl | 2-(4-morpholino)-pyrid-5-yl |
| 446. | ethyl | 2-phenoxypyrid-5-yl |
| 447. | ethyl | (2-isopropyl)-pyrimidin-5-yl |
| 448. | ethyl | (5-isopropyl)-pyrimidin-2-yl |
| 449. | ethyl | 8-quinolyl |
| 450. | ethyl | 5-isoquinolyl |
| 451. | ethyl | 2-(2,2,2-trifluoroacetyl)-1,2,3,4-tetrahydroisoquinolin-7-yl |
| 452. | ethyl | 5-chloro-3-methylbenzothiophen-2-yl |
| 453. | ethyl | 3,4-dihydro-4-methyl-2H-benzo[b][1,4]oxazinyl |
| 454. | ethyl | benzothiazol-6-yl |
| 455. | ethyl | benzo[2,1,3]oxadiazol-4-yl |
| 456. | ethyl | 5-chlorobenzo[1,2,5]oxadiazolyl |
| 457. | ethyl | 7-chlorobenzo[2,1,3]oxadiazol-4-yl |
| 458. | ethyl | benzo[2,1,3]thiadiazol-4-yl |
| 459. | methyl | 4-ethylphenyl |
| 460. | methyl | 4-propylphenyl |
| 461. | methyl | 4-isopropylphenyl |
| 462. | methyl | 4-sec-butylphenyl |
| 463. | methyl | 4-isobutylphenyl |
| 464. | methyl | 4-(1,1-dimethylpropyl)-phenyl |
| 465. | methyl | 4-vinylphenyl |
| 466. | methyl | 4-isopropenylphenyl |
| 467. | methyl | 4-(fluoromethyl)phenyl |
| 468. | methyl | 3-(fluoromethyl)phenyl |
| 469. | methyl | 2-(fluoromethyl)phenyl |
| 470. | methyl | 4-(difluoromethyl)phenyl |
| 471. | methyl | 3-(difluoromethyl)phenyl |
| 472. | methyl | 2-(difluoromethyl)phenyl |
| 473. | methyl | 4-(trifluoromethyl)phenyl |
| 474. | methyl | 3-(trifluoromethyl)phenyl |
| 475. | methyl | 2-(trifluoromethyl)phenyl |
| 476. | methyl | 4-(1-fluoroethyl)-phenyl |
| 477. | methyl | 4-((S)-1-fluoroethyl)-phenyl |
| 478. | methyl | 4-((R)-1-fluoroethyl)-phenyl |
| 479. | methyl | 4-(2-fluoroethyl)-phenyl |
| 480. | methyl | 4-(1,1-difluoroethyl)-phenyl |
| 481. | methyl | 4-(2,2-difluoroethyl)-phenyl |
| 482. | methyl | 4-(2,2,2-trifluoroethyl)-phenyl |
| 483. | methyl | 4-(3-fluoropropyl)-phenyl |
| 484. | methyl | 4-(2-fluoropropyl)-phenyl |
| 485. | methyl | 4-((S)-2-fluoropropyl)-phenyl |
| 486. | methyl | 4-((R)-2-fluoropropyl)-phenyl |
| 487. | methyl | 4-(3,3-difluoropropyl)-phenyl |
| 488. | methyl | 4-(3,3,3-trifluoropropyl)-phenyl |
| 489. | methyl | 4-(1-fluoro-1-methylethyl)-phenyl |
| 490. | methyl | 4-(2-fluoro-1-methylethyl)-phenyl |
| 491. | methyl | 4-((S)-2-fluoro-1-methylethyl)-phenyl |
| 492. | methyl | 4-((R)-2-fluoro-1-methylethyl)-phenyl |
| 493. | methyl | 4-(2,2-difluoro-1-methylethyl)-phenyl |
| 494. | methyl | 4-((S)-2,2-difluoro-1-methylethyl)-phenyl |
| 495. | methyl | 4-((R)-2,2-difluoro-1-methylethyl)-phenyl |
| 496. | methyl | 4-(2,2,2-trifluoro-1-methylethyl)-phenyl |
| 497. | methyl | 4-((S)-2,2,2-trifluoro-1-methylethyl)-phenyl |
| 498. | methyl | 4-((R)-2,2,2-trifluoro-1-methylethyl)-phenyl |
| 499. | methyl | 4-(2-fluoro-1-fluoromethylethyl)-phenyl |
| 500. | methyl | 4-(1-difluoromethyl-2,2-difluoroethyl)-phenyl |
| 501. | methyl | 4-(1,1-dimethyl-2-fluoroethyl)-phenyl |
| 502. | methyl | 4-ethoxyphenyl |
| 503. | methyl | 4-propoxyphenyl |
| 504. | methyl | 4-isopropoxyphenyl |
| 505. | methyl | 4-butoxyphenyl |
| 506. | methyl | 4-(fluoromethoxy)-phenyl |
| 507. | methyl | 4-(difluoromethoxy)-phenyl |
| 508. | methyl | 4-(2-fluoroethoxy)-phenyl |
| 509. | methyl | 4-(2,2-difluoroethoxy)-phenyl |
| 510. | methyl | 4-(2,2,2-trifluoroethoxy)-phenyl |
| 511. | methyl | 4-(1,1,2,2-tetrafluoroethoxy)-phenyl |
| 512. | methyl | 4-cyclopropylphenyl |
| 513. | methyl | 4-cyclobutylphenyl |
| 514. | methyl | 4-cyclopentylphenyl |
| 515. | methyl | 4-(2,2-difluorocyclopropyl)-phenyl |
| 516. | methyl | 2-fluoro-4-isopropylphenyl |
| 517. | methyl | 3-fluoro-4-isopropylphenyl |
| 518. | methyl | 4-(1-hydroxy-1-methylethyl)-phenyl |
| 519. | methyl | 4-(2-hydroxy-2-methylpropyl)-phenyl |
| 520. | methyl | 4-acetylphenyl |
| 521. | methyl | 4-carboxyphenyl |
| 522. | methyl | 4-(O-benzyl)-phenyl |
| 523. | methyl | 4-(2-methoxyethoxy)-phenyl |
| 524. | methyl | 4-(CH$_2$—N(CH$_3$)$_2$)-phenyl |
| 525. | methyl | 4-(NH—CO—NH$_2$)-phenyl |
| 526. | methyl | 4-(methylsulfanyl)-phenyl |
| 527. | methyl | 4-(fluoromethylsulfanyl)-phenyl |
| 528. | methyl | 4-(difluoromethylsulfanyl)-phenyl |
| 529. | methyl | 4-(trifluoromethylsulfanyl)-phenyl |
| 530. | methyl | 4-(methylsulfonyl)-phenyl |
| 531. | methyl | 4-(N-methoxy-N-methyl-amino)-phenyl |
| 532. | methyl | 4-(methoxyamino)-phenyl |
| 533. | methyl | 4-(ethoxyamino)-phenyl |
| 534. | methyl | 4-(N-methylaminooxy)-phenyl |
| 535. | methyl | 4-(N,N-dimethylaminooxy)-phenyl |
| 536. | methyl | 4-(azetidin-1-yl)-phenyl |
| 537. | methyl | 4-(2-methylazetidin-1-yl)-phenyl |
| 538. | methyl | 4-((S)-2-methylazetidin-1-yl)-phenyl |
| 539. | methyl | 4-((R)-2-methylazetidin-1-yl)-phenyl |
| 540. | methyl | 4-(3-fluoroazetidin-1-yl)-phenyl |
| 541. | methyl | 4-(3-methoxyazetidin-1-yl)-phenyl |
| 542. | methyl | 4-(3-hydroxyazetidin-1-yl)-phenyl |
| 543. | methyl | 4-(pyrrolidin-1-yl)-phenyl |
| 544. | methyl | 4-(pyrrolidin-2-yl)-phenyl |
| 545. | methyl | 4-((S)-pyrrolidin-2-yl)-phenyl |
| 546. | methyl | 4-((R)-pyrrolidin-2-yl)-phenyl |
| 547. | methyl | 4-(pyrrolidin-3-yl)-phenyl |
| 548. | methyl | 4-((S)-pyrrolidin-3-yl)-phenyl |
| 549. | methyl | 4-((R)-pyrrolidin-3-yl)-phenyl |
| 550. | methyl | 4-(2-fluoropyrrolidin-1-yl)-phenyl |
| 551. | methyl | 4-((S)-2-fluoropyrrolidin-1-yl)-phenyl |
| 552. | methyl | 4-((R)-2-fluoropyrrolidin-1-yl)-phenyl |
| 553. | methyl | 4-(3-fluoropyrrolidin-1-yl)-phenyl |
| 554. | methyl | 4-((S)-3-fluoropyrrolidin-1-yl)-phenyl |
| 555. | methyl | 4-((R)-3-fluoropyrrolidin-1-yl)-phenyl |
| 556. | methyl | 4-(2,2-difluoropyrrolidin-1-yl)-phenyl |
| 557. | methyl | 4-(3,3-difluoropyrrolidin-1-yl)-phenyl |
| 558. | methyl | 4-(2-methylpyrrolidin-1-yl)-phenyl |
| 559. | methyl | 4-((S)-2-methylpyrrolidin-1-yl)-phenyl |
| 560. | methyl | 4-((R)-2-methylpyrrolidin-1-yl)-phenyl |
| 561. | methyl | 4-(3-methylpyrrolidin-1-yl)-phenyl |
| 562. | methyl | 4-((S)-3-methylpyrrolidin-1-yl)-phenyl |
| 563. | methyl | 4-((R)-3-methylpyrrolidin-1-yl)-phenyl |
| 564. | methyl | 4-(1-methylpyrrolidin-2-yl)-phenyl |
| 565. | methyl | 4-((S)-1-methylpyrrolidin-2-yl)-phenyl |
| 566. | methyl | 4-((R)-1-methylpyrrolidin-2-yl)-phenyl |
| 567. | methyl | 4-(1-methylpyrrolidin-3-yl)-phenyl |
| 568. | methyl | 4-((S)-1-methylpyrrolidin-3-yl)-phenyl |

TABLE A-continued

| No. | R¹ | Ar |
|---|---|---|
| 569. | methyl | 4-((R)-1-methylpyrrolidin-3-yl)-phenyl |
| 570. | methyl | 4-(2,2-dimethylpyrrolidin-1-yl)-phenyl |
| 571. | methyl | 4-(3,3-dimethylpyrrolidin-1-yl)-phenyl |
| 572. | methyl | 4-(2-trifluoromethylpyrrolidin-1-yl)-phenyl |
| 573. | methyl | 4-((S)-2-trifluoromethylpyrrolidin-1-yl)-phenyl |
| 574. | methyl | 4-((R)-2-trifluoromethylpyrrolidin-1-yl)-phenyl |
| 575. | methyl | 4-(3-trifluoromethylpyrrolidin-1-yl)-phenyl |
| 576. | methyl | 4-((S)-3-trifluoromethylpyrrolidin-1-yl)-phenyl |
| 577. | methyl | 4-((R)-3-trifluoromethylpyrrolidin-1-yl)-phenyl |
| 578. | methyl | 4-(2-oxopyrrolidin-1-yl)-phenyl |
| 579. | methyl | 4-(2-oxo-oxazolidin-3-yl)-phenyl |
| 580. | methyl | 4-(piperidin-1-yl)-phenyl |
| 581. | methyl | 4-(2-methylpiperidin-1-yl)-phenyl |
| 582. | methyl | 4-((S)-2-methylpiperidin-1-yl)-phenyl |
| 583. | methyl | 4-((R)-2-methylpiperidin-1-yl)-phenyl |
| 584. | methyl | 4-(piperazin-1-yl)-phenyl |
| 585. | methyl | 4-(4-methylpiperazin-1-yl)-phenyl |
| 586. | methyl | 4-(morpholin-4-yl)-phenyl |
| 587. | methyl | 4-(thiomorpholin-4-yl)-phenyl |
| 588. | methyl | 4-(1-oxo-thiomorpholin-4-yl)-phenyl |
| 589. | methyl | 4-(1,1-dioxo-thiomorpholin-4-yl)-phenyl |
| 590. | methyl | 4-(pyrrol-1-yl)-phenyl |
| 591. | methyl | 4-(pyrrol-2-yl)-phenyl |
| 592. | methyl | 4-(pyrrol-3-yl)-phenyl |
| 593. | methyl | 4-(1-methylpyrrol-2-yl)-phenyl |
| 594. | methyl | 4-(1-methylpyrrol-3-yl)-phenyl |
| 595. | methyl | 4-(furan-2-yl)-phenyl |
| 596. | methyl | 4-(furan-3-yl)-phenyl |
| 597. | methyl | 4-(thiophen-2-yl)-phenyl |
| 598. | methyl | 4-(thiophen-3-yl)-phenyl |
| 599. | methyl | 4-(5-propylthien-2-yl)-phenyl |
| 600. | methyl | 4-(pyrazol-1-yl)-phenyl |
| 601. | methyl | 4-(pyrazol-3-yl)-phenyl |
| 602. | methyl | 4-(pyrazol-4-yl)-phenyl |
| 603. | methyl | 4-(1-methyl-1H-pyrazol-4-yl)-phenyl |
| 604. | methyl | 4-(1-ethyl-1H-pyrazol-4-yl)-phenyl |
| 605. | methyl | 4-(1-methyl-1H-pyrazol-5-yl)-phenyl |
| 606. | methyl | 4-(1H-imidazol-2-yl)-phenyl |
| 607. | methyl | 4-(imidazol-1-yl)-phenyl |
| 608. | methyl | 4-(1-methylimidazol-2-yl)-phenyl |
| 609. | methyl | 4-(oxazol-2-yl)-phenyl |
| 610. | methyl | 4-(oxazol-4-yl)-phenyl |
| 611. | methyl | 4-(oxazol-5-yl)-phenyl |
| 612. | methyl | 4-(isoxazol-3-yl)-phenyl |
| 613. | methyl | 4-(isoxazol-4-yl)-phenyl |
| 614. | methyl | 4-(isoxazol-5-yl)-phenyl |
| 615. | methyl | 4-([1,2,3]-triazol-1-yl)-phenyl |
| 616. | methyl | 4-([1,2,4]-triazol-1-yl)-phenyl |
| 617. | methyl | 4-([1,2,3]-triazol-2-yl)-phenyl |
| 618. | methyl | 4-(4H-[1,2,4]-triazol-3-yl)-phenyl |
| 619. | methyl | 4-([1,2,4]-triazol-4-yl)-phenyl |
| 620. | methyl | 4-(2H-[1,2,3]-triazol-4-yl)-phenyl |
| 621. | methyl | 4-(4-methyl-4H-[1,2,4]-triazol-3-yl)-phenyl |
| 622. | methyl | 4-(2-methyl-2H-[1,2,3]-triazol-4-yl)-phenyl |
| 623. | methyl | 4-([1,3,4]-oxadiazol-2-yl)-phenyl |
| 624. | methyl | 4-([1,2,4]-oxadiazol-3-yl)-phenyl |
| 625. | methyl | 4-([1,2,4]-oxadiazol-5-yl)-phenyl |
| 626. | methyl | 4-([1,2,3]-oxadiazol-4-yl)-phenyl |
| 627. | methyl | 4-([1,2,3]-oxadiazol-5-yl)-phenyl |
| 628. | methyl | 4-([1,2,3]-thiadiazol-4-yl)-phenyl |
| 629. | methyl | 4-(1H-tetrazol-5-yl)-phenyl |
| 630. | methyl | 4-(tetrazol-1-yl)-phenyl |
| 631. | methyl | 4-(2-methyl-2H-tetrazol-5-yl)-phenyl |
| 632. | methyl | 4-(1-methyl-1H-tetrazol-5-yl)-phenyl |
| 633. | methyl | 4-furazan-3-yl-phenyl |
| 634. | methyl | 4-(pyrid-2-yl)-phenyl |
| 635. | methyl | 4-(pyrid-3-yl)-phenyl |
| 636. | methyl | 4-(pyrid-4-yl)-phenyl |
| 637. | methyl | 4-(pyrimidin-2-yl)-phenyl |
| 638. | methyl | 4-(pyrimidin-4-yl)-phenyl |
| 639. | methyl | 4-(pyrimidin-5-yl)-phenyl |
| 640. | methyl | 5-isopropylthiophen-2-yl |
| 641. | methyl | 2-chlorothiophen-5-yl |
| 642. | methyl | 2,5-dichlorothiophen-4-yl |
| 643. | methyl | 2,3-dichlorothiophen-5-yl |
| 644. | methyl | 2-chloro-3-nitrothiophen-5-yl |
| 645. | methyl | 2-(phenylsulfonyl)-thiophen-5-yl |
| 646. | methyl | 2-(pyridin-2-yl)thiophen-5-yl |
| 647. | methyl | 2-(5-(trifluoromethyl)isoxazol-3-yl)-thiophen-5-yl |
| 648. | methyl | 2-(2-methylthiazol-4-yl)-thiophen-5-yl |
| 649. | methyl | 1-methyl-1H-imidazol-4-yl |
| 650. | methyl | 1,2-dimethyl-1H-imidazol-4-yl |
| 651. | methyl | 3,5-dimethylisoxazol-4-yl |
| 652. | methyl | thiazol-2-yl |
| 653. | methyl | 4-methylthiazol-2-yl |
| 654. | methyl | 4-isopropylthiazol-2-yl |
| 655. | methyl | 4-trifluoromethylthiazol-2-yl |
| 656. | methyl | 5-methylthiazol-2-yl |
| 657. | methyl | 5-isopropylthiazol-2-yl |
| 658. | methyl | 5-trifluoromethylthiazol-2-yl |
| 659. | methyl | 2,4-dimethylthiazol-5-yl |
| 660. | methyl | 2-acetamido-4-methylthiazol-5-yl |
| 661. | methyl | 4H-[1,2,4]triazol-3-yl |
| 662. | methyl | 5-methyl-4H-[1,2,4]triazol-3-yl |
| 663. | methyl | 4-methyl-4H-[1,2,4]triazol-3-yl |
| 664. | methyl | 5-isopropyl-4H-[1,2,4]triazol-3-yl |
| 665. | methyl | 5-trifluoromethyl-4H-[1,2,4]triazol-3-yl |
| 666. | methyl | 4,5-dimethyl-4H-[1,2,4]triazol-3-yl |
| 667. | methyl | 5-isopropyl-4-methyl-4H-[1,2,4]triazol-3-yl |
| 668. | methyl | 5-trifluoromethyl-4-methyl-4H-[1,2,4]triazol-3-yl |
| 669. | methyl | [1,3,4]thiadiazol-2-yl |
| 670. | methyl | 5-methyl-[1,3,4]thiadiazol-2-yl |
| 671. | methyl | 5-isopropyl-[1,3,4]thiadiazol-2-yl |
| 672. | methyl | 5-trifluoromethyl-[1,3,4]thiadiazol-2-yl |
| 673. | methyl | 3-bromo-2-chloropyrid-5-yl |
| 674. | methyl | 2-(4-morpholino)-pyrid-5-yl |
| 675. | methyl | 2-phenoxypyrid-5-yl |
| 676. | methyl | (2-isopropyl)-pyrimidin-5-yl |
| 677. | methyl | (5-isopropyl)-pyrimidin-2-yl |
| 678. | methyl | 8-quinolyl |
| 679. | methyl | 5-isoquinolyl |
| 680. | methyl | 2-(2,2,2-trifluoroacetyl)-1,2,3,4-tetrahydroisoquinolin-7-yl |
| 681. | methyl | 5-chloro-3-methylbenzothiophen-2-yl |
| 682. | methyl | 3,4-dihydro-4-methyl-2H-benzo[b][1,4]oxazinyl |
| 683. | methyl | benzothiazol-6-yl |
| 684. | methyl | benzo[2,1,3]oxadiazol-4-yl |
| 685. | methyl | 5-chlorobenzo[1,2,5]oxadiazolyl |
| 686. | methyl | 7-chlorobenzo[2,1,3]oxadiazol-4-yl |
| 687. | methyl | benzo[2,1,3]thiadiazol-4-yl |
| 688. | 3-fluoropropyl | 4-ethylphenyl |
| 689. | 3-fluoropropyl | 4-propylphenyl |
| 690. | 3-fluoropropyl | 4-isopropylphenyl |
| 691. | 3-fluoropropyl | 4-sec-butylphenyl |
| 692. | 3-fluoropropyl | 4-isobutylphenyl |
| 693. | 3-fluoropropyl | 4-(1,1-dimethylpropyl)-phenyl |
| 694. | 3-fluoropropyl | 4-vinylphenyl |
| 695. | 3-fluoropropyl | 4-isopropenylphenyl |
| 696. | 3-fluoropropyl | 4-(fluoromethyl)phenyl |
| 697. | 3-fluoropropyl | 3-(fluoromethyl)phenyl |
| 698. | 3-fluoropropyl | 2-(fluoromethyl)phenyl |
| 699. | 3-fluoropropyl | 4-(difluoromethyl)phenyl |
| 700. | 3-fluoropropyl | 3-(difluoromethyl)phenyl |
| 701. | 3-fluoropropyl | 2-(difluoromethyl)phenyl |
| 702. | 3-fluoropropyl | 4-(trifluoromethyl)phenyl |
| 703. | 3-fluoropropyl | 3-(trifluoromethyl)phenyl |
| 704. | 3-fluoropropyl | 2-(trifluoromethyl)phenyl |
| 705. | 3-fluoropropyl | 4-(1-fluoroethyl)-phenyl |
| 706. | 3-fluoropropyl | 4-((S)-1-fluoroethyl)-phenyl |
| 707. | 3-fluoropropyl | 4-((R)-1-fluoroethyl)-phenyl |
| 708. | 3-fluoropropyl | 4-(2-fluoroethyl)-phenyl |
| 709. | 3-fluoropropyl | 4-(1,1-difluoroethyl)-phenyl |
| 710. | 3-fluoropropyl | 4-(2,2-difluoroethyl)-phenyl |
| 711. | 3-fluoropropyl | 4-(2,2,2-trifluoroethyl)-phenyl |
| 712. | 3-fluoropropyl | 4-(3-fluoropropyl)-phenyl |
| 713. | 3-fluoropropyl | 4-(2-fluoropropyl)-phenyl |
| 714. | 3-fluoropropyl | 4-((S)-2-fluoropropyl)-phenyl |
| 715. | 3-fluoropropyl | 4-((R)-2-fluoropropyl)-phenyl |
| 716. | 3-fluoropropyl | 4-(3,3-difluoropropyl)-phenyl |

TABLE A-continued

| No. | R¹ | Ar |
|---|---|---|
| 717. | 3-fluoropropyl | 4-(3,3,3-trifluoropropyl)-phenyl |
| 718. | 3-fluoropropyl | 4-(1-fluoro-1-methylethyl)-phenyl |
| 719. | 3-fluoropropyl | 4-(2-fluoro-1-methylethyl)-phenyl |
| 720. | 3-fluoropropyl | 4-((S)-2-fluoro-1-methylethyl)-phenyl |
| 721. | 3-fluoropropyl | 4-((R)-2-fluoro-1-methylethyl)-phenyl |
| 722. | 3-fluoropropyl | 4-(2,2-difluoro-1-methylethyl)-phenyl |
| 723. | 3-fluoropropyl | 4-((S)-2,2-difluoro-1-methylethyl)-phenyl |
| 724. | 3-fluoropropyl | 4-((R)-2,2-difluoro-1-methylethyl)-phenyl |
| 725. | 3-fluoropropyl | 4-(2,2,2-trifluoro-1-methylethyl)-phenyl |
| 726. | 3-fluoropropyl | 4-((S)-2,2,2-trifluoro-1-methylethyl)-phenyl |
| 727. | 3-fluoropropyl | 4-((R)-2,2,2-trifluoro-1-methylethyl)-phenyl |
| 728. | 3-fluoropropyl | 4-(2-fluoro-1-fluoromethylethyl)-phenyl |
| 729. | 3-fluoropropyl | 4-(1-difluoromethyl-2,2-difluoroethyl)-phenyl |
| 730. | 3-fluoropropyl | 4-(1,1-dimethyl-2-fluoroethyl)-phenyl |
| 731. | 3-fluoropropyl | 4-ethoxyphenyl |
| 732. | 3-fluoropropyl | 4-propoxyphenyl |
| 733. | 3-fluoropropyl | 4-isopropoxyphenyl |
| 734. | 3-fluoropropyl | 4-butoxyphenyl |
| 735. | 3-fluoropropyl | 4-(fluoromethoxy)-phenyl |
| 736. | 3-fluoropropyl | 4-(difluoromethoxy)-phenyl |
| 737. | 3-fluoropropyl | 4-(2-fluoroethoxy)-phenyl |
| 738. | 3-fluoropropyl | 4-(2,2-difluoroethoxy)-phenyl |
| 739. | 3-fluoropropyl | 4-(2,2,2-trifluoroethoxy)-phenyl |
| 740. | 3-fluoropropyl | 4-(1,1,2,2-tetrafluoroethoxy)-phenyl |
| 741. | 3-fluoropropyl | 4-cyclopropylphenyl |
| 742. | 3-fluoropropyl | 4-cyclobutylphenyl |
| 743. | 3-fluoropropyl | 4-cyclopentylphenyl |
| 744. | 3-fluoropropyl | 4-(2,2-difluorocyclopropyl)-phenyl |
| 745. | 3-fluoropropyl | 2-fluoro-4-isopropylphenyl |
| 746. | 3-fluoropropyl | 3-fluoro-4-isopropylphenyl |
| 747. | 3-fluoropropyl | 4-(1-hydroxy-1-methylethyl)-phenyl |
| 748. | 3-fluoropropyl | 4-(2-hydroxy-2-methylpropyl)-phenyl |
| 749. | 3-fluoropropyl | 4-acetylphenyl |
| 750. | 3-fluoropropyl | 4-carboxyphenyl |
| 751. | 3-fluoropropyl | 4-(O-benzyl)-phenyl |
| 752. | 3-fluoropropyl | 4-(2-methoxyethoxy)-phenyl |
| 753. | 3-fluoropropyl | 4-($CH_2$—$N(CH_3)_2$)-phenyl |
| 754. | 3-fluoropropyl | 4-(NH—CO—$NH_2$)-phenyl |
| 755. | 3-fluoropropyl | 4-(methylsulfanyl)-phenyl |
| 756. | 3-fluoropropyl | 4-(fluoromethylsulfanyl)-phenyl |
| 757. | 3-fluoropropyl | 4-(difluoromethylsulfanyl)-phenyl |
| 758. | 3-fluoropropyl | 4-(trifluoromethylsulfanyl)-phenyl |
| 759. | 3-fluoropropyl | 4-(methylsulfonyl)-phenyl |
| 760. | 3-fluoropropyl | 4-(N-methoxy-N-methyl-amino)-phenyl |
| 761. | 3-fluoropropyl | 4-(methoxyamino)-phenyl |
| 762. | 3-fluoropropyl | 4-(ethoxyamino)-phenyl |
| 763. | 3-fluoropropyl | 4-(N-methylaminooxy)-phenyl |
| 764. | 3-fluoropropyl | 4-(N,N-dimethylaminooxy)-phenyl |
| 765. | 3-fluoropropyl | 4-(azetidin-1-yl)-phenyl |
| 766. | 3-fluoropropyl | 4-(2-methylazetidin-1-yl)-phenyl |
| 767. | 3-fluoropropyl | 4-((S)-2-methylazetidin-1-yl)-phenyl |
| 768. | 3-fluoropropyl | 4-((R)-2-methylazetidin-1-yl)-phenyl |
| 769. | 3-fluoropropyl | 4-(3-fluoroazetidin-1-yl)-phenyl |
| 770. | 3-fluoropropyl | 4-(3-methoxyazetidin-1-yl)-phenyl |
| 771. | 3-fluoropropyl | 4-(3-hydroxyazetidin-1-yl)-phenyl |
| 772. | 3-fluoropropyl | 4-(pyrrolidin-1-yl)-phenyl |
| 773. | 3-fluoropropyl | 4-(pyrrolidin-2-yl)-phenyl |
| 774. | 3-fluoropropyl | 4-((S)-pyrrolidin-2-yl)-phenyl |
| 775. | 3-fluoropropyl | 4-((R)-pyrrolidin-2-yl)-phenyl |
| 776. | 3-fluoropropyl | 4-(pyrrolidin-3-yl)-phenyl |
| 777. | 3-fluoropropyl | 4-((S)-pyrrolidin-3-yl)-phenyl |
| 778. | 3-fluoropropyl | 4-((R)-pyrrolidin-3-yl)-phenyl |
| 779. | 3-fluoropropyl | 4-(2-fluoropyrrolidin-1-yl)-phenyl |
| 780. | 3-fluoropropyl | 4-((S)-2-fluoropyrrolidin-1-yl)-phenyl |
| 781. | 3-fluoropropyl | 4-((R)-2-fluoropyrrolidin-1-yl)-phenyl |
| 782. | 3-fluoropropyl | 4-(3-fluoropyrrolidin-1-yl)-phenyl |
| 783. | 3-fluoropropyl | 4-((S)-3-fluoropyrrolidin-1-yl)-phenyl |
| 784. | 3-fluoropropyl | 4-((R)-3-fluoropyrrolidin-1-yl)-phenyl |
| 785. | 3-fluoropropyl | 4-(2,2-difluoropyrrolidin-1-yl)-phenyl |
| 786. | 3-fluoropropyl | 4-(3,3-difluoropyrrolidin-1-yl)-phenyl |
| 787. | 3-fluoropropyl | 4-(2-methylpyrrolidin-1-yl)-phenyl |
| 788. | 3-fluoropropyl | 4-((S)-2-methylpyrrolidin-1-yl)-phenyl |
| 789. | 3-fluoropropyl | 4-((R)-2-methylpyrrolidin-1-yl)-phenyl |
| 790. | 3-fluoropropyl | 4-(3-methylpyrrolidin-1-yl)-phenyl |
| 791. | 3-fluoropropyl | 4-((S)-3-methylpyrrolidin-1-yl)-phenyl |
| 792. | 3-fluoropropyl | 4-((R)-3-methylpyrrolidin-1-yl)-phenyl |
| 793. | 3-fluoropropyl | 4-(1-methylpyrrolidin-2-yl)-phenyl |
| 794. | 3-fluoropropyl | 4-((S)-1-methylpyrrolidin-2-yl)-phenyl |
| 795. | 3-fluoropropyl | 4-((R)-1-methylpyrrolidin-2-yl)-phenyl |
| 796. | 3-fluoropropyl | 4-(1-methylpyrrolidin-3-yl)-phenyl |
| 797. | 3-fluoropropyl | 4-((S)-1-methylpyrrolidin-3-yl)-phenyl |
| 798. | 3-fluoropropyl | 4-((R)-1-methylpyrrolidin-3-yl)-phenyl |
| 799. | 3-fluoropropyl | 4-(2,2-dimethylpyrrolidin-1-yl)-phenyl |
| 800. | 3-fluoropropyl | 4-(3,3-dimethylpyrrolidin-1-yl)-phenyl |
| 801. | 3-fluoropropyl | 4-(2-trifluoromethylpyrrolidin-1-yl)-phenyl |
| 802. | 3-fluoropropyl | 4-((S)-2-trifluoromethylpyrrolidin-1-yl)-phenyl |
| 803. | 3-fluoropropyl | 4-((R)-2-trifluoromethylpyrrolidin-1-yl)-phenyl |
| 804. | 3-fluoropropyl | 4-(3-trifluoromethylpyrrolidin-1-yl)-phenyl |
| 805. | 3-fluoropropyl | 4-((S)-3-trifluoromethylpyrrolidin-1-yl)-phenyl |
| 806. | 3-fluoropropyl | 4-((R)-3-trifluoromethylpyrrolidin-1-yl)-phenyl |
| 807. | 3-fluoropropyl | 4-(2-oxopyrrolidin-1-yl)-phenyl |
| 808. | 3-fluoropropyl | 4-(2-oxo-oxazolidin-3-yl)-phenyl |
| 809. | 3-fluoropropyl | 4-(piperidin-1-yl)-phenyl |
| 810. | 3-fluoropropyl | 4-(2-methylpiperidin-1-yl)-phenyl |
| 811. | 3-fluoropropyl | 4-((S)-2-methylpiperidin-1-yl)-phenyl |
| 812. | 3-fluoropropyl | 4-((R)-2-methylpiperidin-1-yl)-phenyl |
| 813. | 3-fluoropropyl | 4-(piperazin-1-yl)-phenyl |
| 814. | 3-fluoropropyl | 4-(4-methylpiperazin-1-yl)-phenyl |
| 815. | 3-fluoropropyl | 4-(morpholin-4-yl)-phenyl |
| 816. | 3-fluoropropyl | 4-(thiomorpholin-4-yl)-phenyl |
| 817. | 3-fluoropropyl | 4-(1-oxo-thiomorpholin-4-yl)-phenyl |
| 818. | 3-fluoropropyl | 4-(1,1-dioxo-thiomorpholin-4-yl)-phenyl |
| 819. | 3-fluoropropyl | 4-(pyrrol-1-yl)-phenyl |
| 820. | 3-fluoropropyl | 4-(pyrrol-2-yl)-phenyl |
| 821. | 3-fluoropropyl | 4-(pyrrol-3-yl)-phenyl |
| 822. | 3-fluoropropyl | 4-(1-methylpyrrol-2-yl)-phenyl |
| 823. | 3-fluoropropyl | 4-(1-methylpyrrol-3-yl)-phenyl |
| 824. | 3-fluoropropyl | 4-(furan-2-yl)-phenyl |
| 825. | 3-fluoropropyl | 4-(furan-3-yl)-phenyl |
| 826. | 3-fluoropropyl | 4-(thiophen-2-yl)-phenyl |
| 827. | 3-fluoropropyl | 4-(thiophen-3-yl)-phenyl |
| 828. | 3-fluoropropyl | 4-(5-propylthien-2-yl)-phenyl |
| 829. | 3-fluoropropyl | 4-(pyrazol-1-yl)-phenyl |
| 830. | 3-fluoropropyl | 4-(pyrazol-3-yl)-phenyl |
| 831. | 3-fluoropropyl | 4-(pyrazol-4-yl)-phenyl |
| 832. | 3-fluoropropyl | 4-(1-methyl-1H-pyrazol-4-yl)-phenyl |
| 833. | 3-fluoropropyl | 4-(1-ethyl-1H-pyrazol-4-yl)-phenyl |
| 834. | 3-fluoropropyl | 4-(1-methyl-1H-pyrazol-5-yl)-phenyl |
| 835. | 3-fluoropropyl | 4-(1H-imidazol-2-yl)-phenyl |
| 836. | 3-fluoropropyl | 4-(imidazol-1-yl)-phenyl |
| 837. | 3-fluoropropyl | 4-(1-methylimidazol-2-yl)-phenyl |
| 838. | 3-fluoropropyl | 4-(oxazol-2-yl)-phenyl |
| 839. | 3-fluoropropyl | 4-(oxazol-4-yl)-phenyl |
| 840. | 3-fluoropropyl | 4-(oxazol-5-yl)-phenyl |
| 841. | 3-fluoropropyl | 4-(isoxazol-3-yl)-phenyl |
| 842. | 3-fluoropropyl | 4-(isoxazol-4-yl)-phenyl |
| 843. | 3-fluoropropyl | 4-(isoxazol-5-yl)-phenyl |
| 844. | 3-fluoropropyl | 4-([1,2,3]-triazol-1-yl)-phenyl |
| 845. | 3-fluoropropyl | 4-([1,2,4]-triazol-1-yl)-phenyl |
| 846. | 3-fluoropropyl | 4-([1,2,3]-triazol-2-yl)-phenyl |
| 847. | 3-fluoropropyl | 4-(4H-[1,2,4]-triazol-3-yl)-phenyl |
| 848. | 3-fluoropropyl | 4-([1,2,4]-triazol-4-yl)-phenyl |
| 849. | 3-fluoropropyl | 4-(2H-[1,2,3]-triazol-4-yl)-phenyl |
| 850. | 3-fluoropropyl | 4-(4-methyl-4H-[1,2,4]-triazol-3-yl)-phenyl |
| 851. | 3-fluoropropyl | 4-(2-methyl-2H-[1,2,3]-triazol-4-yl)-phenyl |
| 852. | 3-fluoropropyl | 4-([1,3,4]-oxadiazol-2-yl)-phenyl |
| 853. | 3-fluoropropyl | 4-([1,2,4]-oxadiazol-3-yl)-phenyl |
| 854. | 3-fluoropropyl | 4-([1,2,4]-oxadiazol-4-yl)-phenyl |
| 855. | 3-fluoropropyl | 4-([1,2,3]-oxadiazol-4-yl)-phenyl |
| 856. | 3-fluoropropyl | 4-([1,2,3]-oxadiazol-5-yl)-phenyl |
| 857. | 3-fluoropropyl | 4-([1,2,3]-thiadiazol-4-yl)-phenyl |
| 858. | 3-fluoropropyl | 4-(1H-tetrazol-5-yl)-phenyl |
| 859. | 3-fluoropropyl | 4-(tetrazol-1-yl)-phenyl |
| 860. | 3-fluoropropyl | 4-(2-methyl-2H-tetrazol-5-yl)-phenyl |
| 861. | 3-fluoropropyl | 4-(1-methyl-1H-tetrazol-5-yl)-phenyl |
| 862. | 3-fluoropropyl | 4-furazan-3-yl-phenyl |
| 863. | 3-fluoropropyl | 4-(pyrid-2-yl)-phenyl |
| 864. | 3-fluoropropyl | 4-(pyrid-3-yl)-phenyl |
| 865. | 3-fluoropropyl | 4-(pyrid-4-yl)-phenyl |
| 866. | 3-fluoropropyl | 4-(pyrimidin-2-yl)-phenyl |
| 867. | 3-fluoropropyl | 4-(pyrimidin-4-yl)-phenyl |

TABLE A-continued

| No. | R¹ | Ar |
|---|---|---|
| 868. | 3-fluoropropyl | 4-(pyrimidin-5-yl)-phenyl |
| 869. | 3-fluoropropyl | 5-isopropylthiophen-2-yl |
| 870. | 3-fluoropropyl | 2-chlorothiophen-5-yl |
| 871. | 3-fluoropropyl | 2,5-dichlorothiophen-4-yl |
| 872. | 3-fluoropropyl | 2,3-dichlorothiophen-5-yl |
| 873. | 3-fluoropropyl | 2-chloro-3-nitrothiophen-5-yl |
| 874. | 3-fluoropropyl | 2-(phenylsulfonyl)-thiophen-5-yl |
| 875. | 3-fluoropropyl | 2-(pyridin-2-yl)thiophen-5-yl |
| 876. | 3-fluoropropyl | 2-(5-(trifluoromethyl)isoxazol-3-yl)-thiophen-5-yl |
| 877. | 3-fluoropropyl | 2-(2-methylthiazol-4-yl)-thiophen-5-yl |
| 878. | 3-fluoropropyl | 1-methyl-1H-imidazol-4-yl |
| 879. | 3-fluoropropyl | 1,2-dimethyl-1H-imidazol-4-yl |
| 880. | 3-fluoropropyl | 3,5-dimethylisoxazol-4-yl |
| 881. | 3-fluoropropyl | thiazol-2-yl |
| 882. | 3-fluoropropyl | 4-methylthiazol-2-yl |
| 883. | 3-fluoropropyl | 4-isopropylthiazol-2-yl |
| 884. | 3-fluoropropyl | 4-trifluoromethylthiazol-2-yl |
| 885. | 3-fluoropropyl | 5-methylthiazol-2-yl |
| 886. | 3-fluoropropyl | 5-isopropylthiazol-2-yl |
| 887. | 3-fluoropropyl | 5-trifluoromethylthiazol-2-yl |
| 888. | 3-fluoropropyl | 2,4-dimethylthiazol-5-yl |
| 889. | 3-fluoropropyl | 2-acetamido-4-methylthiazol-5-yl |
| 890. | 3-fluoropropyl | 4H-[1,2,4]triazol-3-yl |
| 891. | 3-fluoropropyl | 5-methyl-4H-[1,2,4]triazol-3-yl |
| 892. | 3-fluoropropyl | 4-methyl-4H-[1,2,4]triazol-3-yl |
| 893. | 3-fluoropropyl | 5-isopropyl-4H-[1,2,4]triazol-3-yl |
| 894. | 3-fluoropropyl | 5-trifluoromethyl-4H-[1,2,4]triazol-3-yl |
| 895. | 3-fluoropropyl | 4,5-dimethyl-4H-[1,2,4]triazol-3-yl |
| 896. | 3-fluoropropyl | 5-isopropyl-4-methyl-4H-[1,2,4]triazol-3-yl |
| 897. | 3-fluoropropyl | 5-trifluoromethyl-4-methyl-4H-[1,2,4]triazol-3-yl |
| 898. | 3-fluoropropyl | [1,3,4]thiadiazol-2-yl |
| 899. | 3-fluoropropyl | 5-methyl-[1,3,4]thiadiazol-2-yl |
| 900. | 3-fluoropropyl | 5-isopropyl-[1,3,4]thiadiazol-2-yl |
| 901. | 3-fluoropropyl | 5-trifluoromethyl-[1,3,4]thiadiazol-2-yl |
| 902. | 3-fluoropropyl | 3-bromo-2-chloropyrid-5-yl |
| 903. | 3-fluoropropyl | 2-(4-morpholino)-pyrid-5-yl |
| 904. | 3-fluoropropyl | 2-phenoxypyrid-5-yl |
| 905. | 3-fluoropropyl | (2-isopropyl)-pyrimidin-5-yl |
| 906. | 3-fluoropropyl | (5-isopropyl)-pyrimidin-2-yl |
| 907. | 3-fluoropropyl | 8-quinolyl |
| 908. | 3-fluoropropyl | 5-isoquinolyl |
| 909. | 3-fluoropropyl | 2-(2,2,2-trifluoroacetyl)-1,2,3,4-tetrahydroisoquinolin-7-yl |
| 910. | 3-fluoropropyl | 5-chloro-3-methylbenzothiophen-2-yl |
| 911. | 3-fluoropropyl | 3,4-dihydro-4-methyl-2H-benzo[b][1,4]oxazinyl |
| 912. | 3-fluoropropyl | benzothiazol-6-yl |
| 913. | 3-fluoropropyl | benzo[2,1,3]oxadiazol-4-yl |
| 914. | 3-fluoropropyl | 5-chlorobenzo[1,2,5]oxadiazolyl |
| 915. | 3-fluoropropyl | 7-chlorobenzo[2,1,3]oxadiazol-4-yl |
| 916. | 3-fluoropropyl | benzo[2,1,3]thiadiazol-4-yl |
| 917. | 2-fluoroethyl | 4-ethylphenyl |
| 918. | 2-fluoroethyl | 4-propylphenyl |
| 919. | 2-fluoroethyl | 4-isopropylphenyl |
| 920. | 2-fluoroethyl | 4-sec-butylphenyl |
| 921. | 2-fluoroethyl | 4-isobutylphenyl |
| 922. | 2-fluoroethyl | 4-(1,1-dimethylpropyl)-phenyl |
| 923. | 2-fluoroethyl | 4-vinylphenyl |
| 924. | 2-fluoroethyl | 4-isopropenylphenyl |
| 925. | 2-fluoroethyl | 4-(fluoromethyl)phenyl |
| 926. | 2-fluoroethyl | 3-(fluoromethyl)phenyl |
| 927. | 2-fluoroethyl | 2-(fluoromethyl)phenyl |
| 928. | 2-fluoroethyl | 4-(difluoromethyl)phenyl |
| 929. | 2-fluoroethyl | 3-(difluoromethyl)phenyl |
| 930. | 2-fluoroethyl | 2-(difluoromethyl)phenyl |
| 931. | 2-fluoroethyl | 4-(trifluoromethyl)phenyl |
| 932. | 2-fluoroethyl | 3-(trifluoromethyl)phenyl |
| 933. | 2-fluoroethyl | 2-(trifluoromethyl)phenyl |
| 934. | 2-fluoroethyl | 4-(1-fluoroethyl)-phenyl |
| 935. | 2-fluoroethyl | 4-((S)-1-fluoroethyl)-phenyl |
| 936. | 2-fluoroethyl | 4-((R)-1-fluoroethyl)-phenyl |
| 937. | 2-fluoroethyl | 4-(2-fluoroethyl)-phenyl |
| 938. | 2-fluoroethyl | 4-(1,1-difluoroethyl)-phenyl |
| 939. | 2-fluoroethyl | 4-(2,2-difluoroethyl)-phenyl |
| 940. | 2-fluoroethyl | 4-(2,2,2-trifluoroethyl)-phenyl |
| 941. | 2-fluoroethyl | 4-(3-fluoropropyl)-phenyl |
| 942. | 2-fluoroethyl | 4-(2-fluoropropyl)-phenyl |
| 943. | 2-fluoroethyl | 4-((S)-2-fluoropropyl)-phenyl |
| 944. | 2-fluoroethyl | 4-((R)-2-fluoropropyl)-phenyl |
| 945. | 2-fluoroethyl | 4-(3,3-difluoropropyl)-phenyl |
| 946. | 2-fluoroethyl | 4-(3,3,3-trifluoropropyl)-phenyl |
| 947. | 2-fluoroethyl | 4-(1-fluoro-1-methylethyl)-phenyl |
| 948. | 2-fluoroethyl | 4-(2-fluoro-1-methylethyl)-phenyl |
| 949. | 2-fluoroethyl | 4-((S)-2-fluoro-1-methylethyl)-phenyl |
| 950. | 2-fluoroethyl | 4-((R)-2-fluoro-1-methylethyl)-phenyl |
| 951. | 2-fluoroethyl | 4-(2,2-difluoro-1-methylethyl)-phenyl |
| 952. | 2-fluoroethyl | 4-((S)-2,2-difluoro-1-methylethyl)-phenyl |
| 953. | 2-fluoroethyl | 4-((R)-2,2-difluoro-1-methylethyl)-phenyl |
| 954. | 2-fluoroethyl | 4-(2,2,2-trifluoro-1-methylethyl)-phenyl |
| 955. | 2-fluoroethyl | 4-((S)-2,2,2-trifluoro-1-methylethyl)-phenyl |
| 956. | 2-fluoroethyl | 4-((R)-2,2,2-trifluoro-1-methylethyl)-phenyl |
| 957. | 2-fluoroethyl | 4-(2-fluoro-1-fluoromethylethyl)-phenyl |
| 958. | 2-fluoroethyl | 4-(1-difluoromethyl-2,2-difluoroethyl)-phenyl |
| 959. | 2-fluoroethyl | 4-(1,1-dimethyl-2-fluoroethyl)-phenyl |
| 960. | 2-fluoroethyl | 4-ethoxyphenyl |
| 961. | 2-fluoroethyl | 4-propoxyphenyl |
| 962. | 2-fluoroethyl | 4-isopropoxyphenyl |
| 963. | 2-fluoroethyl | 4-butoxyphenyl |
| 964. | 2-fluoroethyl | 4-(fluoromethoxy)-phenyl |
| 965. | 2-fluoroethyl | 4-(difluoromethoxy)-phenyl |
| 966. | 2-fluoroethyl | 4-(2-fluoroethoxy)-phenyl |
| 967. | 2-fluoroethyl | 4-(2,2-difluoroethoxy)-phenyl |
| 968. | 2-fluoroethyl | 4-(2,2,2-trifluoroethoxy)-phenyl |
| 969. | 2-fluoroethyl | 4-(1,1,2,2-tetrafluoroethoxy)-phenyl |
| 970. | 2-fluoroethyl | 4-cyclopropylphenyl |
| 971. | 2-fluoroethyl | 4-cyclobutylphenyl |
| 972. | 2-fluoroethyl | 4-cyclopentylphenyl |
| 973. | 2-fluoroethyl | 4-(2,2-difluorocyclopropyl)-phenyl |
| 974. | 2-fluoroethyl | 2-fluoro-4-isopropylphenyl |
| 975. | 2-fluoroethyl | 3-fluoro-4-isopropylphenyl |
| 976. | 2-fluoroethyl | 4-(1-hydroxy-1-methylethyl)-phenyl |
| 977. | 2-fluoroethyl | 4-(2-hydroxy-2-methylpropyl)-phenyl |
| 978. | 2-fluoroethyl | 4-acetylphenyl |
| 979. | 2-fluoroethyl | 4-carboxyphenyl |
| 980. | 2-fluoroethyl | 4-(O-benzyl)-phenyl |
| 981. | 2-fluoroethyl | 4-(2-methoxyethoxy)-phenyl |
| 982. | 2-fluoroethyl | 4-(CH₂—N(CH₃)₂)-phenyl |
| 983. | 2-fluoroethyl | 4-(NH—CO—NH₂)-phenyl |
| 984. | 2-fluoroethyl | 4-(methylsulfanyl)-phenyl |
| 985. | 2-fluoroethyl | 4-(fluoromethylsulfanyl)-phenyl |
| 986. | 2-fluoroethyl | 4-(difluoromethylsulfanyl)-phenyl |
| 987. | 2-fluoroethyl | 4-(trifluoromethylsulfanyl)-phenyl |
| 988. | 2-fluoroethyl | 4-(methylsulfonyl)-phenyl |
| 989. | 2-fluoroethyl | 4-(N-methoxy-N-methyl-amino)-phenyl |
| 990. | 2-fluoroethyl | 4-(methoxyamino)-phenyl |
| 991. | 2-fluoroethyl | 4-(ethoxyamino)-phenyl |
| 992. | 2-fluoroethyl | 4-(N-methylaminooxy)-phenyl |
| 993. | 2-fluoroethyl | 4-(N,N-dimethylaminooxy)-phenyl |
| 994. | 2-fluoroethyl | 4-(azetidin-1-yl)-phenyl |
| 995. | 2-fluoroethyl | 4-(2-methylazetidin-1-yl)-phenyl |
| 996. | 2-fluoroethyl | 4-((S)-2-methylazetidin-1-yl)-phenyl |
| 997. | 2-fluoroethyl | 4-((R)-2-methylazetidin-1-yl)-phenyl |
| 998. | 2-fluoroethyl | 4-(3-fluoroazetidin-1-yl)-phenyl |
| 999. | 2-fluoroethyl | 4-(3-methoxyazetidin-1-yl)-phenyl |
| 1000. | 2-fluoroethyl | 4-(3-hydroxyazetidin-1-yl)-phenyl |
| 1001. | 2-fluoroethyl | 4-(pyrrolidin-1-yl)-phenyl |
| 1002. | 2-fluoroethyl | 4-(pyrrolidin-2-yl)-phenyl |
| 1003. | 2-fluoroethyl | 4-((S)-pyrrolidin-2-yl)-phenyl |
| 1004. | 2-fluoroethyl | 4-((R)-pyrrolidin-2-yl)-phenyl |
| 1005. | 2-fluoroethyl | 4-(pyrrolidin-3-yl)-phenyl |
| 1006. | 2-fluoroethyl | 4-((S)-pyrrolidin-3-yl)-phenyl |
| 1007. | 2-fluoroethyl | 4-((R)-pyrrolidin-3-yl)-phenyl |
| 1008. | 2-fluoroethyl | 4-(2-fluoropyrrolidin-1-yl)-phenyl |
| 1009. | 2-fluoroethyl | 4-((S)-2-fluoropyrrolidin-1-yl)-phenyl |
| 1010. | 2-fluoroethyl | 4-((R)-2-fluoropyrrolidin-1-yl)-phenyl |
| 1011. | 2-fluoroethyl | 4-(3-fluoropyrrolidin-1-yl)-phenyl |
| 1012. | 2-fluoroethyl | 4-((S)-3-fluoropyrrolidin-1-yl)-phenyl |
| 1013. | 2-fluoroethyl | 4-((R)-3-fluoropyrrolidin-1-yl)-phenyl |
| 1014. | 2-fluoroethyl | 4-(2,2-difluoropyrrolidin-1-yl)-phenyl |
| 1015. | 2-fluoroethyl | 4-(3,3-difluoropyrrolidin-1-yl)-phenyl |
| 1016. | 2-fluoroethyl | 4-(2-methylpyrrolidin-1-yl)-phenyl |
| 1017. | 2-fluoroethyl | 4-((S)-2-methylpyrrolidin-1-yl)-phenyl |
| 1018. | 2-fluoroethyl | 4-((R)-2-methylpyrrolidin-1-yl)-phenyl |

TABLE A-continued

| No. | R¹ | Ar |
|---|---|---|
| 1019. | 2-fluoroethyl | 4-(3-methylpyrrolidin-1-yl)-phenyl |
| 1020. | 2-fluoroethyl | 4-((S)-3-methylpyrrolidin-1-yl)-phenyl |
| 1021. | 2-fluoroethyl | 4-((R)-3-methylpyrrolidin-1-yl)-phenyl |
| 1022. | 2-fluoroethyl | 4-(1-methylpyrrolidin-2-yl)-phenyl |
| 1023. | 2-fluoroethyl | 4-((S)-1-methylpyrrolidin-2-yl)-phenyl |
| 1024. | 2-fluoroethyl | 4-((R)-1-methylpyrrolidin-2-yl)-phenyl |
| 1025. | 2-fluoroethyl | 4-(1-methylpyrrolidin-3-yl)-phenyl |
| 1026. | 2-fluoroethyl | 4-((S)-1-methylpyrrolidin-3-yl)-phenyl |
| 1027. | 2-fluoroethyl | 4-((R)-1-methylpyrrolidin-3-yl)-phenyl |
| 1028. | 2-fluoroethyl | 4-(2,2-dimethylpyrrolidin-1-yl)-phenyl |
| 1029. | 2-fluoroethyl | 4-(3,3-dimethylpyrrolidin-1-yl)-phenyl |
| 1030. | 2-fluoroethyl | 4-(2-trifluoromethylpyrrolidin-1-yl)-phenyl |
| 1031. | 2-fluoroethyl | 4-((S)-2-trifluoromethylpyrrolidin-1-yl)-phenyl |
| 1032. | 2-fluoroethyl | 4-((R)-2-trifluoromethylpyrrolidin-1-yl)-phenyl |
| 1033. | 2-fluoroethyl | 4-(3-trifluoromethylpyrrolidin-1-yl)-phenyl |
| 1034. | 2-fluoroethyl | 4-((S)-3-trifluoromethylpyrrolidin-1-yl)-phenyl |
| 1035. | 2-fluoroethyl | 4-((R)-3-trifluoromethylpyrrolidin-1-yl)-phenyl |
| 1036. | 2-fluoroethyl | 4-(2-oxopyrrolidin-1-yl)-phenyl |
| 1037. | 2-fluoroethyl | 4-(2-oxo-oxazolidin-3-yl)-phenyl |
| 1038. | 2-fluoroethyl | 4-(piperidin-1-yl)-phenyl |
| 1039. | 2-fluoroethyl | 4-(2-methylpiperidin-1-yl)-phenyl |
| 1040. | 2-fluoroethyl | 4-((S)-2-methylpiperidin-1-yl)-phenyl |
| 1041. | 2-fluoroethyl | 4-((R)-2-methylpiperidin-1-yl)-phenyl |
| 1042. | 2-fluoroethyl | 4-(piperazin-1-yl)-phenyl |
| 1043. | 2-fluoroethyl | 4-(4-methylpiperazin-1-yl)-phenyl |
| 1044. | 2-fluoroethyl | 4-(morpholin-4-yl)-phenyl |
| 1045. | 2-fluoroethyl | 4-(thiomorpholin-4-yl)-phenyl |
| 1046. | 2-fluoroethyl | 4-(1-oxo-thiomorpholin-4-yl)-phenyl |
| 1047. | 2-fluoroethyl | 4-(1,1-dioxo-thiomorpholin-4-yl)-phenyl |
| 1048. | 2-fluoroethyl | 4-(pyrrol-1-yl)-phenyl |
| 1049. | 2-fluoroethyl | 4-(pyrrol-2-yl)-phenyl |
| 1050. | 2-fluoroethyl | 4-(pyrrol-3-yl)-phenyl |
| 1051. | 2-fluoroethyl | 4-(1-methylpyrrol-2-yl)-phenyl |
| 1052. | 2-fluoroethyl | 4-(1-methylpyrrol-3-yl)-phenyl |
| 1053. | 2-fluoroethyl | 4-(furan-2-yl)-phenyl |
| 1054. | 2-fluoroethyl | 4-(furan-3-yl)-phenyl |
| 1055. | 2-fluoroethyl | 4-(thiophen-2-yl)-phenyl |
| 1056. | 2-fluoroethyl | 4-(thiophen-3-yl)-phenyl |
| 1057. | 2-fluoroethyl | 4-(5-propylthien-2-yl)-phenyl |
| 1058. | 2-fluoroethyl | 4-(pyrazol-1-yl)-phenyl |
| 1059. | 2-fluoroethyl | 4-(pyrazol-3-yl)-phenyl |
| 1060. | 2-fluoroethyl | 4-(pyrazol-4-yl)-phenyl |
| 1061. | 2-fluoroethyl | 4-(1-methyl-1H-pyrazol-4-yl)-phenyl |
| 1062. | 2-fluoroethyl | 4-(1-ethyl-1H-pyrazol-4-yl)-phenyl |
| 1063. | 2-fluoroethyl | 4-(1-methyl-1H-pyrazol-5-yl)-phenyl |
| 1064. | 2-fluoroethyl | 4-(1H-imidazol-2-yl)-phenyl |
| 1065. | 2-fluoroethyl | 4-(imidazol-1-yl)-phenyl |
| 1066. | 2-fluoroethyl | 4-(1-methylimidazol-2-yl)-phenyl |
| 1067. | 2-fluoroethyl | 4-(oxazol-2-yl)-phenyl |
| 1068. | 2-fluoroethyl | 4-(oxazol-4-yl)-phenyl |
| 1069. | 2-fluoroethyl | 4-(oxazol-5-yl)-phenyl |
| 1070. | 2-fluoroethyl | 4-(isoxazol-3-yl)-phenyl |
| 1071. | 2-fluoroethyl | 4-(isoxazol-4-yl)-phenyl |
| 1072. | 2-fluoroethyl | 4-(isoxazol-5-yl)-phenyl |
| 1073. | 2-fluoroethyl | 4-([1,2,3]-triazol-1-yl)-phenyl |
| 1074. | 2-fluoroethyl | 4-([1,2,4]-triazol-1-yl)-phenyl |
| 1075. | 2-fluoroethyl | 4-([1,2,3]-triazol-2-yl)-phenyl |
| 1076. | 2-fluoroethyl | 4-(4H-[1,2,4]-triazol-3-yl)-phenyl |
| 1077. | 2-fluoroethyl | 4-([1,2,4]-triazol-4-yl)-phenyl |
| 1078. | 2-fluoroethyl | 4-(2H-[1,2,3]-triazol-4-yl)-phenyl |
| 1079. | 2-fluoroethyl | 4-methyl-4H-[1,2,4]-triazol-3-yl)-phenyl |
| 1080. | 2-fluoroethyl | 4-(2-methyl-2H-[1,2,3]-triazol-4-yl)-phenyl |
| 1081. | 2-fluoroethyl | 4-([1,3,4]-oxadiazol-2-yl)-phenyl |
| 1082. | 2-fluoroethyl | 4-([1,2,4]-oxadiazol-3-yl)-phenyl |
| 1083. | 2-fluoroethyl | 4-([1,2,4]-oxadiazol-5-yl)-phenyl |
| 1084. | 2-fluoroethyl | 4-([1,2,3]-oxadiazol-4-yl)-phenyl |
| 1085. | 2-fluoroethyl | 4-([1,2,3]-oxadiazol-5-yl)-phenyl |
| 1086. | 2-fluoroethyl | 4-([1,2,3]-thiadiazol-4-yl)-phenyl |
| 1087. | 2-fluoroethyl | 4-(1H-tetrazol-5-yl)-phenyl |
| 1088. | 2-fluoroethyl | 4-(tetrazol-1-yl)-phenyl |
| 1089. | 2-fluoroethyl | 4-(2-methyl-2H-tetrazol-5-yl)-phenyl |
| 1090. | 2-fluoroethyl | 4-(1-methyl-1H-tetrazol-5-yl)-phenyl |
| 1091. | 2-fluoroethyl | 4-furazan-3-yl-phenyl |
| 1092. | 2-fluoroethyl | 4-(pyrid-2-yl)-phenyl |
| 1093. | 2-fluoroethyl | 4-(pyrid-3-yl)-phenyl |
| 1094. | 2-fluoroethyl | 4-(pyrid-4-yl)-phenyl |
| 1095. | 2-fluoroethyl | 4-(pyrimidin-2-yl)-phenyl |
| 1096. | 2-fluoroethyl | 4-(pyrimidin-4-yl)-phenyl |
| 1097. | 2-fluoroethyl | 4-(pyrimidin-5-yl)-phenyl |
| 1098. | 2-fluoroethyl | 5-isopropylthiophen-2-yl |
| 1099. | 2-fluoroethyl | 2-chlorothiophen-5-yl |
| 1100. | 2-fluoroethyl | 2,5-dichlorothiophen-4-yl |
| 1101. | 2-fluoroethyl | 2,3-dichlorothiophen-5-yl |
| 1102. | 2-fluoroethyl | 2-chloro-3-nitrothiophen-5-yl |
| 1103. | 2-fluoroethyl | 2-(phenylsulfonyl)-thiophen-5-yl |
| 1104. | 2-fluoroethyl | 2-(pyridin-2-yl)thiophen-5-yl |
| 1105. | 2-fluoroethyl | 2-(5-(trifluoromethyl)isoxazol-3-yl)-thiophen-5-yl |
| 1106. | 2-fluoroethyl | 2-(2-methylthiazol-4-yl)-thiophen-5-yl |
| 1107. | 2-fluoroethyl | 1-methyl-1H-imidazol-4-yl |
| 1108. | 2-fluoroethyl | 1,2-dimethyl-1H-imidazol-4-yl |
| 1109. | 2-fluoroethyl | 3,5-dimethylisoxazol-4-yl |
| 1110. | 2-fluoroethyl | thiazol-2-yl |
| 1111. | 2-fluoroethyl | 4-methylthiazol-2-yl |
| 1112. | 2-fluoroethyl | 4-isopropylthiazol-2-yl |
| 1113. | 2-fluoroethyl | 4-trifluoromethylthiazol-2-yl |
| 1114. | 2-fluoroethyl | 5-methylthiazol-2-yl |
| 1115. | 2-fluoroethyl | 5-isopropylthiazol-2-yl |
| 1116. | 2-fluoroethyl | 5-trifluoromethylthiazol-2-yl |
| 1117. | 2-fluoroethyl | 2,4-dimethylthiazol-5-yl |
| 1118. | 2-fluoroethyl | 2-acetamido-4-methylthiazol-5-yl |
| 1119. | 2-fluoroethyl | 4H-[1,2,4]triazol-3-yl |
| 1120. | 2-fluoroethyl | 5-methyl-4H-[1,2,4]triazol-3-yl |
| 1121. | 2-fluoroethyl | 4-methyl-4H-[1,2,4]triazol-3-yl |
| 1122. | 2-fluoroethyl | 5-isopropyl-4H-[1,2,4]triazol-3-yl |
| 1123. | 2-fluoroethyl | 5-trifluoromethyl-4H-[1,2,4]triazol-3-yl |
| 1124. | 2-fluoroethyl | 4,5-dimethyl-4H-[1,2,4]triazol-3-yl |
| 1125. | 2-fluoroethyl | 5-isopropyl-4-methyl-4H-[1,2,4]triazol-3-yl |
| 1126. | 2-fluoroethyl | 5-trifluoromethyl-4-methyl-4H-[1,2,4]triazol-3-yl |
| 1127. | 2-fluoroethyl | [1,3,4]thiadiazol-2-yl |
| 1128. | 2-fluoroethyl | 5-methyl-[1,3,4]thiadiazol-2-yl |
| 1129. | 2-fluoroethyl | 5-isopropyl-[1,3,4]thiadiazol-2-yl |
| 1130. | 2-fluoroethyl | 5-trifluoromethyl-[1,3,4]thiadiazol-2-yl |
| 1131. | 2-fluoroethyl | 3-bromo-2-chloropyrid-5-yl |
| 1132. | 2-fluoroethyl | 2-(4-morpholino)-pyrid-5-yl |
| 1133. | 2-fluoroethyl | 2-phenoxypyrid-5-yl |
| 1134. | 2-fluoroethyl | (2-isopropyl)-pyrimidin-5-yl |
| 1135. | 2-fluoroethyl | (5-isopropyl)-pyrimidin-2-yl |
| 1136. | 2-fluoroethyl | 8-quinolyl |
| 1137. | 2-fluoroethyl | 5-isoquinolyl |
| 1138. | 2-fluoroethyl | 2-(2,2,2-trifluoroacetyl)-1,2,3,4-tetrahydroisoquinolin-7-yl |
| 1139. | 2-fluoroethyl | 5-chloro-3-methylbenzothiophen-2-yl |
| 1140. | 2-fluoroethyl | 3,4-dihydro-4-methyl-2H-benzo[b][1,4]oxazinyl |
| 1141. | 2-fluoroethyl | benzothiazol-6-yl |
| 1142. | 2-fluoroethyl | benzo[2,1,3]oxadiazol-4-yl |
| 1143. | 2-fluoroethyl | 5-chlorobenzo[1,2,5]oxadiazolyl |
| 1144. | 2-fluoroethyl | 7-chlorobenzo[2,1,3]oxadiazol-4-yl |
| 1145. | 2-fluoroethyl | benzo[2,1,3]thiadiazol-4-yl |
| 1146. | cyclopropylmethyl | 4-ethylphenyl |
| 1147. | cyclopropylmethyl | 4-propylphenyl |
| 1148. | cyclopropylmethyl | 4-isopropylphenyl |
| 1149. | cyclopropylmethyl | 4-sec-butylphenyl |
| 1150. | cyclopropylmethyl | 4-isobutylphenyl |
| 1151. | cyclopropylmethyl | 4-(1,1-dimethylpropyl)-phenyl |
| 1152. | cyclopropylmethyl | 4-vinylphenyl |
| 1153. | cyclopropylmethyl | 4-isopropenylphenyl |
| 1154. | cyclopropylmethyl | 4-(fluoromethyl)phenyl |
| 1155. | cyclopropylmethyl | 3-(fluoromethyl)phenyl |
| 1156. | cyclopropylmethyl | 2-(fluoromethyl)phenyl |
| 1157. | cyclopropylmethyl | 4-(difluoromethyl)phenyl |
| 1158. | cyclopropylmethyl | 3-(difluoromethyl)phenyl |
| 1159. | cyclopropylmethyl | 2-(difluoromethyl)phenyl |
| 1160. | cyclopropylmethyl | 4-(trifluoromethyl)phenyl |
| 1161. | cyclopropylmethyl | 3-(trifluoromethyl)phenyl |
| 1162. | cyclopropylmethyl | 2-(trifluoromethyl)phenyl |
| 1163. | cyclopropylmethyl | 4-(1-fluoroethyl)-phenyl |
| 1164. | cyclopropylmethyl | 4-((S)-1-fluoroethyl)-phenyl |
| 1165. | cyclopropylmethyl | 4-((R)-1-fluoroethyl)-phenyl |
| 1166. | cyclopropylmethyl | 4-(2-fluoroethyl)-phenyl |

TABLE A-continued

| No. | R¹ | Ar |
|---|---|---|
| 1167. | cyclopropylmethyl | 4-(1,1-difluoroethyl)-phenyl |
| 1168. | cyclopropylmethyl | 4-(2,2-difluoroethyl)-phenyl |
| 1169. | cyclopropylmethyl | 4-(2,2,2-trifluoroethyl)-phenyl |
| 1170. | cyclopropylmethyl | 4-(3-fluoropropyl)-phenyl |
| 1171. | cyclopropylmethyl | 4-(2-fluoropropyl)-phenyl |
| 1172. | cyclopropylmethyl | 4-((S)-2-fluoropropyl)-phenyl |
| 1173. | cyclopropylmethyl | 4-((R)-2-fluoropropyl)-phenyl |
| 1174. | cyclopropylmethyl | 4-(3,3-difluoropropyl)-phenyl |
| 1175. | cyclopropylmethyl | 4-(3,3,3-trifluoropropyl)-phenyl |
| 1176. | cyclopropylmethyl | 4-(1-fluoro-1-methylethyl)-phenyl |
| 1177. | cyclopropylmethyl | 4-(2-fluoro-1-methylethyl)-phenyl |
| 1178. | cyclopropylmethyl | 4-((S)-2-fluoro-1-methylethyl)-phenyl |
| 1179. | cyclopropylmethyl | 4-((R)-2-fluoro-1-methylethyl)-phenyl |
| 1180. | cyclopropylmethyl | 4-(2,2-difluoro-1-methylethyl)-phenyl |
| 1181. | cyclopropylmethyl | 4-((S)-2,2-difluoro-1-methylethyl)-phenyl |
| 1182. | cyclopropylmethyl | 4-((R)-2,2-difluoro-1-methylethyl)-phenyl |
| 1183. | cyclopropylmethyl | 4-(2,2,2-trifluoro-1-methylethyl)-phenyl |
| 1184. | cyclopropylmethyl | 4-((S)-2,2,2-trifluoro-1-methylethyl)-phenyl |
| 1185. | cyclopropylmethyl | 4-((R)-2,2,2-trifluoro-1-methylethyl)-phenyl |
| 1186. | cyclopropylmethyl | 4-(2-fluoro-1-fluoromethylethyl)-phenyl |
| 1187. | cyclopropylmethyl | 4-(1-difluoromethyl-2,2-difluoroethyl)-phenyl |
| 1188. | cyclopropylmethyl | 4-(1,1-dimethyl-2-fluoroethyl)-phenyl |
| 1189. | cyclopropylmethyl | 4-ethoxyphenyl |
| 1190. | cyclopropylmethyl | 4-propoxyphenyl |
| 1191. | cyclopropylmethyl | 4-isopropoxyphenyl |
| 1192. | cyclopropylmethyl | 4-butoxyphenyl |
| 1193. | cyclopropylmethyl | 4-(fluoromethoxy)-phenyl |
| 1194. | cyclopropylmethyl | 4-(difluoromethoxy)-phenyl |
| 1195. | cyclopropylmethyl | 4-(2-fluoroethoxy)-phenyl |
| 1196. | cyclopropylmethyl | 4-(2,2-difluoroethoxy)-phenyl |
| 1197. | cyclopropylmethyl | 4-(2,2,2-trifluoroethoxy)-phenyl |
| 1198. | cyclopropylmethyl | 4-(1,1,2,2-tetrafluoroethoxy)-phenyl |
| 1199. | cyclopropylmethyl | 4-cyclopropylphenyl |
| 1200. | cyclopropylmethyl | 4-cyclobutylphenyl |
| 1201. | cyclopropylmethyl | 4-cyclopentylphenyl |
| 1202. | cyclopropylmethyl | 4-(2,2-difluorocyclopropyl)-phenyl |
| 1203. | cyclopropylmethyl | 2-fluoro-4-isopropylphenyl |
| 1204. | cyclopropylmethyl | 3-fluoro-4-isopropylphenyl |
| 1205. | cyclopropylmethyl | 4-(1-hydroxy-1-methylethyl)-phenyl |
| 1206. | cyclopropylmethyl | 4-(2-hydroxy-2-methylpropyl)-phenyl |
| 1207. | cyclopropylmethyl | 4-acetylphenyl |
| 1208. | cyclopropylmethyl | 4-carboxyphenyl |
| 1209. | cyclopropylmethyl | 4-(O-benzyl)-phenyl |
| 1210. | cyclopropylmethyl | 4-(2-methoxyethoxy)-phenyl |
| 1211. | cyclopropylmethyl | 4-(CH₂—N(CH₃)₂)-phenyl |
| 1212. | cyclopropylmethyl | 4-(NH—CO—NH₂)-phenyl |
| 1213. | cyclopropylmethyl | 4-(methylsulfanyl)-phenyl |
| 1214. | cyclopropylmethyl | 4-(fluoromethylsulfanyl)-phenyl |
| 1215. | cyclopropylmethyl | 4-(difluoromethylsulfanyl)-phenyl |
| 1216. | cyclopropylmethyl | 4-(trifluoromethylsulfanyl)-phenyl |
| 1217. | cyclopropylmethyl | 4-(methylsulfonyl)-phenyl |
| 1218. | cyclopropylmethyl | 4-(N-methoxy-N-methyl-amino)-phenyl |
| 1219. | cyclopropylmethyl | 4-(methoxyamino)-phenyl |
| 1220. | cyclopropylmethyl | 4-(ethoxyamino)-phenyl |
| 1221. | cyclopropylmethyl | 4-(N-methylaminooxy)-phenyl |
| 1222. | cyclopropylmethyl | 4-(N,N-dimethylaminooxy)-phenyl |
| 1223. | cyclopropylmethyl | 4-(azetidin-1-yl)-phenyl |
| 1224. | cyclopropylmethyl | 4-(2-methylazetidin-1-yl)-phenyl |
| 1225. | cyclopropylmethyl | 4-((S)-2-methylazetidin-1-yl)-phenyl |
| 1226. | cyclopropylmethyl | 4-((R)-2-methylazetidin-1-yl)-phenyl |
| 1227. | cyclopropylmethyl | 4-(3-fluoroazetidin-1-yl)-phenyl |
| 1228. | cyclopropylmethyl | 4-(3-methoxyazetidin-1-yl)-phenyl |
| 1229. | cyclopropylmethyl | 4-(3-hydroxyazetidin-1-yl)-phenyl |
| 1230. | cyclopropylmethyl | 4-(pyrrolidin-1-yl)-phenyl |
| 1231. | cyclopropylmethyl | 4-(pyrrolidin-2-yl)-phenyl |
| 1232. | cyclopropylmethyl | 4-((S)-pyrrolidin-2-yl)-phenyl |
| 1233. | cyclopropylmethyl | 4-((R)-pyrrolidin-2-yl)-phenyl |
| 1234. | cyclopropylmethyl | 4-(pyrrolidin-3-yl)-phenyl |
| 1235. | cyclopropylmethyl | 4-((S)-pyrrolidin-3-yl)-phenyl |
| 1236. | cyclopropylmethyl | 4-((R)-pyrrolidin-3-yl)-phenyl |
| 1237. | cyclopropylmethyl | 4-(2-fluoropyrrolidin-1-yl)-phenyl |
| 1238. | cyclopropylmethyl | 4-((S)-2-fluoropyrrolidin-1-yl)-phenyl |
| 1239. | cyclopropylmethyl | 4-((R)-2-fluoropyrrolidin-1-yl)-phenyl |
| 1240. | cyclopropylmethyl | 4-(3-fluoropyrrolidin-1-yl)-phenyl |
| 1241. | cyclopropylmethyl | 4-((S)-3-fluoropyrrolidin-1-yl)-phenyl |
| 1242. | cyclopropylmethyl | 4-((R)-3-fluoropyrrolidin-1-yl)-phenyl |
| 1243. | cyclopropylmethyl | 4-(2,2-difluoropyrrolidin-1-yl)-phenyl |
| 1244. | cyclopropylmethyl | 4-(3,3-difluoropyrrolidin-1-yl)-phenyl |
| 1245. | cyclopropylmethyl | 4-(2-methylpyrrolidin-1-yl)-phenyl |
| 1246. | cyclopropylmethyl | 4-((S)-2-methylpyrrolidin-1-yl)-phenyl |
| 1247. | cyclopropylmethyl | 4-((R)-2-methylpyrrolidin-1-yl)-phenyl |
| 1248. | cyclopropylmethyl | 4-(3-methylpyrrolidin-1-yl)-phenyl |
| 1249. | cyclopropylmethyl | 4-((S)-3-methylpyrrolidin-1-yl)-phenyl |
| 1250. | cyclopropylmethyl | 4-((R)-3-methylpyrrolidin-1-yl)-phenyl |
| 1251. | cyclopropylmethyl | 4-(1-methylpyrrolidin-2-yl)-phenyl |
| 1252. | cyclopropylmethyl | 4-((S)-1-methylpyrrolidin-2-yl)-phenyl |
| 1253. | cyclopropylmethyl | 4-((R)-1-methylpyrrolidin-2-yl)-phenyl |
| 1254. | cyclopropylmethyl | 4-(1-methylpyrrolidin-3-yl)-phenyl |
| 1255. | cyclopropylmethyl | 4-((S)-1-methylpyrrolidin-3-yl)-phenyl |
| 1256. | cyclopropylmethyl | 4-((R)-1-methylpyrrolidin-3-yl)-phenyl |
| 1257. | cyclopropylmethyl | 4-(2,2-dimethylpyrrolidin-1-yl)-phenyl |
| 1258. | cyclopropylmethyl | 4-(3,3-dimethylpyrrolidin-1-yl)-phenyl |
| 1259. | cyclopropylmethyl | 4-(2-trifluoromethylpyrrolidin-1-yl)-phenyl |
| 1260. | cyclopropylmethyl | 4-((S)-2-trifluoromethylpyrrolidin-1-yl)-phenyl |
| 1261. | cyclopropylmethyl | 4-((R)-2-trifluoromethylpyrrolidin-1-yl)-phenyl |
| 1262. | cyclopropylmethyl | 4-(3-trifluoromethylpyrrolidin-1-yl)-phenyl |
| 1263. | cyclopropylmethyl | 4-((S)-3-trifluoromethylpyrrolidin-1-yl)-phenyl |
| 1264. | cyclopropylmethyl | 4-((R)-3-trifluoromethylpyrrolidin-1-yl)-phenyl |
| 1265. | cyclopropylmethyl | 4-(2-oxopyrrolidin-1-yl)-phenyl |
| 1266. | cyclopropylmethyl | 4-(2-oxo-oxazolidin-3-yl)-phenyl |
| 1267. | cyclopropylmethyl | 4-(piperidin-1-yl)-phenyl |
| 1268. | cyclopropylmethyl | 4-(2-methylpiperidin-1-yl)-phenyl |
| 1269. | cyclopropylmethyl | 4-((S)-2-methylpiperidin-1-yl)-phenyl |
| 1270. | cyclopropylmethyl | 4-((R)-2-methylpiperidin-1-yl)-phenyl |
| 1271. | cyclopropylmethyl | 4-(piperazin-1-yl)-phenyl |
| 1272. | cyclopropylmethyl | 4-(4-methylpiperazin-1-yl)-phenyl |
| 1273. | cyclopropylmethyl | 4-(morpholin-4-yl)-phenyl |
| 1274. | cyclopropylmethyl | 4-(thiomorpholin-4-yl)-phenyl |
| 1275. | cyclopropylmethyl | 4-(1-oxo-thiomorpholin-4-yl)-phenyl |
| 1276. | cyclopropylmethyl | 4-(1,1-dioxo-thiomorpholin-4-yl)-phenyl |
| 1277. | cyclopropylmethyl | 4-(pyrrol-1-yl)-phenyl |
| 1278. | cyclopropylmethyl | 4-(pyrrol-2-yl)-phenyl |
| 1279. | cyclopropylmethyl | 4-(pyrrol-3-yl)-phenyl |
| 1280. | cyclopropylmethyl | 4-(1-methylpyrrol-2-yl)-phenyl |
| 1281. | cyclopropylmethyl | 4-(1-methylpyrrol-3-yl)-phenyl |
| 1282. | cyclopropylmethyl | 4-(furan-2-yl)-phenyl |
| 1283. | cyclopropylmethyl | 4-(furan-3-yl)-phenyl |
| 1284. | cyclopropylmethyl | 4-(thiophen-2-yl)-phenyl |
| 1285. | cyclopropylmethyl | 4-(thiophen-3-yl)-phenyl |
| 1286. | cyclopropylmethyl | 4-(5-propylthien-2-yl)-phenyl |
| 1287. | cyclopropylmethyl | 4-(pyrazol-1-yl)-phenyl |
| 1288. | cyclopropylmethyl | 4-(pyrazol-3-yl)-phenyl |
| 1289. | cyclopropylmethyl | 4-(pyrazol-4-yl)-phenyl |
| 1290. | cyclopropylmethyl | 4-(1-methyl-1H-pyrazol-4-yl)-phenyl |
| 1291. | cyclopropylmethyl | 4-(1-ethyl-1H-pyrazol-4-yl)-phenyl |
| 1292. | cyclopropylmethyl | 4-(1-methyl-1H-pyrazol-5-yl)-phenyl |
| 1293. | cyclopropylmethyl | 4-(1H-imidazol-2-yl)-phenyl |
| 1294. | cyclopropylmethyl | 4-(imidazol-1-yl)-phenyl |
| 1295. | cyclopropylmethyl | 4-(1-methylimidazol-2-yl)-phenyl |
| 1296. | cyclopropylmethyl | 4-(oxazol-2-yl)-phenyl |
| 1297. | cyclopropylmethyl | 4-(oxazol-4-yl)-phenyl |
| 1298. | cyclopropylmethyl | 4-(oxazol-5-yl)-phenyl |
| 1299. | cyclopropylmethyl | 4-(isoxazol-3-yl)-phenyl |
| 1300. | cyclopropylmethyl | 4-(isoxazol-4-yl)-phenyl |
| 1301. | cyclopropylmethyl | 4-(isoxazol-5-yl)-phenyl |
| 1302. | cyclopropylmethyl | 4-([1,2,3]-triazol-1-yl)-phenyl |
| 1303. | cyclopropylmethyl | 4-([1,2,4]-triazol-1-yl)-phenyl |
| 1304. | cyclopropylmethyl | 4-([1,2,3]-triazol-2-yl)-phenyl |
| 1305. | cyclopropylmethyl | 4-(4H-[1,2,4]-triazol-3-yl)-phenyl |
| 1306. | cyclopropylmethyl | 4-([1,2,4]-triazol-4-yl)-phenyl |
| 1307. | cyclopropylmethyl | 4-(2H-[1,2,3]-triazol-4-yl)-phenyl |
| 1308. | cyclopropylmethyl | 4-(4-methyl-4H-[1,2,4]-triazol-3-yl)-phenyl |
| 1309. | cyclopropylmethyl | 4-(2-methyl-2H-[1,2,3]-triazol-4-yl)-phenyl |
| 1310. | cyclopropylmethyl | 4-([1,3,4]-oxadiazol-2-yl)-phenyl |
| 1311. | cyclopropylmethyl | 4-([1,2,4]-oxadiazol-3-yl)-phenyl |
| 1312. | cyclopropylmethyl | 4-([1,2,4]-oxadiazol-5-yl)-phenyl |
| 1313. | cyclopropylmethyl | 4-([1,2,3]-oxadiazol-4-yl)-phenyl |
| 1314. | cyclopropylmethyl | 4-([1,2,3]-oxadiazol-5-yl)-phenyl |
| 1315. | cyclopropylmethyl | 4-([1,2,3]-thiadiazol-4-yl)-phenyl |
| 1316. | cyclopropylmethyl | 4-(1H-tetrazol-5-yl)-phenyl |
| 1317. | cyclopropylmethyl | 4-(tetrazol-1-yl)-phenyl |

TABLE A-continued

| No. | R¹ | Ar |
|---|---|---|
| 1318. | cyclopropylmethyl | 4-(2-methyl-2H-tetrazol-5-yl)-phenyl |
| 1319. | cyclopropylmethyl | 4-(1-methyl-1H-tetrazol-5-yl)-phenyl |
| 1320. | cyclopropylmethyl | 4-furazan-3-yl-phenyl |
| 1321. | cyclopropylmethyl | 4-(pyrid-2-yl)-phenyl |
| 1322. | cyclopropylmethyl | 4-(pyrid-3-yl)-phenyl |
| 1323. | cyclopropylmethyl | 4-(pyrid-4-yl)-phenyl |
| 1324. | cyclopropylmethyl | 4-(pyrimidin-2-yl)-phenyl |
| 1325. | cyclopropylmethyl | 4-(pyrimidin-4-yl)-phenyl |
| 1326. | cyclopropylmethyl | 4-(pyrimidin-5-yl)-phenyl |
| 1327. | cyclopropylmethyl | 5-isopropylthiophen-2-yl |
| 1328. | cyclopropylmethyl | 2-chlorothiophen-5-yl |
| 1329. | cyclopropylmethyl | 2,5-dichlorothiophen-4-yl |
| 1330. | cyclopropylmethyl | 2,3-dichlorothiophen-5-yl |
| 1331. | cyclopropylmethyl | 2-chloro-3-nitrothiophen-5-yl |
| 1332. | cyclopropylmethyl | 2-(phenylsulfonyl)-thiophen-5-yl |
| 1333. | cyclopropylmethyl | 2-(pyridin-2-yl)thiophen-5-yl |
| 1334. | cyclopropylmethyl | 2-(5-(trifluoromethyl)isoxazol-3-yl)-thiophen-5-yl |
| 1335. | cyclopropylmethyl | 2-(2-methylthiazol-4-yl)-thiophen-5-yl |
| 1336. | cyclopropylmethyl | 1-methyl-1H-imidazol-4-yl |
| 1337. | cyclopropylmethyl | 1,2-dimethyl-1H-imidazol-4-yl |
| 1338. | cyclopropylmethyl | 3,5-dimethylisoxazol-4-yl |
| 1339. | cyclopropylmethyl | thiazol-2-yl |
| 1340. | cyclopropylmethyl | 4-methylthiazol-2-yl |
| 1341. | cyclopropylmethyl | 4-isopropylthiazol-2-yl |
| 1342. | cyclopropylmethyl | 4-trifluoromethylthiazol-2-yl |
| 1343. | cyclopropylmethyl | 5-methylthiazol-2-yl |
| 1344. | cyclopropylmethyl | 5-isopropylthiazol-2-yl |
| 1345. | cyclopropylmethyl | 5-trifluoromethylthiazol-2-yl |
| 1346. | cyclopropylmethyl | 2,4-dimethylthiazol-5-yl |
| 1347. | cyclopropylmethyl | 2-acetamido-4-methylthiazol-5-yl |
| 1348. | cyclopropylmethyl | 4H-[1,2,4]triazol-3-yl |
| 1349. | cyclopropylmethyl | 5-methyl-4H-[1,2,4]triazol-3-yl |
| 1350. | cyclopropylmethyl | 4-methyl-4H-[1,2,4]triazol-3-yl |
| 1351. | cyclopropylmethyl | 5-isopropyl-4H-[1,2,4]triazol-3-yl |
| 1352. | cyclopropylmethyl | 5-trifluoromethyl-4H-[1,2,4]triazol-3-yl |
| 1353. | cyclopropylmethyl | 4,5-dimethyl-4H-[1,2,4]triazol-3-yl |
| 1354. | cyclopropylmethyl | 5-isopropyl-4-methyl-4H-[1,2,4]triazol-3-yl |
| 1355. | cyclopropylmethyl | 5-trifluoromethyl-4-methyl-4H-[1,2,4]triazol-3-yl |
| 1356. | cyclopropylmethyl | [1,3,4]thiadiazol-2-yl |
| 1357. | cyclopropylmethyl | 5-methyl-[1,3,4]thiadiazol-2-yl |
| 1358. | cyclopropylmethyl | 5-isopropyl-[1,3,4]thiadiazol-2-yl |
| 1359. | cyclopropylmethyl | 5-trifluoromethyl-[1,3,4]thiadiazol-2-yl |
| 1360. | cyclopropylmethyl | 3-bromo-2-chloropyrid-5-yl |
| 1361. | cyclopropylmethyl | 2-(4-morpholino)-pyrid-5-yl |
| 1362. | cyclopropylmethyl | 2-phenoxypyrid-5-yl |
| 1363. | cyclopropylmethyl | (2-isopropyl)-pyrimidin-5-yl |
| 1364. | cyclopropylmethyl | (5-isopropyl)-pyrimidin-2-yl |
| 1365. | cyclopropylmethyl | 8-quinolyl |
| 1366. | cyclopropylmethyl | 5-isoquinolyl |
| 1367. | cyclopropylmethyl | 2-(2,2,2-trifluoroacetyl)-1,2,3,4-tetrahydroisoquinolin-7-yl |
| 1368. | cyclopropylmethyl | 5-chloro-3-methylbenzothiophen-2-yl |
| 1369. | cyclopropylmethyl | 3,4-dihydro-4-methyl-2H-benzo[b][1,4]oxazinyl |
| 1370. | cyclopropylmethyl | benzothiazol-6-yl |
| 1371. | cyclopropylmethyl | benzo[2,1,3]oxadiazol-4-yl |
| 1372. | cyclopropylmethyl | 5-chlorobenzo[1,2,5]oxadiazolyl |
| 1373. | cyclopropylmethyl | 7-chlorobenzo[2,1,3]oxadiazol-4-yl |
| 1374. | cyclopropylmethyl | benzo[2,1,3]thiadiazol-4-yl |
| 1375. | 1-propen-3-yl | 4-ethylphenyl |
| 1376. | 1-propen-3-yl | 4-propylphenyl |
| 1377. | 1-propen-3-yl | 4-isopropylphenyl |
| 1378. | 1-propen-3-yl | 4-sec-butylphenyl |
| 1379. | 1-propen-3-yl | 4-isobutylphenyl |
| 1380. | 1-propen-3-yl | 4-(1,1-dimethylpropyl)-phenyl |
| 1381. | 1-propen-3-yl | 4-vinylphenyl |
| 1382. | 1-propen-3-yl | 4-isopropenylphenyl |
| 1383. | 1-propen-3-yl | 4-(fluoromethyl)phenyl |
| 1384. | 1-propen-3-yl | 3-(fluoromethyl)phenyl |
| 1385. | 1-propen-3-yl | 2-(fluoromethyl)phenyl |
| 1386. | 1-propen-3-yl | 4-(difluoromethyl)phenyl |
| 1387. | 1-propen-3-yl | 3-(difluoromethyl)phenyl |
| 1388. | 1-propen-3-yl | 2-(difluoromethyl)phenyl |
| 1389. | 1-propen-3-yl | 4-(trifluoromethyl)phenyl |
| 1390. | 1-propen-3-yl | 3-(trifluoromethyl)phenyl |
| 1391. | 1-propen-3-yl | 2-(trifluoromethyl)phenyl |
| 1392. | 1-propen-3-yl | 4-(1-fluoroethyl)-phenyl |
| 1393. | 1-propen-3-yl | 4-((S)-1-fluoroethyl)-phenyl |
| 1394. | 1-propen-3-yl | 4-((R)-1-fluoroethyl)-phenyl |
| 1395. | 1-propen-3-yl | 4-(2-fluoroethyl)-phenyl |
| 1396. | 1-propen-3-yl | 4-(1,1-difluoroethyl)-phenyl |
| 1397. | 1-propen-3-yl | 4-(2,2-difluoroethyl)-phenyl |
| 1398. | 1-propen-3-yl | 4-(2,2,2-trifluoroethyl)-phenyl |
| 1399. | 1-propen-3-yl | 4-(3-fluoropropyl)-phenyl |
| 1400. | 1-propen-3-yl | 4-(2-fluoropropyl)-phenyl |
| 1401. | 1-propen-3-yl | 4-((S)-2-fluoropropyl)-phenyl |
| 1402. | 1-propen-3-yl | 4-((R)-2-fluoropropyl)-phenyl |
| 1403. | 1-propen-3-yl | 4-(3,3-difluoropropyl)-phenyl |
| 1404. | 1-propen-3-yl | 4-(3,3,3-trifluoropropyl)-phenyl |
| 1405. | 1-propen-3-yl | 4-(1-fluoro-1-methylethyl)-phenyl |
| 1406. | 1-propen-3-yl | 4-(2-fluoro-1-methylethyl)-phenyl |
| 1407. | 1-propen-3-yl | 4-((S)-2-fluoro-1-methylethyl)-phenyl |
| 1408. | 1-propen-3-yl | 4-((R)-2-fluoro-1-methylethyl)-phenyl |
| 1409. | 1-propen-3-yl | 4-(2,2-difluoro-1-methylethyl)-phenyl |
| 1410. | 1-propen-3-yl | 4-((S)-2,2-difluoro-1-methylethyl)-phenyl |
| 1411. | 1-propen-3-yl | 4-((R)-2,2-difluoro-1-methylethyl)-phenyl |
| 1412. | 1-propen-3-yl | 4-(2,2,2-trifluoro-1-methylethyl)-phenyl |
| 1413. | 1-propen-3-yl | 4-((S)-2,2,2-trifluoro-1-methylethyl)-phenyl |
| 1414. | 1-propen-3-yl | 4-((R)-2,2,2-trifluoro-1-methylethyl)-phenyl |
| 1415. | 1-propen-3-yl | 4-(2-fluoro-1-fluoromethylethyl)-phenyl |
| 1416. | 1-propen-3-yl | 4-(1-difluoromethyl-2,2-difluoroethyl)-phenyl |
| 1417. | 1-propen-3-yl | 4-(1,1-dimethyl-2-fluoroethyl)-phenyl |
| 1418. | 1-propen-3-yl | 4-ethoxyphenyl |
| 1419. | 1-propen-3-yl | 4-propoxyphenyl |
| 1420. | 1-propen-3-yl | 4-isopropoxyphenyl |
| 1421. | 1-propen-3-yl | 4-butoxyphenyl |
| 1422. | 1-propen-3-yl | 4-(fluoromethoxy)-phenyl |
| 1423. | 1-propen-3-yl | 4-(difluoromethoxy)-phenyl |
| 1424. | 1-propen-3-yl | 4-(2-fluoroethoxy)-phenyl |
| 1425. | 1-propen-3-yl | 4-(2,2-difluoroethoxy)-phenyl |
| 1426. | 1-propen-3-yl | 4-(2,2,2-trifluoroethoxy)-phenyl |
| 1427. | 1-propen-3-yl | 4-(1,1,2,2-tetrafluoroethoxy)-phenyl |
| 1428. | 1-propen-3-yl | 4-cyclopropylphenyl |
| 1429. | 1-propen-3-yl | 4-cyclobutylphenyl |
| 1430. | 1-propen-3-yl | 4-cyclopentylphenyl |
| 1431. | 1-propen-3-yl | 4-(2,2-difluorocyclopropyl)-phenyl |
| 1432. | 1-propen-3-yl | 2-fluoro-4-isopropylphenyl |
| 1433. | 1-propen-3-yl | 3-fluoro-4-isopropylphenyl |
| 1434. | 1-propen-3-yl | 4-(1-hydroxy-1-methylethyl)-phenyl |
| 1435. | 1-propen-3-yl | 4-(2-hydroxy-2-methylpropyl)-phenyl |
| 1436. | 1-propen-3-yl | 4-acetylphenyl |
| 1437. | 1-propen-3-yl | 4-carboxyphenyl |
| 1438. | 1-propen-3-yl | 4-(O-benzyl)-phenyl |
| 1439. | 1-propen-3-yl | 4-(2-methoxyethoxy)-phenyl |
| 1440. | 1-propen-3-yl | 4-($CH_2$—$N(CH_3)_2$)-phenyl |
| 1441. | 1-propen-3-yl | 4-(NH—CO—$NH_2$)-phenyl |
| 1442. | 1-propen-3-yl | 4-(methylsulfanyl)-phenyl |
| 1443. | 1-propen-3-yl | 4-(fluoromethylsulfanyl)-phenyl |
| 1444. | 1-propen-3-yl | 4-(difluoromethylsulfanyl)-phenyl |
| 1445. | 1-propen-3-yl | 4-(trifluoromethylsulfanyl)-phenyl |
| 1446. | 1-propen-3-yl | 4-(methylsulfonyl)-phenyl |
| 1447. | 1-propen-3-yl | 4-(N-methoxy-N-methyl-amino)-phenyl |
| 1448. | 1-propen-3-yl | 4-(methoxyamino)-phenyl |
| 1449. | 1-propen-3-yl | 4-(ethoxyamino)-phenyl |
| 1450. | 1-propen-3-yl | 4-(N-methylaminooxy)-phenyl |
| 1451. | 1-propen-3-yl | 4-(N,N-dimethylaminooxy)-phenyl |
| 1452. | 1-propen-3-yl | 4-(azetidin-1-yl)-phenyl |
| 1453. | 1-propen-3-yl | 4-(2-methylazetidin-1-yl)-phenyl |
| 1454. | 1-propen-3-yl | 4-((S)-2-methylazetidin-1-yl)-phenyl |
| 1455. | 1-propen-3-yl | 4-((R)-2-methylazetidin-1-yl)-phenyl |
| 1456. | 1-propen-3-yl | 4-(3-fluoroazetidin-1-yl)-phenyl |
| 1457. | 1-propen-3-yl | 4-(3-methoxyazetidin-1-yl)-phenyl |
| 1458. | 1-propen-3-yl | 4-(3-hydroxyazetidin-1-yl)-phenyl |
| 1459. | 1-propen-3-yl | 4-(pyrrolidin-1-yl)-phenyl |
| 1460. | 1-propen-3-yl | 4-(pyrrolidin-2-yl)-phenyl |
| 1461. | 1-propen-3-yl | 4-((S)-pyrrolidin-2-yl)-phenyl |
| 1462. | 1-propen-3-yl | 4-((R)-pyrrolidin-2-yl)-phenyl |
| 1463. | 1-propen-3-yl | 4-(pyrrolidin-3-yl)-phenyl |
| 1464. | 1-propen-3-yl | 4-((S)-pyrrolidin-3-yl)-phenyl |
| 1465. | 1-propen-3-yl | 4-((R)-pyrrolidin-3-yl)-phenyl |
| 1466. | 1-propen-3-yl | 4-(2-fluoropyrrolidin-1-yl)-phenyl |
| 1467. | 1-propen-3-yl | 4-((S)-2-fluoropyrrolidin-1-yl)-phenyl |
| 1468. | 1-propen-3-yl | 4-((R)-2-fluoropyrrolidin-1-yl)-phenyl |

TABLE A-continued

| No. | R¹ | Ar |
|---|---|---|
| 1469. | 1-propen-3-yl | 4-(3-fluoropyrrolidin-1-yl)-phenyl |
| 1470. | 1-propen-3-yl | 4-((S)-3-fluoropyrrolidin-1-yl)-phenyl |
| 1471. | 1-propen-3-yl | 4-((R)-3-fluoropyrrolidin-1-yl)-phenyl |
| 1472. | 1-propen-3-yl | 4-(2,2-difluoropyrrolidin-1-yl)-phenyl |
| 1473. | 1-propen-3-yl | 4-(3,3-difluoropyrrolidin-1-yl)-phenyl |
| 1474. | 1-propen-3-yl | 4-(2-methylpyrrolidin-1-yl)-phenyl |
| 1475. | 1-propen-3-yl | 4-((S)-2-methylpyrrolidin-1-yl)-phenyl |
| 1476. | 1-propen-3-yl | 4-((R)-2-methylpyrrolidin-1-yl)-phenyl |
| 1477. | 1-propen-3-yl | 4-(3-methylpyrrolidin-1-yl)-phenyl |
| 1478. | 1-propen-3-yl | 4-((S)-3-methylpyrrolidin-1-yl)-phenyl |
| 1479. | 1-propen-3-yl | 4-((R)-3-methylpyrrolidin-1-yl)-phenyl |
| 1480. | 1-propen-3-yl | 4-(1-methylpyrrolidin-2-yl)-phenyl |
| 1481. | 1-propen-3-yl | 4-((S)-1-methylpyrrolidin-2-yl)-phenyl |
| 1482. | 1-propen-3-yl | 4-((R)-1-methylpyrrolidin-2-yl)-phenyl |
| 1483. | 1-propen-3-yl | 4-(1-methylpyrrolidin-3-yl)-phenyl |
| 1484. | 1-propen-3-yl | 4-((S)-1-methylpyrrolidin-3-yl)-phenyl |
| 1485. | 1-propen-3-yl | 4-((R)-1-methylpyrrolidin-3-yl)-phenyl |
| 1486. | 1-propen-3-yl | 4-(2,2-dimethylpyrrolidin-1-yl)-phenyl |
| 1487. | 1-propen-3-yl | 4-(3,3-dimethylpyrrolidin-1-yl)-phenyl |
| 1488. | 1-propen-3-yl | 4-(2-trifluoromethylpyrrolidin-1-yl)-phenyl |
| 1489. | 1-propen-3-yl | 4-((S)-2-trifluoromethylpyrrolidin-1-yl)-phenyl |
| 1490. | 1-propen-3-yl | 4-((R)-2-trifluoromethylpyrrolidin-1-yl)-phenyl |
| 1491. | 1-propen-3-yl | 4-(3-trifluoromethylpyrrolidin-1-yl)-phenyl |
| 1492. | 1-propen-3-yl | 4-((S)-3-trifluoromethylpyrrolidin-1-yl)-phenyl |
| 1493. | 1-propen-3-yl | 4-((R)-3-trifluoromethylpyrrolidin-1-yl)-phenyl |
| 1494. | 1-propen-3-yl | 4-(2-oxopyrrolidin-1-yl)-phenyl |
| 1495. | 1-propen-3-yl | 4-(2-oxo-oxazolidin-3-yl)-phenyl |
| 1496. | 1-propen-3-yl | 4-(piperidin-1-yl)-phenyl |
| 1497. | 1-propen-3-yl | 4-(2-methylpiperidin-1-yl)-phenyl |
| 1498. | 1-propen-3-yl | 4-((S)-2-methylpiperidin-1-yl)-phenyl |
| 1499. | 1-propen-3-yl | 4-((R)-2-methylpiperidin-1-yl)-phenyl |
| 1500. | 1-propen-3-yl | 4-(piperazin-1-yl)-phenyl |
| 1501. | 1-propen-3-yl | 4-(4-methylpiperazin-1-yl)-phenyl |
| 1502. | 1-propen-3-yl | 4-(morpholin-4-yl)-phenyl |
| 1503. | 1-propen-3-yl | 4-(thiomorpholin-4-yl)-phenyl |
| 1504. | 1-propen-3-yl | 4-(1-oxo-thiomorpholin-4-yl)-phenyl |
| 1505. | 1-propen-3-yl | 4-(1,1-dioxo-thiomorpholin-4-yl)-phenyl |
| 1506. | 1-propen-3-yl | 4-(pyrrol-1-yl)-phenyl |
| 1507. | 1-propen-3-yl | 4-(pyrrol-2-yl)-phenyl |
| 1508. | 1-propen-3-yl | 4-(pyrrol-3-yl)-phenyl |
| 1509. | 1-propen-3-yl | 4-(1-methylpyrrol-2-yl)-phenyl |
| 1510. | 1-propen-3-yl | 4-(1-methylpyrrol-3-yl)-phenyl |
| 1511. | 1-propen-3-yl | 4-(furan-2-yl)-phenyl |
| 1512. | 1-propen-3-yl | 4-(furan-3-yl)-phenyl |
| 1513. | 1-propen-3-yl | 4-(thiophen-2-yl)-phenyl |
| 1514. | 1-propen-3-yl | 4-(thiophen-3-yl)-phenyl |
| 1515. | 1-propen-3-yl | 4-(5-propylthien-2-yl)-phenyl |
| 1516. | 1-propen-3-yl | 4-(pyrazol-1-yl)-phenyl |
| 1517. | 1-propen-3-yl | 4-(pyrazol-3-yl)-phenyl |
| 1518. | 1-propen-3-yl | 4-(pyrazol-4-yl)-phenyl |
| 1519. | 1-propen-3-yl | 4-(1-methyl-1H-pyrazol-4-yl)-phenyl |
| 1520. | 1-propen-3-yl | 4-(1-ethyl-1H-pyrazol-4-yl)-phenyl |
| 1521. | 1-propen-3-yl | 4-(1-methyl-1H-pyrazol-5-yl)-phenyl |
| 1522. | 1-propen-3-yl | 4-(1H-imidazol-2-yl)-phenyl |
| 1523. | 1-propen-3-yl | 4-(imidazol-1-yl)-phenyl |
| 1524. | 1-propen-3-yl | 4-(1-methylimidazol-2-yl)-phenyl |
| 1525. | 1-propen-3-yl | 4-(oxazol-2-yl)-phenyl |
| 1526. | 1-propen-3-yl | 4-(oxazol-4-yl)-phenyl |
| 1527. | 1-propen-3-yl | 4-(oxazol-5-yl)-phenyl |
| 1528. | 1-propen-3-yl | 4-(isoxazol-3-yl)-phenyl |
| 1529. | 1-propen-3-yl | 4-(isoxazol-4-yl)-phenyl |
| 1530. | 1-propen-3-yl | 4-(isoxazol-5-yl)-phenyl |
| 1531. | 1-propen-3-yl | 4-([1,2,3]-triazol-1-yl)-phenyl |
| 1532. | 1-propen-3-yl | 4-([1,2,4]-triazol-1-yl)-phenyl |
| 1533. | 1-propen-3-yl | 4-([1,2,3]-triazol-2-yl)-phenyl |
| 1534. | 1-propen-3-yl | 4-(4H-[1,2,4]-triazol-3-yl)-phenyl |
| 1535. | 1-propen-3-yl | 4-([1,2,4]-triazol-4-yl)-phenyl |
| 1536. | 1-propen-3-yl | 4-(2H-[1,2,3]-triazol-4-yl)-phenyl |
| 1537. | 1-propen-3-yl | 4-(4-methyl-4H-[1,2,4]-triazol-3-yl)-phenyl |
| 1538. | 1-propen-3-yl | 4-(2-methyl-2H-[1,2,3]-triazol-4-yl)-phenyl |
| 1539. | 1-propen-3-yl | 4-([1,3,4]-oxadiazol-2-yl)-phenyl |
| 1540. | 1-propen-3-yl | 4-([1,2,4]-oxadiazol-3-yl)-phenyl |
| 1541. | 1-propen-3-yl | 4-([1,2,4]-oxadiazol-5-yl)-phenyl |
| 1542. | 1-propen-3-yl | 4-([1,2,3]-oxadiazol-4-yl)-phenyl |
| 1543. | 1-propen-3-yl | 4-([1,2,3]-oxadiazol-5-yl)-phenyl |
| 1544. | 1-propen-3-yl | 4-([1,2,3]-thiadiazol-4-yl)-phenyl |
| 1545. | 1-propen-3-yl | 4-(1H-tetrazol-5-yl)-phenyl |
| 1546. | 1-propen-3-yl | 4-(tetrazol-1-yl)-phenyl |
| 1547. | 1-propen-3-yl | 4-(2-methyl-2H-tetrazol-5-yl)-phenyl |
| 1548. | 1-propen-3-yl | 4-(1-methyl-1H-tetrazol-5-yl)-phenyl |
| 1549. | 1-propen-3-yl | 4-furazan-3-yl-phenyl |
| 1550. | 1-propen-3-yl | 4-(pyrid-2-yl)-phenyl |
| 1551. | 1-propen-3-yl | 4-(pyrid-3-yl)-phenyl |
| 1552. | 1-propen-3-yl | 4-(pyrid-4-yl)-phenyl |
| 1553. | 1-propen-3-yl | 4-(pyrimidin-2-yl)-phenyl |
| 1554. | 1-propen-3-yl | 4-(pyrimidin-4-yl)-phenyl |
| 1555. | 1-propen-3-yl | 4-(pyrimidin-5-yl)-phenyl |
| 1556. | 1-propen-3-yl | 5-isopropylthiophen-2-yl |
| 1557. | 1-propen-3-yl | 2-chlorothiophen-5-yl |
| 1558. | 1-propen-3-yl | 2,5-dichlorothiophen-4-yl |
| 1559. | 1-propen-3-yl | 2,3-dichlorothiophen-5-yl |
| 1560. | 1-propen-3-yl | 2-chloro-3-nitrothiophen-5-yl |
| 1561. | 1-propen-3-yl | 2-(phenylsulfonyl)-thiophen-5-yl |
| 1562. | 1-propen-3-yl | 2-(pyridin-2-yl)-thiophen-5-yl |
| 1563. | 1-propen-3-yl | 2-(5-(trifluoromethyl)isoxazol-3-yl)-thiophen-5-yl |
| 1564. | 1-propen-3-yl | 2-(2-methylthiazol-4-yl)-thiophen-5-yl |
| 1565. | 1-propen-3-yl | 1-methyl-1H-imidazol-4-yl |
| 1566. | 1-propen-3-yl | 1,2-dimethyl-1H-imidazol-4-yl |
| 1567. | 1-propen-3-yl | 3,5-dimethylisoxazol-4-yl |
| 1568. | 1-propen-3-yl | thiazol-2-yl |
| 1569. | 1-propen-3-yl | 4-methylthiazol-2-yl |
| 1570. | 1-propen-3-yl | 4-isopropylthiazol-2-yl |
| 1571. | 1-propen-3-yl | 4-trifluoromethylthiazol-2-yl |
| 1572. | 1-propen-3-yl | 5-methylthiazol-2-yl |
| 1573. | 1-propen-3-yl | 5-isopropylthiazol-2-yl |
| 1574. | 1-propen-3-yl | 5-trifluoromethylthiazol-2-yl |
| 1575. | 1-propen-3-yl | 2,4-dimethylthiazol-5-yl |
| 1576. | 1-propen-3-yl | 2-acetamido-4-methylthiazol-5-yl |
| 1577. | 1-propen-3-yl | 4H-[1,2,4]triazol-3-yl |
| 1578. | 1-propen-3-yl | 5-methyl-4H-[1,2,4]triazol-3-yl |
| 1579. | 1-propen-3-yl | 4-methyl-4H-[1,2,4]triazol-3-yl |
| 1580. | 1-propen-3-yl | 5-isopropyl-4H-[1,2,4]triazol-3-yl |
| 1581. | 1-propen-3-yl | 5-trifluoromethyl-4H-[1,2,4]triazol-3-yl |
| 1582. | 1-propen-3-yl | 4,5-dimethyl-4H-[1,2,4]triazol-3-yl |
| 1583. | 1-propen-3-yl | 5-isopropyl-4-methyl-4H-[1,2,4]triazol-3-yl |
| 1584. | 1-propen-3-yl | 5-trifluoromethyl-4-methyl-4H-[1,2,4]triazol-3-yl |
| 1585. | 1-propen-3-yl | [1,3,4]thiadiazol-2-yl |
| 1586. | 1-propen-3-yl | 5-methyl-[1,3,4]thiadiazol-2-yl |
| 1587. | 1-propen-3-yl | 5-isopropyl-[1,3,4]thiadiazol-2-yl |
| 1588. | 1-propen-3-yl | 5-trifluoromethyl-[1,3,4]thiadiazol-2-yl |
| 1589. | 1-propen-3-yl | 3-bromo-2-chloropyrid-5-yl |
| 1590. | 1-propen-3-yl | 2-(4-morpholino)-pyrid-5-yl |
| 1591. | 1-propen-3-yl | 2-phenoxypyrid-5-yl |
| 1592. | 1-propen-3-yl | (2-isopropyl)-pyrimidin-5-yl |
| 1593. | 1-propen-3-yl | (5-isopropyl)-pyrimidin-2-yl |
| 1594. | 1-propen-3-yl | 8-quinolyl |
| 1595. | 1-propen-3-yl | 5-isoquinolyl |
| 1596. | 1-propen-3-yl | 2-(2,2,2-trifluoroacetyl)-1,2,3,4-tetrahydroisoquinolin-7-yl |
| 1597. | 1-propen-3-yl | 5-chloro-3-methylbenzothiophen-2-yl |
| 1598. | 1-propen-3-yl | 3,4-dihydro-4-methyl-2H-benzo[b][1,4]oxazinyl |
| 1599. | 1-propen-3-yl | benzothiazol-6-yl |
| 1600. | 1-propen-3-yl | benzo[2,1,3]oxadiazol-4-yl |
| 1601. | 1-propen-3-yl | 5-chlorobenzo[1,2,5]oxadiazolyl |
| 1602. | 1-propen-3-yl | 7-chlorobenzo[2,1,3]oxadiazol-4-yl |
| 1603. | 1-propen-3-yl | benzo[2,1,3]thiadiazol-4-yl |

The compounds of the formula I where E is NH and $R^{1a}$ is hydrogen can be prepared by analogy to methods which are well known in the art, e.g. from the international patent applications cited in the introductory part. A preferred method for the preparation of compounds I is outlined in scheme 1:

Scheme 1

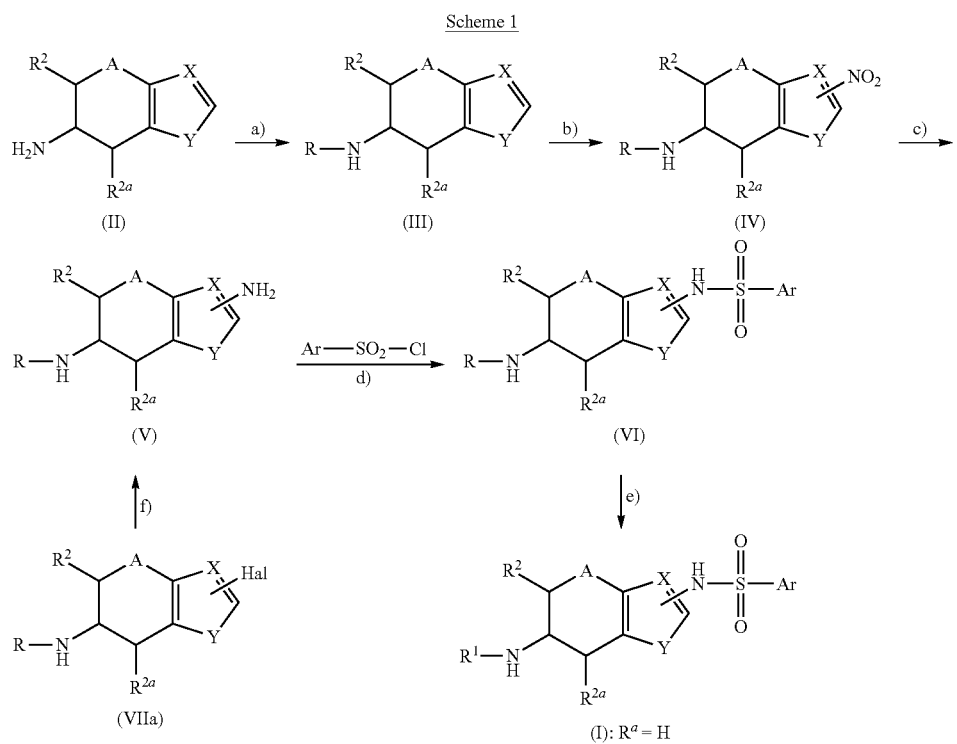

In scheme 1, $R^1$, $R^2$, $R^{2a}$, A, X, Y and Ar have the meanings as given above. Hal is halogene in particular bromine or iodine. R is $C_1$-$C_3$-alkylcarbonyl, fluorinated $C_1$-$C_3$-alkylcarbonyl or may also be also an amino-protecting group PG such as tert.-butoxycarbonyl. Suitable protecting groups are disclosed, for example, in P. Kocienski, Protecting Groups, Thieme-Verlag, Stuttgart 2000, Chapter 6.

In step a) of scheme 1 the amino group of the compound of formula II is reacted with an optionally fluorinated $C_2$-$C_4$-acyl halide in the presence of a base to obtain a compound of the formula III, wherein R is optionally fluorinated $C_1$-$C_3$-alkylcarbonyl. Acylation can be achieved by standard methods, which are discussed e.g. in J. March, Advanced Organic Chemistry, 3rd ed. J. Wiley & Sons, New York 1985, p. 370 and 373 (acylation) and p. 1099 f. and in the literature cited in this publication (see also Synth. Commun. 1986, 16, p. 267). Likewise, the amino group may be protected by standard methods with a conventional amino-protecting group PG, e.g. by reacting II with pivaloyl anhydride in the presence of a tertiary amine such as triethylamine (for reaction conditions see the literature cited in P. Kocienski, Protecting Groups, loc. cit.).

The reaction depicted in step b) in scheme 2 takes place under the reaction conditions which are customary for a nitration of an aromatic radical and which are described, for example, in J. March, Advanced Organic Chemistry, 3rd ed., John Wiley & Sons, New York 1985, pp 468-470 and the literature cited therein).

In step c), the nitro group in IV is reduced to the $NH_2$ group in V. Subsequently, in step c), the $NH_2$ group may be converted into a —$NR^{3'}H$ group, in which $R^{3'}$ has the meanings different from hydrogen which are specified for $R^3$. The reaction conditions which are required for step c) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction is achieved, for example, by reacting the nitro compound IV with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of IV to V can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of compound IV, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of IV with tin(II) chloride is preferably carried out in an inert organic solvent, preferably an alcohol such as methanol, ethanol, isopropanol or butanol.

The thus obtained compound V is reacted with an arylchlorosulfonylchloride Cl—$SO_2$—Ar, preferably in the presence of a base, according to standard procedures in the art to obtain compound VI. The reaction depicted in scheme 1 step d) takes place under the reaction conditions which are customary for preparing arylsulfonamide compounds or arylsulfonic esters, respectively, and which are described, for example, in J. March, Advanced Organic Chemistry, 3$^{rd}$ edition, John Wiley & Sons, New York, 1985 p 444 and the literature cited therein, European Journal of Medicinal Chemistry (1977), 12(1), 81-66, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of V with Cl—$SO_2$—Ar is customarily carried out in the presence of an auxiliary base. Suitable bases are inorganic bases, such as sodium carbonate or potassium carbonate, or sodium hydrogencarbonate or potassium hydrogencarbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound V.

The amino compounds of the formula V can also be prepared from the corresponding bromine compounds VIIa by reacting VIIa with an alkalimetal salt of a bis(trialkylsilyl) amine such as lithium bis(trimethylsilyl)amide in the presence of a palladium catalyst and subsequent hydrolysis. An example for a suitable palladium catalyst is tris(dibenzylideneacetone)dipalladium(0), optionally in the presence of a tri(substituted)phosphine, e.g. a triarylphosphine such as triphenylphosphine or tritolylphosphine, tri(cyclo)alkylphosphine such as tris-n-butylphosphine, tris(tert.-butyl)phosphine or tris(cyclohexylphosphine), or $PdCl_2$(dppf). The reaction of VIIa with the alkalimetal-bis(trialkylsilyl)amide can be performed by analogy to a Buchwald-Hartwig coupling. the alkalimetal-bis(trialkylsilyl)amide can be generated in-situ from the corresponding amine by a strong base such an alkalimetal alkoxide, e.g. potassium tert.-butylat or an alkalimetal hydride such as lithium hydride, sodium hydride and the like. Hydrolysis is simply achieved by aqueous work-up.

If R is optionally fluorinated $C_1$-$C_3$-alkylcarbonyl, the carbonyl group in these compounds can be reduced to a $CH_2$-moiety either with diborane, borane-dimethylsulfide or lithium aluminium hydride to obtain compounds of the general formula I, wherein R is $CH_2$-(optionally fluorinated $C_1$-$C_3$-alkyl) (see e.g. see also J. Heterocycl. Chem. 1979, 16, p. 1525). The carbonyl group can also be reacted with a fluorinating agent to obtain a compound I wherein $R^1$ is 1,1-difluoroalkyl.

If R is a protecting group, this group can be cleaved by standard methods, whereby a compound of the formula I is obtained, wherein both $R^1$ and $R^{1a}$ are hydrogen. This compound can then be reacted, in a known manner, in the sense of an alkylation, with a compound $R^1$-L. In this compound, $R^1$ is $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, fluorinated $C_3$-$C_4$-alkenyl and L is a nucleophilically displaceable leaving group, e.g. halogen, trifluoroacetate, alkylsulfonate, arylsulfonate, alkyl sulfate and the like. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

The introduction of $C_2$-$C_4$-alkyl or fluorinated $C_2$-$C_4$-alkyl as a radical $R^1$ into a compound of formula I, wherein both $R^1$ and $R^{1a}$ are hydrogen, can also be achieved, in the sense of a reductive amination, by reacting I [$R^1$=$R^{1a}$=H] with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

A skilled person will appreciate, that a compound I, wherein $R^1$ is alkenyl can be converted into a compound wherein $R^1$ is alkyl or fluorinated alkyl by hydrogenation or by addition of hydrogen fluoride or by fluorination with suitable fluorinating agents such as $XeF_2$ or $CoF_3$.

A skilled person will further appreciate, that a radical $R_3$, which is different from hydrogen, can be introduced in either compound I of scheme I or at an earlier stage of the synthesis by a conventional alkylation.

Compounds of the general formula I, wherein E is N—$R^3$ can also be obtained by the synthetic route outlined in scheme 2.

Scheme 2:

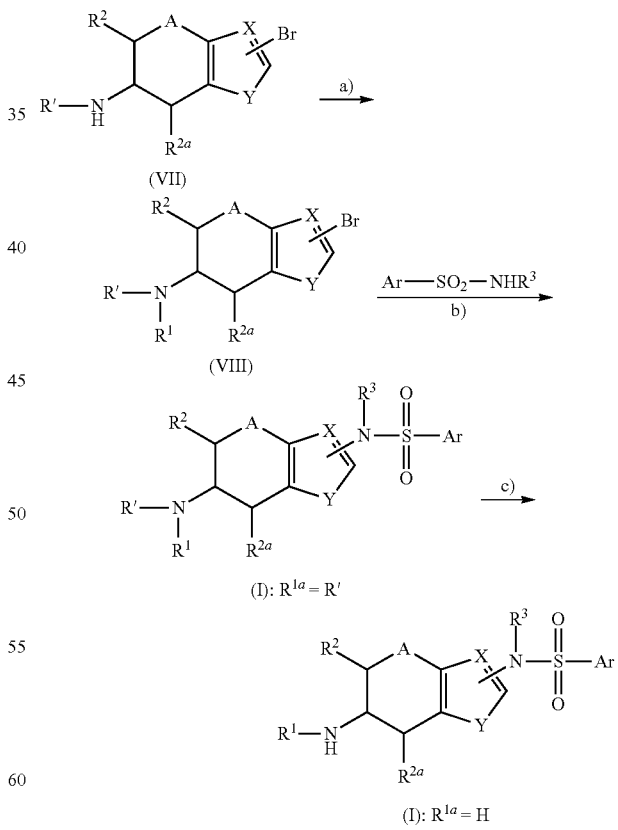

In scheme 2, R' is an amino-protecting group or has one of the meanings given for $R^{1a}$, provided that R' is different from hydrogen. $R^2$, $R^{2a}$, $R^3$, A, X, Y and Ar have the meanings given above.

In step a) of scheme 2 a radical $R^1$ is introduced into compound VII either by acylation or by alkylation as outlined for scheme 1.

In step b) of scheme 2, compound VIII is reacted with an arylsulfonylamide Ar—$SO_2$—$NH_2$ or the lithium salt thereof in the presence of a palladium(0) compound such as tris (dibenzylideneacetone)dipalladium(0) in the presence of a tri(substituted)phosphine, e.g. a triarylphosphine such as triphenylphosphine or tritolylphosphine, tri(cyclo)alkylphosphine such as tris-n-butylphosphine, tris(tert.-butyl)phosphine or tris(cyclohexylphosphine), preferably in the presence of a base such as sodium hydride according to the method described in J. Org. Chem., 68 (2993) pp 8274-8276, and outlined below.

If R' is an amino-protecting group, R' can be cleaved by standard methods to obtain a compound of the formula I, wherein $R^{1a}$ is hydrogen (step c).

A skilled person will appreciate, that the radical $R^1$ compounds I shown in scheme 2, can be further modified as described for scheme 1.

Compounds of the formula I, wherein $R^{1a}$ and $R^2$ together are $(CH_2)_n$ with n being 2 or 3 can be prepared in manner similar to the method outlined in scheme 1 starting from a compound of the formula IX, by the method outlined in scheme 3:

Scheme 3:

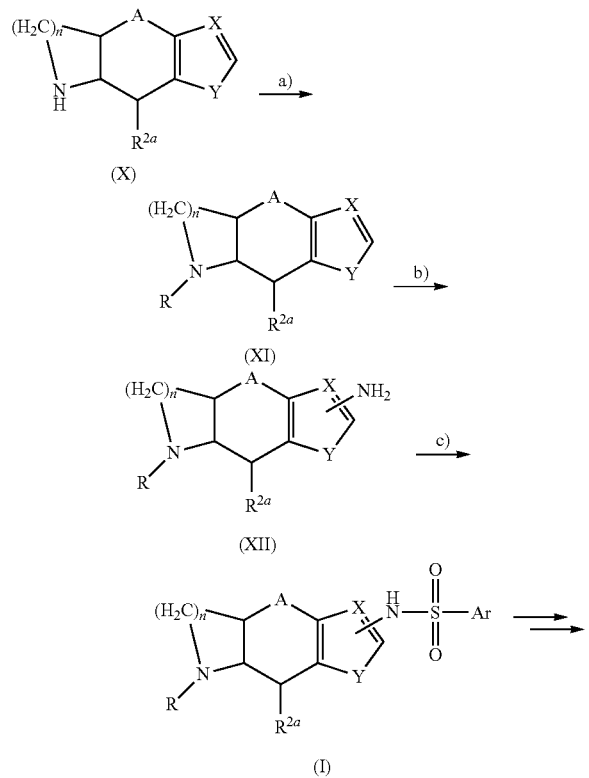

In scheme 3, $R^{2a}$, n, A, X, Y and Ar have the meanings given above. R is a radical $R^1$ or an amino protecting group. In particular $R^1$ is $C_1$-$C_3$-alkylcarbonyl. In step a) a radical $R^1$ is introduced in compound X by a method corresponding to the methods described for step e) in scheme 1. Compound XI is converted into the amino compound XII by a nitration/reduction sequence described for steps b and c of scheme 1. Step c) of scheme 3 can by performed by analogy to a method described for step d in scheme 1.

A skilled person will appreciate that compound I of scheme 3 can be further reacted as described for scheme 1. A skilled person will further appreciate, that compounds wherein $R^{1a}$ and $R^{2a}$ together are $(CH_2)_n$ can be prepared by a similar approach.

Compounds of the formula I, where X is CH, Y is N=CH and E is $NR^3$ can be also obtained by the synthetic approach outlined in scheme 4:

Scheme 4:

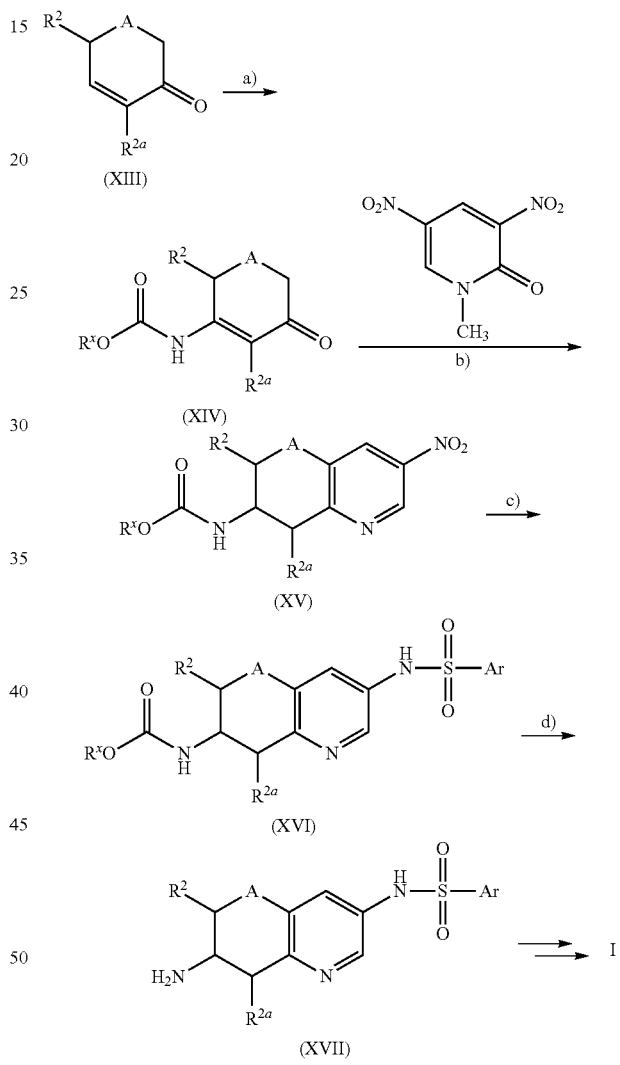

Starting from cyclohex-2-enone XIII (or the corresponding pyranon (A=O) or thianon (A=S)), selective Michael addition of a carbamate $R^xO$—C(O)—$NH_2$, in the presence of bismuth nitrate, generates the requisite β-amino ketone XIV (step a, see e.g. (J. Org. Chem. 2003, 68, 2109-2114). In step b), compound XIV undergoes Tohda reaction with dinitropyridone to give the azabicyclic nitro derivative XV (step c), see e.g. Bull. Chem. Soc. Jpn. 1990, 63, 2820-2827; J. Med. Chem. 1996, 39, 2844-2851; Synth. Commun. 2001, 31, 787-797; Bioorg. Med. Chem. Lett. 2003, 13, 529-532). This generates a mixture of the 5- and 7-amino isomers which can be separated as either the amino or sulfonamide product. The mixture can then be reduced to the amine by the methods disclosed for step b in scheme 2, e.g. via tin chloride or catalytic hydrogenation (e.g. Pd—C/H$_2$) and subsequently converted to the desired sulfonamide by reaction with the appropriate sulfonyl chloride as outlined for step b) in scheme 1 to yield a compound of the formula XVI. The amine XVI may be generated by cleavage of the carbamate in the presence of an acid such as trifluoroacetic acid and converted to the target N-alkyl derivatives by processes of alkylation, acylation/reduction or reductive amination as outlined for scheme 1.

Compounds of the formulae II, VII and X are known in the art or they can be prepared in case of VII by subsequent amino-protection of the corresponding amines and bromination. The preparation of compounds X can be achieved e.g. by the method disclosed in Organic Process Research and Development 7(6) (2003) 904-912.

Compounds V, wherein R is alkylcarbonyl, A is CH$_2$, X is N and Y is S, can be prepared by the following reaction scheme:

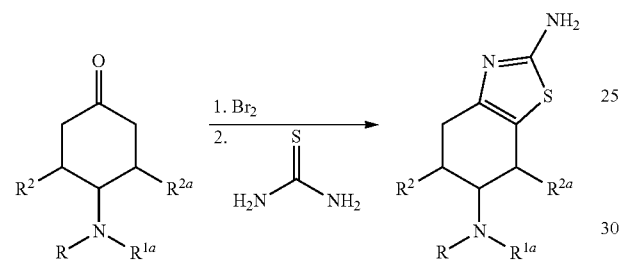

Compounds V, wherein R is an aminoprotecting group PG, A is CH$_2$, X is N and Y is CH═N, can be prepared by the following reaction scheme:

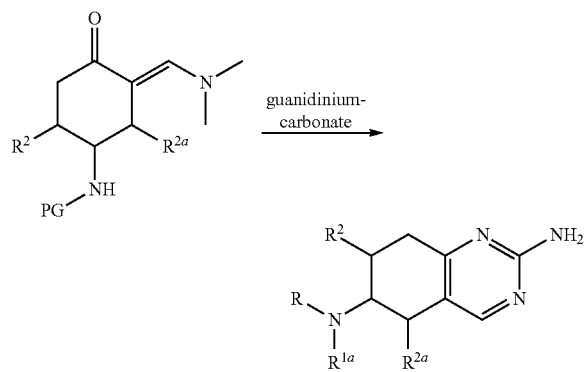

The compounds of the formula I where E is CR$^6$R$^7$ can be prepared as outlined in scheme 5:

Scheme 5:

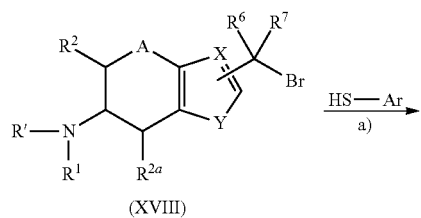

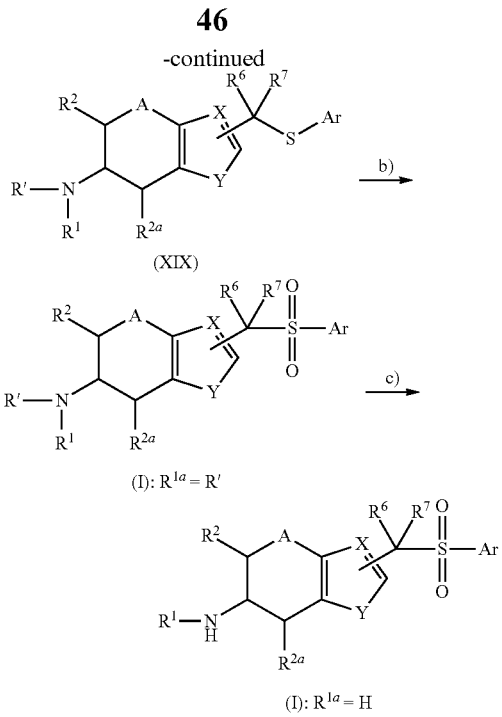

In scheme 5, R$^1$, R$^2$, R$^{2a}$, R$^6$, R$^7$, Ar, A, X and Y have the meanings given above. R' is a radical R$^{1a}$ or a protective group. According to scheme 5, compound XVIII is reacted in step b) with a mercapto compound HS—Ar in the presence of a base, such as sodium hydride or sodium alkoxide or with an alkali metal salt thereof thereby yielding thioether compound XIX. The thioether moiety in compound is oxidized to a sulfone moiety, e.g. by oxone (step b). If R' is a protective group, R' can be cleaved, thereby obtaining compound I, wherein R$^{1a}$ is H. A skilled person understands that I can be further transformed as outlined for scheme 1.

A skilled person will readily appreciate that compounds of the formula I can also be obtained from structurally similar compounds by functional group interconversion. In particular N-bound radicals R$^a$ can be introduced into compounds of the formula I by reacting the corresponding halogen compound, i.e. a compound of the formula I, which instead of R$^a$ carries a halogen atom, in particular a bromine or iodine atom, with a primary or secondary amine in the presence of a base, preferably also in the presence of a palladium catalyst in terms of a Buchwald-Hartwig reaction.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The sulfonylchlorides Cl—SO$_2$—Ar are either commercially available or can be prepared according to standard synthetic methods. Sulfonylchlorides containing a fluorinated radical R$^a$ may be prepared by different synthetic routes, e.g. by reacting suitable hydroxy or oxo precursor (e.g. a compound Cl—SO$_2$—Ar, carrying a hydroxy or oxo substituted radical) with fluorinating reagents like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377). More conventionally, the hydroxy group of an aromatic compound which carries a hydroxy substituted radical but not a chlorosulfonyl group, is transformed into a leaving group which is then replace by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21)). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorour pentachloride (Eur. J. Med. Chem., 2002, 36, 809-828) and the like, yields the desired sulfonylchloride (Tetrahedron Letters, 1991, 33, 50 7787-7788)) Sulfonylchlorides may also be prepared by diazotation of suitable amine precursor Ar—NH$_2$ with sodium nitrite under acidic conditions and reaction with sulfur dioxide in acetic acid (scheme (iii); J. Org. Chem., 1960, 25, 1824-26); by oxidation of suitable heteroaryl-thiols HS—Ar or heteroaryl-benzyl-thioethers C$_6$H$_5$—CH$_2$—S—Ar with chlorine (Synthesis, 1998, 36-38; J. Am. Chem. Soc., 1950, 74, 4890-92) directly to the corresponding sulfonyl chlorides. The further are known in the art or may be prepared by standard methods. E.g. mercapto-pyrimidines or pyrimidinyl-benzylthioether precursors can e.g. be prepared according to literature (Chemische Berichte, 1960, 1208-11; Chemische Berichte, 1960, 95, 230-235; Collection Czechoslow. Chem. Comm., 1959, 24, 1667-1671; Austr. J. Chem., 1966, 19, 2321-30; Chemiker-Zeitung, 101, 6, 1977, 305-7; Tetrahedron, 2002, 58, 887-890; Synthesis, 1983, 641-645.

In the following schemes 6 to 8 several routes are shown which are suitable to prepare benzenesulfonyl chlorides carrying a fluorinated propyl radical.

verted to the 1,1-difluoro-2-propyl derivative by reaction with a suitable fluorinating reagent like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377) (step b). The thus obtained 1,1-difluoro-2-phenylpropane can be converted into 4-(1,1-difluoro-2-propyl)benzenesulfonyl chloride by either direct chlorosulfonylation with chlorosulfonic acid (Heterocycles, 2001, 55, 9, 1789-1803; J. Org. Chem., 2000, 65, 1399-1406) (step c) or by a two step process preparing first the sulfonic acid derivatives (step d) which are then transformed to the sulfonylchlorides (step e) by reaction with e.g. chlorosulfonic acid, phosphorous pentachloride (Eur. J. Med. Chem., 2002, 36, 809-828); through diazotisation of suitable amine precursors with sodium nitrite under acidic conditions and reaction with sulfur dioxide in acetic acid (J. Org. Chem., 1960, 25, 1824-26); oxidation of suitable heteroaryl-thiols or heteroaryl-benzyl-thioethers with chlorine (Synthesis, 1998, 36-38; J. Am. Chem. Soc., 1950, 74, 4890-92) directly to the corresponding sulfonyl chlorides.

The synthesis shown in scheme 6 can also be performed using (R)-2-phenylpropanic acid and (S)-2-phenylpropanic acid respectively to give the corresponding chiral 4-(1,1-difluoropropan-2-yl)benzene-1-sulfonyl chlorides.

Scheme 7:

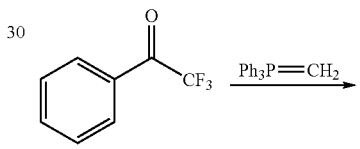

Scheme 6:

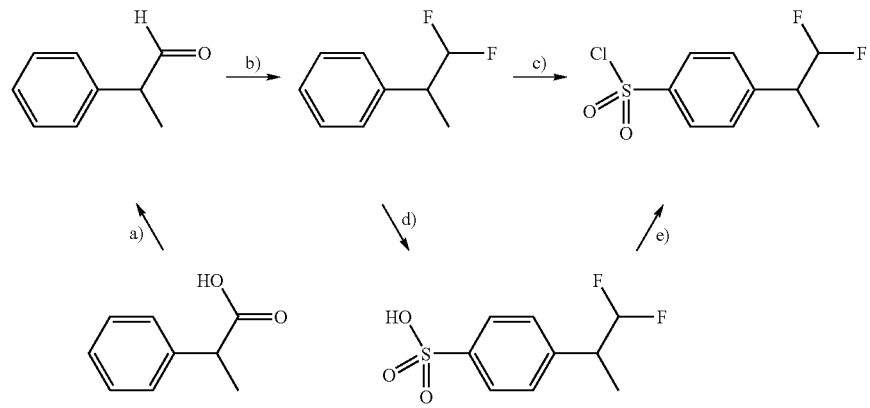

The 4-(1,1-difluoropropan-2-yl)benzene-1-sulfonyl chloride intermediate can be prepared from the commercially available 2-phenylpropanoic acid. In the first step a) the 2-phenylpropanic acid is converted to the alkyl ester by esterification with an alcohol (e.g. methanol or ethanol) under acid catalysis (e.g. HCl, SO$_2$Cl$_2$). The ester can be reduced to the corresponding 2-phenyl propanal by a reducing agent such as DIBAL (diisobutylaluminium hydride). The aldehyde is con- -continued

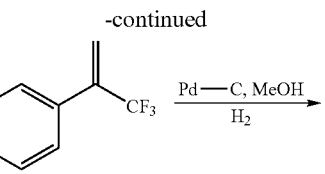

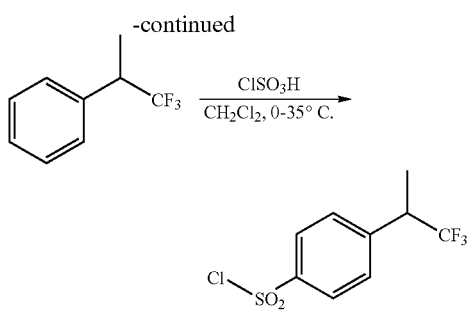

4-(1,1,1-Trifluoropropan-2-yl)benzene-1-sulfonyl chloride intermediate can be prepared from the commercially available 2,2,2-trifluoro-1-phenylethanone by a synthetic route shown in scheme 7. The ketone can be converted to the 3,3,3-trifluoro-2-phenylpropene by a Wittig reaction with a suitable ylide such as methylene-triphenylphosphane (prepared by reaction of methyltriphenylphosphonium halide and a suitable base such as lithium diisopropylamide or potassium tert-butoxide) or according to a Horner-Emmons reaction by reacting the ketone with a suitable phosphonate such as diethyl methylphosphonate and a suitable base such as lithium diisopropylamide or potassium tert-butoxide. The thus obtained 3,3,3-trifluoro-2-phenylpropene can then be reduced to the saturated alkane by catalytic hydrogenation (eg Pd—C) followed by conversion to the sulfonyl chloride by the methods described in scheme 6.

The synthesis of scheme 7 can also be performed using a chiral catalyst for the alkene hydrogenation to allow the preparation of the corresponding chiral 4-(1,1,1-trifluoropropan-2-yl)benzene-1-sulfonyl chlorides.

Scheme 8:

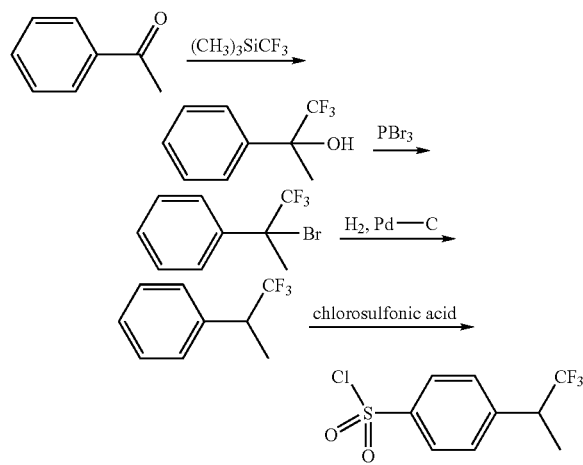

The 4-(1,1,1-trifluoropropan-2-yl)benzene-1-sulfonyl chloride can be also prepared from the commercially available 1-phenyl-ethanone by a four step procedure as shown in scheme 8. The ketone can be converted to the trifluoromethyl hydroxyl intermediate by reaction with trimethyl-trifluoromethyl-silane (Journal of Organic Chemistry, 2000, 65, 8848-8856; Journal of Fluorine Chemistry, 2003, 122, 243-246) which can then be converted to the trifluoromethyl bromide (Journal of the American Chemical Society, 1987, 109, 2435-4). Dehalogenation by catalytic hydrogenation (eg Pd—C) can then be followed by conversion to the sulfonyl chloride by the methods discussed above.

Examples of solvents which can be used are ethers, such as diethyl ether, diisopropyl ether, methyl tert-butyl ether or tetrahydrofuran, aprotic polar solvent, such as dimethylformamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are surprisingly highly selective dopamine $D_3$ receptor ligands which, because of their low affinity for other receptors such as $D_1$ receptors, $D_4$ receptors, α1-adrenergic and/or α2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists. A compound of the invention can be a dopamine $D_3$ receptor agonist, including partial agonistic activity, or a dopamine $D_3$ receptor antagonist, including partial antagonistic activity.

The high affinity of the compounds according to the invention for $D_3$ receptors is reflected in very low in vitro receptor binding constants ($K_i(D_3)$ values) of as a rule less than 50 nM (nmol/l), preferably of less than 10 nM and, in particular of less than 5 nM. The displacement of [$^{125}$I]-iodosulpride can, for example, be used in receptor binding studies for determining binding affinities for $D_3$ receptors.

The selectivity of the compounds according to the invention, i.e. the ratio $K_i(D_2)/K_i(D_3)$ of the receptor binding constants, is as a rule at least 50, preferably at least 100, even better at least 150. The displacement of [$^3$H]SCH23390, [$^{125}$I] iodosulpride or [$^{125}$I] spiperone can be used, for example, for carrying out receptor binding studies on $D_1$, $D_2$ and $D_4$ receptors.

Because of their binding profile, the compounds can be used for treating diseases which respond to dopamine $D_3$ receptor ligands (or which are susceptible to treatment with a dopamine $D_3$ receptor ligand, respectively), i.e. they are effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disorders which can be treated in accordance with the invention also include Parkinson's disease and epilepsy and, in particular, the affective disturbances connected thereto.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogenously administered binding partners (ligands) to dopamine $D_3$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional liability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Therefore the compounds according to the invention are preferentially suitable for treating diseases of the central nervous system, in particular for treating affective disorder neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney-function which are caused by diabetes mellitus (see WO 00/67847) and, especially, diabetic nephropathy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet(s), broad singlet (s. br.), doublet (d), broad doublet (d br.), triplet (t), broad triplet (t br.), quartet (q), quintet (quint.) and multiplet (m).

PREPARATION EXAMPLES

I. Preparation of Intermediates a. Synthesis of Sulfonyl Chlorides a.1 4-((S)-2-Fluoro-1-methyl-ethyl)-benzenesulfonyl chloride a.1.1 Toluene-4-sulfonic acid (S)-2-phenyl-propyl ester To a solution of 20 g of (S)-(−)-2-phenyl-1-propanol in 240 ml of dichloromethane was added in portions 28 g of p-toluenesulfonyl chloride (146.8 mmol). After stirring for 18 h at room temperature, the organic phase was washed with 100 ml of water, dried over magnesium sulfate, filtered, and the solvent evaporated under reduced pressure to yield 43 g of the title compound.

$^1$H-NMR (CDCl$_3$, 400 MHz): δ [ppm] 7.65 (d, 2H), 7.15-7.3 (m, 5H), 7.1 (d, 2H), 4.0-4.1 (m, 2H), 3.1 (m, 1H), 2.4 (s, 3H), 1.3 (d, 3H).

a.1.2 ((S)-2-Fluoro-1-methyl-ethyl)-benzene 9.62 g of toluene-4-sulfonic acid (S)-2-phenyl-propyl ester (33.13 mmol) were dissolved in 80 ml of polyethyleneglycol 400. 9.62 g of potassium fluoride (165.6 mmol) were added and the reaction mixture was stirred at 50° C. for 3 days and another 2 days at 55-70° C. The reaction was treated with 150 ml of saturated aqueous sodium chloride solution, extracted three times with diethyl ether, and the combined organic layers were dried over magnesium sulfate, filtered, and the solvent was evaporated under reduced pressure. The crude product was purified via silica gel chromatography using cyclohexane/ethyl acetate 15% as eluent. 2.85 g of the desired product were isolated, containing ~25% of the elimination side product.

$^1$H-NMR (CDCl$_3$, 400 MHz): δ [ppm] 7.2-7.4 (m, 5H), 4.3-4.6 (several m, 2H), 3.15 (m, 1H). 1.3 (m, 3H).

a.1.3 4-((S)-2-Fluoro-1-methyl-ethyl)-benzenesulfonyl chloride 3.5 g of ((S)-2-fluoro-1-methyl-ethyl)-benzene (25.32 mmol) were dissolved in 80 ml of dichloromethane. At 0-5°

C., 11.81 g of chlorosulfonic acid (101.31 mmol), dissolved in 20 ml of dichloromethane, were added dropwise. The reaction mixture was stirred for 30 min at room temperature and 2 h at 30° C. The solvent was evaporated. 150 ml of diethyl ether were added to the residue, washed once with 150 ml water, and the organic layer was dried over magnesium sulfate, filtered, and the solvent evaporated under reduced pressure. The crude product was purified via silica gel chromatography with n-heptane-dichloromethane (6:4) as eluent to give 1.5 g of the title compound.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.2 4-((R)-2-Fluoro-1-methyl-ethyl)-benzenesulfonyl chloride a.2.1 Toluene-4-sulfonic acid (R)-2-phenyl-propyl ester

Following the procedure analogous to that used for the synthesis of toluene-4-sulfonic acid (S)-2-phenyl-propyl ester, but using (R)-2-phenyl-1-propanol, the title compound was prepared a.2.2 ((R)-2-Fluoro-1-methyl-ethyl)-benzene

The title compound was prepared as described above for the synthesis of ((S)-2-fluoro-1-methyl-ethyl)-benzene, but using toluene-4-sulfonic acid (R)-2-phenyl-propyl ester instead of toluene-4-sulfonic acid (S)-2-phenyl-propyl ester.

$^1$H-NMR (CDCl$_3$, 400 MHz): δ [ppm] 7.2-7.4 (m, 5H), 4.3-4.6 (several m, 2H), 3.15 (m, 1H). 1.3 (m, 3H).

a.2.3 4-((R)-2-Fluoro-1-methyl-ethyl)-benzenesulfonyl chloride 1.3 g of ((R)-2-fluoro-1-methyl-ethyl)-benzene (9.4 mmol) were dissolved in 50 ml of dichloromethane. At 0-5° C., 1.1 g of chlorosulfonic acid (9.4 mmol), dissolved in 10 ml of dichloromethane, were added dropwise. The reaction mixture was stirred for 20 min at 0-5° C. and then added to a solution of 2.15 g of phosphorous pentachloride dissolved in 40 ml of dichloromethane. The reaction mixture was stirred for 30 min at 0-5° C. and 1 h at room temperature. The solvent was evaporated, 100 ml of diethyl ether were added, the mixture was washed once with 150 ml of water, and the organic layer dried over magnesium sulfate, filtered, and the solvent evaporated under reduced pressure. The crude product was purified via silica gel chromatography with n-heptane-dichloromethane (1:1) as eluent to give 0.261 g of the title compound.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.3 4-(2-Fluoro-1-methyl-ethyl)-benzenesulfonyl chloride

Following the procedures analogous to that used for the preparation of 4-((S)-2-fluoro-1-methyl-ethyl)-benzenesulfonyl chloride, but starting with 2-phenyl-1-propanol in step a.3.1, the title compound was prepared.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

a.4 4-(2-Fluoro-1-fluoromethyl-ethyl)-benzenesulfonyl chloride a.4.1 (2-Fluoro-1-fluoromethyl-ethyl)-benzene 4 g of 3-phenylglutaric acid (19.21 mmol) were suspended in 350 ml of dichloromethane. At room temperature, 6.5 g of xenon difluoride (38.42 mmol) were added and the reaction mixture was stirred at room temperature for 18 h. The organic phase was washed once with 975 ml of 6% aqueous sodium hydrogencarbonate, dried over magnesium sulfate, filtered, and the solvent evaporated. The remaining residue was distilled at a bath temperature of 123° C. at 21 mm to yield 0.78 g of the title compound that contained ~50% of 4-(2-Fluoro-1-methyl-ethyl)-benzene.

$^1$H-NMR (CDCl$_3$, 400 MHz): δ [ppm] 7.2-7.4 (m, 5H), 4.6-4.8 (dd, 4H), 3.3 (m, 1H).

a.4.2 4-(2-Fluoro-1-fluoromethyl-ethyl)-benzenesulfonyl chloride

Following the procedures analogous to that used for the preparation of 4-((S)-2-fluoro-1-methyl-ethyl)-benzenesulfonyl chloride, but using 5 equivalents. of chlorosulfonic acid, 0.12 g of the title compound were obtained.

$^1$H-NMR (CDCl$_3$, 400 MHz): δ [ppm] 8.05 (d, 2H), 7.55 (d, 2H), 4.75 (dd, 4H), 3.4 (m, 1H).

a.5 4-(3,3,3-Trifluoropropyl)-benzenesulfonyl chloride 2.9 g were obtained from commercially available (3,3,3-trifluoropropyl)-benzene following the procedure used for the synthesis of 4-((S)-2-fluoro-1-methyl-ethyl)benzenesulfonyl chloride described above.

$^1$H-NMR (CDCl$_3$, 400 MHz): δ [ppm] 8.0 (d, 2H), 7.45 (d, 2H), 3.0 (t, 2H), 2.45 (m, 2H).

a.6 4-(2,2,2-Trifluoroethyl)-benzenesulfonyl chloride

The product was obtained from commercially available (2,2,2-trifluoroethyl)-benzene following the procedure as described in J. Org. Chem., 1960, 25, 1824-26.

$^1$H-NMR (CDCl$_3$, 400 MHz): δ [ppm] 8.05 (d, 2H), 7.55 (d, 2H), 3.5 (q, 2H).

a.7 4-(3-Fluoropropyl)-benzenesulfonyl chloride a.7.1 (3-Fluoropropyl)-benzene 15.6 g of diethylaminosulfurtrifluoride (DAST, 96.91 mmol) were dissolved in 18 ml of dichloromethane. At 0-5° C., 12 g of 3-phenyl-1-propanol (88.1 mmol) dissolved in 30 ml of dichloromethane, were added dropwise. The reaction mixture was stirred for 18 h, and, after addition of 30 ml of dichloromethane, poured onto 100 ml of ice water. The organic layer was separated, dried over magnesium sulfate, filtered, and the solvent evaporated. The crude product was purified by distillation at a bath temperature of 106° C. at 20 mm to yield 7.4 g of the title compound.

$^1$H-NMR (CDCl$_3$, 400 MHz): δ [ppm] 7.1-7.3 (m, 5H), 4.4 (dt, 2H), 2.7 (m, 2H). 2.0 (m, 2H).

a.7.2 4-(3-Fluoropropyl)-benzenesulfonyl chloride 4.1 g of (3-fluoro-propyl)-benzene (29.67 mmol) were dissolved in 40 ml of dichloromethane. At 0-5° C., 6.91 g of chlorosulfonic acid (59.34 mmol), dissolved in 10 ml of dichloromethane, were added dropwise. The reaction mixture was stirred for 45 min at 0-5° C. and then added to a solution of 6.8 g of phosphorous pentachloride (32.63 mmol) dissolved in 50 ml of dichloromethane. The reaction mixture was stirred for 1 h rat 5-10° C. The solvent was evaporated, 150 ml of diethyl ether added, washed once with 150 ml of ice water, and the organic layer dried over magnesium sulfate, filtered, and the solvent evaporated under reduced pressure. The crude product was purified via silica gel chromatography with n-heptane-dichloromethane (11:9) as eluent to give 5.5 g of the title compound.

$^1$H-NMR (CDCl$_3$, 400 MHz): δ [ppm] 7.95 (d, 2H), 7.45 (d, 2H), 4.5 (dt, 2H), 2.9 (t, 2H), 2.05 (m, 2H).

a.8 4-(2,2-Difluoro-cyclopropyl)-benzenesulfonyl chloride 2.07 g of were obtained from commercially available (2,2-difluorocyclopropyl)benzene following the procedure used for the synthesis of (3-fluoropropyl)benzenesulfonyl chloride with the exception that only 1.1 equivalents of phosphorous pentachloride were used.

$^1$H-NMR (CDCl$_3$, 400 MHz): δ [ppm] 8.0 (d, 2H), 7.45 (d, 2H), 2.85 (m, 1H), 2.0 (m, 1H), 1.75 (m, 1H).

a.9 3-Bromo-4-trifluoromethoxy-benzenesulfonyl chloride 2.0 g of 1-bromo-2-(trifluoro-methoxy)benzene (8.3 mmol) were dissolved in 30 ml of dichloromethane. At 0-5° C., 1.06 g of chlorosulfonic acid (9.13 mmol), dissolved in 3 ml of dichloromethane, were added dropwise. The reaction mixture was stirred for 30 min at room temperature. Additional 5.5 equivalents of chlorosulfonic in dichloromethane were added to drive the reaction to completion. Standard work-up was followed and silica gel chromatography with n-heptane-dichloromethane (6:4) as eluent gave 2.19 g of the title compound.

$^1$H-NMR (CDCl$_3$, 400 MHz): δ [ppm] 8.3 (d, 1H), 8.05 (dd, 1H), 7.5 (dd, 1H).

a.10 4-(2-Fluoroethyl)-benzenesulfonyl chloride a.10.1 (2-Fluoroethyl)-benzene 6.8 g of the title compound were obtained from commercially available 2-phenylethanol following the procedure used for the synthesis of (3-fluoropropyl)-benzene.

$^1$H-NMR (CDCl$_3$, 400 MHz): δ [ppm] 7.1-7.3 (m, 5H), 4.6 (m, 1H), 4.45 (m, 1H), 2.95 (m, 1H), 2.9 (m, 1H).

a.10.2 4-(2-Fluoroethyl)-benzenesulfonyl chloride 3.55 g were obtained following the procedure used for the synthesis of 4-((R)-2-fluoro-1-methyl-ethyl)-benzenesulfonyl chloride.

$^1$H-NMR (CDCl$_3$, 400 MHz): δ [ppm] 8.0 (d, 2H), 7.5 (d, 2H), 4.7 (dt, 2H), 3.05-3.2 (dt, 2H).

a.11 5-Propylthiophene-2-sulfonyl chloride

Following the procedures analogous to that used for the preparation of (3-fluoropropyl)-benzenesulfonyl chloride, but using only 1 equivalent of phosphorous pentachloride, the title compound was prepared.

$^1$H-NMR (CDCl$_3$, 400-MHz): δ [ppm] 7.7 (d, 1H), 6.85 (d, 1H), 2.9 (t, 2H), 1.75 (m, 2H), 1.0 (t, 3H).

a.12 4-(1-Methyl-1H-pyrazol-4-yl)-benzenesulfonyl chloride a.12.1 1-Methyl-4-phenyl-1H-pyrazole 1 g of 2-phenylmalonaldehyde (6.75 mmol) were dissolved in 25 ml of ethanol. 0.36 ml of N-methyl-hydrazine (6.75 mmol) were added, the reaction mixture was stirred under reflux for 4 h, the solvent evaporated under reduced pressure to yield 1.09 g of the product.

ESI-MS: 159.1 [M+H]+
$^1$H-NMR (CDCl$_3$, 400 MHz): δ [ppm] 7.75 (s, 1H), 7.6 (s, 1H), 7.45 (d, 2H), 7.35 (t, 2H), 7.2 (t, 1H), 3.9 (s, 3H)

a.12.2 4-(1-Methyl-1H-pyrazol-4-yl)-benzenesulfonyl chloride 0.5 g of 1-methyl-4-phenyl-1H-pyrazole (3.16 mmol) were dissolved in 20 ml of dichloromethane. At 0° C., 0.232 ml of chlorosulfonic acid were added and the reaction mixture was stirred for 1 h under ice cooling. Additional 0.7 ml of chlorosulfonic acid were added, the mixture was stirred at 0° C. for 30 minutes and then 90 minutes at 50° C. The two phases were separated and the lower layer put on ice, extracted twice with diethyl ether, dried over magnesium sulfate, filtered, and the solvent evaporated under reduced pressure to yield 0.496 g of the product.

$^1$H-NMR (CDCl$_3$, 400 MHz): δ [ppm] 8.0 (d, 2H), 7.85 (s, 1H), 7.75 (s, 1H), 7.65 (d, 2H), 4.0 (s, 3H).

a.13 4-(1,1,1-Trifluoropropan-2-yl)benzenesulfonyl chloride and 2-(1,1,1-trifluoropropan-2-yl)benzenesulfonyl chloride Prepared on a 14 g scale following the procedure outlined in Scheme 7. 2-(1,1,1-Trifluoropropan-2-yl)benzenesulfonyl chloride is a by-product of the reaction.

4-(1,1,1-Trifluoropropan-2-yl)benzenesulfonyl chloride

MS (ESI) m/z: 273.1 [M+H]$^+$
$^1$H-NMR (DMSO): δ [ppm] 7.62 (d, 2H), 7.33 (d, 2H), 3.81 (m, 1H), 1.42 (d, 3H).

2-(1,1,1-Trifluoropropan-2-yl)benzenesulfonyl chloride

MS (ESI) m/z: 273.1 [M+H]$^+$ a.14 4-(1,1-Difluoropropan-2-yl)benzenesulfonyl chloride and 2-(1,1-Difluoropropan-2-yl)benzene-1-sulfonyl chloride Prepared on an 11 g scale following the procedure outlined in Scheme 6. 2-(1,1-Difluoropropan-2-yl)benzene-1-sulfonyl chloride is a by-product of the reaction.

4-(1,1-Difluoropropan-2-yl)benzenesulfonyl chloride

MS (ESI) m/z: 255.0 [M+H]$^+$
$^1$H-NMR (DMSO): δ [ppm] 8.03 (d, 2H), 7.55 (d, 2H), 5.88 (dt, 1H), 3.34 (m, 1H), 1.47 (d, 3H).

$^{13}$C-NMR (DMSO): δ [ppm] 146.43, 143.54, 129.77, 127.28, 117.06 (t), 43.76, 13.78.

2-(1,1-difluoropropan-2-yl)benzene-1-sulfonyl chloride

Isolated by chromatography on 110 mg scale.
MS (ESI) m/z: 255.0 [M+H]$^+$
$^1$H-NMR (DMSO-d$_6$): δ [ppm] 8.15 (d, 1H), 7.77 (t, 1H), 7.70 (d, 1H), 7.54 (t, 1H), 5.99 (dt, 1H), 4.43 (m, 1H), 1.51 (d, 3H).
$^{13}$C-NMR (DMSO-d$_6$): δ [ppm] 143.45, 138.63, 135.53, 130.93, 129.04, 128.17, 116.61 (t), 38.38, 13.68.

II. Preparation of Compounds I

Example 1

(R)—N-[7-(4-Isopropyl-benzenesulfonylamino)-1,2,3,4-tetrahydro-naphthalen-2-yl]-propionamide 1.1 (R)—N-(1,2,3,4-Tetrahydro-naphthalen-2-yl)-propionamide A solution of (R)-2-aminotetralin hydrochloride (2.50 g, 13.6 mmol) and triethylamine (3.42 g, 33.77 mmol) in tetrahydrofuran (THF) (30 mL) was stirred at −5° C. and propionic anhydride (1.78 g, 13.7 mmol) added dropwise. After the mixture was stirred for 18 h at room temperature, the solvent was removed and ethyl acetate/water were added. The organic layer was washed with citric acid solution (5%) and dried over MgSO$_4$. The filtered solution was concentrated to give a white solid (2.69 g, 97%).
$^1$H-NMR (CDCl$_3$): δ [ppm] 7.12 (m, 4H), 5.49 (br s, 1H), 4.30 (m, 1H), 3.12 (m, 1H), 2.87 (m, 1H), 2.63 (m, 1H), 2.18 (q, 2H), 2.03 (m, 1H), 1.76 (m, 1H), 1.13 (t, 3H).
MS (ESI) m/z: 204.1 [M+H]$^+$ 1.2 (R)—N-(7-Nitro-1,2,3,4-tetrahydro-naphthalen-2-yl)-propionamide and 5-nitro isomer, 6-nitro isomer and 8-nitro isomer N-(1,2,3,4-Tetrahydro-naphthalen-2-yl)-propionamide (3.00 g, 14.8 mmol) was dissolved in nitromethane (45 mL) and cooled to 5° C. A solution of concentrated H$_2$SO$_4$ (14.5 mL), nitric acid (1.05 mL, 65%) and water (2.40 mL) was added dropwise over 30 mins. After stirring for a further 2 hours, the solution was poured into water and and extracted with ethyl acetate. The organic phase was dried over MgSO$_4$, filtered, and the filtrate was evaporated in vacuo to give the product as a yellow oil (3.56 g, 97%).
$^1$H-NMR (CDCl$_3$): δ [ppm] regioisomers (1:1) 9.15 (br s, 1H), 7.92 (m, 3H), 7.70 (d, 1H), 7.20 (m, 3H), 6.15 (br m, 1H), 4.26 (m, 4H), 3.20 (m, 2H), 3.10 (m, 1H), 2.98 (m, 3H), 2.72 (m, 2H), 2.25 (q, 4H), 2.15 (m, 2H), 1.60 (m, 2H), 1.15 (t, 6H).
MS (ESI) m/z: 249.1 [M+H]$^+$ 1.3 (R)—N-(7-Amino-1,2,3,4-tetrahydro-naphthalen-2-yl)-propionamide and 5-amino isomer, 6-amino isomer and 8-amino isomer The mixture of nitro isomers (3.50 g, 14.1 mmol) were dissolved in methanol (MeOH) (100 mL) and Pd—C (0.40 g, 10%) added. The solution was stirred under an H$_2$ atmosphere for 6 h. The solution was filtered and the filtrate concentrated to give an oil which was separated by preparative HPLC (20-95% MeOH) to all 4 amino isomers. The products were obtained as yellow oils: 8-amino isomer (0.05 g, 2%), 7-amino isomer (0.38 g, 12%), 6-amino isomer (0.19 g, 6%) and 5-amino isomer (0.34 g, 10%).

8-Amino isomer

MS (ESI) m/z: 219.1 [M+H]$^+$

7-Amino Isomer

MS (ESI) m/z: 219.1 [M+H]$^+$
$^1$H-NMR (DMSO-d$_6$): δ [ppm] 7.72 (d, NH), 6.71 (d, 2H), 6.35 (d, 1H), 6.25 (s, 1H), 4.72 (s, NH$_2$), 3.84 (m, 1H), 2.75 (m, 1H), 2.62 (m, 2H), 2.48 (m, 1H), 2.05 (q, 2H), 1.85 (m, 1H), 1.51 (m, 1H), 0.98 (t, 3H).

6-Amino Isomer

MS (ESI) m/z: 219.1 [M+H]$^+$
$^1$H-NMR (DMSO-d$_6$): δ [ppm] 7.74 (d, 1H), 6.71 (d, 2H), 6.50 (br s, NH), 6.33 (d, 1H), 6.31 (s, 1H), 3.84 (m, 1H), 2.75 (m, 1H), 2.68 (m, 2H), 2.42 (m, 1H), 2.08 (q, 2H), 1.85 (m, 1H), 1.51 (m, 1H), 0.99 (t, 3H).

5-Amino Isomer

MS (ESI) m/z: 219.1 [M+H]$^+$
$^1$H-NMR (DMSO): δ [ppm] 7.74 (d, NH), 6.79 (t, 1H), 6.44 (d, 1H), 6.26 (d, 1H), 4.71 (s, NH$_2$), 3.84 (m, 1H), 2.81 (m, 1H), 2.52 (m, 2H), 2.36 (m, 1H), 2.07 (q, 2H), 1.94 (m, 1H), 1.59 (m, 1H), 1.00 (t, 3H).

1.4 (R)—N-[7-(4-Isopropyl-benzenesulfonylamino)-1,2,3,4-tetrahydro-naphthalen-2-yl]-propionamide (R)—N-(7-Amino-1,2,3,4-tetrahydro-naphthalen-2-yl)-propionamide (0.34 g, 1.56 mmol) was dissolved in pyridine-dichloromethane (1:2, 30 mL) and cooled to 5° C. 4-Isopropylbenzenesulfonyl chloride (0.37 g, 1.69 mmol) was added and the solution stirred at 5° C. for 3 h. Solution was evaporated, partitioned between ethyl acetate and water, and the organic phase separated and dried over MgSO$_4$. The filtered solution was concentrated to give the product as a yellow oil (0.56 g, 90%).
7-Amino: MS (ESI) m/z: 401.1 [M+H]$^+$ Example 2

(R)-4-Isopropyl-N—((R)-7-propylamino-5,6,7,8-tetrahydro-naphthalen-2-yl)benzenesulfonamide (R)—N-[7-(4-Isopropyl-benzenesulfonylamino)-1,2,3,4-tetrahydro-naphthalen-2-yl]-propionamide (0.56 g, 1.40 mmol) was dissolved in 15 mL of tetrahydrofuran (THF) and 7.5 mL (78.4 mmol) of a borane-THF complex was introduced dropwise over 15 min. The resulting mixture was stirred at reflux for 1 h. The solution was cooled, 5 mL of 2 N HCl was added slowly, and the mixture was stirred at 40° C. for 2 h. The cooled solution was quenched with water, then NaOH (2N) and extracted with ethyl acetate. The organic phase was dried over MgSO$_4$, filtered, and the filtrate was evaporated in vacuo to give product as a white solid which was further purified recrystallization from MeOH— isopropanol to give a white solid (100 mg, 18%).
MS (ESI) m/z: 387.2 [M+H]$^+$
$^1$H-NMR (DMSO-d$_6$): δ [ppm] 14.3 (br s, 1H), 12.0 (br s, 1H), 7.68 (d, 2H), 7.43 (d, 2H), 6.88 (m, 2H), 6.76 (s, 1H), 2.82 (m, 2H), 2.65 (m, 1H), 2.52 (m, 3H), 2.36 (m, 1H), 1.88 (m, 1H), 1.40 (m, 3H), 1.15 (d, 6H), 0.84 (t, 3H).

$^{13}$C-NMR (DMSO): δ [ppm] 153.4 (s), 137.4 (s), 136.0 (s), 135.3 (s), 131.8 (s), 129.0 (d), 127.1 (d), 126.7 (d), 120.4 (d), 117.5 (d), 52.7 (d), 48.2 (t), 35.7 (t), 33.2 (d), 28.5 (t), 26.5 (t), 23.3 (q), 22.6 (t), 11.8 (q).

Example 3

4-Isopropyl-N—((R)-6-propylamino-5,6,7,8-tetrahydro-naphthalen-2-yl)-benzenesulfonamide N-[6-(4-Isopropyl-benzenesulfonylamino)-1,2,3,4-tetrahydro-naphthalen-2-yl]-propionamide (0.19 g, 0.47 mmol) was dissolved in 10 mL of tetrahydrofuran (THF) and 3 mL (31.3 mmol) of a borane-THF complex was introduced dropwise over 20 min. The resulting mixture was stirred at reflux for 3 h. The solution was cooled, 3 mL of 2 N HCl was added slowly, and the mixture was stirred at 40° C. for 1 h. The cooled solution was quenched with water, then NaOH (2N) and extracted with ethyl acetate. The organic phase was dried over MgSO$_4$, filtered, and the filtrate was evaporated in vacuo to give the product as a colorless oil (100 mg, 55%).

MS (ESI) m/z: 387.1 [M+H]$^+$ $^1$H-NMR (DMSO-d$_6$): δ [ppm] 7.68 (d, J 8.4, 2H), 7.39 (d, J 8.4, 2H), 6.90-6.75 (m, 3H), 2.92 (m, 2H), 2.69 (m, 1H), 2.52 (m, 3H), 2.38 (m, 1H), 1.88 (m, 1H), 1.40 (m, 3H), 1.15 (d, 6H), 0.84 (t, 3H).

Example 4

(R)—N-[5-(4-Isopropyl-benzenesulfonylamino)-1,2,3,4-tetrahydro-naphthalen-2-yl]-propionamide The 5-amine isomer (0.26 g, 1.19 mmol) from 1.3 was dissolved in pyridinedichloromethane (1:2, 30 mL) and cooled to 5° C. 4-Isopropylbenzenesulfonyl chloride (0.29 g, 1.31 mmol) was added and the solution stirred at 5° C. for 3 h. Solution was evaporated, partitioned between ethyl acetate and water, and the organic phase separated and dried over MgSO$_4$. The filtered solution was concentrated to give the product as a yellow oil (0.61 g, 100%).

MS (ESI) m/z: 401.1 [M+H]$^+$

Example 5

(R)-4-Isopropyl-N-(6-propylamino-5,6,7,8-tetrahydro-naphthalen-1-yl)-benzenesulfonamide (R)—N-[5-(4-Isopropyl-benzenesulfonylamino)-1,2,3,4-tetrahydro-naphthalen-2-yl]-propionamide (0.48 g, 1.20 mmol) was dissolved in 10 mL of THF and 5 mL (8.36 mmol) of a borane-THF complex was introduced dropwise over 20 min. The resulting mixture was stirred at reflux for 3 h. The solution was cooled, 5 mL of 2 N HCl was added slowly, and the mixture was stirred at 40° C. for 1 h. The cooled solution was quenched with water, then NaOH (2N) and extracted with ethyl acetate. The organic phase was dried over MgSO$_4$, filtered, and the filtrate was evaporated in vacuo to give the product as a colorless oil (130 mg, 28%).

MS (ESI) m/z: 387.4 [M+H]$^+$ $^1$H-NMR (DMSO-d$_6$): δ [ppm] 7.56 (d, J 8.4, 2H), 7.39 (d, J 8.4, 2H), 6.98 (m, 1H), 6.83 (m, 2H), 2.83 (m, 1H), 2.70-2.52 (m, 3H), 2.37 (m, 1H), 2.15 (m, 1H), 1.75 (m, 1H), 1.40 (m, 2H), 1.15 (d, 6H), 0.82 (t, 3H).

$^{13}$C-NMR (DMSO-d$_6$): δ [ppm] 153.1 (s), 138.7 (s), 136.6 (s), 135.2 (s), 132.4 (s), 126.8 (d), 126.5 (d), 125.5 (d), 123.2 (d), 52.4 (d), 48.3 (t), 35.2 (t), 33.3 (d), 28.3 (t), 23.5 (q), 23.0 (t), 22.8 (t), 11.8 (q).

Example 6

N—((R)-6-Allylamino-5,6,7,8-tetrahydro-naphthalen-2-yl)-4-isopropyl-benzenesulfonamide, hydrochloride 6.1 ((R)-6-Bromo-1,2,3,4-tetrahydro-naphthalen-2-yl)-carbamic acid tert-butyl ester (R)-6-Bromo-1,2,3,4-tetrahydro-naphthalen-2-ylamine hydrochloride (5.25 g, 20 mmol) was dissolved in dichloromethane (100 ml). Subsequently, triethylamine (11.14 ml, 80 mmol) and di-tert-butyldicarbonate (5.45 g, 25 mmol) were added and the reaction mixture was stirred at room temperature overnight. The reaction mixture was extracted with aqueous NaHCO$_3$ solution. The organic layer was dried over magnesium sulfate, filtered, and evaporated to dryness to yield the desired crystalline product (6.4 g, 98%).

6.2 Allyl-((R)-6-Bromo-1,2,3,4-tetrahydro-naphthalen-2-yl)-carbamic acid tert-butyl ester ((R)-6-Bromo-1,2,3,4-tetrahydro-naphthalen-2-yl)-carbamic acid tert-butyl ester (3.26 g, 10 mmol) was dissolved in dimethylformamide (30 ml). Sodium hydride (50% in oil) (528 mg, 11 mmol) was added and stirred for 15 minutes at room temperature. Allyl bromide (0.95 ml, 11 mmol) was added and the reaction mixture was stirred at room temperature overnight. To the reaction mixture was added H$_2$O (400 ml) and extracted twice with 150 ml diethylether. The organic layer was dried over magnesium sulfate, filtered, and evaporated to dryness to yield the crude product (3.25 g). The crude product was purified with silica gel chromatography with cyclohexane/ethyl acetate (9:1) as eluent, yielding the purified product (2.7 g, 66%).

6.3 Allyl-[(R)-6-(4-isopropyl-benzenesulfonylamino)-1,2,3,4-tetrahydro-naphthalen-2-yl]-carbamic acid tert-butyl ester In an inert atmosphere (argon), allyl-((R)-6-bromo-1,2,3,4-tetrahydro-naphthalen-2-yl)-carbamic acid tert-butyl ester (2.04 g, 5.5 mmol) was dissolved in trifluortoluol (10 ml) at room temperature. Tris(dibenzylideneacetone)dipalladium (230 mg, 0.25 mmol) and tri-tert-butyl-phosphane (152 mg, 0.75 mmol) were added to the reaction mixture. In a separate flask, 4-isopropyl-benzenesulfonamide (996 mg, 5 mmol) was dissolved in trifluortoluol (20 ml) at 65° C. Sodium hydride (50% in oil) (240 mg, 5 mmol) was added, stirred for 5 minutes and added to the reaction mixture. The reaction mixture was dispensed into 5 vials and stirred for 1 hour at 160° C. in the microwave (CEM). The combined reaction mixture was evaporated to dryness. H$_2$0 (50 ml) was added and extracted three times with 50 ml diethylether. The organic layer was dried over magnesium sulfate, filtered, and evaporated to dryness to yield 2.8 g of crude product. The crude product was purified with silica gel chromatography with cyclohexane/ethyl acetate (85:15) as eluent, yielding the purified product (1.13 g, 45

6.4 N—((R)-6-Allylamino-5,6,7,8-tetrahydro-naphthalen-2-yl)-4-isopropylbenzenesulfonamide, hydrochloride Allyl-[(R)-6-(4-isopropyl-benzenesulfonylamino)-1,2,3,4-tetrahydro-naphthalen-2-yl]-carbamic acid tert-butyl ester (2.04 g, 5.5 mmol) was dissolved in dichloromethane (50 ml). Trifluoroacetic acid (2 ml) was added and the reaction mixture was stirred at room temperature for 3 hours. The reaction mixture was evaporated to dryness. Ethyl acetate (100 ml) was added and extracted with NaOH (2M). The organic layer was dried over magnesium sulfate, filtered, and evaporated to dryness to yield 790 mg of crude product. The crude product was purified with silica gel chromatography with ethyl acetate/methanol (90:10) as eluent, yielding the purified product (300 mg, 30% yield).

50 mg were dissolved in diethyl ether and dichloromethane. A solution of 1 N HCl in diethyl ether was added, and after formation of a precipitate, the suspension evaporated under reduced pressure to yield 36 mg of a white precipitate.

ESI-MS: 385.1 [M+H]$^+$ $^1$H-NMR (DMSO-$d_6$): δ [ppm] 10.2 (s, 1H), 9.2 (bs, 2H), 7.7 (d, 2H), 7.4 (d, 2H), 7.0 (d, 1H), 6.9 (d, 1H), 6.8 (s, 1H), 6.0 (m, 1H), 5.5 (d, 1H), 5.4 (d, 1H), 3.7 (d, 2H), 3.3 (bs, 1H), 3.1 (dd, 1H), 2.9 (m, 1H), 2.7 (m, 3H), 2.2 (m, 1H), 1.7 (m, 1H), 1.2 (d, 6H).

Example 7

N—((S)-6-Allylamino-5,6,7,8-tetrahydro-naphthalen-2-yl)-4-isopropyl-benzenesulfonamide, hydrochloride

7.1 ((S)-6-Bromo-1,2,3,4-tetrahydro-naphthalen-2-yl)-carbamic acid tert-butyl ester (S)-6-Bromo-1,2,3,4-tetrahydro-naphthalen-2-ylamine hydrochloride (3.94 g, 15 mmol) was dissolved in dichloromethane (75 ml). Subsequently, triethylamine (8.32 ml, 60 mmol) and di-tert-butyldicarbonate (4.09 g, 18.75 mmol) were added and the reaction mixture was stirred at room temperature overnight. The reaction mixture was extracted with aqueous NaHCO$_3$ solution. The organic layer was dried over magnesium sulfate, filtered, and evaporated to dryness to yield the desired crystalline product (4.85 g, 99%).

7.2 Allyl-((S)-6-Bromo-1,2,3,4-tetrahydro-naphthalen-2-yl)-carbamic acid tert-butyl ester ((S)-6-Bromo-1,2,3,4-tetrahydro-naphthalen-2-yl)-carbamic acid tert-butyl ester (4.85 g, 14.87 mmol) was dissolved in dimethylformamide (40 ml). Sodium hydride (50% in oil) (785 mg, 16.35 mmol) was added and stirred for 15 minutes at room temperature. Allyl bromide (1.41 ml, 16.35 mmol) was added and the reaction mixture was stirred at room temperature overnight. To the reaction mixture was added H$_2$0 (500 ml) and extracted three times with 100 ml diethylether. The organic layer was dried over magnesium sulfate, filtered, and evaporated to dryness to yield 5.5 g of crude product. The crude product was purified with silica gel chromatography with cyclohexane/ethyl acetate (95:5) as eluent, yielding the purified product (3.9 g, 68%).

7.3 Allyl-[(S)-6-(4-isopropyl-benzenesulfonylamino)-1,2,3,4-tetrahydro-naphthalen-2-yl]-carbamic acid tert-butyl ester In an inert atmosphere (argon), allyl-((S)-6-bromo-1,2,3,4-tetrahydro-naphthalen-2-yl)-carbamic acid tert-butyl ester (1.94 g, 5.3 mmol) was dissolved in trifluortoluol (10 ml) at room temperature. Tris(dibenzylideneacetone)dipalladium (230 mg, 0.25 mmol) and tri-tert-butyl-phosphane (152 mg, 0.75 mmol) were added to the reaction mixture. In a separate flask, 4-Isopropyl-benzenesulfonamide (996 mg, 5 mmol) was dissolved in trifluortoluol (20 ml) at 65° C. Sodium hydride (50% in oil) (240 mg, 5 mmol) was added, stirred for 5 minutes and added to the reaction mixture. The reaction mixture was dispensed into 8 vials and stirred for 1 hour at 150° C. in the microwave (CEM). The combined reaction mixture was evaporated to dryness. H$_2$0 (50 ml) was added and extracted three times with 50 ml diethylether. The organic layer was dried over magnesium sulfate, filtered, and evaporated to dryness to yield 4.3 g of crude product. The crude product was purified with silica gel chromatography with cyclohexane/ethyl acetate (85:15) as eluent, yielding the product (1.5 g, 50% purity, 31% yield).

7.4 N—((S)-6-Allylamino-5,6,7,8-tetrahydro-naphthalen-2-yl)-4-isopropylbenzenesulfonamide, hydrochloride Allyl-[(R)-6-(4-isopropyl-benzenesulfonylamino)-1,2,3,4-tetrahydro-naphthalen-2-yl]-carbamic acid tert-butyl ester (1.5 g, 1.5 mmol) was dissolved in dichloromethane (50 ml). Trifluoroacetic acid (2 ml) was added and the reaction mixture was stirred at room temperature for 3 hours. The reaction mixture was evaporated to dryness. Ethyl acetate (100 ml) was added and extracted with NaOH (2M). The organic layer was dried over magnesium sulfate, filtered, and evaporated to dryness to yield 1.05 g of crude product. The crude product was purified with silica gel chromatography with ethyl acetate/methanol (90:10) as eluent, yielding the purified product (290 mg, 34% yield).

50 mg were dissolved in diethyl ether and dichloromethane. A solution of 1 N HCl in diethyl ether was added, and after formation of a precipitate, the suspension evaporated under reduced pressure to yield 36 mg of a white precipitate.

ESI-MS: 385.1 [M+H]$^+$ $^1$H-NMR (DMSO-$d_6$): δ [ppm] 10.2 (s, 1H), 9.2 (bs, 2H), 7.7 (d, 2H), 7.4 (d, 2H), 7.0 (d, 1H), 6.9 (d, 1H), 6.8 (s, 1H), 6.0 (m, 1H), 5.5 (d, 1H), 5.4 (d, 1H), 3.7 (d, 2H), 3.1 (dd, 1H), 2.9 (m, 1H), 2.7 (m, 3H), 2.5 (m, 1H), 2.2 (m, 1H), 1.7 (m, 1H), 1.2 (d, 6H).

Example 8

4-Isopropyl-N—((S)-6-propylamino-5,6,7,8-tetrahydro-naphthalen-2-yl)-benzenesulfonamide, hydrochloride A mixture of N—((S)-6-Allylamino-5,6,7,8-tetrahydro-naphthalen-2-yl)-4-isopropylbenzenesulfonamide (240 mg, 0.48 mmol) and 10% palladium on carbon (25 mg) in ethyl acetate (25 ml) was hydrogenated overnight. The catalyst was filtered, and the solvent was removed under vacuum to yield an oil (190 mg). The residue was dissolved in H$_2$O (20 ml) and HCl (1N, 1 ml) and extracted twice with ethyl ether (20 ml). The aqueous phase was made alkaline and extracted with ethyl acetate. The organic phase was separated, dried over magnesium sulfate, filtered, and evaporated to dryness to yield a foam (120 mg, 58%). 50 mg of this foam were dissolved in distilled H$_2$O (30 ml) and a few drops of concentrated HCl were added. This solution was lyophilised to yield the desired product.

ESI-MS: 387.4 [M+H]$^+$
$^1$H-NMR (DMSO-d$_6$): δ [ppm] 10.2 (s, 1H), 8.9 (m, 2H), 7.7 (d, 2H), 7.4 (d, 2H), 7.0 (d, 1H), 6.9 (d, 1H), 6.8 (s, 1H), 3.1 (dd, 1H), 3.0 (m, 3H), 2.8 (m, 3H), 2.5 (m, 1H), 2.2 (m, 1H), 1.7 (m, 3H), 1.2 (d, 6H), 0.9 (t, 3H).

Example 9

N—((S)-6-Allylamino-5,6,7,8-tetrahydro-naphthalen-2-yl)-4-isopropyl-N-methylbenzenesulfonamide 9.1 Allyl-{(S)-6-[(4-isopropyl-benzenesulfonyl)-methyl-amino]-1,2,3,4-tetrahydronaphthalen-2-yl}-carbamic acid tert-butyl ester In an inert atmosphere (argon), allyl-((S)-6-bromo-1,2,3,4-tetrahydro-naphthalen-2-yl)-carbamic acid tert-butyl ester (749 mg, 2.0 mmol) was dissolved in trifluortoluol (20 ml) at room temperature. Tris(dibenzylideneacetone)dipalladium (92 mg, 0.1 mmol) and tri-tert-butyl-phosphane (61 mg, 0.3 mmol) were added to the reaction mixture. In a separate flask, 4-Isopropyl-N-methyl-benzenesulfonamide (427 mg, 2 mmol) was dissolved in trifluortoluol (20 ml) at 65° C. Sodium hydride (50% in oil) (96 mg, 2 mmol) was added, stirred for 5 minutes and added to the reaction mixture. The reaction mixture was dispensed into 3 vials and stirred for 1 hour at 150° C. in the microwave (CEM). The combined reaction mixture was evaporated to dryness. H$_2$0 (50 ml) was added and extracted three times with 50 ml diethylether. The organic layer was dried over magnesium sulfate, filtered, and evaporated to dryness to yield crude product (1.12 g, 68%).

9.2 N—((S)-6-Allylamino-5,6,7,8-tetrahydro-naphthalen-2-yl)-4-isopropyl-N-methylbenzenesulfonamide Allyl-{(S)-6-[(4-isopropyl-benzenesulfonyl)-methyl-amino]-1,2,3,4-tetrahydronaphthalen-2-yl}-carbamic acid tert-butyl ester (672 mg, 1.35 mmol) was dissolved in dichloromethane (30 ml). Trifluoroacetic acid (1 ml) was added and the reaction mixture was stirred at room temperature overnight. The reaction mixture was evaporated to dryness. Ethyl acetate (100 ml) was added and extracted with NaOH (2M). The organic layer was dried over magnesium sulfate, filtered, and evaporated to dryness to yield 1.05 g of crude product. The crude product was dissolved in ethyl acetate (20 ml) and the precipitate was collected to yield the desired compound (270 mg, 50%). The mother liquid was reduced in vacuo to yield an oil (840 mg, 54% purity).
ESI-MS: 399.1 [M+H]$^+$
$^1$H-NMR (CDCl$_3$): δ [ppm] 9.8 (bs, 2H), 7.5 (d, 2H), 7.3 (d, 2H), 7.0 (d, 1H), 6.9 (s, 1H), 6.8 (dd, 1H), 6.0 (m, 1H), 5.5 (m, 2H), 3.7 (m, 2H), 3.4 (m, 1H), 3.2 (dd, 1H), 3.1 (s, 3H), 3.0-2.8 (m, 4H), 2.3 (m, 1H), 1.9 (m, 1H), 1.3 (d, 6H).

Example 10

4-Isopropyl-N-methyl-N—((S)-6-propylamino-5,6,7,8-tetrahydro-naphthalen-2-yl)benzenesulfonamide A mixture of N—((S)-6-Allylamino-5,6,7,8-tetrahydro-naphthalen-2-yl)-4-isopropyl-N-methyl-benzenesulfonamide (840 mg, 54% purity, 1.13 mmol) and 10% palladium on carbon (50 mg) in ethyl acetate (25 ml) was hydrogenated overnight. The catalyst was filtered, and the solvent was removed under vacuum to yield an oil (720 mg). The crude product was dissolved in ethyl acetate (20 ml) and the precipitate was collected to yield the desired compound (100 mg, 22%).
ESI-MS: 401.2 [M+H]$^+$
$^1$H-NMR (CDCl$_3$): δ [ppm] 9.5 (bs, 2H), 7.5 (d, 2H), 7.3 (d, 2H), 7.0 (d, 1H), 6.9 (s, 1H), 6.8 (d, 1H), 3.4 (m, 1H), 3.2 (dd, 1H), 3.1 (s 3H), 3.0-2.8 (m, 6H), 2.3 (m, 1H), 1.9 (m, 1H), 1.8 (m, 2H), 1.3 (d, 6H), 1.0 (t, 3H).

Example 11

Reference

N-[3-(4-Trifluoromethoxy-benzenesulfonylamino)-5,6,7,8-tetrahydro-quinolin-7-yl]-propionamide and its 5-regioisomer 11.1 (3-Oxo-cyclohexyl)-carbamic acid benzyl ester Bismuth nitrate pentahydrate (1.02 g, 2.10 mmol) was added to a mixture of benzylcarbamate (3.2 g, 21.16 mmol) and cyclohex-2-enone (2 ml, 20.59 mmol) in CH$_2$Cl$_2$ (2 ml) and the resulting syrup was vigorously stirred at room temperature overnight. CH$_2$Cl$_2$ (20 ml) was then added to the mix and it was filtered through a pad of celite. The filtrate was washed with saturated aqueous NaHCO$_3$, the organic layer was dried over Na$_2$SO$_4$ and evaporated. Purification of the crude product by flash column chromatography (heptane:ethyl acetate, 3:1) provides the title compound (4.81 g, 94%) as a pale yellow gum.
MS (ESI+) m/z=248.3 [M+H]$^+$
$^1$H NMR (400 MHz, CDCl$_3$): δ (ppm) 1.71 (m, 2H), 1.97 (m, 1H), 2.10 (m, 1H), 2.27 (m, 2H), 2.37 (m, 1H), 2.71 (dd, J=14.0, 4.4 Hz, 1H), 3.99 (bs, 1H), 4.77 (bs, 1H), 5.09 (s, 2H), 7.35 (m, 5H).

11.2 (3-Nitro-5,6,7,8-tetrahydro-quinolin-5 and 7-yl)-carbamic acid benzyl ester A mixture of 1-methyl-3,5-dinitro-2-pyridone (3.66 g, 18.38 mmol) and (3-oxocyclohexyl)-carbamic acid benzyl ester (4.55 g, 18.39 mmol) in methanolic ammonia (1 M, 140 ml) was heated at 65° C. for 1.5 h. It was then concentrated and digested in CH$_2$Cl$_2$. The organic layer was washed with H$_2$O (×2), dried (Na$_2$SO$_4$) and evaporated. The residue was chromatographed on silica gel (heptane:ethyl acetate, 3:1) to afford a mixture ½ of the 5 and 7 regioisomers (4.51 g, 75% for two steps) as a pale yellow gum.
MS (ESI+) m/z=328.1 [M+H]$^+$
$^1$H NMR (400 MHz, CDCl$_3$): δ (ppm) 1.83 (m, 1.5H), 2.01 (m, 1H), 2.20 (m, 1.5H), 2.90 (dd, J=18.1, 8.7 Hz, 1H), 3.00 (t, J=6.4 Hz, 2H), 3.05 (t, J=6.4 Hz, 1H), 3.43 (dd, J=18.1, 5.2 Hz, 1H), 4.16 (m, 1H), 4.81 (bs, 1H), 5.03 (bs, 1H), 5.12 (s, 2H), 5.19 (s, 1H), 7.36 (m, 7.5H), 8.19 (bs, 1H), 8.46 (bs, 0.5H), 9.20 (d, J=1.9 Hz, 1H), 9.23 (d, J=2.1 Hz, 0.5H).

11.3 [3-(4-Trifluoromethoxy-benzenesulfonylamino)-5,6,7,8-tetrahydro-quinolin-5 and 7-yl]-carbamic acid benzyl ester (3-Nitro-5,6,7,8-tetrahydro-quinolin-5 and 7-yl)-carbamic acid benzyl ester (1 g, 3.05 mmol) was dissolved in EtOH (25 ml) and SnCl$_2$.2H$_2$O (3.44 g, 15.24 mmol) was added. The resulting mixture was refluxed for 14 h and the solvent next removed under vacuum. The raw material was dissolved in ethyl acetate and washed successively with 2N aqueous NaOH (×2) and water. The organic layer was dried (Na₂SO₄), filtered through a pad of celite and evaporated. The crude material was then dissolved in CH₂Cl₂ (60 ml) and pyridine (370 µl, 4.53 mmol) followed by 4-(trifluoromethoxy)benzenesulfonyl chloride (620 µl, 3.65 mmol) were added dropwise. After stirring at room temperature overnight, the reaction mixture was diluted with CH₂Cl₂ and washed successively with 1N aqueous HCl, saturated aqueous NaHCO₃ and water. The organic layer was dried (Na₂SO₄) and evaporated. The residue was chromatographed on silica gel (heptane:ethyl acetate, 1:1) to afford a mixture ½ of the 5 and 7 regioisomers (1.32 g, 83% for two steps) as a light yellow gum.

MS (ESI+) m/z=522.2 [M+H]$^+$ $^1$H NMR (400 MHz, CDCl₃): δ (ppm) 1.74 (m, 1.5H), 1.89 (m, 1H), 2.08 (m, 1.5H), 2.72 (dd, J=17.2, 8.6 Hz, 1H), 2.82 (m, 3H), 3.21 (dd, J=17.2, 5.0 Hz, 1H), 4.06 (m, 1H), 4.86 (d, J=7.2 Hz, 1.5H), 5.10 (m, 3.5H), 7.23 (d, J=8.5 Hz, 1H), 7.27 (d, J=8.5 Hz, 2H), 7.34 (m, 8.5H), 7.47 (s, 0.5H), 7.81 (d, J=8.6 Hz, 3H), 7.99 (s, 1H), 8.15 (s, 0.5H).

11.4 N-[3-(4-Trifluoromethoxy-benzenesulfonylamino)-5,6,7,8-tetrahydro-quinolin-7-yl]-propionamide and its 5-regioisomer 10% Pd/C (150 mg) was suspended in a solution of [3-(4-trifluoromethoxybenzenesulfonylamino)-5,6,7,8-tetrahydro-quinolin-5 and 7-yl]-carbamic acid benzyl ester (558 mg, 1.07 mmol) in MeOH (25 ml) and the resulting mixture stirred under H₂ (1 atm) at room temperature for 3 h. It was then filtered through celite and concentrated in vacuo to yield the free base. The latter was next dissolved in THF (20 ml) and the solution cooled to 0° C. Propionyl chloride (94 µl, 1.07 mmol) and triethylamine (150 µl, 1.07 mmol) were next added, the mixture allowed to reach 20° C. and stirred for a further 2 h. It was then diluted with CH₂Cl₂ and washed successively with 1N aqueous HCl, saturated aqueous NaHCO₃ and water. The organic layer was dried (Na₂SO₄) and evaporated. The residue was chromatographed on silica gel (heptane:ethyl acetate, 1:4) to afford the title compound (268 mg, 56% for two steps) as a white solid and its 5-regioisomer (130 mg, 27% for two steps) as a gum.

N-[3-(4-Trifluoromethoxy-benzenesulfonylamino)-5,6,7,8-tetrahydro-quinolin-7-yl]-propionamide MS (ESI+) m/z=444.0 [M+H]$^+$ $^1$H NMR (400 MHz, CDCl₃): δ (ppm) 1.17 (t, J=7.6 Hz, 3H), 1.71 (m, 1H), 2.08 (m, 1H), 2.23 (q, J=7.6 Hz, 2H), 2.68 (dd, J=17.1, 9.2 Hz, 1H), 2.82 (m, 2H), 3.18 (dd, J=17.2, 5.2 Hz, 1H), 4.28 (m, 1H), 5.51 (d, J=7.6 Hz, 1H), 7.29 (d, J=8.3 Hz, 2H), 7.34 (d, J=1.7 Hz, 1H), 7.82 (d, J=8.8 Hz, 2H), 8.02 (d, J=2.0 Hz, 1H).

N-[3-(4-Trifluoromethoxy-benzenesulfonylamino)-5,6,7,8-tetrahydro-quinolin-5-yl]-propionamide MS (ESI+) m/z=444.0 [M+H]$^+$ $^1$H NMR (400 MHz, CDCl₃): δ (ppm) 1.19 (t, J=7.6 Hz, 3H), 1.70 (m, 2H), 1.92 (m, 2H), 2.07 (m, 1H), 2.25 (m, 2H), 2.88 (m, 2H), 5.16 (dd, J=14.0, 8.2 Hz, 1H), 5.69 (d, J=8.7 Hz, 1H), 7.29 (d, J=8.4 Hz, 2H), 7.41 (bs, 1H), 7.85 (d, J=8.8 Hz, 2H), 8.18 (d, J=1.8 Hz, 1H).

Example 12

Reference

N-(7-Propylamino-5,6,7,8-tetrahydro-quinolin-3-yl)-4-trifluoromethoxy-benzenesulfonamide To a solution of N-[3-(4-trifluoromethoxy-benzenesulfonylamino)-5,6,7,8-tetrahydroquinolin-7-yl]-propionamide (260 mg, 0.58 mmol) in THF (10 ml) was added dropwise 1M BH₃.THF (5.8 ml) and the mixture was stirred at room temperature for 6 h. It was then quenched by careful addition of 1N aqueous HCl (10 ml) and the resulting solution was heated at reflux for 4 h. The solution was next cooled to room temperature, adjusted to pH~8 with 2 N NaOH solution and diluted with CH₂Cl₂. Separation of the layers, drying (Na₂SO₄) of the organic phase and evaporation in vacuo provided the crude material, which was purified by flash column chromatography (CH₂Cl₂:MeOH, 95:5) to give the title compound (160 mg, 64%) as a white solid.

MS (ESI+) m/z=430.1 [M+H]$^+$ $^1$H NMR (400 MHz, CDCl₃): δ (ppm) 0.93 (t, J=7.4 Hz, 3H), 1.53 (m, 2H), 1.65 (m, 1H), 2.04 (m, 1H), 2.69 (m, 4H), 2.84 (m, 1H), 3.10 (m, 2H), 3.67 (bs, 2H), 7.27 (m, 3H), 7.81 (d, J=8.6 Hz, 2H), 7.95 (bs, 1H).

Example 13

Reference

N-(5-Propylamino-5,6,7,8-tetrahydro-quinolin-3-yl)-4-trifluoromethoxy-benzenesulfonamide Following the same procedure as described previously, N-[3-(4-trifluoromethoxy-benzenesulfonylamino)-5,6,7,8-tetrahydro-quinolin-5-yl]-propionamide (120 mg, 0.27 mmol) in THF (10 ml) was treated with 1M BH₃.THF (2.7 ml). Purification of the crude product by flash column chromatography (heptane:ethyl acetate, 1:2) provides the title compound (66 mg, 57%) as a white solid.

MS (ESI+) m/z=430.1 [M+H]$^+$ $^1$H NMR (400 MHz, (CD₃)₂SO): δ (ppm) 0.85 (t, J=7.4 Hz, 3H), 1.40 (m, 3H), 1.67 (m, 2H), 2.86 (m, 2H), 2.43 (m, 2H), 2.68 (m, 2H), 3.68 (bs, 1H), 7.46 (d, J=2.0 Hz, 1H), 7.53 (d, J=8.4 Hz, 2H), 7.85 (d, J=8.8 Hz, 2H), 8.04 (d, J=2.3 Hz, 1H).

Example 14

N-[3-(4-Isopropyl-benzenesulfonylamino)-5,6,7,8-tetrahydro-quinolin-7-yl]-propionamide and N-[3-(4-Isopropyl-benzenesulfonylamino)-5,6,7,8-tetrahydro-quinolin-5-yl]-propionamide

Reference

14.1 [3-(4-Isopropyl-benzenesulfonylamino)-5,6,7,8-tetrahydro-quinolin-5 and 7-yl]-carbamic acid benzyl ester and its 5-regioisomer Following the same procedure as described in example 11.3, (3-nitro-5,6,7,8-tetrahydro-quinolin-5 and 7-yl)-carbamic acid benzyl ester (1 g, 3.05 mmol) in EtOH (25 ml) was treated with SnCl₂.2H₂O (3.44 g, 15.24 mmol). The resulting amine in CH₂Cl₂ (50 ml) was then treated with pyridine (500 µl, 6.13 mmol) and 4-isopropylbenzenesulfonylchloride (655 µl, 3.65 mmol). Purification of the crude product by flash column chromatography (heptane:ethyl acetate, 1:1) provides a mixture ½ of the 5 and 7 regioisomers (872 mg, 60% for two steps) as a light yellow gum.

MS (ESI+) m/z=480.1 [M+H]$^+$.

14.2 N-[3-(4-Isopropyl-benzenesulfonylamino)-5,6,7,8-tetrahydro-quinolin-7-yl]-propionamide and N-[3-(4-Isopropyl-benzenesulfonylamino)-5,6,7,8-tetrahydroquinolin-5-yl]-propionamide Following the same procedure as described previously, [3-(4-isopropylbenzenesulfonylamino)-5,6,7,8-tetrahydro-quinolin-5 and 7-yl]-carbamic acid benzyl ester (412 mg, 0.86 mmol) in MeOH (18 ml) was hydrogenated in the presence of 10% Pd/C (100 mg) under $H_2$ (1 atm). The resulting amine in THF (15 ml) was next treated with propionyl chloride (75 μl, 0.86 mmol) and triethylamine (120 μl, 0.86 mmol). Purification of the crude product by flash column chromatography (heptane:ethyl acetate, 1:9) provides the title compound (290 mg, 58% for two steps) as a white solid and its 5-regioisomer (136 mg, 27% for two steps) as a white solid.

N-[3-(4-Isopropyl-benzenesulfonylamino)-5,6,7,8-tetrahydro-quinolin-7-yl]-propionamide MS (ESI+) m/z=402.1 [M+H]$^+$ $^1$H NMR (400 MHz, CDCl$_3$): δ (ppm) 1.16 (t, J=7.6 Hz, 3H), 1.24 (d, J=6.9 Hz, 6H), 1.72 (m, 1H), 2.07 (m, 1H), 2.21 (q, J=7.6 Hz, 2H), 2.68 (dd, J=17.1, 8.9 Hz, 1H), 2.81 (m, 2H), 2.95 (m, 1H), 3.17 (dd, J=17.1, 5.2 Hz, 1H), 4.30 (m, 1H), 5.53 (d, J=7.6 Hz, 1H), 7.31 (d, J=8.3 Hz, 2H), 7.35 (d, J=1.9 Hz, 1H), 7.68 (d, J=8.4 Hz, 2H), 7.99 (d, J=2.1 Hz, 1H).

N-[3-(4-Isopropyl-benzenesulfonylamino)-5,6,7,8-tetrahydro-quinolin-5-yl]-propionamide MS (ESI+) m/z=402.1 [M+H]$^+$ $^1$H NMR (400 MHz, CDCl$_3$): δ (ppm) 1.19 (t, J=7.6 Hz, 3H), 1.24 (d, J=7.0 Hz, 6H), 1.70 (m, 2H), 1.91 (m, 2H), 2.06 (m, 1H), 2.26 (q, J=7.6 Hz, 2H), 2.86 (m, 2H), 2.94 (m, 1H), 5.16 (dd, J=13.8, 8.2 Hz, 1H), 5.75 (d, J=8.7 Hz, 1H), 7.31 (d, J=8.3 Hz, 2H), 7.41 (d, J=2.1 Hz, 1H), 7.71 (d, J=8.4 Hz, 2H), 8.14 (d, J=2.3 Hz, 1H).

Example 15

4-Isopropyl-N-(7-propylamino-5,6,7,8-tetrahydro-quinolin-3-yl)-benzenesulfonamide Following the same procedure as described above, N-[3-(4-isopropylbenzenesulfonylamino)-5,6,7,8-tetrahydro-quinolin-7-yl]-propionamide (90 mg, 0.22 mmol) in THF (5 ml) was treated with 1M BH$_3$.THF (2.2 ml). Purification of the crude product by flash column chromatography (CH$_2$Cl$_2$:MeOH, 95:5) provides the title compound (52 mg, 60%) as a white solid.

MS (ESI+) m/z=388.1 [M+H]$^+$ $^1$H NMR (400 MHz, CDCl$_3$): δ (ppm) 0.94 (t, J=7.4 Hz, 3H), 1.24 (d, J=6.9 Hz, 6H), 1.56 (m, 2H), 1.66 (m, 1H), 2.06 (m, 1H), 2.72 (m, 4H), 2.85 (dt, J=17.1, 5.3 Hz, 1H), 2.94 (m, 1H), 3.06 (m, 1H), 3.14 (dd, J=16.8, 4.6 Hz, 1H), 3.62 (bs, 2H), 7.30 (d, J=8.3 Hz, 2H), 7.32 (d, J=2.1 Hz, 1H), 7.68 (d, J=8.4 Hz, 2H), 7.94 (d, J=2.3 Hz, 1H).

Example 16

Reference

4-Isopropyl-N-(5-propylamino-5,6,7,8-tetrahydro-quinolin-3-yl)-benzenesulfonamide Following the same procedure as described above, N-[3-(4-isopropylbenzenesulfonylamino)-5,6,7,8-tetrahydro-quinolin-5-yl]-propionamide (136 mg, 0.33 mmol) in THF (10 ml) was treated with 1M BH$_3$.THF (3.3 ml). Purification of the crude product by flash column chromatography (heptane:ethyl acetate, 1:2) provides the title compound (74 mg, 56%) as a white solid.

MS (ESI+) m/z=388.1 [M+H]$^+$ $^1$H NMR (400 MHz, CDCl$_3$): δ (ppm) 0.94 (t, J=7.4 Hz, 3H), 1.24 (d, J=6.9 Hz, 6H), 1.51 (m, 2H), 1.75 (m, 3H), 1.96 (m, 3H), 2.59 (m, 2H), 2.86 (m, 3H), 3.73 (m, 1H), 7.30 (d, J=8.3 Hz, 2H), 7.68 (d, J=1.9 Hz, 1H), 7.68 (d, J=8.3 Hz, 2H), 8.02 (d, J=2.2 Hz, 1H).

Example 17

N-[6-(4-Isopropyl-benzenesulfonylamino)-chroman-3-yl]-propionamide

17.1 N-Chroman-3-yl-propionamide

A solution of chroman-3-ylamine (5.00 g, 33.5 mmol) and triethylamine (5.09 g, 50.27 mmol) in THF (70 mL) was stirred at −5° C. and propionic anhydride (4.36 g, 33.5 mmol) added dropwise. After the mixture was stirred for 2 h at room temperature, the solvent was removed and ethyl acetate/water were added. The organic layer was washed with citric acid solution (5%) and dried over MgSO$_4$. The filtered solution was concentrated to give a yellow-brown solid (5.40 g, 78%).

MS (ESI) m/z: 206.1 [M+H]$^+$ $^1$H-NMR (CDCl$_3$): δ [ppm] 7.15 (t, 1H), 7.06 (d, 1H), 6.88 (t, 1H), 6.82 (d, 1H), 5.76 (brs, 1H), 4.50 (m, 1H), 4.12 (m, 2H), 3.12 (dd, 1H), 2.72 (d, 1H), 2.16 (q, 2H), 1.25 (t, 3H).

17.2 N-(6-Nitro-chroman-3-yl)-propionamide

The nitration was carried out by the aforementioned procedure. The product was obtained as a red oil (1.40 g).

MS (ESI) m/z: 251.1 [M+H]$^+$ $^1$H-NMR (DMSO-d$_6$): δ [ppm] 8.07 (s, 1H), 8.00 (m, 2H), 6.97 (d, 1H), 4.22 (m, 2H), 3.12 (dd, 1H), 2.80 (dd, 1H), 2.14 (q, 2H), 1.16 (t, 3H).

17.3 N-(6-Amino-chroman-3-yl)-propionamide

The SnCl$_2$ reduction was carried out by the aforementioned procedure. The product was obtained as a brown solid (3.63 g, 65%).

MS (ESI) m/z: 221.1 [M+H]+

17.4 N-[6-(4-Isopropyl-benzenesulfonylamino)-chroman-3-yl]-propionamide

The sulfonamide coupling was carried out by the aforementioned procedure. The product was obtained as a yellow oil (0.46 g, 31%).

MS (ESI) m/z: 403.1 [M+H]$^+$

¹H-NMR (DMSO-d₆): δ [ppm] 7.66 (d, J 8.2, 2H), 7.39 (d, J 8.2, 2H), 7.00 (s, 1H), 6.81 (m, 2H), 6.70 (m, 1H), 5.83 (d, 1H), 4.40 (m, 1H), 2.92 (m, 2H), 2.65 (m, 1H), 2.15 (m, 2H), 1.15 (m, 9H).

Example 18

4-Isopropyl-N-(3-propylamino-chroman-6-yl)-benzenesulfonamide

N-[6-(4-Isopropyl-benzenesulfonylamino)-chroman-3-yl]-propionamide (0.48 g, 1.20 mmol) was dissolved in THF (5 mL) and added dropwise to a stirred suspension of LiAlH4 (0.43 g, 11.3 mmol) in THF (5 mL) at 0° C. The resulting mixture was stirred at room temperature for 18 h. The solution was heated to reflux for 3 h, cooled and quenched by addition of water and 2 N HCl. The mixture was extracted with ethyl acetate and the organic phase dried over MgSO₄, filtered, and the filtrate was evaporated in vacuo to give the product which was further purified by preparative HPLC (20-90% MeOH) to give a white solid (10 mg, 6%).

MS (ESI) m/z: 389.1 [M+H]⁺

Example 19

N-((4aS,10bS)-4-Allyl-1,2,3,4,4a,5,6,10b-octahydro-benzo[f]quinolin-8-yl)-4-isopropylbenzenesulfonamide 19.1 (4aS,10bS)-8-Nitro-1,2,3,4,4a,5,6,10b-octahydro-benzo[f]quinoline Trans-(4a,10b)-1,2,3,4,4a,5,6,10b-octahydrobenzo[f]quinoline (5.00 g, 26.7 mmol) was dissolved in concentrated H₂SO₄ (14.2 mL) cooled to 5° C. After stirring for 15 min, potassium nitrate (2.90 g, 29.0 mmol) was added in small portions as a solid so that the temperature was maintained below 5° C. The reaction mixture was stirred at 5° C. for 1 h then allowed to reach room temperature and stirred for 18 hours. The reaction solution was poured over ice (200 g) and a yellow precipitate (3.92 g) collected. This was determined to be the sulfate salt of the desired product. The solution was adjusted to pH 11 with 50% NaOH/H₂O, extracted with ethyl acetate (150 mL) and the organic phase separated and dried over MgSO₄. The filtered solution was concentrated to give a red oil (1.96 g). Total yield 76%.

MS (ESI) m/z: 233.1 [M+H]⁺

¹H-NMR (DMSO-d₆): δ [ppm] regioisomers 8.08-7.95 (m, 1H), 7.73-7.58 (m, 1H), 7.41 (m, 1H), 3.05 (m, 3H), 2.60 (m, 2H), 2.42 (m, 2H), 1.92 (m, 1H), 1.80 (m, 1H), 1.64 (m, 2H), 1.22 (m, 1H).

19.2 (4aS,10bS)-4-Allyl-8-nitro-1,2,3,4,4a,5,6,10b-octahydro-benzo[f]quinoline (4aS,10bS)-8-Nitro-1,2,3,4,4a,5,6,10b-octahydro-benzo[f]quinoline (0.50 g, 1.51 mmol) was dissolved in THF (30 mL) and allyl bromide (0.40 g, 3.30 mmol) added. The solution was stirred at 50° C. for 8 h, room temperature for 18 h and then evaporated. The residue was partitioned between ethyl acetate and NaOH (2M), and the organic phase separated and dried over MgSO₄. The filtered solution was concentrated and separated by column chromatography (dichloromethane: 0-3% MeOH) to give the product as a yellow oil (0.40 g, 97%).

MS (ESI) m/z: 273.2 [M+H]⁺

19.3 (4aS,10bS)-4-Allyl-1,2,3,4,4a,5,6,10b-octahydro-benzo[f]quinolin-8-ylamine (4aS,10bS)-4-Allyl-8-nitro-1,2,3,4,4a,5,6,10b-octahydro-benzo[f]quinoline (0.85 g, 3.12 mmol) was dissolved in MeOH (50 mL) and tin chloride (3.50 g, 15.5 mmol) added. The solution was heated to reflux for 3 h and then evaporated. The residue was partitioned between ethyl acetate and NaOH (2M), and the organic phase separated and dried over MgSO₄. The filtered solution was concentrated and separated by preparative HPLC (20-90% MeOH) to give the 3 amino isomers. The product was obtained as a yellow oil (0.35 g, 46%).

MS (ESI) m/z: 243.3 [M+H]⁺

¹H-NMR (DMSO-d₆): δ [ppm] 6.90 (d, 1H), 6.35 (d, 1H), 6.25 (s, 1H), 5.87 (m, 1H), 5.12 (m, 2H), 3.42 (m, 1H), 3.04 (m, 1H), 2.90 (m, 1H), 2.64 (m, 2H), 2.34 (m, 2H), 2.13 (m, 2H), 1.95 (m, 1H), 1.62 (m, 2H), 1.39 (m, 1H), 1.00 (m, 1H).

¹³C-NMR (DMSO-d₆): δ [ppm] 146.1 (s), 135.7 (s), 135.3 (d), 126.4 (s), 125.6 (d), 117.1 (t), 113.2 (d), 112.2 (d), 63.9 (d), 55.4 (t), 52.8 (t), 41.3 (d), 29.4 (t), 28.6 (t), 26.3 (t), 24.9 (t).

19.4 N-((4aS,10bS)-4-Allyl-1,2,3,4,4a,5,6,10b-octahydro-benzo[f]quinolin-8-yl)-4-isopropyl-benzenesulfonamide (4aS,10bS)-4-Allyl-1,2,3,4,4a,5,6,10b-octahydro-benzo[f]quinolin-8-ylamine (60 mg, 0.23 mmol) was dissolved in pyridine-dichloromethane (1:2, 7.5 mL) and cooled to 5° C. 4-Isopropylbenzenesulfonyl chloride (50 mg, 0.24 mmol) was added and the solution stirred at 5° C. for 3 h. Solution was evaporated, partitioned between ethyl acetate and water, and the organic phase separated and dried over MgSO₄. The filtered solution was concentrated and separated by column chromatography (dichloromethane-3% MeOH) to give an oil. The oil was dissolved in ethyl acetate and HCl (4M, dioxane) was added to give the product as a white solid (20 mg, 15%).

MS (ESI) m/z: 425.2 [M+H]⁺

The procedure described in example 19 was used to prepare the compounds of examples 20 and 21. The compounds were characterized by the following physical data:

Example 20

N-((4aS,10bS)-4-Allyl-1,2,3,4,4a,5,6,10b-octahydro-benzo[f]quinolin-9-yl)-4-isopropylbenzenesulfonamide 20.1 (4aS,10bS)-9-Nitro-1,2,3,4,4a,5,6,10b-octahydro-benzo[f]quinoline MS (ESI) m/z: 233.1 [M+H]⁺

¹H-NMR (DMSO-d₆): δ [ppm] 8.13 (s, 1H), 8.03 (d, 1H), 7.43 (d, 1H), 4.05 (br s, 1H), 3.38 (m, 1H), 2.97 (m, 3H), 2.64 (m, 1H), 2.15 (d, 1H), 1.99 (m, 1H), 1.88 (m, 2H), 1.46 (m, 2H).

¹³C-NMR (DMSO-d₆): δ [ppm] 146.1 (s), 143.7 (s), 138.2 (d), 130.1 (d), 121.3 (d), 120.6 (d), 56.3 (d), 43.7 (t), 27.6 (t), 26.4 (t), 25.5 (t), 22.1 (t).

20.2 (4aS,10bS)-4-Allyl-9-nitro-1,2,3,4,4a,5,6,10b-octahydro-benzo[f]quinoline Scale 1.51 g. Yield: 97%
MS (ESI) m/z: 273.0 [M+H]+

20.3 (4aS,10bS)-4-Allyl-1,2,3,4,4a,5,6,10b-octahydro-benzo[f]quinolin-9-ylamine Scale 0.73 g. Yield 59%
MS (ESI) m/z: 243.3 [M+H]$^+$
$^1$H-NMR (DMSO-d$_6$): δ [ppm] 6.47 (d, 1H), 6.28 (s, 1H), 6.13 (d, 1H), 5.67 (m, 1H), 5.40 (brs, 2H), 4.93 (m, 2H), 3.18 (m, 1H), 2.82 (m, 1H), 2.70 (d, 1H), 2.41 (m, 2H), 2.11 (m, 2H), 1.93 (m, 2H), 1.85 (m, 1H), 1.47 (m, 2H), 1.15 (m, 1H), 0.82 (m, 1H).
$^{13}$C-NMR (DMSO-d$_6$): δ [ppm] 146.2 (s), 139.1 (s), 135.1 (d), 128.4 (d), 122.8 (s), 117.2 (t), 112.2 (d), 110.9 (d), 63.7 (d), 55.4 (t), 52.7 (t), 41.9 (d), 29.3 (t), 27.6 (t), 26.5 (t), 24.9 (t).

20.4 N-((4aS,10bS)-4-Allyl-1,2,3,4,4a,5,6,10b-octahydro-benzo[f]quinolin-9-yl)-4-isopropyl-benzene-sulfonamide Procedure described above. Scale 0.73 g. Yield 45%.
MS (ESI) m/z: 425.2 [M+H]$^+$
$^1$H-NMR (DMSO-d$_6$): δ [ppm] 7.68 (d, 2H), 7.42 (d, 2H), 6.92 (m, 3H), 6.00 (m, 1H), 5.52 (m, 2H), 3.90 (m, 1H), 3.78 (m, 1H), 3.41 (m, 1H), 3.05-2.85 (m, 4H), 2.75 (m, 2H), 2.40 (m, 1H), 2.22 (m, 1H), 2.00 (m, 2H), 1.78 (m, 1H), 1.30 (m, 1H), 1.19 (d, 6H).

Example 21

N-((4aS,10bS)-4-Allyl-1,2,3,4,4a,5,6,10b-octahydro-benzo[f]quinolin-7-yl)-4-isopropylbenzenesulfonamide

21.1 (4aS,10bS)-4-Allyl-7-nitro-1,2,3,4,4a,5,6,10b-octahydro-benzo[f]quinoline Procedure described above except: room temperature reaction for 18 h. Yield 51%.
MS (ESI) m/z: 273.0 [M+H]$^+$

21.2 (4aS,10bS)-4-Allyl-1,2,3,4,4a,5,6,10b-octahydro-benzo[f]quinolin-7-ylamine Scale 0.85 g. Yield: 46%
MS (ESI) m/z: 243.3 [M+H]$^+$

21.3 N-((4aS,10bS)-4-Allyl-1,2,3,4,4a,5,6,10b-octahydro-benzo[f]quinolin-7-yl)-4-isopropyl-benzene-sulfonamide Procedure described above. Scale 0.26 g. Yield 53%. Converted to HCl salt.
MS (ESI) m/z: 425.1 [M+H]$^+$
$^1$H-NMR (DMSO-d$_6$): δ [ppm] 11.38 (br s, 1H), 9.56 (br s, 1H), 7.60 (d, 2H), 7.44 (d, 2H), 7.21 (d, 2H), 7.11 (t, 1H), 6.84 (d, 1H), 6.00 (m, 1H), 5.50 (m, 2H), 3.85 (m, 1H), 3.75 (m, 1H), 3.15 (m, 1H), 2.95 (m, 3H), 2.60 (m, 2H), 2.28 (m, 1H), 2.00 (m, 2H), 1.68 (m, 1H), 1.40 (m, 1H), 1.19 (d, 6H).

$^{13}$C-NMR (DMSO-d$_6$): δ [ppm] 153.5 (s), 138.0 (s), 134.1 (s), 132.0 (s), 127.0 (d), 126.5 (d), 126.3 (d), 124.6 (t), 124.4 (d), 123.9 (d), 62.8 (d), 53.8 (t), 51.2 (t), 35.2 (d), 33.3 (d), 26.8 (t), 23.3 (q), 22.6 (t), 22.1 (t).

Example 22 trans-4-Isopropyl-N-(1-propionyl-1,2,3,4,4a,5,10,10a-octahydro-benzo[g]quinolin-7-yl)benzene-sulfonamide

22.1 trans-1,2,3,4,4a,5,10,10a-Octahydro-benzo[g]quinoline

This compound was prepared as described for (4aR,10aR)-9-methoxy-1-methyl-6-trimethylsilanyl-1,2,3,4,4a,5,10,10a-octahydrobenzo[g]quinoline in Organic Process Research & Development, 2003, 904-12.
ESI-MS: [M+H]$^+$
$^1$H-NMR (CDCl$_3$): δ [ppm] 7.1-8.0 (several m, 4H), 3.15 (m, 1H), 3.0 (m, 1H), 2.9 (m, 1H), 2.6-2.8 (several m, 3H), 2.55 (m, 1H), 2.0 (m, 1H), 1.75 (m, 1H), 1.6 (m, 2H), 1.2 (m, 1H).
$^1$H-NMR (DMSO-d$_6$): δ [ppm] 7.0-7.1 (several m, 4H), 2.95 (m, 1H), 2.8 (m, 1H), 2.7 (m, 1H), 2.3-2.6 (several m, 4H), 1.85 (m, 1H), 1.55 (m, 1H), 1.45 (m, 1H), 1.35 (m, 1H), 1.05 (m, 1H).

22.2 trans-1-(3,4,4a,5,10,10a-Hexahydro-2H-benzo[g]quinolin-1-yl)-propan-1-one 5.33 g of trans-1,2,3,4,4a,5,10,10a-Octahydro-benzo[g]quinoline (28.46 mmol) were dissolved in 70 ml tetrahydrofuran, and subsequently 5.76 g of triethylamine (56.9 mmol) and, at −5° C., 4.07 g propionic acid anhydride (31.3 mmol) in 10 ml of tetrahydrofuran were added. After stirring for 2 h at −5° C., 4 ml of concentrated aqueous ammonia were added, the reaction mixture evaporated to dryness, 100 ml ethyl acetate added, and washed with 60 ml water. The organic layer was dried over magnesium sulfate, filtered, and evaporated to dryness to yield 7.79 g of the desired product.
ESI-MS: 244.2 [M+H]$^+$
$^1$H-NMR (CDCl$_3$): δ [ppm]

22.3 trans-1-(7-Nitro-3,4,4a,5,10,10a-hexahydro-2H-benzo[g]quinolin-1-yl)-propan-1-one 2.5 g trans-1-(3,4,4a,5,10,10a-Hexahydro-2H-benzo[g]quinolin-1-yl)-propan-1-one (10.27 mmol) were dissolved in 25 ml nitromethane. At −5° C. to −10° C., a mixture of 0.71 ml of nitric acid (10.27 mmol), 1.5 ml of water, and 9.5 ml of sulphuric acid (170 mmol) were added within 30 minutes. Stirring continued for 1.5 h under cooling conditions before the mixture was poured onto crushed ice. The aqueous phase was extracted twice with ethyl acetate, the combined organic layer was dried over magnesium sulfate, filtered, and the solvent evaporated under reduced pressure to yield 2.7 g of the nitrated product as a mixture of several nitro-isomers, which was used in the subsequent reaction without further separation.
ESI-MS: 289.1 [M+H]$^+$

22.4 trans-1-(7-amino-3,4,4a,5,10,10a-hexahydro-2H-benzo[g]quinolin-1-yl)-propan-1-one 2.7 g trans-1-(7-Nitro-3,4,4a,5,10,10a-hexahydro-2H-benzo[g]quinolin-1-yl)-propan-1-one including its regioisomers (9.36 mmol) were dissolved in 100 ml of methanol, 11 g of stannous dichloride (48.75 mmol) added, and the reaction mixture stirred under reflux for 1.5 h. Methanol was removed, the residue treated with 1 N aqueous sodium hydroxide and ethyl acetate, filtered through celite, the phases separated and the aqueous phase extracted twice with ethyl acetate. The combined organic layers were dried over magnesium sulfate, filtered, and the solvent evaporated under reduced pressure. The crude product was purified via preparative HPLC (DeltaPak, 40 mm diameter) with methanol/water/ 1% acetic acid as eluent to yield 0.04 g of the 6-amino-isomer, 0.1 g of the 7-amino-isomer, 0.14 g of the 8-amino-isomer, and 0.19 g of the 9-amino-isomer.

6-amino-isomer

ESI-MS: 259.1 [M+H]$^+$
$^1$H-NMR (CDCl$_3$): δ [ppm] 6.95 (m, 1H), 6.5 (m, 2H), 3.8 (m, very broad, 2H), 3.55 (m, very broad, 2H), 3.1 (m, very broad, 2H), 2.6-2.8 (m, 2H), 2.3-2.5 (m, 2H), 2.15 (m, 1H), 1.7-2.0 (several m, 4H), 1.3 (m, 1H), 1.15 (m, 3H).

7-amino-isomer

ESI-MS: 259.1 [M+H]$^+$
$^1$H-NMR (CDCl$_3$): δ [ppm] 6.9 (m, 1H), 6.5 (m, 1H), 6.4 (m, 1H), 3.7 (m, very broad, 2H), 3.55 (m, very broad, 2H), 3.1 (m, very broad, 2H), 2.3-2.8 (several m, 5H), 1.65-2.0 (several m, 4H), 1.3 (m, 1H), 1.15 (m, 3H).

8-amino-isomer

ESI-MS: 259.1 [M+H]$^+$
$^1$H-NMR (CDCl$_3$): δ [ppm] 6.85 (m, 1H), 6.5 (m, 1H), 6.4 (m, 1H), 3.3-4.2 (m, very broad, 4H), 3.1 (m, very broad, 2H), 2.55-2.8 (m, 2H), 2.25-2.5 (m, 3H), 1.9 (m, 2H), 1.75 (m, 2H), 1.25 (m, 1H), 1.15 (m, 3H).

9-amino-isomer

ESI-MS: 259.1 [M+H]$^+$
$^1$H-NMR (CDCl$_3$): δ [ppm] 6.95 (m, 1H), 6.5 (m, 2H), 3.4-4.0 (m, very broad, 4H), 3.0-3.3 (m, very broad, 2H), 2.8 (m, 1H), 2.55 (m, 1H), 2.2-2.45 (m, 3H), 1.95 (m, 2H), 1.75 (m, 2H), 1.25 (m, 1H), 1.15 (m, 3H).

22.5 trans-4-Isopropyl-N-(1-propionyl-1,2,3,4,4a,5, 10,10a-octahydro-benzo[g]quinolin-7-yl)-benzenesulfonamide 1.21 g of trans-1-(7-amino-3,4,4a,5,10,10a-hexahydro-2H-benzo[g]quinolin-1-yl)propan-1-one (0.38 mmol) were dissolved in 2 ml of pyridine. At 0-4° C., 0.08 g of 4-isopropyl-benzene sulfonylchloride (0.4 mmol) were added, and the reaction stirred for 1 h under cooling. 40 ml of aqueous 1 N hydrochloride acid and diethyl ether were added, the phases separated, and the aqueous layer extracted twice with diethyl ether. The organic phases were combined, washed three times with water acidified with 1 N aqueous hydrochloric acid, dried over magnesium sulfate, filtered, and the solvent evaporated under reduced pressure to yield 0.118 g of the product.

ESI-MS: 441.1 [M+H]$^+$

Example 23 trans-4-Isopropyl-N-(1-propyl-1,2,3,4,4a,5,10,10a-octahydro-benzo[g]quinolin-7-yl)benzenesulfonamide 0.18 mg of trans-4-isopropyl-N-(1-propionyl-1,2,3,4,4a,5, 10,10a-octahydrobenzo[g]quinolin-7-yl)-benzenesulfonamide (0.268 mmol) were dissolved in 7 ml of tetrahydrofuran. 1.4 ml of 1 M borane-tetrahydrofuran-complex in tetrahydrofurane were added and the reaction stirred under reflux for 30 min. 2 ml of 2 N aqueous hydrochloric acid were added, the reaction further stirred for 3 h under reflux, and the solvent removed under reduced pressure. Water adjusted to pH 9 with sodium hydroxide was added and the aqueous phase extracted three times with diethyl ether. The combined organic layers were dried over magnesium sulfate, filtered, and the solvent removed. The residue was purified via silica gel chromatography on chroma-bond column with cyclohexane/ethyl acetate 1:3 as eluent to yield 0.0155 g of the desired product ESI-MS: 427.1 [M+H]$^+$
$^1$H-NMR (CDCl$_3$): δ [ppm] 7.6 (d, 2H), 7.2 (d, 2H), 6.9 (m, 1H), 6.7 (m, 3H), 3.05 (m, 1H), 2.95 (m, 1H), 2.85 (m, 1H), 2.5-2.75 (several m, 3H), 2.05-2.5 (several m, 4H), 1.8 (m, 1H), 1.6 (m, 3H), 1.45 (m, 2H), 1.2 (m, 6H), 0.8 (m, 3H).

Example 24 trans-4-Isopropyl-N-(1,2,3,4,4a,5,10,10a-octahydro-benzo[g]quinolin-7-yl)benzenesulfonamide From that same chromatography of example 20, 0.0227 g of the secondary amine could be obtained.
ESI-MS: 385.1 [M+H]$^+$
$^1$H-NMR (CDCl$_3$): δ [ppm] 7.7 (d, 2H), 7.25 (d, 2H), 6.9 (m, 1H), 6.75 (m, 2H), 3.1 (m, 1H), 2.9 (m, 1H), 2.8 (m, 1H), 2.7 (m, 2H), 2.6 (m, 2H), 2.35 (m, 1H), 1.9 (m, 1H), 1.7 (m, 1H), 1.6 (m, 1H), 1.45 (m, 1H), 1.2 (m, 6H), 1.1 (m, 1H).

Example 25 trans-4-trifluoromethyl-N-(1-propionyl-1,2,3,4,4a,5, 10,10a-octahydro-benzo[g]quinolin-7-yl)-benzenesulfonamide 0.792 g (3.065 mmol) of a 1:1 mixture trans-(7-amino-3, 4,4a,5,10,10a-hexahydro-2H-benzo[g]quinolin-1-yl)-propan-1-one and trans-(8-amino-3,4,4a,5,10,10a-hexahydro-2H-benzo[g]quinolin-1-yl)-propan-1-one were dissolved in 20 ml pyridine. At 0-4° C., 0.75 g of 4-trifluoromethyl-benzene sulfonylchloride (3.066 mmol) were added, and the reaction stirred for 2 h under cooling. Pyridine was evaporated and the residue partitioned between 20% aqueous citric acid and diethylether. The aqueous layer was extracted twice with diethylether, the combined organic phases washed with 20% aqueous citric acid, dried over magnesium sulfate, filtered, and the solvent evaporated under reduced pressure to yield 1.327 g of the product. MSD: 467.1 g/mol
ESI-MS: 467.1 [M]$^+$ Example 26 trans-4-trifluoromethyl-N-(1-propyl-1,2,3,4,4a,5,10, 10a-octahydro-benzo[g]quinolin-7-yl)benzenesulfonamide 22.5 mg of the compound were obtained from the chromatographic purification of example 27 which describes the reduction of a 1:1 mixture of the 7- and 8-isomers of the corresponding propionyl precursors

Example 27 trans-4-trifluoromethyl-N-(1-propyl-1,2,3,4,4a,5,10,10a-octahydro-benzo[g]quinolin-8-yl)benzenesulfonamide To a suspension of 0.035 g of lithium aluminium hydride (0.922 mmol) in 2.5 ml tetrahydrofurane were added at 4° C. a solution of 0.2 g of the 1:1 mixture of trans-4-trifluoromethyl-N-(1-propionyl-1,2,3,4,4a,5,10,10a-octahydro-benzo[g]quinolin-7-yl)benzenesulfonamide and trans-4-trifluoromethyl-N-(1-propionyl-1,2,3,4,4a,5,10,10a-octahydro-benzo[g]quinolin-8-yl)-benzenesulfonamide (0.429 mmol) in 2.5 ml tetra-hydrofuran. After stirring for 5 minutes at 10° C., 1 mL water was cautiously added, the solvent evaporated and the residue treated with diethyl ether and water. The aqueous phase was reextracted with diethylether, and the combined organic layers dried over magnesium sulfate, filtered and the solvent evaporated under reduced pressure. The crude product was purified via preparative HPLC (compression column, Delta Pack 40 mm diameter) using a gradient consisting of methanol/water/0.1% acetic as eluent; fraction 3, m=31.9 mg (8-isomer), fraction. 4, m=22.4 mg, fractions. 5-7, m=22.5 mg (7-isomer),

ESI-MS: 453.3 [M+H]$^+$

Example 28

N—((S)-6-Amino-5,6,7,8-tetrahydro-naphthalen-2-yl)-4-isopropyl-benzenesulfonamide, hydrochloride A mixture of N—((S)-6-Allylamino-5,6,7,8-tetrahydro-naphthalen-2-yl)-4-isopropylbenzenesulfonamide (108 mg, 0.26 mmol) and 10% palladium on carbon (25 mg) in a mixture of ethyl acetate (12 ml) and methanol (3 ml) was hydrogenated overnight. The catalyst was filtered, and the solvent was removed under vacuum to yield an oil. This oil was dissolved in destined H$_2$O (30 ml) and a few drops of concentrated HCl were added. This solution was lyophilisated to yield the deallylated product (60 mg, 61%).

ESI-MS: 345.2 [M+H]$^+$ $^1$H-NMR (DMSO-d$_6$): δ [ppm] 10.2 (bs, 1H), 8.2 (bs, 1H), 7.7 (d, 2H), 7.4 (d, 2H), 7.0 (d, 1H), 6.9 (d, 1H), 6.8 (s, 1H), 3.7 (m, 1H), 3.0 (m, 2H), 2.7 (m, 3H), 2.1 (m, 1H), 1.7 (m, 1H), 1.2 (d, 6H).

Example 29

N—((R)-6-Dipropylamino-5,6,7,8-tetrahydro-naphthalen-2-yl)-4-isopropyl-benzenesulfonamide, hydrochloride 4-Isopropyl-N—((R)-6-propylamino-5,6,7,8-tetrahydro-naphthalen-2-yl)benzenesulfonamide (150 mg, 0.39 mmol) and propionaldehyde (42 μl, 0.58 mmol) were dissolved in THF (20 ml). Acetic acid (30 μl, 0.58 mmol) and sodium trisacetoxyborohydride (165 mg, 0.78 mmol) were sequentially added to the reaction mixture and stirred overnight. The reaction mixture was concentrated and the residue was dissolved in H$_2$O (10 ml) and ethyl acetate (50 ml). With NaOH (2M) the ph was adjusted to 9. The organic phase was separated, dried over magnesium sulfate, filtered, and evaporated to dryness to yield an oil (95 mg). This oil was dissolved in destined H$_2$O (30 ml) and a few drops of concentrated HCl were added. This solution was lyophilisated to yield the desired product (92 mg, 54%).

ESI-MS: 429.2 [M+H]$^+$ $^1$H-NMR (DMSO-d$_6$): δ [ppm] 10.2 (s, 1H), 9.9 (bs, 1H), 7.7 (d, 2H), 7.4 (d, 2H), 7.0 (d, 1H), 6.9 (d, 1H), 6.8 (s, 1H), 3.6 (m, 1H), 3.1-2.9 (m, 6H), 2.8 (m, 2H), 2.5 (m, 1H), 2.2 (m, 1H), 1.7 (m, 5H), 1.2 (d, 6H), 0.9 (t, 6H).

Example 30

N—((S)-6-Dipropylamino-5,6,7,8-tetrahydro-naphthalen-2-yl)-4-isopropylbenzenesulfonamide, hydrochloride 4-Isopropyl-N—((S)-6-propylamino-5,6,7,8-tetrahydro-naphthalen-2-yl)benzenesulfonamide (70 mg, 0.18 mmol) and propionaldehyde (42 μl, 0.58 mmol) was dissolved in THF (20 ml). Acetic acid (19 μl, 0.27 mmol) and sodium trisacetoxyborohydride (75 mg, 0.35 mmol) were sequentially added to the reaction mixture and stirred overnight. The reaction mixture was concentrated and the residue was dissolved in H$_2$O (10 ml) and ethyl acetate (50 ml). With NaOH (2M) the ph was adjusted to 9. The organic phase was separated, dried over magnesium sulfate, filtered, and evaporated to dryness to yield an oil (95 mg). This oil was dissolved in destilled H$_2$O (30 ml) and a few drops of concentrated HCl were added. This solution was lyophilisated to yield the desired product (21 mg, 25%).

ESI-MS: 429.2 [M+H]$^+$ $^1$H-NMR (DMSO-d$_6$): δ [ppm] 10.2 (s, 1H), 9.9 (bs, 1H), 7.7 (d, 2H), 7.4 (d, 2H), 7.0 (d, 1H), 6.9 (d, 1H), 6.8 (s, 1H), 3.6 (m, 1H), 3.1-2.9 (m, 6H), 2.8 (m, 2H), 2.5 (m, 1H), 2.2 (m, 1H), 1.7 (m, 5H), 1.2 (d, 6H), 0.9 (t, 6H).

Example 31

N-[7-(4-Trifluoromethoxy-benzenesulfonylamino)-3,4-dihydro-2H-pyrano[3,2-b]pyridin-3-yl]-propionamide

31.1 (5-Oxo-tetrahydro-pyran-3-yl)-carbamic acid benzyl ester

Following the same procedure as described in example 11.1, 6H-pyran-3-one (5 g, 50.96 mmol) in CH$_2$Cl$_2$ (5 ml) was treated with bismuth nitrate pentahydrate (5 g, 10.30 mmol) and benzylcarbamate (8.5 g, 56.22 mmol). Purification of the crude product by flash column chromatography (heptane:ethyl acetate, 3:1) gave the title compound (8.11 g, 64%) as a colorless oil.

MS (ESI+) m/z=250.1 [M+H]$^+$ $^1$H NMR (400 MHz, CDCl$_3$) δ 2.67 (dd, J=16.6, 2.5 Hz, 1H), 2.75 (dd, J=16.6, 5.4 Hz, 1H), 3.84 (br d, J=11.5 Hz, 1H), 3.92 (dd, J=11.8, 2.7 Hz, 1H), 3.99 (d, J=16.1 Hz, 1H), 4.06 (d, J=16.2 Hz, 1H), 4.30 (br s, 1H), 5.10 (m, 2H), 5.19 (m, 1H), 7.35 (m, 5H); $^{13}$C NMR (100 MHz, CDCl$_3$) 044.1, 47.9, 67.0, 69.3, 74.9, 128.1 (2 C), 128.2, 128.5 (2 C), 136.0, 155.4, 204.7.

31.2 Benzyl 3,4-dihydro-7-nitro-2H-pyrano[3,2-b]pyridin-3-ylcarbamate and benzyl 6,8-dihydro-3-nitro-5H-pyrano[3,4-b]pyridin-5-ylcarbamate A solution of (5-oxo-tetrahydro-pyran-3-yl)-carbamic acid benzyl ester (750 mg, 3 mmol) and 1-methyl-3,5-dinitro-2-pyridone (660 g, 3.31 mmol) in methanolic ammonia (1M, 6 ml) was irradiated in a sealed vial at 120° C. for 20 min. The mixture was then concentrated and the resulting residue was dissolved in CH₂Cl₂. The organic layer was washed with saturated aqueous NaHCO₃ and water, dried over Na₂SO₄ and evaporated. Purification of the resulting residue by chromatography on silica gel (heptane:ethyl acetate, 3:1) afforded a mixture 7.5/1 (632 mg, 64%) of benzyl 6,8-dihydro-3-nitro-5H-pyrano[3,4-b]pyridin-5-ylcarbamate as major product along with benzyl 3,4-dihydro-7-nitro-2H-pyrano[3,2-b]pyridin-3-ylcarbamate as minor adduct. A small fraction of each was isolated to afford full characterization.

Benzyl 3,4-dihydro-7-nitro-2H-pyrano[3,2-b]pyridin-3-yl-carbamate: white solid
MS (ESI+) m/z=330.1 [M+H]⁺.
$^1$H NMR (400 MHz, CDCl₃) δ 3.10 (dd, J=18.1, 3.5 Hz, 1H), 3.34 (dd, J=18.2, 5.3 Hz, 1H), 4.25 (s, 2H), 4.39 (br s, 1H), 5.02 (br s, 1H), 5.10 (s, 2H), 7.33 (m, 5H), 7.90 (d, J=2.0 Hz, 1H), 8.98 (d, J=2.0 Hz, 1H);
$^{13}$C NMR (100 MHz, CDCl₃) δ 34.9, 43.7, 67.2, 68.7, 118.6, 128.2 (2 C), 128.3, 128.5 (2 C), 135.8, 137.2, 143.6, 148.0, 150.3, 155.4.
Anal. calcd. for C₁₆H₁₅N₃O₅: C, 58.36; H, 4.59; N, 12.76; O, 24.29. Found: C, 58.76; H, 5.00; N, 12.23; O, 24.12.

Benzyl 6,8-dihydro-3-nitro-5H-pyrano[3,4-b]pyridin-5-yl-carbamate: light yellow solid
MS (ESI+) m/z=330.1 [M+H]⁺.
$^1$H NMR (400 MHz, CDCl₃) δ 3.96 (dd, J=11.9, 3.2 Hz; 1H), 4.07 (dd, J=11.9, 2.9 Hz, 1H), 4.80 (d, J=17.4 Hz, 1H), 4.94 (d, J=17.4 Hz, 1H), 5.00 (m, 1H), 5.13 (d, J=12.3 Hz, 1H), 5.17 (d, J=12.3 Hz, 1H), 5.38 (d, J=9.0 Hz, 1H), 7.35 (m, 5H), 8.61 (d, J=1.6 Hz, 1H), 9.29 (d, J=1.9 Hz, 1H);
$^{13}$C NMR (100 MHz, CDCl₃) δ46.7, 67.3, 68.8, 69.8, 128.1 (2 C), 128.3, 128.5 (2 C), 130.9, 131.8, 135.8, 143.2, 144.1, 155.8, 160.8;
Anal. calcd for C₁₆H₁₅N₃O₅: C, 58.36; H, 4.59; N, 12.76; O, 24.29. Found: C, 58.46; H, 4.80; N, 12.59; O, 23.98.

31.3 N-(3,4-dihydro-7-nitro-2H-pyrano[3,2-b]pyridin-3-yl)propionamide and N-(6,8-dihydro-3-nitro-5H-pyrano[3,4-b]pyridin-5-yl)propionamide A mixture of benzyl 3,4-dihydro-7-nitro-2H-pyrano[3,2-b]pyridin-3-ylcarbamate and benzyl 6,8-dihydro-3-nitro-5H-pyrano[3,4-b]pyridine-5-ylcarbamate (6.54 g, 26.23 mmol) in CH₂Cl₂ (55 ml) was stirred at 0° C. and 33% HBr in acetic acid (45 ml) was added. The solution was further stirred at 0° C. for 1 h then at room temperature for 2 h. The solvents were then removed. The crude mixture was dissolved in CH₂Cl₂/H₂O 1/1 (80 ml) and the aqueous mixture adjusted to pH~10 with 2N NaOH solution. After separation of the layers, the organic phase was washed with H₂O (×2), dried over Na₂SO₄ and evaporated. The residue was dissolved in CH₂Cl₂ (400 ml) and the solution cooled to 0° C. Propionyl chloride (4.54 ml, 52 mmol) and triethylamine (7.22 ml, 52 mmol) were added and then the mixture was allowed to reach 20° C. and stirred for 4.5 h. The solution was washed successively with 1 N aqueous HCl, saturated aqueous NaHCO₃ and water. The organic layer was dried (Na₂SO₄) and evaporated. Immediate recrystallization in acetone gave a pure fraction of N-(6,8-dihydro-3-nitro-5H-pyrano[3,4-b]pyridin-5-yl)propionamide (2.2 g, 33% for two steps) as a white solid. The remaining mixture was subjected to chromatography on silica gel (heptane:ethyl acetate, 1.5:3.5 then CH₂Cl₂:CH₃OH, 95:5) to afford another portion of N-(6,8-dihydro-3-nitro-5H-pyrano[3,4-b]pyridin-5-yl)propionamide (1.15 mg, 17% for two steps) and N-(3,4-dihydro-7-nitro-2H-pyrano[3,2-b]pyridin-3-yl)propionamide (445 mg, 7% for two steps) as a white solid.

N-(3,4-dihydro-7-nitro-2H-pyrano[3,2-b]pyridin-3-yl)propionamide

MS (ESI+) m/z=252.1 [M+H]⁺
$^1$H-NMR (400 MHz, CDCl₃) δ 1.14 (t, J=7.6 Hz, 3H), 2.21 (q, J=7.6 Hz, 2H), 3.08 (dd, J=18.3, 4.0 Hz, 1H), 3.35 (dd, J=18.3, 5.5 Hz, 1H), 4.25 (m, 2H), 4.65 (m, 1H), 5.57 (br s, 1H), 7.93 (d, J=1.9 Hz, 1H), 9.01 (d, J=2.0 Hz, 1H).

31.4 N-(7-Amino-3,4-dihydro-2H-pyrano[3,2-b]pyridin-3-yl)-propionamide

N-(3,4-Dihydro-7-nitro-2H-pyrano[3,2-b]pyridin-3-yl) propionamide (445 mg, 1.76 mmol) was dissolved in ethanol (80 ml) and SnCl₂.2H₂O (2 g, 8.82 mmol) was added. The resulting mixture was refluxed for 8 h and then the solvent was removed under vacuum. The raw material was dissolved in ethyl acetate and washed successively with 2 N aqueous NaOH (2×) and water. The organic layer was dried (Na₂SO₄), filtered through a pad of celite and evaporated to afford the crude N-(7-amino-3,4-dihydro-2H-pyrano[3,2-b]pyridin-3-yl)-propionamide (390 mg, 99%) as a pale yellow powder.

31.5 N-[7-(4-Trifluoromethoxy-benzenesulfonylamino)-3,4-dihydro-2H-pyrano[3,2-b]pyridin-3-yl]-propionamide A portion of the raw N-(7-amino-3,4-dihydro-2H-pyrano[3,2-b]pyridin-3-yl)propionamide (100 mg, 0.45 mmol) was dissolved in CH₂Cl₂/pyridine 9/1 (20 ml) and 4-(trifluoromethoxy)benzenesulfonyl chloride (100 μl, 0.58 mmol) was added dropwise. After stirring at room temperature overnight, the reaction mixture was concentrated and the purification of the residue by chromatography on silica gel (CH₂Cl₂:CH₃OH, 97:3) gave the title compound (94 mg, 47% for steps 31.4 and 31.5) as a gum.
MS (ESI+) m/z=446.1 [M+H]⁺

Example 32

N-[7-(4-Isopropyl-benzenesulfonylamino)-3,4-dihydro-2H-pyrano[3,2-b]pyridin-3-yl]-propionamide Following the same procedure as described in example 31.5, a portion of crude N-(7-amino-3,4-dihydro-2H-pyrano[3,2-b]pyridin-3-yl)-propionamide (100 mg, 0.45 mmol) in CH₂Cl₂/pyridine 9/1 (20 ml) was treated with 4-isopropyl-benzenesulfonyl chloride (130 μl, 0.72 mmol). Purification by flash column chromatography (CH₂Cl₂:methanol, 97:3) gave the title compound (85 mg, 47% for steps 31.4 and this step) as a gum.
MS (ESI+) m/z=404.1 [M+H]⁺

Example 33

N-{7-[4-((S)-2-Fluoro-1-methyl-ethyl)-benzenesulfonylamino]-3,4-dihydro-2H-pyrano[3,2-b]pyridin-3-yl}-propionamide Following the same procedure as described in example 31.5, a portion of crude N-(7-amino-3,4-dihydro-2H-pyrano[3,2-b]pyridin-3-yl)-propionamide (95 mg, 0.43 mmol) in CH₂Cl₂/pyridine 9/1 (10 ml) was treated with 4-((S)-2- fluoro-1-methyl-ethyl)benzenesulfonyl chloride (132 mg, 0.55 mmol). Purification by flash column chromatography (CH$_2$Cl$_2$:MeOH, 97:3) gave the title compound (100 mg, 55% for step 31.4 and this step) as a gum.

MS (ESI+) m/z=422.1 [M+H]$^+$

Example 34

N-(3-Propylamino-3,4-dihydro-2H-pyrano[3,2-b]pyridin-7-yl)-4-trifluoromethoxybenzenesulfonamide To a solution of N-[7-(4-trifluoromethoxy-benzenesulfonylamino)-3,4-dihydro-2H-pyrano[3,2-b]pyridin-3-yl]-propionamide (93 mg, 0.20 mmol) in THF (20 ml) was added dropwise 1M BH$_3$.THF (2.08 ml, 2.08 mmol) and the mixture was stirred at room temperature for 12 h. It was then quenched by adding carefully 1N aqueous HCl (8 ml) and then the resulting solution was heated at reflux for 4 h. The solution was cooled to room temperature, the aqueous mixture was adjusted to pH~8 with 2 N NaOH solution and diluted with CH$_2$Cl$_2$. Separation of the layers, drying (Na$_2$SO$_4$) of the organic phase and evaporation in vacuo provided the crude material, which was purified by flash column chromatography (CH$_2$Cl$_2$:methanol, 97:3) to give the title compound (70 mg, 78%) as a white amorphous solid.

MS (ESI+) m/z=432.1 [M+H]$^+$ $^1$H NMR (400 MHz, CDCl$_3$): δ (ppm) 0.92 (t, J=7.3 Hz, 3H), 1.53 (m, 2H), 2.69 (t, 1H, J=7.3 Hz, 2H), 2.78 (dd, J=16.9, 6.5 Hz, 1H), 3.10 (dd, J=16.9, 4.8 Hz, 1H), 3.24 (m, 1H), 3.96 (dd, J=10.8, 6.4 Hz, 1H), 4.16 (m, 3H), 6.97 (d, J=1.7 Hz, 1H), 7.27 (d, J=8.3 Hz, 2H), 7.77 (d, J=1.2 Hz, 1H), 7.84 (d, J=8.7 Hz, 2H).

Example 35

4-Isopropyl-N-(3-propylamino-3,4-dihydro-2H-pyrano[3,2-b]pyridin-7-yl)benzenesulfonamide Following the same procedure as described in example 34, N-[7-(4-isopropylbenzenesulfonylamino)-3,4-dihydro-2H-pyrano[3,2-b]pyridin-3-yl]-propionamide (85 mg, 0.21 mmol) in THF (10 ml) was treated with 1M BH$_3$.THF (2.1 ml, 2.1 mmol). Purification of the crude product by flash column chromatography (CH$_2$Cl$_2$:methanol, 97:3) gave the title compound (50 mg, 61%) as a white amorphous solid.

MS (ESI+) m/z=390.1 [M+H]$^+$ $^1$H NMR (400 MHz, CDCl$_3$): δ (ppm) 0.92 (t, J=7.4 Hz, 3H), 1.23 (d, J=6.9 Hz, 6H), 1.52 (m, 2H), 2.69 (t, 1H, J=7.3 Hz, 2H), 2.78 (dd, J=16.9, 6.9 Hz, 1H), 2.93 (m, 1H), 3.09 (dd, J=16.8, 4.8 Hz, 1H), 3.28 (m, 1H), 3.90 (m, 1H), 3.92 (dd, J=10.8, 6.8 Hz, 1H), 4.17 (d, J=10.1 Hz, 1H), 7.02 (d, J=2.1 Hz, 1H), 7.30 (d, J=8.3 Hz, 2H), 7.71 (d, J=8.3 Hz, 2H), 7.79 (d, J=2.0 Hz, 1H).

Example 36

4-((S)-2-Fluoro-1-methyl-ethyl)-N-(3-propylamino-3,4-dihydro-2H-pyrano[3,2-b]pyridin-7-yl)-benzenesulfonamide Following the same procedure as described in example 34, N-{7-[4-((S)-2-fluoro-1-methyl-ethyl)-benzenesulfonylamino]-3,4-dihydro-2H-pyrano[3,2-b]pyridin-3-yl}-propionamide (100 mg, 0.27 mmol) in THF (15 ml) was treated with 1M BH$_3$.THF (2.3 ml, 2.3 mmol). Purification of the crude product by flash column chromatography (CH$_2$Cl$_2$:methanol, 97:3) gave the title compound (50 mg, 52%) as a white solid.

MS (ESI+) m/z=408.1 [M+H]$^+$ $^1$H NMR (400 MHz, CH$_3$OH-d$_4$): δ (ppm) 0.92 (t, J=7.4 Hz, 3H), 1.18 (d, J=6.9 Hz, 3H), 1.61 (m, 2H), 2.93 (m, 1H), 3.00 (m, 2H), 3.09 (m, 1H), 3.28 (dd, J=18.1, 5.9 Hz, 1H), 3.81 (m, 1H), 4.18 (m, 1H), 4.31 (d, J=6.2 Hz, 1H), 4.34 (m, 1H), 4.43 (d, J=6.2 Hz, 1H), 7.11 (d, J=1.9 Hz, 1H), 7.36 (d, J=8.3 Hz, 2H), 7.67 (d, J=8.3 Hz, 2H), 7.83 (bs, 1 m).

Example 37

4-Oxazol-5-yl-N—((S)-6-propylamino-5,6,7,8-tetrahydro-naphthalen-2-yl)benzenesulfonamide Step 1. Sulfonamide coupling; following a procedure described above, e.g. example 6.3. yield: 1.57 g (88%)

Step 2. Removal of the BOC (tert-butoxycarbonyl) group was achieved by following a procedure as described above, e.g. example 6.4 (HCl/dioxane/CH$_2$Cl$_2$). Scale 0.59 g. Yield: 40%.

HCl salt.

MS (ESI) m/z: 449.1 [M+H]$^+$ $^1$H-NMR (DMSO-d$_6$): δ [ppm] 10.24 (s, 1H), 8.80 (m, 2H), 8.53 (s, 1H), 7.84 (m, 4H), 6.98 (d, 1H), 6.88 (m, 2H), 3.39 (m, 1H), 3.07 (m, 1H), 2.91 (m, 2H), 2.72 (m, 3H), 2.16 (m, 1H), 1.63 (m, 3H), 0.91 (t, J=7.3 Hz, 3H).

Example 38

5-Oxazol-5-yl-thiophene-2-sulfonic acid ((S)-6-propylamino-5,6,7,8-tetrahydro-naphthalen-2-yl)-amide Step 1. Sulfonamide coupling; following a procedure described above, e.g. example 6.3

Step 2. Removal of the BOC (tert-butoxycarbonyl) group was achieved by following a procedure as described above, e.g. example 6.4. Yield: 110 mg (74% based for two steps MS (ESI) m/z: 418.0 [M+H]$^+$ $^1$H-NMR (DMSO-d$_6$): δ [ppm] 10.50 (s, 1H), 8.62 (br s, 1H), 8.48 (s, 1H), 7.72 (s, 1H), 7.50 (m, 2H), 7.00 (m, 4H), 3.12 (m, 1H), 2.93 (m, 2H), 2.76 (t, 1H, J=7.3 Hz, 2H), 2.16 (m, 1H), 1.63 (m, 3H), 1.47 (m, 1H), 0.92 (t, J=7.3 Hz, 3H).

Example 39

5-Isoxazol-5-yl-thiophene-2-sulfonic acid ((S)-6-propylamino-5,6,7,8-tetrahydronaphthalen-2-yl)-amide Step 1. Sulfonamide coupling; following a procedure described above, e.g. example 6.3.

Step 2. BOC deprotection; following a procedure described above, e.g. example 6.4. Amount 130 mg. Yield: 87% calculated for two steps.

Converted to HCl salt.

MS (ESI) m/z: 418.1 [M+H]$^+$ $^1$H-NMR (DMSO-d$_6$): δ [ppm] 10.55 (s, 1H), 8.70 (br s, 2H), 7.67 (d, 1H), 7.62 (d, 1H), 7.06 (m, 2H), 6.96 (m, 2H), 3.10 (m, 1H), 2.92 (m, 2H), 2.76 (m, 3H), 2.15 (m, 1H), 1.63 (m, 3H), 0.93 (t, J=7.3 Hz, 3H).

Example 40

N—((S)-6-Propylamino-5,6,7,8-tetrahydro-naphthalen-2-yl)-4-(2,2,2-trifluoro-1-methyl-ethyl)benzenesulfonamide-racemate Step 1. Sulfonamide coupling; following a procedure described above, e.g. example 6.3 Amount 900 mg. Yield 100%

Step 2. BOC deprotection; following a procedure described above, e.g. example 6.4.
Amount 700 mg. Yield: 88%
Converted to HCl salt.
MS (ESI) m/z: 441.1 [M+H]$^+$
$^1$H-NMR (DMSO-d$_6$): δ [ppm] 10.23 (br s, 1H), 8.72 (br s, 1H), 7.78 (d, 2H), 7.59 (d, 2H), 6.88 (m, 3H), 3.92 (m, 1H), 3.32 (m, 1H), 3.08 (m, 1H), 2.90 (m, 2H), 2.70 (m, 3H), 2.16 (m, 1H), 1.63 (m, 3H), 1.41 (d, 3H), 0.91 (t, J=7.3 Hz, 3H).

Example 41

N—((S)-6-Propylamino-5,6,7,8-tetrahydro-naphthalen-2-yl)-4-((R)-2,2,2-trifluoro-1-methylethyl)-benzenesulfonamide The racemic compound obtained in example 40 was separated by chiral HPLC. Amount 40 mg. 80% recovery.
MS (ESI) m/z: 441.1 [M+H]$^+$
$^1$H-NMR (DMSO-d$_6$): δ [ppm] 10.23 (br s, 1H), 8.72 (br s, 1H), 7.78 (d, 2H), 7.59 (d, 2H), 6.88 (m, 3H), 3.92 (m, 1H), 3.32 (m, 1H), 3.08 (m, 1H), 2.90 (m, 2H), 2.70 (m, 3H), 2.16 (m, 1H), 1.63 (m, 3H), 1.41 (d, 3H), 0.91 (t, J=7.3 Hz, 3H).

Example 42

N—((S)-6-Propylamino-5,6,7,8-tetrahydro-naphthalen-2-yl)-4-((S)-2,2,2-trifluoro-1-methylethyl)-benzenesulfonamide The racemic compound of example 40 was separated by chiral HPLC. Amount 50 mg. 100% recovery.
MS (ESI) m/z: 441.1 [M+H]$^+$
$^1$H-NMR (DMSO-d$_6$): δ [ppm] 10.23 (br s, 1H), 8.72 (br s, 1H), 7.78 (d, 2H), 7.59 (d, 2H), 6.88 (m, 3H), 3.92 (m, 1H), 3.32 (m, 1H), 3.08 (m, 1H), 2.90 (m, 2H), 2.70 (m, 3H), 2.16 (m, 1H), 1.63 (m, 3H), 1.41 (d, 3H), 0.91 (t, J=7.3 Hz, 3H).

Example 43

5-Isoxazol-3-yl-thiophene-2-sulfonic acid ((S)-6-propylamino-5,6,7,8-tetrahydro-naphthalen-2-yl)-amide Step 1. Sulfonamide coupling; following a procedure described above, e.g. example 6.3 Amount 100 mg. Yield: 59%

Step 2. BOC deprotection; following a procedure described above, e.g. example 6.4 Amount 50 mg. Yield: 57%
MS (ESI) m/z: 418.0 [M+H]$^+$
$^1$H-NMR (DMSO-d$_6$): δ [ppm] 7.28 (d, 1H), 7.07 (br s, 1H), 6.90 (m, 4H), 6.60 (d, 2H), 4.10 (m, 1H), 3.94 (m, 1H), 3.03 (m, 1H), 2.75 (m, 5H), 2.06 (m, 2H), 1.53 (m, 3H), 0.92 (t, J=7.3 Hz, 3H).

Example 44

4-((R)-3-Fluoro-pyrrolidin-1-yl)-N—((S)-6-propylamino-5,6,7,8-tetrahydro-naphthalen-2-yl)benzenesulfonamide Step 1. Buchwald coupling reaction using (R)-3-fluoropyrrolidine, Reaction of 0.200 g of [(S)-6-(4-bromo-benzenesulfonylamino)-1,2,3,4-tetrahydronaphthalen-2-yl]-propyl-carbamic acid tert-butyl ester (0.38 mmol), 72 mg of (R)-3-fluoropyrrolidine (0.57 mmol), 51 mg of NaOtC$_4$H$_9$ (1.53 mmol), 39 mg of Pd$_2$(dba)$_3$ (tris(dibenzylideneacetone)dipalladium(0) (0.04 mmol)), 47 mg of BINAP (2,2'-bis(diphenylphosphino)-1,1'-binaphthyl) (0.08 mmol) in 5 ml tetrahydrofuran at 80° C. for 48 hours yielded 95 mg (47%) of {(S)-6-[4-((R)-3-fluoro-pyrrolidin-1-yl)benzenesulfonylamino]-1,2,3,4-tetrahydro-naphthalen-2-yl}-propyl-carbamic acid tert-butyl ester as a yellow solid.

Step 2. BOC deprotection; following a procedure described below, see example 47.2. Amount: 39 mg. Yield: 49%
MS (ESI) m/z: 432.0 [M+H]$^+$

Example 45

4-Morpholin-4-yl-N—((S)-6-propylamino-5,6,7,8-tetrahydro-naphthalen-2-yl)benzenesulfonamide Step 1. Buchwald coupling using morpholine, following a procedure as described in example 44, step 1. Amount: 40 mg. Yield 20%

Step 2. BOC deprotection; following a procedure described below, see example 47.2. Amount: 11 mg. Yield 31%
MS (ESI) m/z: 430.0 [M+H]$^+$

Example 46

4-Difluoromethoxy-N—((S)-6-propylamino-5,6,7,8-tetrahydro-naphthalen-2-yl)benzenesulfonamide, hydrochloride 46.1 ((S)-6-Bromo-1,2,3,4-tetrahydro-naphthalen-2-yl)-propyl-carbamic acid tert-butyl ester ((S)-6-Bromo-1,2,3,4-tetrahydro-naphthalen-2-yl)-carbamic acid tert-butyl ester (12.2 g, 37.4 mmol) was dissolved in N,N-dimethylformamide (1000 ml). Sodium hydride (50% in oil) (1.975 g, 41.14 mmol) was added and the mixture was stirred for 15 minutes at room temperature. Propyl bromide (3.74 ml, 41.14 mmol) was added and the reaction mixture was stirred at room temperature over night. The reaction mixture was poured into a mixture of ice and H$_2$O (400 ml) and extracted twice with 200 ml of diethyl ether. The organic layer was dried over magnesium sulfate, filtered, and evaporated to dryness to yield 14.4 g of crude product. The crude product was purified by chromatography on silica gel using cyclohexane/ethyl acetate (95:5) as eluent, yielding the title compound (10.5 g, 76%).

46.2 ((S)-6-Amino-1,2,3,4-tetrahydro-naphthalen-2-yl)-propyl-carbamic acid tert-butyl ester In an inert atmosphere (argon), ((S)-6-bromo-1,2,3,4-tetrahydro-naphthalen-2-yl)propyl-carbamic acid tert-butyl ester (5.0 g, 13.58 mmol) was dissolved in toluene (150 ml) at room temperature. Tris(dibenzylideneacetone)dipalladium (622 mg, 0.68 mmol) and tri-tert-butyl-phosphane (412 mg, 2.04 mmol) were added to the reaction mixture. After 15 minutes bis-(trimethylsilyl)lithiumamide (29.86 ml of a 1 M solution in THF) was added slowly and the reaction mixture was stirred for 1 hour at 100° C. The reaction mixture was cooled and H$_2$O (150 ml) was added slowly and the aqueous mixture was extracted several times with diethyl ether. The organic layer was dried over magnesium sulfate, filtered, and evaporated to dryness to yield 6.9 g of crude product (95% yield, 57% purity).

46.3 [(S)-6-(4-Difluoromethoxy-benzenesulfonylamino)-1,2,3,4-tetrahydro-naphthalen-2-yl]-propyl-carbamic acid tert-butyl ester ((S)-6-Amino-1,2,3,4-tetrahydro-naphthalen-2-yl)-propyl-carbamic acid tert-butyl ester (1.5 g, 4.93 mmol) was dissolved in tetrahydrofuran (50 ml). Then, dimethylaminopyridine (100 mg, 0.82 mmol) and difluoromethoxy-benzenesulfonyl chloride (1.195 g, 4.93 mmol) were added and the reaction mixture was stirred over night at room temperature. The solvent was evaporated under reduced pressure, the residue treated with water and diethyl ether. The organic layer was dried over magnesium sulfate, filtered, and the solvent evaporated under reduced pressure to give the crude product (2.5 g). The crude product was purified by chromatography on silica gel using dichloromethane/methanol (100:0 to 96:4) as eluent, yielding the purified product (2.08 g, 83%).

46.4 4-Difluoromethoxy-N—((S)-6-propylamino-5,6,7,8-tetrahydro-naphthalen-2-yl)benzenesulfonamide, hydrochloride

[(S)-6-(4-Difluoromethoxy-benzenesulfonylamino)-1,2,3,4-tetrahydro-naphthalen-2-yl]-propyl-carbamic acid tert-butyl ester (2.08 g, 4.07 mmol) were dissolved in dichloromethane (100 ml). Trifluoroacetic acid (10 ml) was added and the reaction mixture was stirred at room temperature for 1 hour. The reaction mixture was evaporated to dryness. Diethyl ether (100 ml) was added and the mixture was extracted with saturated NaHCO$_3$ solution. To the organic layer was added ethereal hydrochloride solution and the solvent evaporated. To the residue was added diethyl ether (25 ml) and the resulting crystalline product was filtered off to give pure product (1.41 g, 77% yield).

ESI-MS: 411.15 [M+H]$^+$ $^1$H-NMR (DMSO-d$_6$, 400 MHz): δ [ppm] 10.25 (s, 1H), 9.0 (m, 2H), 7.8 (d, 2H), 7.35 (t, J=70 Hz, 1H), 7.3 (d, 2H), 7.0 (d, 1H), 6.9 (d, 1H), 6.85 (s, 1H), 3.4 (m, 1H), 3.1 (dd, 1H), 2.95 (m, 2H), 2.75 (m, 3H), 2.2 (m, 1H), 1.7 (m, 3H), 0.9 (t, 3H).

Example 47

N—((S)-6-Propylamino-5,6,7,8-tetrahydro-naphthalen-2-yl)-4-(2,2,2-trifluoro-ethyl)benzenesulfonamide, hydrochloride

47.1 Propyl-{(S)-6-[4-(2,2,2-trifluoro-ethyl)-benzenesulfonylamino]-1,2,3,4-tetrahydronaphthalen-2-yl}-carbamic acid tert-butyl ester ((S)-6-Amino-1,2,3,4-tetrahydro-naphthalen-2-yl)-propyl-carbamic acid tert-butyl ester (720 mg, 2.37 mmol) was dissolved in tetrahydrofurane (50 ml). Then, dimethylamino pyridine (100 mg, 0.82 mmol) and 4-(2,2,2-trifluoro-ethyl) benzenesulfonyl chloride (761 mg, 2.37 mmol) were added and the reaction mixture was stirred for 30 minutes at room temperature. The solvent was evaporated under reduced pressure, the residue treated with water and diethyl ether. The organic layer was dried over magnesium sulfate, filtered, and the solvent evaporated under reduced pressure to give the crude product (1.22 g, 95% purity, 93% yield).

47.2 N—((S)-6-Propylamino-5,6,7,8-tetrahydro-naphthalen-2-yl)-4-(2,2,2-trifluoro-ethyl)benzenesulfonamide, hydrochloride Propyl-{(S)-6-[4-(2,2,2-trifluoro-ethyl)-benzenesulfonylamino]-1,2,3,4-tetrahydronaphthalen-2-yl}-carbamic acid tert-butyl ester (1.22 g, 2.07 mmol) was dissolved in dichloromethane (40 ml). Trifluoroacetic acid (2 ml) was added and the reaction mixture was stirred at room temperature for 1 hour. The reaction mixture was evaporated to dryness. Diethyl ether (100 ml) was added and the mixture was extracted with saturated NaHCO$_3$ solution. The organic layer was dried over magnesium sulfate, filtered, and the solvent evaporated under reduced pressure. The residue was dissolved with ethyl acetate and ethereal hydrochloride solution was added. The crystalline product was filtered off to give pure product (625 mg, 65% yield).

ESI-MS: 427.15 [M+H]$^+$ $^1$H-NMR (DMSO-d$_6$, 400 MHz): δ [ppm] 10.25 (s, 1H), 8.9 (m, 2H), 7.8 (d, 2H), 7.55 (d, 2H), 7.0 (d, 1H), 6.9 (d, 1H), 6.85 (s, 1H), 3.75 (q, 2H), 3.35 (m, 1H), 3.1 (dd, 1H), 2.95 (m, 2H), 2.75 (m, 3H), 2.2 (m, 1H), 1.95 (m, 4H), 1.7 (m, 3H), 0.95 (t, 3H).

The procedure described in example 46 was used to prepare the compounds of examples 48 to 57. The compounds were characterized by the following physical data:

Example 48

4-(2,2-Difluoro-cyclopropyl)-N—((S)-6-propylamino-5,6,7,8-tetrahydro-naphthalen-2-yl)benzenesulfonamide, hydrochloride

ESI-MS: 421.35 [M+H]$^+$

Example 49

N—((S)-6-Propylamino-5,6,7,8-tetrahydro-naphthalen-2-yl)-4-pyrrolidin-1-ylbenzenesulfonamide, hydrochloride

ESI-MS: 414.25 [M+H]$^+$ $^1$H-NMR (DMSO-d$_6$, 400 MHz): δ [ppm] 9.8 (s, 1H), 8.85 (m, 2H), 7.5 (d, 2H), 6.95 (d, 1H), 6.9 (d, 1H), 6.85 (s, 1H), 6.55 (d, 1H), 3.35 (m, 1H), 3.25 (m, 4H), 3.1 (dd, 1H), 2.95 (m, 2H), 2.75 (m, 3H), 2.2 (m, 1H), 1.95 (m, 4H), 1.7 (m, 3H), 0.95 (t, 3H).

Example 50

4-Dimethylamino-N—((S)-6-propylamino-5,6,7,8-tetrahydro-naphthalen-2-yl)benzenesulfonamide, hydrochloride

ESI-MS: 388.25 [M+H]$^+$ $^1$H-NMR (DMSO-d$_6$, 400 MHz): δ [ppm] 9.85 (s, 1H), 9.05 (m, 2H), 7.55 (d, 2H), 6.95 (d, 1H), 6.9 (d, 1H), 6.85 (s, 1H), 6.7 (d, 2H), 3.35 (m, 1H), 3.1 (dd, 1H), 2.95 (m, 7H), 2.75 (m, 4H), 2.2 (m, 1H), 1.65 (m, 3H), 0.95 (t, 3H).

Example 51

4-(3-Fluoro-propyl)-N—((S)-6-propylamino-5,6,7,8-tetrahydro-naphthalen-2-yl)benzenesulfonamide ESI-MS: 405.2 [M+H]$^+$
$^1$H-NMR (DMSO-d$_6$, 400 MHz): δ [ppm] 10.1 (m, 1H), 8.9 (m, 1H), 7.7 (d, 2H), 7.4 (d, 2H), 7.0 (d, 1H), 6.9 (d, 1H), 6.85 (s, 1H), 4.5 (t, 1H), 4.4 (t, 1H), 3.35 (m, 1H), 3.05 (dd, 1H), 2.9 (m, 2H), 2.75 (m, 5H), 2.2 (m, 1H), 1.95 (m, 2H), 1.65 (m, 3H), 0.95 (t, 3H).

Example 52

5-Propyl-thiophene-sulfonic acid ((S)-6-propylamino-5,6,7,8-tetrahydro-naphthalen-2-yl)amide, hydrochloride The crude product was purified by chromatography on silica gel using dichloromethane/methanol (9:1) as eluent and subsequently conversion into the hydrochloride salt.

ESI-MS: 393.15 [M+H]$^+$
$^1$H-NMR (DMSO-d$_6$, 400 MHz): δ [ppm] 10.25 (s, 1H), 8.95 (m, 2H), 7.35 (d, 1H), 7.05 (d, 1H), 6.95 (d, 1H), 6.85 (m, 2H), 3.4 (m, 1H), 3.1 (dd, 1H), 2.95 (m, 2H), 2.8 (m, 5H), 2.2 (m, 1H), 1.8-1.55 (m, 5H), 0.95 (t, 3H), 0.9 (t, 3H).

Example 53 Reference

4-Chloro-N—((S)-6-propylamino-5,6,7,8-tetrahydro-naphthalen-2-yl)-benzenesulfonamide, hydrochloride ESI-MS: 379.15 [M+H]$^+$
$^1$H-NMR (DMSO-d$_6$, 400 MHz): δ [ppm] 10.3 (s, 1H), 8.9 (m, 2H), 7.75 (d, 2H), 7.65 (d, 2H), 7.0 (d, 1H), 6.9 (d, 1H), 6.85 (s, 1H), 3.4 (m, 1H), 3.1 (dd, 1H), 2.95 (m, 2H), 2.75 (m, 3H), 2.2 (m, 1H), 1.7 (m, 3H), 0.95 (t, 3H).

Example 54 Reference

N—((S)-6-Propylamino-5,6,7,8-tetrahydro-naphthalen-2-yl)-4-trifluoromethylbenzenesulfonamide, hydrochloride ESI-MS: 413.15 [M+H]$^+$
$^1$H-NMR (DMSO-d$_6$, 400 MHz): δ [ppm] 10.45 (s, 1H), 8.9 (m, 2H), 8.0 (s, 4H), 7.0 (d, 1H), 6.9 (d, 1H), 6.85 (s, 1H), 3.4 (m, 1H), 3.1 (dd, 1H), 2.95 (m, 2H), 2.75 (m, 3H), 2.2 (m, 1H), 1.65 (m, 3H), 0.95 (t, 3H).

Example 55

4-((S)-2-Fluoro-1-methyl-ethyl)-N—((S)-6-propylamino-5,6,7,8-tetrahydro-naphthalen-2-yl)benzenesulfonamide, hydrochloride ESI-MS: 405.15 [M+H]$^+$
$^1$H-NMR (DMSO-d$_6$, 400 MHz): δ [ppm] 10.2 (s, 1H), 8.9 (m, 2H), 7.75 (d, 2H), 7.5 (d, 2H), 7.0 (d, 1H), 6.9 (d, 1H), 6.85 (s, 1H), 4.6 (d, 1H), 4.45 (d, 1H), 3.4 (m, 1H), 3.2 (m, 1H), 3.1 (dd, 1H), 2.9 (m, 2H), 2.75 (m, 3H), 2.2 (m, 1H), 1.7 (m, 3H), 1.2 (d, 3H), 0.95 (t, 3H).

Example 56

4-((R)-2-Fluoro-1-methyl-ethyl)-N—((S)-6-propylamino-5,6,7,8-tetrahydro-naphthalen-2-yl)benzenesulfonamide, hydrochloride ESI-MS: 405.15 [M+H]$^+$
$^1$H-NMR (DMSO-d$_6$, 400 MHz): δ [ppm] 10.2 (s, 1H), 8.85 (m, 2H), 7.75 (d, 2H), 7.5 (d, 2H), 7.0 (d, 1H), 6.9 (d, 1H), 6.85 (s, 1H), 4.6 (d, 1H), 4.45 (d, 1H), 3.4 (m, 1H), 3.2 (m, 1H), 3.1 (dd, 1H), 2.95 (m, 2H), 2.75 (m, 3H), 2.2 (m, 1H), 1.7 (m, 3H), 1.2 (d, 3H), 0.95 (t, 3H).

Example 57

4-(1-Methyl-1H-pyrazol-4-yl)-N—((S)-6-propylamino-5,6,7,8-tetrahydro-naphthalen-2-yl)benzenesulfonamide, hydrochloride ESI-MS: 425.15 [M+H]$^+$
$^1$H-NMR (DMSO-d$_6$, 400 MHz): δ [ppm] 10.15 (s, 1H), 9.0 (m, 2H), 8.35 (s, 1H), 7.7 (s, 4H), 7.0 (d, 1H), 6.9 (d, 1H), 6.85 (s, 1H), 3.9 (s, 3H), 3.35 (m, 1H), 3.1 (dd, 1H), 2.9 (m, 2H), 2.75 (m, 3H), 2.2 (m, 1H), 1.65 (m, 3H), 0.95 (t, 3H).

Example 58

4-(3-Fluoro-propyl)-N—((R)-6-propylamino-5,6,7,8-tetrahydro-naphthalen-2-yl)benzenesulfonamide, hydrochloride

58.1 ((R)-6-Bromo-1,2,3,4-tetrahydro-naphthalen-2-yl)-carbamic acid tert-butyl ester To (R)-6-bromo-1,2,3,4-tetrahydro-naphthalen-2-ylamine (5.252 g, 20.0 mmol) and di-tert-butyldicarbonate (5.456 g, 25.0 mmol) in dichloromethane (100 ml) was added triethylamine (21.12 ml, 152.34 mmol). The reaction mixture was stirred over night at room temperature and then extracted twice with aqueous NaHCO$_3$ solution. The organic layer was dried over magnesium sulfate, filtered, and evaporated to dryness to yield the pure product (6.4 g, 98% yield).

ESI-MS: 270.05/272.05 [M+H−C(CH$_3$)$_3$]$^+$

58.2 ((R)-6-Bromo-1,2,3,4-tetrahydro-naphthalen-2-yl)-propyl-carbamic acid tert-butyl ester ((R)-6-Bromo-1,2,3,4-tetrahydro-naphthalen-2-yl)-carbamic acid tert-butyl ester (3.4 g, 10.42 mmol) was dissolved in dimethylformamide (40 ml). Sodium hydride (60% in oil) (625 mg, 15.63 mmol) was added and stirred for 1 hour at 0° C. Propyl bromide (1.04 ml, 11.46 mmol) dissolved in N,N-dimethylformamide (DMF) was added at 0° C. to the reaction mixture. After 2 hours propyl bromide was added (0.2 ml, 2.20 mmol) and the reaction mixture was stirred at room temperature over night. To the reaction mixture was added water and three times extracted with diethyl ether. The organic layer was dried over magnesium sulfate, filtered, and evaporated to dryness to yield the crude product. The crude product was purified by chromatography on silica gel using cyclohexane/ethyl acetate (92:8) as eluent, yielding the purified product (3.54 g, 92%).
ESI-MS: 312.05/314.05 [M+H–C(CH$_3$)$_3$]$^+$

58.3 ((R)-6-Amino-1,2,3,4-tetrahydro-naphthalen-2-yl)-propyl-carbamic acid tert-butyl ester Under an inert atmosphere (argon), ((R)-6-bromo-1,2,3,4-tetrahydro-naphthalen-2-yl)-propyl-carbamic acid tert-butyl ester (3.54 g, 9.61 mmol) was dissolved in toluene (50 ml) at room temperature. Tris(dibenzylideneacetone)dipalladium (440 mg, 0.48 mmol) and tri-tert-butyl-phosphane (292 mg, 1.44 mmol) were added to the reaction mixture. After 10 minutes bis-(trimethylsilyl)lithiumamide (21.14 ml of a 1 molar solution in THF) was added slowly and the reaction mixture was stirred for 1 hour at 100° C. The reaction mixture was cooled and slowly water was added. The organic phase was extracted twice with water. The organic layer was dried over magnesium sulfate, filtered, and evaporated to dryness to yield 6.06 g of crude product (93% yield, 45% purity).
ESI-MS: 249.15 [M+H–C(CH$_3$)$_3$]$^+$

58.4 {(R)-6-[4-(3-Fluoro-propyl)-benzenesulfonylamino]-1,2,3,4-tetrahydro-naphthalen-2-yl}-propyl-carbamic acid tert-butyl ester ((R)-6-Amino-1,2,3,4-tetrahydro-naphthalen-2-yl)-propyl-carbamic acid tert-butyl ester (200 mg, 0.66 mmol) was dissolved in tetrahydrofuran (10 ml). Then, dimethylamino pyridine (80 mg, 0.66 mmol) and 4-(3-fluoro-propyl)-benzenesulfonyl chloride (156 mg, 0.66 mmol) were added and the reaction mixture was stirred over night at room temperature. The solvent was evaporated under reduced pressure, the residue treated with water and ethyl acetate. The organic layer was dried over magnesium sulfate, filtered, and the solvent evaporated under reduced pressure to give the crude product. The crude product was purified with silica gel chromatography with dichloromethane/methanol (100:0 to 96:4) as eluent, yielding the purified product (150 mg, 45%).
ESI-MS: 455.15 [M+H–C(CH$_3$)$_3$]$^+$

58.5 4-(3-Fluoro-propyl)-N—((R)-6-propylamino-5,6,7,8-tetrahydro-naphthalen-2-yl)benzenesulfonamide, hydrochloride Following the procedure analogous to that described in example 46.4, the title compound was obtained.
ESI-MS: 405.55 [M+H]$^+$
$^1$H-NMR (CH$_3$OH-d$_4$, 400 MHz): δ [ppm] 7.55 (d, 2H), 7.25 (d, 2H), 6.9 (d, 2H), 6.8 (s, 1H), 4.35 (t, 1H), 4.25 (t, 1H), 3.35 (m, 1H), 3.1 (dd, 1H), 3.0 (t, 2H), 2.75 (m, 3H), 2.65 (m, 3H), 2.2 (m, 1H), 1.85 (m, 2H), 1.65 (m, 3H), 0.95 (t, 3H).

Example 59

4-(2-Fluoro-ethyl)-N—((R)-6-propylamino-5,6,7,8-tetrahydro-naphthalen-2-yl)benzenesulfonamide, hydrochloride Following the procedure analogous to that described in example 46, the title compound was obtained.
ESI-MS: 391.15 [M+H]$^+$
$^1$H-NMR (CH$_3$OH-d$_4$, 400 MHz): δ [ppm] 7.6 (d, 2H), 7.3 (d, 2H), 6.9 (d, 1H), 6.8 (m, 2H), 4.6 (t, 1H), 4.45 (t, 1H), 3.35 (m, 1H), 3.1 (dd, 1H), 2.95 (m, 3H), 2.9 (m, 1H), 2.75 (m, 3H), 2.2 (m, 1H), 1.65 (m, 3H), 0.95 (t, 3H).

Example 60

4-Acetyl-N—((S)-6-propylamino-5,6,7,8-tetrahydro-naphthalen-2-yl)-benzenesulfonamide Following the procedure analogous to that described in example 46, the title compound was obtained.
ESI-MS: 387.15 [M+H]$^+$
$^1$H-NMR (DMSO-d$_6$, 400 MHz): δ [ppm] 8.05 (d, 2H), 7.85 (d, 2H), 6.9 (d, 1H), 6.8 (d, 1H), 6.75 (s, 1H), 3.4 (m, 1H), 2.9 (m, 2H), 2.65 (m, 6H), 2.45 (m, 1H), 1.95 (m, 1H), 1.45 (m, 3H), 0.85 (t, 3H).

Example 61

4-(1-Hydroxy-1-methyl-ethyl)-N—((S)-6-propylamino-5,6,7,8-tetrahydro-naphthalen-2-yl)-benzenesulfonamide, acetate

61.1 {(S)-6-[4-(1-Hydroxy-1-methyl-ethyl)-benzenesulfonylamino]-1,2,3,4-tetrahydronaphthalen-2-yl}-propyl-carbamic acid tert-butyl ester

[(S)-6-(4-Acetyl-benzenesulfonylamino)-1,2,3,4-tetrahydro-naphthalen-2-yl]-propyl-carbamic acid tert-butyl ester (400 mg, 0.71 mmol) was dissolved in tetrahydrofuran (15 ml) at 0° C. A 3 molar solution of methylmagnesium bromide in diethyl ether (2.82 ml, 7.12 mmol) was added slowly and the reaction mixture was stirred for 3 hours at room temperature. Another portion of a 3 molar solution of methylmagnesium bromide in diethyl ether (0.5 ml, 1.26 mmol) was added. Since no further conversion was observed, the reaction mixture was evaporated to dryness. Water (20 ml) was added to the residue and the aqueous phase was extracted with diethyl ether (50 ml) twice. The organic layer was dried over magnesium sulfate, filtered, and evaporated to dryness to yield the crude product. The crude product was purified by MPLC chromatography using dichloromethane/methanol (100:0-70:30) as eluent, yielding the product (300 mg, 47% purity, 39%).

61.2 4-(1-Hydroxy-1-methyl-ethyl)-N—((S)-6-propylamino-5,6,7,8-tetrahydro-naphthalen-2-yl)-benzenesulfonamide, acetate {(S)-6-[4-(1-Hydroxy-1-methyl-ethyl)-benzenesulfonylamino]-1,2,3,4-tetrahydronaphthalen-2-yl}-propyl-carbamic acid tert-butyl ester (115 mg, 47% purity, 0.11 mmol) was dissolved in dichloromethane (10 ml). Trifluoroacetic acid (1 ml) was added and the reaction mixture was stirred at room temperature for 1 hour. The reaction mixture was evaporated to dryness. Ethyl acetate (15 ml) was added and extracted with saturated NaHCO$_3$ solution (5 ml). The organic layer was dried over magnesium sulfate, filtered, and evaporated to dryness to yield the crude product (65 mg). The crude product was purified via HPLC chromatography yielding the purified product (22 mg, 42%).
ESI-MS: 403.2 [M+H]$^+$

Example 62

4-(1-Fluoro-1-methyl-ethyl)-N—((S)-6-propylamino-5,6,7,8-tetrahydro-naphthalen-2-yl)benzenesulfonamide, trifluoro acetate

62.1 {(S)-6-[4-(1-Fluoro-1-methyl-ethyl)-benzenesulfonylamino]-1,2,3,4-tetrahydronaphthalen-2-yl}-propyl-carbamic acid tert-butyl ester {(S)-6-[4-(1-Hydroxy-1-methyl-ethyl)-benzenesulfonylamino]-1,2,3,4-tetrahydronaphthalen-2-yl}-propyl-carbamic acid tert-butyl ester (50 mg, 92% purity, 0.09 mmol) was dissolved in dichloromethane (10 ml) and cooled to −78° C. Diethylaminosulfurtrifluoride (59 mg, 0.36 mmol) was added and the reaction mixture was allowed to reach 0° C. over 30 minutes. The reaction mixture was evaporated to dryness. The residue was dissolved in saturated NaHCO$_3$ solution (10 ml) and extracted with diethyl ether (20 ml). The organic layer was dried over magnesium sulfate, filtered, and evaporated to dryness to yield the crude product (49 mg, 83% purity, 88%).

62.1 4-(1-Fluoro-1-methyl-ethyl)-N—((S)-6-propylamino-5,6,7,8-tetrahydro-naphthalen-2-yl)-benzenesulfonamide, trifluoro acetate {(S)-6-[4-(1-Fluoro-1-methyl-ethyl)-benzenesulfonylamino]-1,2,3,4-tetrahydronaphthalen-2-yl}-propyl-carbamic acid tert-butyl ester (49 mg, 83% purity, 0.08 mmol) was dissolved in dichloromethane (10 ml). Trifluoroacetic acid (1 ml) was added and the reaction mixture was stirred at room temperature for 1 hour. The reaction mixture was evaporated to dryness. Ethyl acetate (15 ml) was added and extracted with saturated NaHCO$_3$ solution (5 ml). The organic layer was dried over magnesium sulfate, filtered, and evaporated to dryness to yield the crude product (33 mg). The crude product was purified via HPLC chromatography yielding the purified product (19 mg, 46%).

ESI-MS: 405.25 [M+H]$^+$ $^1$H-NMR (DMSO-d$_6$, 400 MHz): δ [ppm] 10.25 (s, 1H), 8.45 (m, 2H), 7.8 (d, 2H), 7.6 (d, 2H), 7.0 (d, 1H), 6.9 (d, 1H), 6.85 (s, 1H), 3.4 (m, 1H), 3.05 (dd, 1H), 2.95 (m, 2H), 2.75 (m, 3H), 2.15 (m, 1H), 1.65 (m, 9H), 0.95 (t, 3H).

The procedure described in example 46 was used to prepare the compounds of examples 63 to 70. The compounds were characterized by the following physical data:

Example 63

N—((S)-6-Ethylamino-5,6,7,8-tetrahydro-naphthalen-2-yl)-4-trifluoromethoxybenzenesulfonamide, hydrochloride

ESI-MS: 415.15 [M+H]$^+$ $^1$H-NMR (DMSO-d$_6$, 400 MHz): δ [ppm] 10.35 (s, 1H), 8.95 (m, 2H), 7.9 (d, 2H), 7.55 (d, 2H), 7.0 (d, 1H), 6.9 (d, 1H), 6.85 (s, 1H), 3.35 (m, 1H), 3.05 (m, 3H), 2.75 (m, 3H), 2.2 (m, 1H), 1.7 (m, 1H), 1.25 (t, 3H).

Example 64

N—((S)-6-Ethylamino-5,6,7,8-tetrahydro-naphthalen-2-yl)-4-isopropyl-benzenesulfonamide, hydrochloride

ESI-MS: 373.15 [M+H]$^+$ $^1$H-NMR (DMSO-d$_6$, 400 MHz): δ [ppm] 10.15 (s, 1H), 8.95 (m, 2H), 7.7 (d, 2H), 7.45 (d, 2H), 7.0 (d, 1H), 6.9 (d, 1H), 6.85 (s, 1H), 3.4 (m, 1H), 3.05 (m, 3H), 2.95 (sept, 1H), 2.75 (m, 3H), 2.2 (m, 1H), 1.7 (m, 1H), 1.25 (t, 3H), 1.2 (d, 6H).

Example 65

N—[(S)-6-(2-Fluoro-ethylamino)-5,6,7,8-tetrahydro-naphthalen-2-yl]-4-trifluoromethoxybenzenesulfonamide, hydrochloride

ESI-MS: 433.15 [M+H]$^+$ $^1$H-NMR (DMSO-d$_6$, 400 MHz): δ [ppm] 10.35 (s, 1H), 9.3 (m, 2H), 7.9 (d, 2H), 7.55 (d, 2H), 7.0 (d, 1H), 6.9 (d, 1H), 6.85 (s, 1H), 4.85 (t, 1H), 4.75 (t, 1H), 3.45 (m, 2H), 3.15 (dd, 1H), 2.75 (m, 4H), 2.25 (m, 1H), 1.75 (m, 1H).

Example 66

N—[(S)-6-(2-Fluoro-ethylamino)-5,6,7,8-tetrahydro-naphthalen-2-yl]-4-isopropylbenzenesulfonamide, hydrochloride

ESI-MS: 391.15 [M+H]$^+$ $^1$H-NMR (DMSO-d$_6$, 400 MHz): δ [ppm] 10.15 (s, 1H), 9.3 (m, 2H), 7.7 (d, 2H), 7.45 (d, 2H), 7.0 (d, 1H), 6.9 (d, 1H), 6.85 (s, 1H), 4.85 (t, 1H), 4.75 (t, 1H), 3.4 (m, 2H), 3.1 (dd, 1H), 2.95 (m, 1H), 2.75 (m, 4H), 2.25 (m, 1H), 1.75 (m, 1H), 1.2 (d, 6H).

Example 67

N—[(S)-6-(3-Fluoro-propylamino)-5,6,7,8-tetrahydro-naphthalen-2-yl]-4-trifluoromethoxybenzenesulfonamide, hydrochloride

ESI-MS: 447.15 [M+H]$^+$ $^1$H-NMR (DMSO-d$_6$, 400 MHz): δ [ppm] 10.35 (s, 1H), 9.05 (m, 2H), 7.9 (d, 2H), 7.55 (d, 2H), 7.0 (d, 1H), 6.9 (d, 1H), 6.85 (s, 1H), 4.65 (t, 1H), 4.5 (t, 1H), 3.45 (m, 1H), 3.1 (m, 3H), 2.75 (m, 3H), 2.2 (m, 1H), 2.05 (m, 2H), 1.75 (m, 1H).

Example 68

N—[(S)-6-(3-Fluoro-propylamino)-5,6,7,8-tetrahydro-naphthalen-2-yl]-4-isopropylbenzenesulfonamide, hydrochloride

ESI-MS: 405.15 [M+H]$^+$ $^1$H-NMR (DMSO-d$_6$, 400 MHz): δ [ppm] 10.15 (s, 1H), 9.1 (m, 2H), 7.7 (d, 2H), 7.45 (d, 2H), 7.0 (d, 1H), 6.9 (d, 1H), 6.85 (s, 1H), 4.65 (t, 1H), 4.5 (t, 1H), 3.4 (m, 1H), 3.1 (m, 3H), 2.95 (sept, 1H), 2.75 (m, 3H), 2.2 (m, 1H), 2.1 (m, 2H), 1.75 (m, 1H), 1.2 (d, 6H).

Example 69

N—((S)-6-Ethylamino-5,6,7,8-tetrahydro-naphthalen-2-yl)-4-(2-oxo-pyrrolidin-1-yl)benzenesulfonamide, hydrochloride

ESI-MS: 414.2 [M+H]$^+$

Example 70

N—((S)-6-Ethylamino-5,6,7,8-tetrahydro-naphthalen-2-yl)-4-pyrrolidin-1-ylbenzenesulfonamide, hydrochloride ESI-MS: 400.15 [M+H]$^+$
$^1$H-NMR (DMSO-d$_6$, 400 MHz): δ [ppm] 9.8 (s, 1H), 8.95 (m, 2H), 7.55 (d, 2H), 6.95 (d, 1H), 6.9 (d, 1H), 6.85 (s, 1H), 6.55 (d, 2H), 3.4 (m, 1H), 3.25 (m, 4H), 3.05 (m, 3H), 2.75 (m, 3H), 2.2 (m, 1H), 1.95 (m, 4H), 1.7 (m, 1H), 1.25 (t, 3H).

Example 71

4-Isopropyl-N-(3-propylamino-chroman-7-yl)-benzenesulfonamide, hydrochloride

71.1 7-Methoxy-2H-chromene-3-carbonitrile

To 2-hydroxy-4-methoxy-benzaldehyde (10.0 g, 65.72 mmol) and DABCO (1,4-diazabicyclo[2.2.2]octane) (1.84 g, 16.43 mmol) was added acrylonitrile (17.44 g, 328.62 mmol). The reaction mixture was refluxed for 20 h. The reaction mixture was diluted with ethyl acetate and the resulting rheum was separated. The organic phase was washed with a 1 molar solution of NaOH and then with a 1 molar solution of HCl. The organic layer was dried over magnesium sulfate, filtered, and the solvent evaporated under reduced pressure to give the crude product (8.89 g, 72% yield).

71.2 7-Methoxy-2H-chromene-3-carboxylic acid

To 7-methoxy-2H-chromene-3-carbonitrile (8.89 g, 47.49 mmol) was added a 10 molar solution of NaOH (40 ml). The reaction mixture was refluxed for 6 h. After cooling to room temperature, the reaction mixture was adjusted to pH=2 with concentrated HCl. The precipitate was filtered off and washed with water to give the pure product (6.07 g, 62% yield).

71.3 7-Methoxy-chroman-3-one

7-Methoxy-2H-chromene-3-carboxylic acid (6.07 g, 29.44 mmol) and triethylamine (4.8 ml, 34.48 mmol) were dissolved in dichloromethane (60 ml). Diphenylphosphoryl azide (6.54 ml, 29.44 mmol) was dissolved in toluene (24 ml) and added dropwise to the reaction mixture while slowly increasing the temperature to 60° C. 60 ml of toluene were added and the reaction mixture was stirred at 70° C. for 90 minutes. A 10 molar HCl solution (28 ml) was then added and the reaction mixture was stirred at reflux for 2 hours. After cooling to room temperature the phases were separated. The organic phase was extracted with an aq. NaHCO$_3$ solution. The organic layer was dried over magnesium sulfate, filtered, and the solvent evaporated under reduced pressure. The crude product was purified by chromatography using silica gel with cyclohexane/ethyl acetate (100:0 to 95:5) as eluent, yielding the title product (1.47 g, 24% yield).
ESI-MS: 179.05 [M+H]$^+$

71.4 (7-Methoxy-chroman-3-yl)-propyl-amine

7-Methoxy-chroman-3-one (1.47 g, 8.25 mmol) and propylamine (748 μl, 9.07 mmol) were dissolved in dichloromethane (20 ml). Acetic acid (710 μl, 12.37 mmol) and sodium trisacetoxyborohydride (3.5 g, 16.51 mmol) were sequentially added to the reaction mixture and the mixture was stirred for 1 hour at room temperature. To the reaction mixture was added dichloromethane and water. The aqueous phase was made alkaline with a 1 molar solution of NaOH. The aqueous phase was separated and extracted (3 times) with dichloromethane. The combined organic phases were dried over magnesium sulfate, filtered, and evaporated to dryness to yield the crude product (1.68 g, 92% yield).
ESI-MS: 222.15 [M+H]$^+$

71.5 3-Propylamino-chroman-7-ol, hydrobromide (7-Methoxy-chroman-3-yl)-propyl-amine (1.3 g, 5.87 mmol) was dissolved in dichloromethane (100 ml) and cooled to −78° C. Boron tribromide (11.7 ml, 122.52 mmol) was added and the reaction mixture was allowed to reach room temperature over night. The reaction mixture was cooled to −78° C. and a mixture of methanol and dichloromethane (2:3) was slowly added. The reaction mixture was allowed to reach room temperature and was then evaporated to dryness to yield the crude product (1.69 g, 5.86 mmol)
ESI-MS: 208.15 [M+H]$^+$

71.6 (7-Hydroxy-chroman-3-yl)-propyl-carbamic acid tert-butyl ester

3-Propylamino-chroman-7-ol, hydrobromide (1.69 g, 5.86 mmol) was dissolved in dichloromethane (50 ml). Subsequently, triethylamine (4.08 ml, 29.32 mmol) and ditert-butyldicarbonate (1.28 g, 5.86 mmol) were added and the reaction mixture was stirred at room temperature over night. The reaction mixture was concentrated in vacuo and then dissolved in diethyl ether and water. The aqueous phase was adjusted to pH=4 with a 5% citric acid solution. The organic phase was then separated and washed with water and brine. The organic layer was dried over magnesium sulfate, filtered, and evaporated to dryness to yield the desired product (1.61 g, 89%).
ESI-MS: 252.15 [M+H−C(CH$_3$)$_3$]$^+$

71.7 Trifluoro-methanesulfonic acid 3-(tert-butoxycarbonyl-propyl-amino)-chroman-7-yl ester (7-Hydroxy-chroman-3-yl)-propyl-carbamic acid tert-butyl ester (1.58 g, 5.14 mmol) and triethylamine (2.15 ml, 15.42 mmol) were dissolved in dichloromethane (40 ml) and cooled to −78° C. Trifluoromethanesulfonic anhydride (1.45 g, 5.14 mmol) was dissolved in dichloromethane (10 ml) and slowly added to the reaction mixture. Stirring was continued for 2 hours. The reaction mixture was allowed to reach room temperature, diluted with dichloromethane and washed twice with aqueous citric acid solution (pH=4). The organic phase was then separated and washed with brine. The organic layer was dried over magnesium sulfate, filtered, and evaporated to dryness to yield the desired product (2.57 g, 88% purity, 100% yield).
ESI-MS: 384.05 [M+H−C(CH$_3$)$_3$]$^+$

71.8 Trifluoro-methanesulfonic acid 3-propylamino-chroman-7-yl ester

Trifluoro-methanesulfonic acid 3-(tert-butoxycarbonyl-propyl-amino)-chroman-7-yl ester (2.1 g, 4.78 mmol) was dissolved in dichloromethane (30 ml). Trifluoroacetic acid (3 ml) was added and the reaction mixture was stirred at room temperature for 3 hours. The reaction mixture was evaporated to dryness. Dichloromethane was added (twice) and the reaction mixture was evaporated to dryness to give the product (2.6 g, 65% purity).

ESI-MS: 340.05 [M+H]$^+$

71.9 Trifluoro-methanesulfonic acid 3-(benzyl-propyl-amino)-chroman-7-yl ester Trifluoro-methanesulfonic acid 3-propylamino-chroman-7-yl ester (1.62 g, 4.78 mmol) and benzaldehyde (975 µl, 9.56 mmol) were dissolved in dichloromethane (60 ml). Acetic acid (710 µl, 12.37 mmol) and sodium trisacetoxyborohydride (3.04 g, 14.34 mmol) were sequentially added to the reaction mixture and stirred over the weekend at room temperature. Dichloromethane and water were added to the reaction mixture. The aqueous phase was adjusted to a pH=6 with a 1 molar solution of NaOH. The organic phase was separated, dried over magnesium sulfate, filtered, and evaporated to dryness to yield the crude product. The crude product was purified by chromatography on silica gel using cyclohexane/ethyl acetate (100:0 to 95:5) as eluent, yielding the purified product (1.24 g, 50% purity, 30% yield).

ESI-MS: 430.15 [M+H]$^+$

71.10 N-3-Benzyl-N-3-propyl-chroman-3,7-yl-diamine

In an inert atmosphere (argon), trifluoromethanesulfonic acid 3-(benzyl-propyl-amino)-chroman-7-yl ester (1.25 g, 2.91 mmol), benzhydrylideneamine (528 mg, 2.91 mmol) and sodium tert.-butoxide (420 mg, 4.37 mmol) were dissolved in toluene (15 ml) at room temperature. Tris(dibenzylideneacetone)dipalladium (320 mg, 0.35 mmol) and BINAP (2,2'-bis(diphenylphosphino)-1,1'-binaphthyl) (326 mg, 0.52 mmol) were dissolved in toluene (5 ml) and then added to the reaction mixture. The reaction mixture was refluxed under stirring for 4 hours. The reaction mixture was cooled and filtered. The reaction mixture was evaporated to dryness. The residue was treated with tetrahydrofuran and a 1 molar solution of HCl (40 ml). The tetrahydrofuran was evaporated and diethyl ether was added. The aqueous phase was separated and twice extracted with diethyl ether. The aqueous phase was made alkaline with a 1 molar solution of NaOH and then extracted several times with diethyl ether. The combined organic layers were dried over magnesium sulfate, filtered, and evaporated to dryness to yield the crude product. The crude product was purified by chromatography on silica gel with dichloromethane/methanol (100:0 to 95:5) as eluent, yielding the product (110 mg, 35% purity, 5% yield).

ESI-MS: 297.15 [M+H]$^+$

71.11 N-[3-(Benzyl-propyl-amino)-chroman-7-yl]-4-isopropyl-benzenesulfonamide N-3-Benzyl-N-3-propyl-chroman-3,7-yl-diamine (110 mg, 0.13 mmol) was dissolved in tetrahydrofuran (5 ml). Subsequently, dimethylaminopyridine (17 mg, 0.13 mmol) and 4-isopropyl-benzenesulfonyl chloride (57 mg, 0.26 mmol) were added and the reaction mixture stirred was over night at room temperature. The solvent was evaporated under reduced pressure, the residue treated with water and diethyl ether. The organic layer was dried over magnesium sulfate, filtered, and the solvent evaporated under reduced pressure to give the crude product (2.5 g). The crude product was purified by chromatography on silica gel using dichloromethane/methanol (100:0 to 0:100) as eluent, yielding the purified product (25 mg, 40%).

ESI-MS: 479.25 [M+H]$^+$

71.12 4-Isopropyl-N-(3-propylamino-chroman-7-yl)-benzenesulfonamide, hydrochloride A mixture of N-[3-(benzylpropyl-amino)-chroman-7-yl]-4-isopropylbenzenesulfonamide (25 mg, 0.05 mmol) and 10% palladium on carbon (3 mg) in methanol (5 ml) was hydrogenated over night. The catalyst was filtered off, and the solvent was removed under vacuum to yield the crude product. The crude product was purified by reversed phase chromatography. The purified product was then converted into its hydrochloride salt (5.8 mg, 26% yield).

ESI-MS: 389.15 [M+H]$^+$ $^1$H-NMR, measured from free base: $^1$H-NMR (CH$_3$OH-d$_4$, 400 MHz): δ [ppm] 7.75 (d, 2H), 7.4 (d, 2H), 7.05 (d, 1H), 6.75 (m, 2H), 4.35 (m, 1H), 4.25 (m, 1H), 3.8 (m, 1H), 3.35 (dd, 1H), 3.1 (m, 2H), 2.95 (m, 2H), 1.75 (m, 2H), 1.25 (d, 6H), 1.05 (t, 3H).

The procedure described in example 46 was used to prepare the compounds of examples 72 and 73. The compounds were characterized by the following physical data

Example 72

4-((S)-2-Fluoro-1-methyl-ethyl)-N—((R)-6-propylamino-5,6,7,8-tetrahydro-naphthalen-2-yl)benzenesulfonamide, hydrochloride

ESI-MS: 405.15 [M+H]$^+$ $^1$H-NMR (CH$_3$OH-d$_4$, 400 MHz): δ [ppm] 7.6 (d, 2H), 7.3 (d, 2H), 6.9 (d, 1H), 6.85 (d, 1H), 6.8 (s, 1H), 4.45 (d, 1H), 4.3 (d, 1H), 3.35 (m, 1H), 3.1 (m, 2H), 3.0 (m, 2H), 2.75 (m, 3H), 2.2 (m, 1H), 1.65 (m, 3H), 1.2 (d, 3H), 0.95 (t, 3H).

Example 73

N—((R)-6-Propylamino-5,6,7,8-tetrahydro-naphthalen-2-yl)-4-(2,2,2-trifluoro-1-methyl-ethyl)benzenesulfonamide

ESI-MS: 441.15 [M+H]$^+$ $^1$H-NMR (CH$_3$OH-d$_4$, 400 MHz): δ [ppm] 7.75 (d, 2H), 7.5 (d, 2H), 6.95 (d, 1H), 6.85 (d, 1H), 6.8 (s, 1H), 3.7 (m, 1H), 2.95 (m, 2H), 2.7 (m, 4H), 2.5 (m, 1H), 2.1 (m, 1H), 1.55 (m, 3H), 1.5 (d, 3H), 1.0 (t, 3H).

Example 74

4-Difluoromethoxy-N—((S)-6-propylamino-5,6,7,8-tetrahydro-naphthalen-2-yl)benzenesulfonamide, hydrochloride

74.1 ((S)-6-Bromo-1,2,3,4-tetrahydro-naphthalen-2-yl)-carbamic acid tert-butyl ester To (S)-6-bromo-1,2,3,4-tetrahydro-naphthalen-2-ylamine (10.0 g, 38.08 mmol) and di-tert-butyldicarbonate (10.39 g, 47.6 mmol) in dichloromethane (200 ml) was added triethylamine (21.12 ml, 152.34 mmol). The reaction mixture was stirred for 1 hour at room temperature and then extracted twice with water (50 ml). The organic layer was dried over magnesium sulfate, filtered, and evaporated to dryness to yield pure product (12.2 g, 98% yield).

ESI-MS: 310.95/312.95 [M+H−CH$_3$]$^+$

74.2 ((S)-6-Bromo-1,2,3,4-tetrahydro-naphthalen-2-yl)-propyl-carbamic acid tert-butyl ester ((S)-6-Bromo-1,2,3,4-tetrahydro-naphthalen-2-yl)-carbamic acid tert-butyl ester (12.2 g, 37.4 mmol) was dissolved in N,N-dimethylformamide (1000 ml). Sodium hydride (50% in oil) (1.975 g, 41.14 mmol) was added and stirred for 15 minutes at room temperature. Propyl bromide (3.74 ml, 41.14 mmol) was added and the reaction mixture was stirred at room temperature overnight. The reaction mixture was poured into a mixture of ice and $H_2O$ (400 ml) and twice extracted with 200 ml diethyl ether. The organic layer was dried over magnesium sulfate, filtered, and evaporated to dryness to yield 14.4 g of crude product. The crude product was purified with silica gel chromatography with cyclohexane/ethyl acetate (95:5) as eluent, yielding the purified product (10.5 g, 76%).

74.3 ((S)-6-Amino-1,2,3,4-tetrahydro-naphthalen-2-yl)-propyl-carbamic acid tert-butyl ester In an inert atmosphere (argon), ((S)-6-bromo-1,2,3,4-tetrahydro-naphthalen-2-yl)propyl-carbamic acid tert-butyl ester (5.0 g, 13.58 mmol) was dissolved in toluene (150 ml) at room temperature. Tris(dibenzylideneacetone)dipalladium (622 mg, 0.68 mmol) and tri-tert-butyl-phosphane (412 mg, 2.04 mmol) were added to the reaction mixture. After 15 minutes bis-(trimethylsilyl)lithiumamide (29.86 ml of a 1 molar solution in tetrahydrofuran) was added slowly and the reaction mixture was stirred for 1 hour at 100° C. The reaction mixture was cooled and slowly $H_2O$ (150 ml) was added and extracted several times with diethyl ether. The organic layer was dried over magnesium sulfate, filtered, and evaporated to dryness to yield 6.9 g of crude product (95% yield, 57% purity).

ESI-MS: 249.15 $[M+H-C(CH_3)_3]^+$

74.4 [(S)-6-(4-Difluoromethoxy-benzenesulfonylamino)-1,2,3,4-tetrahydro-naphthalen-2-yl]-propyl-carbamic acid tert-butyl ester ((S)-6-Amino-1,2,3,4-tetrahydro-naphthalen-2-yl)-propyl-carbamic acid tert-butyl ester (1.5 g, 4.93 mmol) was dissolved in tetrahydrofuran (50 ml). Subsequently, dimethylamino pyridine (100 mg, 0.82 mmol) and difluoromethoxy-benzenesulfonyl chloride (1.195 g, 4.93 mmol) were added and the reaction mixture stirred over night at room temperature. The solvent was evaporated under reduced pressure, the residue treated with water and diethyl ether. The organic layer was dried over magnesium sulfate, filtered, and the solvent evaporated under reduced pressure to give the crude product (2.5 g). The crude product was purified with silica gel chromatography with dichloromethane/methanol (100:0 to 96:4) as eluent, yielding the purified product (2.08 g, 83%).

74.5 4-Difluoromethoxy-N—((S)-6-propylamino-5,6,7,8-tetrahydro-naphthalen-2-yl)benzenesulfonamide, hydrochloride

[(S)-6-(4-Difluoromethoxy-benzenesulfonylamino)-1,2,3,4-tetrahydro-naphthalen-2-yl]-propyl-carbamic acid tert-butyl ester (2.08 g, 4.07 mmol) was dissolved in dichloromethane (100 ml). Trifluoroacetic acid (10 ml) was added and the reaction mixture was stirred at room temperature for 1 hour. The reaction mixture was evaporated to dryness. Diethyl ether (100 ml) was added and extracted with saturated $NaHCO_3$ solution. To the organic layer was added ethereal hydrochloride solution and the solvent evaporated. To the residue was added diethyl ether (25 ml) and the crystalline product was filtered off to give pure product (1.41 g, 77% yield).

ESI-MS: 411.15 $[M+H]^+$ $^1$H-NMR (DMSO-$d_6$, 400 MHz): δ [ppm] 10.25 (s, 1H), 9.0 (m, 2H), 7.8 (d, 2H), 7.35 (t, J=70 Hz, 1H), 7.3 (d, 2H), 7.0 (d, 1H), 6.9 (d, 1H), 6.85 (s, 1H), 3.4 (m, 1H), 3.1 (dd, 1H), 2.95 (m, 2H), 2.75 (m, 3H), 2.2 (m, 1H), 1.7 (m, 3H), 0.9 (t, 3H).

Example 75

4-Difluoromethoxy-N—((R)-6-propylamino-5,6,7,8-tetrahydro-naphthalen-2-yl)benzenesulfonamide, hydrochloride Example 75 was prepared analogous to the procedure described for Example 74, except that in step 75.1 (R)-6-bromo-1,2,3,4-tetrahydro-naphthalen-2-ylamine was used instead of (S)-6-bromo-1,2,3,4-tetrahydro-naphthalen-2-ylamine.

The procedure described in example 47 was used to prepare the compounds of examples 76 to 81. The compounds were characterized by the following physical data.

Example 76

N—((S)-6-Propylamino-5,6,7,8-tetrahydro-naphthalen-2-yl)-4-pyrazol-1-ylbenzenesulfonamide, hydrochloride Sulfonamide coupling: yield 14% (amount 24 mg); removal of tert-butoxy carbonyl protection group: yield: 45% (amount 12 mg);

ESI-MS: 411.2 $[M+H]^+$;

$^1$H-NMR (DMSO-$d_6$, 400 MHz): δ [ppm] 10.22 (s, 1H), 8.70 (br m, 2H), 8.59 (s, 1H), 8.03 (d, 2H), 7.84 (d, 2H), 7.82 (s, 1H), 6.90 (m, 3H), 6.60 (s, 1H), 2.92 (m, 2H), 2.72 (m, 2H), 2.15 (m, 1H), 1.68 (m, 2H), 0.92 (t, 3H).

Example 77

4-(2,2-Difluoro-1-methyl-ethyl)-N—((S)-6-propylamino-5,6,7,8-tetrahydro-naphthalen-2-yl)benzenesulfonamide, hydrochloride Sulfonamide coupling: amount obtained 300 mg; yield 97%; removal of tert-butoxy carbonyl protection group: amount obtained 190 mg; yield: 72%.

ESI-MS: 423.1 $[M+H]^+$ $^1$H-NMR (DMSO-$d_6$, 400 MHz): δ [ppm] 10.22 (s, 1H), 8.75 (br m, 2H), 7.74 (d, 2H), 7.50 (d, 2H), 6.92 (m, 3H), 6.19 (t, 1H), 3.36 (m, 1H), 3.09 (m, 1H), 2.93 (m, 2H), 2.72 (m, 2H), 2.18 (m, 1H), 1.68 (m, 3H), 1.30 (m, 3H), 0.92 (t, 3H).

Example 78

4-Oxazol-5-yl-N—((R)-6-propylamino-5,6,7,8-tetrahydro-naphthalen-2-yl)benzenesulfonamide

78.1 [(R)-6-(4-Oxazol-5-yl-benzenesulfonylamino)-1,2,3,4-tetrahydro-naphthalen-2-yl]-propyl-carbamic acid tert-butyl ester Amount obtained: 165 mg, yield 75%.
ESI-MS: 512.1 $[M+H]^+$

78.2 4-Oxazol-5-yl-N—((R)-6-propylamino-5,6,7,8-tetrahydro-naphthalen-2-yl)benzenesulfonamide Amount obtained: 150 mg, yield 100%.
ESI-MS: 412.1 [M+H]$^+$

Example 79

5-Oxazol-5-yl-thiophene-2-sulfonic acid ((R)-6-propylamino-5,6,7,8-tetrahydro-naphthalen-2-yl)-amide

79.1 [(R)-6-(5-Oxazol-5-yl-thiophene-2-sulfonylamino)-1,2,3,4-tetrahydro-naphthalen-2-yl]-propyl-carbamic acid tert-butyl ester Amount obtained: 201 mg, yield 91%.
ESI-MS: 518.1 [M+H]$^+$

79.2 5-Oxazol-5-yl-thiophene-2-sulfonic acid ((R)-6-propylamino-5,6,7,8-tetrahydronaphthalen-2-yl)-amide Amount obtained: 172 mg; yield: 100%
ESI-MS: 418.1 [M+H]$^+$

Example 80

4-(2,2-Difluoro-1-methyl-ethyl)-N—((R)-6-propylamino-5,6,7,8-tetrahydro-naphthalen-2-yl)benzenesulfonamide

80.1 {(R)-6-[4-(2,2-Difluoro-1-methyl-ethyl)-benzenesulfonylamino]-1,2,3,4-tetrahydronaphthalen-2-yl}-propyl-carbamic acid tert-butyl ester Amount obtained: 247 mg; yield: 100%.
ESI-MS: 523.1 [M+H]$^+$

80.2 4-(2,2-Difluoro-1-methyl-ethyl)-N—((R)-6-propylamino-5,6,7,8-tetrahydro-naphthalen-2-yl)-benzenesulfonamide Amount obtained: 235 mg; yield: 100%.
ESI-MS: 423.1 [M+H]$^+$

Example 81

4-(Bromo)-N—((R)-6-propylamino-5,6,7,8-tetrahydronaphthalen-2-yl)-benzenesulfonamide

81.1 [(R)-6-(4-Bromo-benzenesulfonylamino)-1,2,3,4-tetrahydronaphthalen-2-yl]-propyl-carbamic acid tert-butyl ester Amount obtained: 317 mg; yield: 62%.
ESI-MS: 523.1, 525.1 1 [M+H]$^+$

81.2 4-(Bromo)-N—((R)-6-propylamino-5,6,7,8-tetrahydro-naphthalen-2-yl)benzenesulfonamide Examples of Galenic Administration Forms
A) Tablets
Tablets of the following composition are pressed on a tablet press in the customary manner:
40 mg of substance from Example 8
120 mg of corn starch
13.5 mg of gelatin
45 mg of lactose
2.25 mg of Aerosil® (chemically pure silicic acid in submicroscopically fine dispersion)
6.75 mg of potato starch (as a 6% paste)
B) Sugar-Coated Tablets
20 mg of substance from Example 8
60 mg of core composition
70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

Biological Investigations
Receptor Binding Studies:
The substance to be tested was either dissolved in methanol/Chremophor® (BASF-AG) or in dimethyl sulfoxide and then diluted with water to the desired concentration.

Dopamine $D_3$ Receptor:
The assay mixture (0.250 ml) was composed of membranes derived from ~10$^6$ HEK-293 cells possessing stably expressed human dopamine $D_3$ receptors, 0.1 nM [$^{125}$I]-iodosulpride and incubation buffer (total binding) or, in addition, test substance (inhibition curve) or 1 μM spiperone (nonspecific binding). Each assay mixture was run in triplicate.

The incubation buffer contained 50 mM tris, 120 mM NaCl, 5 mM KCl, 2 mM CaCl$_2$, 2 mM MgCl$_2$ and 0.1% bovine serum albumin, 10 μM quinolone and 0.1% ascorbic acid (prepared fresh daily). The buffer was adjusted to pH 7.4 with HCl.

Dopamine $D_{2L}$ Receptor:
The assay mixture (1 ml) was composed of membranes from ~10$^6$ HEK-293 cells possessing stably expressed human dopamine $D_{2L}$ receptors (long isoform) and 0.01 nM [$^{125}$I] iodospiperone and incubation buffer (total binding) or, in addition, test substance (inhibition curve) or 1 μM haloperidol (nonspecific binding). Each assay mixture was run in triplicate.

The incubation buffer contained 50 mM tris, 120 mM NaCl, 5 mM KCl, 2 mM CaCl$_2$, 2 mM MgCl$_2$ and 0.1% bovine serum albumin. The buffer was adjusted to pH 7.4 with HCl.

Measurement and Analysis:
After having been incubated at 25° C. for 60 minutes, the assay mixtures were filtered through a Whatman GF/B glass fiber filter under vacuum using a cell collecting device. The filters were transferred to scintillation vials using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptro binding studies are expressed as receptor binding constants $K_i(D_2)$ and $K_i(D_3)$, respectively, as herein before described, and given in table 2.

In these tests, the compounds according to the invention exhibit very good affinities for the $D_3$ receptor (frequently <20 nM, in particular <5 nM) and bind selectively to the $D_3$ receptor.

The results of the binding tests are given in table %.

TABLE 5

| Example | $K_i(D3)^*$ [nM] | $K_i(D2)^*$ [nM] | $K_i(D2)^*/K_i(D3)^*$ |
|---|---|---|---|
| 2 | 14 | 442 | 32 |
| 3 | 0.34 | 10.3 | 30 |
| 6 | 0.28 | 14.5 | 52 |
| 7 | 1.97 | 152 | 77 |
| 8 | 0.50 | 50.6 | 102 |
| 9 | 15.3 | 416 | 27 |
| 10 | 8.2 | 238 | 29 |
| 15 | 11.3 | 476 | 42 |
| 19 | 2.5 | 51 | 21 |
| 20 | 7.5 | 339 | 45 |
| 22 | 19.0 | 1829 | 96 |
| 23 | 2.3 | 116 | 50 |
| 29 | 0.37 | 1.39 | 4 |
| 30 | 0.39 | 11.3 | 29 |
| 35 | 30.4 | 12342 | 406 |
| 38 | 4.81 | 727 | 151 |
| 40 | 1.40 | 309 | 221 |
| 41 | 12.2 | 1232.27 | 101 |
| 42 | 1.95 | 514 | 263 |
| 43 | 30.7 | 3477 | 113 |
| 44 | 0.62 | 258 | 416 |
| 45 | 13.9 | 1309 | 94 |
| 46 | 2.5 | | 100 |
| 47 | 5.1 | | 70 |
| 48 | 1.5 | | 128 |
| 49 | 1.3 | | 63 |
| 50 | 1.8 | | 95 |
| 51 | 1.7 | | 56 |
| 52 | 0.7 | | 71 |
| 55 | 1.7 | | 230 |
| 56 | 2.4 | | 161 |
| 58 | 0.15 | | 229 |
| 60 | 9.4 | | 274 |
| 62 | 6.2 | | 77 |
| 63 | 30.9 | | 40 |
| 64 | 3.4 | | 70 |
| 68 | 2 | | 42 |
| 70 | 3.6 | | 61 |
| 74 | 2.5 | 250 | 100 |
| 76 | 8.62 | 728 | 84 |
| 77 | 1.65 | 501 | 304 |

*Receptor binding constants obtained according to the assays described herein before

We claim:

1. An aromatic compound of the formula I

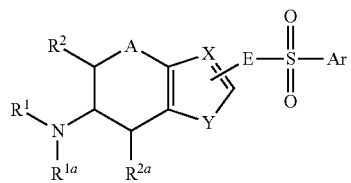

(I)

wherein

Ar is phenyl or an aromatic 5- or 6-membered C-bound heteroaromatic radical, wherein Ar is substituted with 1 radical $R^a$, wherein $R^a$ is selected from the group consisting of $C_2$-$C_6$ alkyl, fluorinated $C_2$-$C_6$ alkyl, fluorinated $C_3$-$C_6$ cycloalkyl, fluoromethyl, difluoromethyl, fluoromethoxy, difluoromethoxy, $C_1$-$C_6$ hydroxyalkyl and a 3- to 7-membered heterocyclic radical, wherein the 3- to 7-membered heterocyclic radical is optionally substituted with 1, 2, 3 or 4 radicals selected from the group consisting of halogen, cyano, OH, oxo, CN, and $C_1$-$C_6$ alkyl;

X is CH;
Y is —CH=CH—;
A is $CH_2$;
E is $NR^3$;

$R^1$ is selected from the group consisting of $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl and $C_1$-$C_3$ alkylcarbonyl;

$R^{1a}$ is selected from the group consisting of H, $C_2$-$C_4$-alkyl, $C_3$-$C_4$-cycloalkyl, $C_3$-$C_4$-alkenyl, fluorinated $C_1$-$C_4$-alkyl, and fluorinated $C_3$-$C_4$-cycloalkyl, or $R^{1a}$ and $R^2$ together are $(CH_2)_n$ wherein n is 2 or 3, or $R^{1a}$ and $R^{2a}$ together are $(CH_2)_n$ with n being 2 or 3;

$R^2$ and $R^{2a}$ are each independently selected from the group consisting of H, $CH_3$, $CH_2F$, $CHF_2$ and $CF_3$;

$R^3$ is H or $C_1$-$C_4$-alkyl;

or a physiologically tolerated acid addition salt thereof.

2. The compound as claimed in claim 1, wherein $R^1$ is selected from the group consisting of $C_2$-$C_4$-alkyl, $C_3$-$C_4$-alkenyl, fluorinated $C_1$-$C_4$-alkyl, and $C_1$-$C_3$-alkylcarbonyl;

$R^{1a}$ is hydrogen or $C_2$-$C_4$-alkyl, or $R^{1a}$ and $R^2$ together are $(CH_2)_3$, or $R^{1a}$ and $R^{2a}$ together are $(CH_2)_3$.

3. The compound as claimed in claim 1, wherein the radical $R^a$ is selected from the group consisting of isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-fluoro-1-methylethyl cyclopropyl, 1 fluorocyclopropyl, (R)-2,2-difluorocyclopropyl, (S)-2,2-difluorocyclopropyl (R)-, and (S)-2-fluorocyclopropyl.

4. The compound as claimed in claim 1, wherein the radical $R^a$ is selected from the group consisting of 4-morpholinyl, 4-thiomorpholinyl, 4-(1,1-dioxo)thiomorpholinyl, piperazin-1-yl, 4-methylpiperazin-1-yl, azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, pyrrolidin-2-yl, (S)pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl, (R)-1-methylpyrrolidin-3-yl, 2,2-dimethylpyrrolidin-1-yl, 3,3-dimethylpyrrolidin-1-yl, 2-oxopyrrolidin-1-yl, 2-oxooxazolidin-3-yl, piperidin-1-yl, 2-methylpiperidin-1-yl, (S)-2-methylpiperidin-1-yl, and (R)-2-methylpiperidin-1-yl.

5. The compound as claimed in claim 1, wherein Ar is substituted by one radical $R^a$, which is selected from the group consisting of $CHF_2$, $CH_2F$, $OCHF_2$, and $OCH_2F$.

6. The compound as claimed in claim 1, wherein Ar is substituted by one radical $R^a$, which is selected from 5- or 6-membered heteroaromatic radicals having as ring members 1 heteroatom selected from O, S, and N, and which optionally further contains 1, 2 or 3 nitrogen atoms as ring members, and wherein the 5- or 6-membered heteroaromatic radical is unsubstituted or substituted with 1, 2 or 3 substituents selected from halogen, OH, CN, and $C_1$-$C_6$-alkyl.

7. The compound as claimed in claim 6, wherein Ar is substituted by one heteroaromatic radical $R^a$, which is selected from the group consisting of furanyl, thienyl, pyrrolyl, pyrazolyl, imidazolyl, oxazolyl, isoxazolyl, 1,3,4-thiadiazolyl, 1,2,4-triazolyl, 1,2,3-triazolyl, and tetrazolyl, wherein the heteroaromatic radical is optionally substituted with 1, 2, or 3 substituents selected from the group consisting of halogen and $C_2$-$C_4$-alkyl.

8. The compound as claimed in claim 1, wherein Ar is phenyl.

9. The compound as claimed in claim 1, wherein Ar is phenyl that is substituted by a radical $R^a$ in the 4-position of the phenyl ring.

10. The compounds as claimed in claim 1, wherein $R^1$ is n-propyl, fluorinated linear $C_2$-$C_3$-alkyl, or 1-propen-3-yl.

11. The compound as claimed in claim 1, wherein $R^{1a}$ is hydrogen.

12. The compound as claimed in claim 1, wherein $R^{1a}$ is n-propyl or 1-propen-3-yl.

13. The compounds as claimed in claim 1, wherein either $R^{1a}$ and $R^2$ or $R^{1a}$ and $R^{2a}$ form a moiety $(CH_2)_n$ with n being 2 or 3.

14. The compound as claimed in claim 1 of the formula Ia

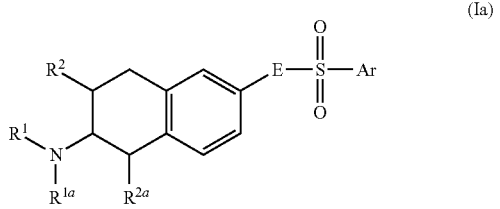

(Ia)

wherein $R^1$, $R^{1a}$, $R^2$, $R^{2a}$, $R^3$, E and Ar have the meanings given in claim 1 or a physiologically tolerated acid addition salt thereof.

15. The compound of the formula Ia and the physiologically tolerated acid addition salts thereof as claimed in claim 14, wherein $R^2$ and $R^{2a}$ are hydrogen, Ar is 4-difluoromethoxyphenyl, and $R^1$ is n-propyl, fluorinated linear $C_2$-$C_3$-alkyl, or 1-propen-3-yl.

16. The compound as claimed in claim 15, wherein $R^{1a}$ is hydrogen.

17. The compound as claimed in claim 15, wherein $R^1$ is propyl.

18. The compound as claimed in claim 1, wherein $R^2$ and $R^{2a}$ are hydrogen.

19. The compound as claimed in claim 18, wherein Ar is 4-difluoromethoxyphenyl.

20. The compound as claimed in claim 18, wherein $R^1$ is n-propyl, fluorinated linear $C_2$-$C_3$-alkyl, or 1-propen-3-yl.

21. The compound as claimed in claim 18, wherein $R^{1a}$ is hydrogen.

22. A compound selected from the group consisting of:
(R)—N-[7-(4-Isopropylbenzenesulfonylamino)-1,2,3,4-tetrahydro-naphthalen-2-yl]-propionamide;
(R)-4-Isopropyl-N-((R)-7-propylamino-5,6,7,8-tetrahydro-naphthalen-2-yl)benzenesulfonamide;
4-Isopropyl-N-((R)-6-propylamino-5,6,7,8-tetrahydro-naphthalen-2-yl)-benzenesulfonamide;
(R)—N-[5-(4-Isopropyl-benzenesulfonylamino)-1,2,3,4-tetrahydro-naphthalen-2-yl]-propionamide;
(R)-4-Isopropyl-N-(6-propylamino-5,6,7,8-tetrahydro-naphthalen-1-yl)-benzenesulfonamide;
N—((R)-6-Allylamino-5,6,7,8-tetrahydro-naphthalen-2-yl)-4-isopropyl-benzenesulfonamide;
N—((S)-6-Allylamino-5,6,7,8-tetrahydro-naphthalen-2-yl)-4-isopropyl-benzenesulfonamide;
4-Isopropyl-N-((S)-6-propylamino-5,6,7,8-tetrahydro-naphthalen-2-yl)-benzenesulfonamide;
N—((S)-6-Allylamino-5,6,7,8-tetrahydro-naphthalen-2-yl)-4-isopropyl-N-methylbenzenesulfonamide;
4-Isopropyl-N-methyl-N-((S)-6-propylamino-5,6,7,8-tetrahydro-naphthalen-2-yl)benzenesulfonamide;
N-((4aS,10bS)-4-Allyl-1,2,3,4,4a,5,6,10b-octahydro-benzo[f]quinolin-8-yl)-4-isopropylbenzenesulfonamide;
N-((4aS,10bS)-4-Allyl-1,2,3,4,4a,5,6,10b-octahydro-benzo[f]quinolin-9-yl)-4-isopropylbenzenesulfonamide;
N-((4aS,10bS)-4-Allyl-1,2,3,4,4a,5,6,10b-octahydro-benzo[f]quinolin-7-yl)-4-isopropylbenzenesulfonamide;
trans-4-Isopropyl-N-(1-propionyl-1,2,3,4,4a,5,10,10a-octahydro-benzo[g]quinolin-7-yl)benzenesulfonamide;
trans-4-Isopropyl-N-(1-propyl-1,2,3,4,4a,5,10,10a-octahydro-benzo[g]quinolin-7-yl)benzenesulfonamide;
N—((R)-6-Dipropylamino-5,6,7,8-tetrahydro-naphthalen-2-yl)-4-isopropyl-benzenesulfonamide;
N—((S)-6-Dipropylamino-5,6,7,8-tetrahydro-naphthalen-2-yl)-4-isopropyl-benzenesulfonamide;
4-Oxazol-5-yl-N-((S)-6-propylamino-5,6,7,8-tetrahydro-naphthalen-2-yl)benzenesulfonamide;
5-Oxazol-5-yl-thiophene-2-sulfonic acid ((S)-6-propylamino-5,6,7,8-tetrahydro-naphthalen-2-yl)amide;
5-Isoxazol-5-yl-thiophene-2-sulfonic acid ((S)-6-propylamino-5,6,7,8-tetrahydronaphthalen-2-yl)amide;
N—((S)-6-Propylamino-5,6,7,8-tetrahydro-naphthalen-2-yl)-4-(2,2,2-trifluoro-1-methyl-ethyl)benzenesulfonamide racemate;
N—((S)-6-Propylamino-5,6,7,8-tetrahydro-naphthalen-2-yl)-4-((R)-2,2,2-trifluoro-1-methylethyl)-benzenesulfonamide;
N—((S)-6-Propylamino-5,6,7,8-tetrahydro-naphthalen-2-yl)-4-((S)-2,2,2-trifluoro-1-methylethyl)-benzenesulfonamide;
5-Isoxazol-3-yl-thiophene-2-sulfonic acid ((S)-6-propylamino-5,6,7,8-tetrahydro-naphthalen-2-yl)amide;
4-((R)-3-Fluoro-pyrrolidin-1-yl)-N-((S)-6-propylamino-5,6,7,8-tetrahydro-naphthalen-2-yl)benzenesulfonamide;
4-Morpholin-4-yl-N-((S)-6-propylamino-5,6,7,8-tetrahydro-naphthalen-2-yl)benzenesulfonamide;
4-Difluoromethoxy-N-((S)-6-propylamino-5,6,7,8-tetrahydro-naphthalen-2-yl)benzenesulfonamide;
N—((S)-6-Propylamino-5,6,7,8-tetrahydro-naphthalen-2-yl)-4-(2,2,2-trifluoroethyl)benzenesulfonamide;
4-(2,2-Difluoro-cyclopropyl)-N-((S)-6-propylamino-5,6,7,8-tetrahydro-naphthalen-2-yl)benzenesulfonamide;
N—((S)-6-Propylamino-5,6,7,8-tetrahydro-naphthalen-2-yl)-4-pyrrolidin-1-ylbenzenesulfonamide;
4-(3-Fluoro-propyl)-N-((S)-6-propylamino-5,6,7,8-tetrahydro-naphthalen-2-yl)benzenesulfonamide;
5-Propyl-thiophene-sulfonic acid ((S)-6-propylamino-5,6,7,8-tetrahydro-naphthalen-2-yl)amide;

4-((S)-2-Fluoro-1-methyl-ethyl)-N-((S)-6-propylamino-5,6,7,8-tetrahydro-naphthalen-2-yl)benzenesulfonamide;

4-((R)-2-Fluoro-1-methyl-ethyl)-N-((S)-6-propylamino-5,6,7,8-tetrahydro-naphthalen-2-yl)benzenesulfonamide;

4-(1-Methyl-1H-pyrazol-4-yl)-N-((S)-6-propylamino-5,6,7,8-tetrahydro-naphthalen-2-yl)benzenesulfonamide;

4-(3-Fluoro-propyl)-N-((R)-6-propylamino-5,6,7,8-tetrahydro-naphthalen-2-yl)benzenesulfonamide;

4-(2-Fluoro-ethyl)-N-((R)-6-propylamino-5,6,7,8-tetrahydro-naphthalen-2-yl)benzenesulfonamide;

4-(1-Hydroxy-1-methyl-ethyl)-N-((S)-6-propylamino-5,6,7,8-tetrahydro-naphthalen-2-yl)benzenesulfonamide;

4-(1-Fluoro-1-methyl-ethyl)-N-((S)-6-propylamino-5,6,7,8-tetrahydro-naphthalen-2-yl)benzenesulfonamide;

N—((S)-6-Ethylamino-5,6,7,8-tetrahydro-naphthalen-2-yl)-4-isopropyl-benzenesulfonamide;

N—[(S)-6-(2-Fluoro-ethylamino)-5,6,7,8-tetrahydro-naphthalen-2-yl]-4-isopropylbenzenesulfonamide;

N—[(S)-6-(3-Fluoro-propylamino)-5,6,7,8-tetrahydro-naphthalen-2-yl]-4-isopropylbenzenesulfonamide;

N—((S)-6-Ethylamino-5,6,7,8-tetrahydro-naphthalen-2-yl)-4-(2-oxo-pyrrolidin-1-yl)benzenesulfonamide;

N—((S)-6-Ethylamino-5,6,7,8-tetrahydro-naphthalen-2-yl)-4-pyrrolidin-1-yl benzenesulfonamide;

4-((S)-2-Fluoro-1-methyl-ethyl)-N-((R)-6-propylamino-5,6,7,8-tetrahydro-naphthalen-2-yl)benzenesulfonamide;

N—((R)-6-Propylamino-5,6,7,8-tetrahydro-naphthalen-2-yl)-4-(2,2,2-trifluoro-1-methylethyl)benzenesulfonamide;

4-Difluoromethoxy-N-((R)-6-propylamino-5,6,7,8-tetrahydro-naphthalen-2-yl)benzenesulfonamide;

N—((S)-6-Propylamino-5,6,7,8-tetrahydro-naphthalen-2-yl)-4-pyrazol-1-yl benzenesulfonamide;

4-(2,2-Difluoro-1-methyl-ethyl)-N-((S)-6-propylamino-5,6,7,8-tetrahydro-naphthalen-2-yl)benzenesulfonamide;

4-Oxazol-5-yl-N-((R)-6-propylamino-5,6,7,8-tetrahydro-naphthalen-2-yl)benzenesulfonamide;

5-Oxazol-5-yl-thiophene-2-sulfonic acid ((R)-6-propylamino-5,6,7,8-tetrahydro-naphthalen-2-yl)amide; and 4-(2,2-Difluoro-1-methyl-ethyl)-N-((R)-6-propylamino-5,6,7,8-tetrahydro-naphthalen-2-yl)benzenesulfonamide;

or a physiologically tolerated acid addition salt thereof.

23. The compound 4-difluoromethoxy-N-((S)-6-propylamino-5,6,7,8-tetrahydro-naphthalen-2-yl)benzenesulfonamide or a physiologically tolerated acid addition salt thereof.

24. The compound 4-difluoromethoxy-N-((S)-6-propylamino-5,6,7,8-tetrahydro-naphthalen-2-yl)benzenesulfonamide, hydrochloride.

25. A pharmaceutical composition comprising at least one compound of the formula I or a pharmaceutically acceptable salt thereof as claimed in claim 1, optionally together with at least one physiologically acceptable carrier or auxiliary substance.

\* \* \* \* \*